US012389888B2

(12) United States Patent
McWhirter et al.

(10) Patent No.: US 12,389,888 B2
(45) **Date of Patent: *Aug. 19, 2025**

(54) MICE EXPRESSING A LIMITED IMMUNOGLOBULIN LIGHT CHAIN REPERTOIRE

(71) Applicant: Regeneron Pharmaceuticals, Inc., Tarrytown, NY (US)

(72) Inventors: John McWhirter, Sanremo (IT); Lynn Macdonald, Harrison, NY (US); Sean Stevens, Del Mar, CA (US); Andrew J. Murphy, Croton-on-Hudson, NY (US)

(73) Assignee: Regeneron Pharmaceuticals, Inc., Tarrytown, NY (US)

( * ) Notice: Subject to any disclaimer, the term of this patent is extended or adjusted under 35 U.S.C. 154(b) by 1129 days.

This patent is subject to a terminal disclaimer.

(21) Appl. No.: 17/238,710

(22) Filed: Apr. 23, 2021

(65) Prior Publication Data

US 2021/0315189 A1 Oct. 14, 2021

Related U.S. Application Data

(63) Continuation of application No. 16/530,030, filed on Aug. 2, 2019, now Pat. No. 11,026,407, which is a continuation of application No. 16/128,360, filed on Sep. 11, 2018, now Pat. No. 10,412,940, which is a continuation of application No. 15/700,973, filed on Sep. 11, 2017, now Pat. No. 10,167,344, which is a continuation of application No. 13/798,455, filed on Mar. 13, 2013, now Pat. No. 9,796,788, which is a continuation-in-part of application No. 13/488,628, filed on Jun. 5, 2012, now abandoned, which is a continuation-in-part of application No. 13/412,936, filed on Mar. 6, 2012, now abandoned, which is a continuation-in-part of application No. 13/093,156, filed on Apr. 25, 2011, now abandoned, which is a continuation-in-part of application No. 13/022,759, filed on Feb. 8, 2011, now Pat. No. 10,143,186.

(60) Provisional application No. 61/302,282, filed on Feb. 8, 2010.

(51) Int. Cl.

| | |
|---|---|
| ***A01K 67/0278*** | (2024.01) |
| ***A01K 67/0275*** | (2024.01) |
| ***C07K 16/00*** | (2006.01) |
| ***C07K 16/46*** | (2006.01) |
| ***C12N 15/85*** | (2006.01) |

(52) U.S. Cl.

CPC ...... *A01K 67/0278* (2013.01); *A01K 67/0275* (2013.01); *C07K 16/00* (2013.01); *C07K 16/462* (2013.01); *C12N 15/8509* (2013.01); *A01K 2207/15* (2013.01); *A01K 2217/072* (2013.01); *A01K 2217/15* (2013.01); *A01K 2227/105* (2013.01); *A01K 2267/01* (2013.01); *C07K 2317/21* (2013.01); *C07K 2317/24* (2013.01); *C07K 2317/515* (2013.01)

(58) Field of Classification Search

CPC ............ A01K 67/0278; A01K 67/0275; A01K 2207/15; A01K 2217/072; A01K 2217/15; A01K 2227/105; A01K 2267/01; C07K 16/00; C07K 16/462; C07K 2317/21; C07K 2317/24; C07K 2317/515; C12N 15/8509

USPC ................................................ 800/18, 21, 6

See application file for complete search history.

(56) References Cited

U.S. PATENT DOCUMENTS

| | | | |
|---|---|---|---|
| 5,545,807 | A | 8/1996 | Surani et al. |
| 5,574,205 | A | 11/1996 | Kucherlapati et al. |
| 5,667,988 | A | 9/1997 | Barbas et al. |
| 5,770,429 | A | 6/1998 | Lonberg et al. |
| 5,789,208 | A | 8/1998 | Sharon |
| 5,888,789 | A | 3/1999 | Rodriguez |
| 5,939,598 | A | 8/1999 | Kucherlapati et al. |
| 6,075,181 | A | 6/2000 | Kucherlapati et al. |
| 6,080,560 | A | 6/2000 | Russell et al. |
| 6,096,551 | A | 8/2000 | Barbas et al. |
| 6,114,598 | A | 9/2000 | Kucherlapati et al. |
| 6,139,835 | A | 10/2000 | Kucherlapati et al. |
| 6,150,584 | A | 11/2000 | Kucherlapati et al. |
| 6,162,963 | A | 12/2000 | Kucherlapati et al. |
| 6,514,752 | B1 | 2/2003 | Kucherlapati et al. |

(Continued)

FOREIGN PATENT DOCUMENTS

| | | | |
|---|---|---|---|
| CN | 1277632 | A | 12/2000 |
| CN | 1484707 | A | 3/2004 |

(Continued)

OTHER PUBLICATIONS

De Wildt et al. (1999) J. Mol. Biol., vol. 285, 895-901.*

(Continued)

*Primary Examiner* — Anne Marie S Wehbe

(74) *Attorney, Agent, or Firm* — Choate, Hall & Stewart LLP; Stephanie L. Schonewald; Dana M. Daukss

(57) ABSTRACT

A genetically modified mouse is provided, wherein the mouse expresses an immunoglobulin light chain repertoire characterized by a limited number of light chain variable domains. Mice are provided that present a choice of two human light chain variable gene segments such that the immunoglobulin light chains expresses by the mouse comprise one of the two human light chain variable gene segments. Methods for making bispecific antibodies having universal light chains using mice as described herein, including human light chain variable regions, are provided. Methods for making human variable regions suitable for use in multispecific binding proteins, e.g., bispecific antibodies, and host cells are provided.

12 Claims, 29 Drawing Sheets

Specification includes a Sequence Listing.

(56) References Cited

U.S. PATENT DOCUMENTS 6,551,592 B2 4/2003 Lindhofer et al.
6,596,541 B2 7/2003 Murphy et al.
6,657,103 B1 12/2003 Kucherlapati et al.
6,673,986 B1 1/2004 Kucherlapati et al.
6,713,610 B1 3/2004 Kucherlapati et al.
6,914,128 B1 7/2005 Salfeld et al.
6,998,514 B2 2/2006 Bruggemann
7,052,873 B2 5/2006 Tsuchiya
7,064,244 B2 6/2006 Jakobovits et al.
7,067,284 B1 6/2006 Barbas et al.
7,084,260 B1 8/2006 Lonberg et al.
7,105,348 B2 9/2006 Murphy et al.
7,119,248 B1 10/2006 Rajewsky et al.
7,129,084 B2 10/2006 Buelow et al.
7,183,076 B2 2/2007 Arathoon et al.
7,262,028 B2 8/2007 Van Berkel et al.
7,435,871 B2 10/2008 Green et al.
7,501,552 B2 3/2009 Lonberg et al.
7,534,604 B2 5/2009 Fandl et al.
7,585,668 B2 9/2009 Buelow et al.
7,605,237 B2 10/2009 Stevens et al.
7,642,228 B2 1/2010 Carter et al.
7,704,498 B2 4/2010 Gerritsen et al.
7,879,985 B2 2/2011 Urso et al.
7,910,798 B2 3/2011 Tanamachi et al.
8,158,419 B2 4/2012 Lonberg et al.
8,502,018 B2 8/2013 Murphy et al.
8,592,562 B2 11/2013 Kannan et al.
8,642,835 B2 2/2014 MacDonald et al.
9,248,182 B2 2/2016 De Kruif et al.
9,796,788 B2 * 10/2017 McWhirter ............ C07K 16/00
10,167,344 B2 * 1/2019 McWhirter ........ A01K 67/0278
10,412,940 B2 * 9/2019 McWhirter ........ A01K 67/0278
11,026,407 B2 * 6/2021 McWhirter ............ C07K 16/00
2002/0088016 A1 7/2002 Bruggemann
2003/0017534 A1 1/2003 Buelow et al.
2003/0078385 A1 4/2003 Arathoon et al.
2003/0108925 A1 6/2003 Dix et al.
2003/0138440 A1 7/2003 Fang et al.
2003/0217373 A1 11/2003 Green et al.
2004/0015880 A1 1/2004 Floyd et al.
2004/0018626 A1 1/2004 Murphy et al.
2004/0052773 A1 3/2004 Bogen et al.
2004/0146991 A1 7/2004 Tsuji et al.
2005/0059082 A1 3/2005 Breitling et al.
2005/0153392 A1 7/2005 Buelow et al.
2005/0170398 A1 8/2005 Van Berkel et al.
2005/0229263 A1 10/2005 Buelow
2006/0015949 A1 1/2006 Lonberg et al.
2006/0015957 A1 * 1/2006 Lonberg .............. C07K 16/462 800/18
2006/0021074 A1 1/2006 Kellermann et al.
2006/0026696 A1 2/2006 Buelow et al.
2006/0083747 A1 4/2006 Winter et al.
2006/0099207 A1 5/2006 Wu et al.
2006/0117398 A1 6/2006 Buelow et al.
2006/0153826 A1 7/2006 Arnould et al.
2006/0199204 A1 9/2006 Dix et al.
2007/0009957 A1 1/2007 Bowdish et al.
2007/0280945 A1 12/2007 Stevens et al.
2008/0069822 A1 * 3/2008 Jensen ................ C07K 16/081 435/339
2009/0083879 A1 3/2009 Dhugga
2009/0092582 A1 4/2009 Bogin et al.
2009/0093059 A1 4/2009 Baszczynski et al.
2009/0181855 A1 7/2009 Vasquez et al.
2009/0258392 A1 10/2009 Gallo et al.
2010/0069614 A1 3/2010 Houtzager et al.
2010/0146647 A1 6/2010 Logtenberg et al.
2010/0286374 A1 11/2010 Kannan et al.
2010/0310586 A1 12/2010 Dolcetti et al.
2010/0331527 A1 12/2010 Davis et al.
2011/0195454 A1 8/2011 McWhirter et al.
2012/0021409 A1 1/2012 McWhirter et al.
2012/0070861 A1 3/2012 Macdonald et al.
2012/0167237 A1 6/2012 Bradley et al.
2012/0192300 A1 7/2012 Babb et al.
2012/0204278 A1 8/2012 Bradley et al.
2012/0222140 A1 8/2012 Kuroiwa et al.
2013/0045492 A1 2/2013 Babb et al.
2013/0096020 A1 4/2013 Throsby et al.
2013/0096287 A1 4/2013 Macdonald et al.
2013/0145484 A1 6/2013 Logtenberg et al.
2013/0198879 A1 8/2013 McWhirter et al.
2014/0322756 A1 10/2014 Arathoon et al.
2016/0238600 A1 8/2016 Hoogenboom et al.
2024/0156070 A1 5/2024 Babb et al.

FOREIGN PATENT DOCUMENTS

CN 1560081 A 1/2005
CN 101962408 A 2/2011
EP 0364096 A2 4/1990
EP 1298207 A1 4/2003
EP 1439234 A1 7/2004
EP 1605058 A1 12/2005
EP 1505148 B1 4/2009
EP 2147594 A1 1/2010
EP 2501817 A1 9/2012
EP 2505654 A1 10/2012
EP 2517556 A2 10/2012
EP 2517557 A2 10/2012
EP 2556747 A2 2/2013
EP 2564695 A1 3/2013
EP 2582230 A1 4/2013
RU 2434882 C2 11/2011
WO WO-90/04036 A1 4/1990
WO WO-91/00906 A1 1/1991
WO WO-91/08216 A1 6/1991
WO WO-92/03918 A1 3/1992
WO WO-94/02602 A1 2/1994
WO WO-94/04690 A1 3/1994
WO WO-94/25585 A1 11/1994
WO WO-95/17085 A1 6/1995
WO WO-95/17500 A1 6/1995
WO WO-97/13852 A1 4/1997
WO WO-97/42313 A1 11/1997
WO WO-98/24893 A2 6/1998
WO WO-98/39416 A1 9/1998
WO WO-98/46645 A2 10/1998
WO WO-1998/50431 A2 11/1998
WO WO-1999/018212 A1 4/1999
WO WO-99/45962 A1 9/1999
WO WO-00/63403 A2 10/2000
WO WO-01/64929 A1 9/2001
WO WO-02/08409 A2 1/2002
WO WO-02/12437 A2 2/2002
WO WO-02/18948 A2 3/2002
WO WO-2002/036789 A2 5/2002
WO WO-02/053596 A2 7/2002
WO WO 02/066630 * 8/2002
WO WO-02/066630 A1 8/2002
WO WO-02/085944 A2 10/2002
WO WO-02/085945 A2 10/2002
WO WO-03/002609 A2 1/2003
WO WO-03/052416 A2 6/2003
WO WO-03/061363 A2 7/2003
WO WO-03/106495 A2 12/2003
WO WO-2004/006955 A1 1/2004
WO WO-2004/009618 A2 1/2004
WO WO-2004/049794 A2 6/2004
WO WO-2004/050838 A2 6/2004
WO WO-2004/058820 A2 7/2004
WO WO-2004/106375 A1 12/2004
WO WO-2005/007696 A2 1/2005
WO WO-2005/019463 A1 3/2005
WO WO-2005/038001 A2 4/2005
WO WO-2006/117699 A2 11/2006
WO WO-2006/122442 A1 11/2006
WO WO-2007/096779 A2 8/2007
WO WO-2007/117410 A2 10/2007
WO WO-2008/022391 A1 2/2008
WO WO-2008/054606 A2 5/2008
WO WO-2008/076379 A2 6/2008

(56) References Cited

FOREIGN PATENT DOCUMENTS

WO WO-2008/081197 A1 7/2008
WO WO-2008/112922 A2 9/2008
WO WO-2008/151081 A1 12/2008
WO WO-2009/013620 A2 1/2009
WO WO-2009/051974 A1 4/2009
WO WO-2009/089004 A1 7/2009
WO WO-2009/097006 A2 8/2009
WO WO-2009/129247 A2 10/2009
WO WO-2009/143472 A2 11/2009
WO WO-2009/157771 A2 12/2009
WO WO-2010/039900 A2 4/2010
WO WO-2010/053751 A1 5/2010
WO WO-2010/054007 A1 5/2010
WO WO-2010/070263 A1 6/2010
WO WO-2010/097385 A1 9/2010
WO WO-2010/136598 A1 12/2010
WO WO-2010/151792 A1 12/2010
WO WO-2011/004192 A1 1/2011
WO WO-2011/062207 A1 5/2011
WO WO-2011/072204 A1 6/2011
WO WO-2011/097603 A1 8/2011
WO WO-2011/143545 A1 11/2011
WO WO-2011/158009 A1 12/2011
WO WO-2011/163311 A1 12/2011
WO WO-2011/163314 A1 12/2011
WO WO-2012/018764 A1 2/2012
WO WO-2012/141798 A1 10/2012
WO WO-2012/148873 A2 11/2012
WO WO-2013/022782 A1 2/2013
WO WO-2013/059230 A1 4/2013
WO WO-2013/079953 A1 6/2013
WO WO-2013/134263 A1 9/2013
WO WO-2013/184761 A1 12/2013
WO WO-2014/160179 A1 10/2014
WO WO-2014/160202 A1 10/2014

OTHER PUBLICATIONS

Merchant et al. (1998) Nat. Biotech., vol. 16, 677-681.*
Adderson, E. et al., Restricted immunoglobulin VH usage and VDJ combinations in the human response to Haemophilus influenzae type b capsular polysaccharide. Nucleotide sequences of monospecific anti-Haemophilus antibodies and polyspecific antibodies cross-reacting with self antigens, J Clin Invest., 91(6):2734-43 (1993).
Al-Lazikani, B. et al., Standard conformations for the canonical structures of immunoglobulins, J. Mol. Biol., 273(4):927-48 (1997).
Applicant's Written Submissions for AU2009263082, 49 pages (Sep. 6, 2016).
Arnaout, R. et al., High-resolution description of antibody heavy-chain repertoires in; humans PLoS One, 6(8):e22365 (2011).
Arnold, L. et al., Development of B-1 cells: segregation of phosphatidyl choline-specific B cells to the B-1 population occurs after immunoglobulin gene expression, J. Exp. Med., 179:1585-1595 (1994).
Askew, G.R. et al., Site-directed point mutations in embryonic stem cells: a gene-targeting tag-and-exchange strategy, Mol. Cell Biol., 13(7):4115-24 (1993).
Aucouturier, P.et al., Monoclonal Ig L chain and L chain V domain fragment crystallization in myeloma-associated Fanconi's syndrome, J. Immunol., 150( 8):3561-3568 (1993).
Author Not Known, Additional post-filing data and letter filed by the Applicant/Patentee for corresponding European application 09075279.1, now opposed patent EP 2147594 B1, 4 pages (Jun. 13 2013).
Author Not Known, Chapter 6: The Development of B Lymphocytes, Immuno Biology: The Immune System in Health and Disease, 4th Edition, Janeway et al. ed., pp. 195-208 (1999).
Author Not Known, Chapter 8: The Development and Survival of Lymphocytes, Janeway's Immunobiology, 8th Edition, Eds. Kenneth Murphy et al, Garland Science (ISBN: 9780815342434), whole document, in particular p. 279 and Figure 8.4, (2011).
Author Not Known, Mouse strain, document #3 submitted with Third Party Observation, filed in GB2012052956, 4 pages (Mar. 26, 2014).
Author Not Known, Next generation transgenic mice for therapeutic human antibodies, Description of MeMoTM, filed by the Applicant/Patentee in prosecution for corresponding European application 09075279.1, now opposed patent EP 2147594 B1, 2 pages (Dec. 22, 2011).
Author Not Known, V-BASE Sequence Directory, 6 pages, retrieved on Jun. 6, 2016 <http://www2.mrc-lmb.cam.ac.uk/vbase/list2.php.
Baeuerle, P.A. and Reinhardt, C., Bispecific T-cell engaging antibodies for cancer; therapy, Cancer Res., 69(12):4941-4 (2009).
Bauer, S. et al., Structure and pre-B lymphocyte restricted expression of the VpreB gene in humans and conservation of its structure in other mammalian species, The EMBO Journal, 7(1):111-116 (1988).
Billiard, F. et al., Ongoing DII4-Notch signaling is required for T-cell homeostasis in the adult thymus, Eur. J. Immunol., 41(8):2207-16 (2011).
Blaas, L. et al., Bacterial artificial chromosomes improve recombinant protein production in mammalian cells, BMC Biotechnol., 9:3 (2009).
Bode, J. et al., The transgeneticist's toolbox: novel methods for the targeted modification of eukaryotic genomes, Biol. Chem., 381(9-10):801-13 (2000).
Bot, A. et al., V2-Light Chain Genes Reconstitute Immune Responses to Defined Carbohydrate Antigens or Haptens by Utilizing Different VH Genes, Molecular Immunology, 33(17/18):1359-1368 (1996).
Brezinschek, H. et al., Pairing of variable heavy and variable kappa chains in individual naïve and memory B cells, J. Immunol., 160(10):4762-4767 (1998).
Brezinschek, H.P. et al., Analysis of the human VH gene repertoire. Differential effects of selection and somatic hypermutation on human peripheral CD5(+)/IgM+ and CD5(−)/IgM+ B; Cells, J. Clin. Invest., 99(10):2488-501 (1997).
Brief comments on third party observations, EP 11703799.1-1410, submitted to EPO by David Power, 3 pages (Apr. 20, 2015).
Brüggemann, M. and Neuberger, M.S., Strategies for expressing human antibody repertoires in transgenic mice, Immunol. Today, 17(8):391-7 (1996).
Bruggemann, M. et al., A repertoire of monoclonal antibodies with human heavy chains from transgenic mice, Proceedings of the National of Academy of Science USA, 86:6709-6713 (1989).
Bruggemann, M., Human Antibody Expression in Transgenic Mice, Archivum Immunologiae et Therapiae Experimentalis, 49:203-208 (2001).
Brüggemann, M., Human Monoclonal Antibodies from Translocus Mice, Molecular Biology of B Cells, Eds. Honjo, T. and Neuberger, M.S., New York, NY: Academic Press, pp. 547-561 (2004).
Campbell, K.H. et al., Sheep cloned by nuclear transfer from a cultured cell line, Nature, 380(6569):64-6 (1996).
Carmack, C. et al., Influence of a V kappa 8 L chain transgene on endogenous rearrangements and the immune response to the HA(Sb) determinant of influenza virus, J. Immunol., 147(6):2024-2033 (1991).
Carter, P., Bispecific human IgG by design, Journal of Immunological Methods, 248(1-2):7-15 (2001).
Cascalho, M. et al., A quasi-monoclonal mouse, Science, 272(5268):1649-1652 (1996).
Casellas, R. et al., Contribution of receptor editing to the antibody repertoire, Science, 291(5508):1541-4 (2001).
Chen, C. et al., Deletion and Editing of B Cells that Express Antibodies to DNA, Journal of Immunology, 152(4):1970-1982 (1994).
Choi, I. et al., Characterization and comparative genomic analysis of intronless Adams with testicular gene expression, Genomics, 83(4):636-46 (2004).
Chothia, C. and Lesk, A.M., Canonical structures for the hypervariable regions of; Immunoglobulins, J. Mol. Biol., 196(4):901-17 (1987).
Choulika, A. et al., Induction of homologous recombination in mammalian chromosomes by using the I-Scel system of *Saccharomyces cerevisiae*, Mol. Cell. Biol., 15:4 1968-73 (1995).

(56) References Cited

OTHER PUBLICATIONS

Cohen-Tannoudji, M. et al., I-Scel-induced gene replacement at a natural locus in; embryonic stem cells, Mol. Cell. Biol., 18(3):1444-8 (1998).
Collins, A. et al., The reported germline repertoire of human immunoglobulin kappa chain genes is relatively complete and accurate, Immunogenetics, 60:669-676 (2008).
Combriato, G. and Klobeck, H.G., Regulation of human Ig lambda light chain gene expression by NF-kappa B, J. Immunol., 168(3):1259-66 (2002).
Conrath, K. et al., Camel single-domain antibodies as modular building units in bispecific and bivalent antibody constructs, J. Biol. Chem., 276(10):7346-50 (2001).
Corcos, D. et al., Pre-B-cell development in the absence of lambda 5 in transgenic mice expressing a heavy-chain disease protein, Curr. Biol., 5(10):1140-8 (1995).
Corrected Claims in JP5749161 (English and Japanese), 6 pages.
Cover Letter—Applicant Post-Hearing Submissions in AU2009263082, 1 page (Oct. 19, 2016).
Cowen, N.J. et al., Purification and Sequence Analysis of the mRNA Coding for an Immunoglobulin Heavy Chain, European J. of Biochem., 61(2): 355-368 (1976).
Davies, N. et al., Creation of Mice Expressing Human Antibody Light Chains by Introduction of a Yeast Artificial Chromosome Containing the Core Region of the Human Immunoglobulin κ Locus, Nature Biotechnology 11:911-914, (1993).
De Kruif, J. et al., Human Immunoglobulin Repertoires against Tetanus Toxoid Contain a Large and Diverse Fraction of High-Affinity Promiscuous VH Genes, Journal of Molecular Biology, 387:548-558 (2009).
De Kruif, J. et al., Rapid selection of cell subpopulation-specific human monoclonal antibodies from a synthetic phage antibody library, Proc. Natl. Acad. Sci. U S A, 92(9):3938-42 (1995).
De Wildt, R. et al., Analysis of heavy and light chain pairings indicates that receptor editing shapes the human antibody repertoire, J. Mol. Biol., 285(3):895-901 (1999).
Dechiara, T.M. et al., Chapter 16: VelociMouse: Fully ES Cell-Derived FO Generation Mice Obtained from the Injection of ES Cells into 8-Cell Stage Embryos, Gene Knockout Protocols: Second Edition, vol. 530, Humana Press (2009).
Declaration Appendix as filed in U.S. Appl. No. 13/798,310, on Jul. 18, 2014 (7 pages).
Declaration of Andrew M. Scharenberg, M.D., filed in prosecution of U.S. Appl. No. 12/130,818, 21 pages, signed Oct. 4, 2010.
Declaration of Brink dated Apr. 30, 2015, as filed in AU Application No. 2009263082, 34 pages.
Declaration of Brink dated Jun. 2, 2015, as filed in AU Application No. 2009263082, 38 pages.
Declaration of Brink dated Sep. 27, 2016, as filed against EP Patent No. 2,147,594 B1 (European patent application No. 09075279.1), 33 pages.
Declaration of DeFranco dated Dec. 21, 2014, as filed in AU Application No. 2009263082, 56 pages.
Declaration of DeFranco dated Oct. 19, 2015, as filed in AU Application No. 2009263082, 31 pages.
Declaration of Denley dated May 1, 2015, as filed in AU Application No. 2009263082, 493 pages.
Declaration of Dr. Joel Martin, Opposition filed against European Patent No. EP 2314629 B1, 13 pages (May 18, 2016).
Declaration of Dr. Ton Logtenberg filed in U.S. Appl. No. 13/750,753, 10 pages (Dec. 18, 2015).
Declaration of Dr. Ton Logtenberg filed in U.S. Appl. No. 13/750,753, 4 pages (Sep. 15, 2015).
Declaration of Goodnow dated Oct. 19, 2015, as filed in AU Application No. 2009263082, 81 pages.
Declaration of Hudson dated Jun. 2, 2015, as filed in AU Application No. 2009263082, 81 pages.
Declaration of Hudson dated May 1, 2015, as filed in AU Application No. 2009263082, 52 pages.
Declaration of Lynn E. Macdonald, including Annexes 1-4, as together made publicly available at least upon submission to and online publication by the European Patent Office on Mar. 12, 2015, 13 pages, signed Mar. 3, 2015.
Declaration of Murphy dated Dec. 19, 2014, as filed in AU Application No. 2009263082, 18 pages.
Declaration of Professor Ton Logtenberg for EP2314629, 7 pages (May 4, 2016).
Declaration of Robert Brink in AU 2009263082, 19 pages (Oct. 19, 2016).
Declaration of Tarlinton dated Dec. 21, 2014, as filed in AU Application No. 2009263082, 40 pages.
Declaration of Tarlinton dated Oct. 19, 2015, as filed in AU Application No. 2009263082, 24 pages.
Declaration under 37 CFR 1.131 as filed in U.S. Appl. No. 13/798,310 on Jul. 18, 2014 (21 Pages).
Deisenhofer, J., Crystallographic Refinement and Atomic Models of a Human Fc Fragment and Its Complex with Fragment B of Protein A from *Staphylococcus aureus* at 2.9- and 2.8-? Resolution, Biochemistry, 20(9):2361-2370 (1981).
Desmyter, A. et al., Crystal structure of a camel single-domain VH antibody fragment in complex with lysozyme, Nat. Struct. Biol., 3(9):803-11 (1996).
Dinnyés, A. et al., Somatic cell nuclear transfer: recent progress and challenges, Cloning Stem Cells, 4(1):81-90 (2002).
Donoho, G. et al., Analysis of gene targeting and intrachromosomal homologous recombination stimulated by genomic double-strand breaks in mouse embryonic stem cells, Mol. Cell. Biol., 18(7):4070-8 (1998).
Donohoe, M. et al., Transgenic Human Lambda5 Rescues the Murine Lambda5 Nullizygous Phenotype, Journal of Immunology, 164:5269-5276 (2000).
Echelard, Y., Year of the ox, Nat. Biotechnol., 27(2):146-7 (2009).
Edwards D.R. et al., The ADAM metalloproteinases, Molecular Aspects of Medicine, 29(5):258-89 (2008).
Engel, P. et al., Abnormal B Lymphocyte Development, Activation, and Differentiation in Mice that Lack or Overexpress the CD19 Signal Transduction Molecule, Immunity, 3:39-50 (1995).
English Translation of Arguments dated Jan. 14, 2014, as filed in Merus Japanese Patent No. 5749161, 6 pages.
English Translation of Arguments dated Jan. 5, 2015, as filed in Merus Japanese Patent No. 5749161, 9 pages.
Epinat, J.C., et al. A novel engineered meganuclease induces homologous recombination in yeast and mammalian cells, Nucleic Acids Res., 31(11):2952-62 (2003).
Ewert, S. et al., Biophysical properties of human antibody variable domains, J. Mol. Biol., 325(3):531-53 (2003).
Exhibit A as filed in U.S. Appl. No. 13/798,310 on Jul. 18, 2014 (2 pages).
Exhibit B as filed in U.S. Appl. No. 13/798,310 on Jul. 18, 2014 (2 pages).
Exhibit C as filed in U.S. Appl. No. 13/798,310 on Jul. 18, 2014 (1 page).
Exhibit D as filed in U.S. Appl. No. 13/798,310 on Jul. 18, 2014 (1 page).
Exhibit E as filed in U.S. Appl. No. 13/798,310 on Jul. 18, 2014 (3 pages).
Extended European Search Report for 12 173 456.0, 9 pages (Aug. 21, 2012).
Extended European Search Report for EP 15186515.1, 8 pages (Feb. 3, 2016).
Farner, N.L. et al., Molecular mechanisms and selection influence the generation of the human V lambda J lambda repertoire, J. Immunol., 162(4):2137-45 (1999).
Featherstone, K. et al., The mouse immunoglobulin heavy chain V-D intergenic sequence contains insulators that may regulate ordered V(D)J recombination, J. Biol. Chem. 285(13):9327-9338 (2010).
Fell, H.P. et al., Homologous recombination in hybridoma cells: heavy chain chimeric antibody produced by gene targeting, Proc. Natl. Acad. Sci. U S A., 86(21):8507-11 (1989).
Final Post-Hearing Submission—DeFranco Declaration Annexure in AU2009263082, 10 pages (Oct. 18, 2016).

(56) References Cited

OTHER PUBLICATIONS

Final Post-Hearing Submission—Opponent in AU2009263082, 4 pages (Oct. 19, 2016).
Final Response to Opposition in EP2501817, 27 pages (Dec. 23, 2016).
Final Written Submissions for Oral Proceedings Scheduled for Jun. 22, 2016, Opposition to Merus B.V.'s EP 2314629 B1, 13 pages (May 20, 2016).
Final Written Submissions Oral Proceedings Scheduled for Oct. 28, 2016 in EP2147594, 40 pages.
Fischer, N. and Léger, O., Bispecific antibodies: molecules that enable novel therapeutic strategies, Pathobiology, 74(1):3-14 (2007).
Fishwild, D. et al., High-avidity human IgGk monoclonal antibodies from a novel strain of minilocus transgenic mice, Nature Biotechnology, 14:845-851 (1996).
Flavell, D.J., et al., Therapy of human T-cell acute lymphoblastic leukaemia with a combination of anti-CD7 and anti-CD38-SAPORIN immunotoxins is significantly better than therapy with each individual immunotoxin, Br. J. Cancer., 84(4):571-8 (2001).
Forrest, K. B., Opinion of the United States District Court, *Regeneron Pharmaceuticals, Inc.* v. *Merus B.V.*, 114 pages (Nov. 2, 2015).
Fraenkel, S. et al., Allelic 'choice' governs somatic hypermutation in vivo at the immunoglobulin kappa-chain locus, Nat. Immunol., 8(7):715-722 (2007).
Fussenegger, M. et al., Genetic optimization of recombinant glycoprotein production by mammalian cells, Tibtech, 17:35-42 (1999).
Gallo, M.L. et al., The human immunoglobulin loci introduced into mice: V (D) and J gene segment usage similar to that of adult humans, Eur. J. Immunol., 30(2):534-40 (2000).
Gay, D. et al., Receptor editing: an approach by autoreactive B cells to escape tolerance, J. Exp. Med., 177(4):999-1008 (1993).
GenBank Accession No. X97051, GI:564822, first referenced Jan. 9, 1997, updated Nov. 14, 2006 (29 pages).
GenBank Accession No. ABA26122, immunoglobulin light chain variable region, partial [*Homo sapiens*], Rabquer et al., 2 pages, first referenced Dec. 31, 2005.
GenBank Accession No. M87478, Human rearranged IgK mRNA VJC region, Aucouturier et al., 1 page, first referenced Mar. 3, 1992, first seen at NCBI Apr. 27, 1993.
Giallourakis, C.C. et al., Elements between the IgH variable (V) and diversity (D) clusters influence antisense transcription and lineage-specific V(D)K recombination, PNAS, 107(51):22207-22212 (2010).
Giddings, G. et al., Transgenic plants as factories for biopharmaceuticals, Nat. Biotechnol., 18(11):1151-5 (2000).
Goletz, S. et al., Selection of Large Diversities of Antiidiotypic Antibody Fragments by Phage Display, J. Mol. Biol. 315:1087-97, (2002).
Gonzalez-Fernandez, A. and Milstein, C., Analysis of somatic hypermutation in mouse Peyer's patches using immunoglobulin kappa light-chain transgenes, PNAS USA, 90:9862-9866 (1993).
Goodhardt et al., Rearrangement and Expression of rabbit immunoglobulin K light chain gene in transgenic mice; Jun. 1987; PNAS, 84: 4229-4233.
Goyenechea, B. and Milstein, C., Modifying the sequence of an immunoglobulin V-gene alters the resulting pattern of hypermutation, PNAS USA, 93:13979-13984 (1996).
Goyenechea, B. et al., Cells strongly expressing Ig(kappa) transgenes show clonal recruitment of hypermutation: a role for both MAR and the enhancers, EMBO J., 16(13):3987-94 (1997).
Green, L. and Jakobovits, A., Regulation of B cell development by variable gene complexity in mice reconstituted with human immunoglobulin yeast artificial chromosomes, J. Exp. Med., 188(3):483-495 (1998).
Green, L. et al., Antigen-specific human monoclonal antibodies from mice engineered with human Ig heavy and light chain YACs, Nature Genetics, 7(1):13-21 (1994).
Hagiwara, S., Transgenic expression of VpreB-3 under the control of the immunoglobulin heavy chain enhancer and SV40 promoter, Kobe J. Med. Sci., 42(1):43-59 (1996).
Han, C. et al., Comprehensive analysis of reproductive ADAMs: relationship of ADAM4 and ADAM6; with an ADAM complex required for fertilization in mice, Biology of Reproduction, 80(5):1001-8 (2009).
Harding, F.A. and Lonberg, N., Class switching in human immunoglobulin transgenic Mice, Ann. N Y Acad. Sci., 764:536-46 (1995).
Hardy, R.R. and Hayakawa, K., B cell development pathways, Annu. Rev. Immunol., 19:595-621 (2001).
Hartley, S. and Goodnow, C., Censoring of self-reactive B cells with a range of receptor affinities in transgenic mice expressing heavy chains for a lysozyme-specific antibody, International Immunology, 6:1417-1425 (1994).
Hendricks J. et al., Organization of the variable region of the immunoglobulin heavy-chain gene locus of the rat, Immunogenetics, 62(7):479-86 (2010).
Hengstschlager, M. et al., A lambda1 transgene under the control of a heavy chain promoter and enhancer does not undergo somatic hypermutation, Eur. J. Immunol., 24:1649-1656 (1994).
Hiatt, A. et al. Production of antibodies in transgenic plants, Nature, 342(6245):76-8 (1989).
Hochedlinger, K. and R. Jaenisch, Monoclonal Mice Generated by Nuclear Transfer from Mature B and T Donor Cells, Nature, 415(6875):1035-1038, (2002).
Hömig-Hölzel, C. et al., Constitutive CD40 signaling in B cells selectively activates the noncanonical NF-kappaB pathway and promotes lymphomagenesis, J. Exp. Med., 205(6):1317-29 (2008).
Houdebine, L.M. Transgenic Animals: Generation and Use. Amsterdam: Harwood Academic Publishers. pp. 397-403 (1997).
Huls, G. et al., Antitumor immune effector mechanisms recruited by phage display-derived fully human IgG1 and IgA1 monoclonal antibodies, Cancer Res., 59(22):5778-84 (1999).
IMGT V-Quest Analysis of Sequence of GenBank M87478, 7 pages.
Initial Determination in EP Application No. 10186063.3, 11 pages (Nov. 19, 2015).
Initial Post-Hearing Submissions—DeFranco Declaration Annexure for Australian patent application No. 2009263082, 41 pages (Oct. 4, 2016).
Initial Post-Hearing Submissions—Goodnow Declaration Annexure for Australian patent application No. 2009263082, 13 pages (Oct. 4, 2016).
Initial Post-Hearing Submissions (Applicant) Brink Declaration Annex for Australian patent application No. 2009263082, 36 pages (Oct. 4, 2016).
Initial Post-Hearing Submissions (Applicant) for Australian patent application No. 2009263082, 5 pages (Oct. 5, 2016).
Initial Post-Hearing Submissions (Opponent's Initial Supplementary Submissions) for Australian patent application No. 2009263082, 7 pages (Oct. 5, 2016).
Inlay, M. et al., Essential roles of the kappa light chain intronic enhancer and 3' enhancer in kappa rearrangement and demethylation, Nat. Immunol., 3(5):463-8 (2002).
International Search Report and Written Opinion for PCT Application No. PCT/US2013/044257 mailed Sep. 4, 2013.
International Search Report for PCT/US2011/023971, 5 pages (Apr. 11, 2011).
International Search Report for PCT/US2012/034737, 7 pages (Dec. 6, 2012).
International Search Report for PCT/US2012/049600 (7 pages), mailed Nov. 23, 2012.
International Search Report for PCT/US2013/029125, 6 pages (Jun. 20, 2013).
International Search Report for PCT/US2013/044257, 4 pages (Sep. 4, 2013).
International Search Report for PCT/US2014/025982 dated Jul. 22, 2014 (6 pages).
International Search Report for PCT/US2014/026040 dated Jul. 29, 2014 (5 pages).
Irving, R.A. et al., Ribosome display and affinity maturation: from antibodies to single V-domains and steps towards cancer therapeutics, J. Immunol. Methods, 248(1-2):31-45 (2001).

(56) References Cited

OTHER PUBLICATIONS

Jakobovits, A. et al., From XenoMouse technology to panitumumab, the first fully human antibody product from transgenic mice, Nature Biotechnology, 25(10):1134-1143 (2007).
Jakobovits, A., Production of fully human antibodies by transgenic mice, Curr. Opin. Biotechnol., 6(5):561-6 (1995).
Jakobovits, Therapeutic Antibodies from XenoMouse Transgenic Mice, Recombinant Antibodies for Immunotherapy, Ed. Little, M., New York, NY: Cambridge University Press, Chapter 7, pp. 89-99 (2009).
Janeway's Immunobiology, Seventh Edition, Murphy, Travers and Walpot, eds., Garland Science, New York and London, Ch. 4, pp. 145-155, and Ch. 7, pp. 266-267 (2008).
Jendreyko, N. et al., Intradiabodies, bispecific, tetravalent antibodies for the simultaneous functional knockout of two cell surface receptors, J. Biol. Chem., 278(48):47812-47819 (2003).
Jolly, C. et al., Rapid methods for the analysis of immunoglobulin gene hypermutation: application to transgenic and gene targeted mice, Nucleic Acids Research, 25(10):1913-1919 (1997).
Jones, D. et al., High-level expression of recombinant IgG in the human cell line per.c6, Biotechnol. Prog., 19(1):163-8 (2003).
Joyner, A.L. ed., Gene Targeting: A Practical Approach, Second Edition, Oxford University Press, entire book, 193 pages (2000).
JP Opposition Decision in JP5749161 (English and Japanese), 54 pages (Sep. 7, 2016).
Kabat, E.A., and Wu, T.T., Identical V region amino acid sequences and segments of sequences in antibodies of different specificities. Relative contributions of VH and VL genes, minigenes, and complementarity-determining regions to binding of antibody-combining sites, J. Immunol., 147(5):1709-19 (1991).
Kasprzyk, P.G. et al., Therapy of an animal model of human gastric cancer using a combination of anti-erbB-2 monoclonal antibodies, Cancer Res., 52(10):2771-6 (1992).
Kaushik et al, "Stochastic pairing of heavy-chain and K light-chain variable gene families occurs in polyclonally activated B cells," Proc. Natl. Acad. Sci. USA, vol. 87: 4932-4936 (1990).
Klohn, P.C. et al., IBC's 23rd Annual Antibody Engineering, 10th Annual Antibody Therapeutics international conferences and the 2012 Annual Meeting of The Antibody Society: Dec. 3-6, 2012, San Diego, CA, Mabs, 5(2):178-201 (2013).
Klotz, E. et al., Somatic hypermutation of a lambda2 transgene under the control of the lambda enhancer or the heavy chain intron enhancer, J. Immunol., 157:4458-4463 (1996).
Klotz, E. et al., Somatic hypermutation of an artificial test substrate within an Ig kappa transgene, J. Immunol., 161:782-790 (1998).
Knappik, A. et al., Fully synthetic human combinatorial antibody libraries (HuCAL) based on modular consensus frameworks and CDRs randomized with trinucleotides, J. Mol. Biol., 296(1):57-86 (2000).
Kong, Q. et al., A lambda 3' enhancer drives active and untemplated somatic hypermutation of a lambda1 transgene, J. Immunol., 161:294-301 (1998).
Kontermann, R.E., Dual targeting strategies with bispecific antibodies, MAbs., 4(2):182-97 (2012).
Kroesen, B.J. et al., Bispecific antibodies for treatment of cancer in experimental animal models and man, Adv. Drug Deliv. Rev., 31(1-2):105-129 (1998).
Kuroiwa, Y. et al., Cloned transchromosomic calves producing human immunoglobulin, Nat. Biotechnol., 20(9):889-94 (2002).
Lam, K. et al., In Vivo Ablation of Surface Immunoglobulin on Mature B Cells by Inducible Gene Targeting Results in Rapid Cell Death, Cell, 90:1073-1083 (1997).
Lantto, J. et al., Capturing the natural diversity of the human antibody response against vaccinia virus, J Virol, 85(4):1820-33 (2011).
Larrick, J.W. and Thomas, D.W., Producing proteins in transgenic plants and animals, Curr. Opin. Biotechnol., 12(4):411-8 (2001).
Le Gall, F. et al., Effect of linker sequences between the antibody variable domains on the formation, stability and biological activity of a bispecific tandem diabody, Protein Eng. Des. Sel., 17(4):357-66 (2004).
Lee, E.C. et al., Complete humanization of the mouse immunoglobulin loci enables efficient therapeutic antibody discovery, Nat. Biotechnol., 32(4):356-63 (2014).
Lee, H. et al., Human C5aR knock-in mice facilitate the production and assessment of anti-inflammatory monoclonal antibodies, Nat. Biotechnol., 24(10):1279-1284 (2006).
Lefranc, M.P. and Lefranc, G., Immunoglobulin Facts Book, London: Academic Press, pp. 3-44, 98-100, and 102 (2001).
Lefranc, M.P. Nomenclature of the human immunoglobulin heavy (IGH) genes, Exp. Clin. Immunogenet., 18(2):100-16 (2001).
Lefranc, M.P., Nomenclature of the Human Immunoglobulin Genes Current Protocols in Immunology, Supplement 40:A.1P.1-A.1P.37 (2000).
Lefranc, M.P., Nomenclature of the human immunoglobulin kappa (IGK) genes, Exp. Clin. Immunogenet., 18(3):161-74 (2001).
Lefranc, M-P. and Lefranc, G., The Immunoblobulin Facts Books, San Diego, CA: Academic Press, entire book, pp. 1-457 (2001).
Leitzgen, K. et al., Assembly of immunoglobulin Light Chains as a Prerequisite for Secretion, Journal of Biological Chemistry, 272(5):3117-3123 (1997).
Letter Accompanying Initial Post-Hearing Submissions (Applicant) for Australian patent application No. 2009263082, 1 page (Oct. 5, 2016).
Letter in Reply to Merus Response in EP2147594, 9 pages (Aug. 20, 2015).
Liao, M.J. and Van Dyke, T., Critical role for Atm in suppressing V(D)J recombination-driven thymic lymphoma, Genes Dev., 13(10):1246-50 (1999).
Lindhofer, H. et al., Preferential Species-Restricted Heavy/Light Chain Pairing in Rat/Mouse Quadromas, The Journal of Immunology, 155:219-225 (1995).
Logtenberg, T., Antibody cocktails: next-generation biopharmaceuticals with improved potency, Trends Biotechnol., 25(9):390-4 (2007).
Lonberg, N. et al., Antigen-specific Human Antibodies from Mice Comprising Four Distinct Genetic Modifications, Nature, 368:856-859, (1994).
Lonberg, N., Fully human antibodies from transgenic mouse and phage display platforms, Curr. Opin. Immunol., 20(4):450-9, and supplemental material, 16 pages (2008).
Lonberg, N., Human antibodies from transgenic animals, Nature Biotechnology, 23(9):1117-1125 (2005).
Lonberg, N., Human Monoclonal Antibodies from Transgenic Mice, Therapeutic Antibodies, Handbook of Experimental Pharmacology, Eds. Chernajovsky, Y and Nissim, A., Berlin Heidelberg: Springer-Verlag, 181: 69-97 (2008).
Longo, N. et al., Characterization of immunoglobulin gene somatic hypermutation in the absence of activation-induced cytidine deaminase, J. Immunol., 181(2):1299-1306 (2008).
Luby, T.M. et al., The mu Switch Region Tandem Repeats Are Important, but Not Required, for Antibody Class Switch Recombination, J. Exp. Med., 193(2):159-168 (2001).
MacDonald, L. et al., Velocigene Technology Extended to Humanization of Several Megabases of Complex Gene Loci, First International MUGEN Conference of Animal Models for Human Immunological Disease, Sep. 10-13, 2006—Athens, Greece, Abstract 21 and Poster, 2 pages (2006).
Manis, J.P. et al., Mechanism and control of class-switch recombination, Trends. Immunol., 23(1):31-9 (2002).
Martinez-Jean, C. et al., Nomenclature and overview of the mouse (*Mus musculus* and *Mus* sp.) immunoglobulin kappa (IGK) genes, Exp. Clin. Immunogenet., 18(4):255-79 (2001).
Marvin, J. and Zhu, Z., Recombinant approaches to IgG-like bispecific antibodies, Acta Pharmacologica Sinica, 26(6):649-658 (2005).
Matsuda, F. et al., The Complete Nucleotide Sequence of the Human Immunoglobulin Heavy Chain Variable Region Locus, J. Exp. Med., 188(11): 2151-2162 (1998).

(56) References Cited

OTHER PUBLICATIONS

Mendez M.J., et al., Functional transplant of megabase human immunoglobulin loci recapitulates human antibody response in mice, Nat Genet. 15(2):146-56 (1997).
Merchant, A. et al., An efficient route to human bispecific IgG, Nature Biotechnology, 16(7):677-681 (1998).
Merus Final Written Submissions as filed in EP2147594 / 09075279. 1-1405, 32 pages (Aug. 26, 2016).
Merus Response to REGN Opposition in EP2147594, 35 pages (Apr. 2, 2015).
Moran N., Mouse platforms jostle for slice of humanized antibody market, Nature Biotechnology, 31(4): 267-268, (2013).
Murphy, A., VelocImmune: Immunoglobulin Variable Region Humanized Mice, Recombinant Antibodies for Immunotherapy, Ed. Little, M., New York, NY: Cambridge University Press, Chapter 8, pp. 100-107 (2009).
Murphy, Kenneth, Janeway's Immunobiology, 8th Edition., New York: Garland Science, Chapter 5, Sections 5-1 to 5-4, pp. 157-162 (2012).
Muyldermans, S. et al., Sequence and structure of VH domain from naturally occurring camel heavy chain immunoglobulins lacking light chains, Protein Eng., 7(9):1129-35 (1994).
Muyldermans, S., Single domain camel antibodies: current status, J. Biotechnol., 74(4):277-302 (2001).
Nelson, A.L. et al., Development trends for human monoclonal antibody therapeutics, Nat. Rev. Drug. Discov., 9(10):767-74 (2010).
Nemazee, D., Receptor editing in B cells, Adv. Immunol., 74:89-126 (2000).
Nemazee, D., Receptor editing in lymphocyte development and central tolerance, Nat. Rev. Immunol., 6(10):728-40 (2006).
News In Brief Article (2007) Big Pharma vies for mice, Nature Biotechnology 2007, 25(6): 613—Published Jun. 2007.
Nguyen, V.K. et al., Heavy-chain only antibodies derived from dromedary are secreted and displayed by mouse B cells, Immunology, 109(1):93-101 (2003).
Nicholson, I. et al., Antibody Repertoires of Four- and Five-Feature Translocus Mice Carrying Human Immunoglobulin Heavy Chain and ? and ? Light Chain Yeast Artificial Chromosomes, Journal of Immunology, 163:6898-6906 (1999).
Nissim et al., Antibody fragments from a 'single pot' phage display library as immunochemical reagents, Embo J., 13(3): 692-698 (1994).
Notice of Opposition for EP 2501817, 28 pages (May 25, 2016).
Notice of Opposition in EP2701499, 27 pages (Nov. 10, 2016).
Notice of Opposition in JP5749161 (English and Japanese), 188 pages (Jan. 15, 2016).
Notice of Opposition to a European patent for EP 2314629, Merus B.V. v. Regeneron Pharmaceuticals, Inc., 38 pages (Jul. 15, 2014).
Notice of Reasons for Revocation in JP5749161, (English and Japanese), 18 pages (Mar. 17, 2016).
Notice of Receipt of Correction Request in JP5749161 (English and Japanese), 2 pages (Jul. 1, 2016).
Nucleotide Sequence RID Y55HBK1 W114, last accessed Aug. 6, 2014 (2 pages).
O'Brien, R. et al., Somatic hypermutation of an immunoglobulin transgene in kappa mice, Nature, 326(6111):405-409 (1987).
Opposition dated Aug. 11, 2014, in EP Application No. 09075279.1, 983 pages.
Opposition dated Aug. 20, 2015, in EP Application No. 09075279.1, 25 pages.
Opposition dated Jan. 15, 2016, in JP Patent No. 5749161 and English translation, 188 pages.
Opposition dated Sep. 22, 2014, in AU Application No. 2009263082, 35 pages.
Opposition filed in European Application No. 10186063.3, 1351 pages (Jul. 15, 2014).
Opposition's rebuttal to Proprietor's submissions in Opposition No. 700031/2016 (English and Japanese), 64 pages (Aug. 22, 2016).
Orban, P.C. et al., Tissue- and site-specific DNA recombination in transgenic mice, Proc. Natl. Acad. Sci. U S A., 89(15):6861-5 (1992).
Patent Owner Final Submissions in response to the Summons to attend Oral Proceedings dated Nov. 19, 2015 and in preparation of the Hearing of Jun. 22, 2016 for EP2314629, 16 pages (May 20, 2016).
Patentee's Arguments against Opposition No. 700031/2016 (English and Japanese), 29 pages (Jun. 21, 2016).
Patentee's Exhibit 1 submitted with Argument against Opposition No. 700031/2016 on Jun. 21, 2016, "Really Essential Medical Immunology", Blackwell Science Ltd. Cover, colophon, Contents and Chapter 3 (pp. 23-25) (English and Japanese), 17 pages (2000).
Patentee's Exhibit 2 submitted with Argument against Opposition No. 700031/2016 on Jun. 21, 2016, Communication to the EPO submitted by the Opponent in connection with prosecution of EP2505654 (English and Japanese), 7 pages (Sep. 29, 2014).
Patentee's Exhibit 3 submitted with Argument against Opposition No. 700031/2016 on Jun. 21, 2016, Declaration of Peter Hudson (English and Japanese), 15 pages (Jun. 17, 2016).
Peeters, K. et al., Production of antibodies and antibody fragments in plants, Vaccine, 19(17-19):2756-61 (2001).
Pelanda, R. et al., A prematurely expressed Ig(kappa) transgene, but not V(kappa)J(kappa) gene segment targeted into the Ig(kappa) locus, can rescue B cell development in lambda5-deficient mice, Immunity, 5(3):229-239 (1996).
Phan, T. et al., Altered Migration, Recruitment, and Somatic Hypermutation in the Early Response of Marginal Zone B Cells to T Cell-Dependent Antigen, The Journal of Immunology, 174(8):4567-78 (2005).
Phan, T. et al., B Cell Receptor-independent Stimuli Trigger Immunoglobulin (Ig) Class Switch Recombination and Production of IgG Autoantibodies by Anergic Self-Reactive B Cells, The Journal of Experimental Medicine, 197(7):845-860 (2003).
Phan, T.G. et al., High affinity germinal center B cells are actively selected into the plasma cell compartment, J. Exp. Med., 203(11):2419-24 (2006).
Phelps, J. et al., Expression and Characterization of a Chimeric Bifunctional Antibody with Therapeutic Applications, The Journal of Immunology, 145:1200-1204 (1990).
Pollock, D.P. et al., Transgenic milk as a method for the production of recombinant antibodies, J. Immunol. Methods., 231(1-2):147-57 (1999).
Popov, A.V. et al., A human immunoglobulin lambda locus is similarly well expressed in mice and humans, J. Exp. Med., 189(10):1611-20 (1999).
Porteus, M.H. and Carroll, D., Gene targeting using zinc finger nucleases, Nat.; Biotechnol., 23(8):967-73 (2005).
Prak, E. and Weigert, M., Light chain replacement: a new model for antibody gene rearrangement, J. Exp. Med., 182(2):541-548 (1995).
Preliminary Opinion of the Opposition Division in EP2147594, 11 pages (Jan. 19, 2016).
Prelle, K. et al., Pluripotent stem cells—model of embryonic development, tool for gene targeting, and basis of cell therapy, Anat. Histol. Embryol., 31(3):169-86 (2002).
Radic, M.Z. et al., Ig H and L chain contributions to autoimmune specificities, J. Immunol., 146(1):176-82 (1991).
Ramsden, D.A et al., Conservation of sequence in recombination signal sequence spacers. Nucleic Acids Res., 22(10):1785-96 (1994).
Ravetch, J.V., Structure of the human immunoglobulin mu locus: characterization of embryonic and rearranged J and D genes, Cell, 27(3 Pt 2):583-91 (1981).
Reply to Communication in EP12173456.0, 12 pages (mailed Apr. 12, 2013).
Reply to Third Party Observations on EP2501817 (May 20, 2013).
Request for Correction in JP5749161 (English and Japanese), 29 pages (Jun. 21, 2016).
Request to provoke an interference U.S. Appl. No. 13/750,753, filed Jan. 25, 2013.
Response Post-Hearing Submissions by Applicant in AU2009263082, 15 pages (Oct. 19, 2016).
Response to Notice of Opposition dated Aug. 22, 2014 for EP2314629, 20 pages (Feb. 24, 2015).

(56) References Cited

OTHER PUBLICATIONS

Response to Opponent's Submission dated Aug. 26, 2016 and in Preparation of the Hearing scheduled for Oct. 28, 2016 in EP2147594, 14 pages (Sep. 28, 2016).
Reusch, et al., Beyond mAbs with TandAbs, Innovations in Pharmaceutical Technology, 4 pages (Jun. 2011).
Rickert, R. et al., Impairment of T-cell-dependent B-cell responses and B-1 cell development in CD19-deficient mice, Nature, 376(6538):352-5 (1995).
Rickert, R.C. et al., B lymphocyte-specific, Cre-mediated mutagenesis in mice, Nucleic Acids Res., 25(6):1317-8 (1997).
Riechmann, L. and Muyldermans, S., Single domain antibodies: comparison of camel VH and camelised human VH domains, J. Immunol. Methods., 231(1-2):25-38 (1999).
Ritchie, K. et al., Allelic exclusion and control of endogenous immunoglobulin gene rearrangement in kappa transgenic mice, Nature, 312:517-520 (1984).
Rodríguez, C.I., et al., High-efficiency deleter mice show that FLPe is an alternative to Cre-loxP, Nat. Genet., 25(2):139-40 (2000).
Rojas, G. et al., Phage antibody fragments library combining a single human light chain variable region with immune mouse heavy chain variable regions, Journal of Biotechnology, 94:287-298 (2002).
Rosner, K. et al., Third complementarity-determining region of mutated VH immunoglobulin genes contains shorter V, D, J, P, and N components than non-mutated genes, Immunology, 103(2):179-187 (2001).
Rouet, P., et al. Introduction of double-strand breaks into the genome of mouse cells by expression of a rare-cutting endonuclease, Mol. Cell. Biol., 14:12 8096-8106 (1994).
Sasaki et al., "Canonical NF-KB Activity, Dispensable for B Cell Development, Replaces BAFF-Receptor Signals and Promotes B Cell Proliferation upon Activation," Immunity 24: 729-739 (2006).
Schnieke, A.E. et al., Human factor IX transgenic sheep produced by transfer of nuclei from transfected fetal fibroblasts, Science, 278(5346):2130-3 (1997).
Schroeder, H.W. Jr., Similarity and divergence in the development and expression; of the mouse and human antibody repertoires, Dev. Comp. Immunol., 30(1-2):119-35 (2006).
Scott, Christopher T., "Mice with a human touch," Nature Biotechnology, 25(10): 1075-1077 (2007).
Seals D.F. and Courtneidge S.A., The ADAMs family of metalloproteases: multidomain; proteins with multiple functions, Genes and Development, 17(1):7-30 (2003).
Segal, D. et al., Introduction: bispecific antibodies, Journal of Immunological Methods, 248(1-2):1-6 (2001).
Sekiguchi, et al. Mechanism of V(D)J Recombination, Molecular Biology of B Cells, Eds. Honjo, Alt, and Neuberger, London, UK: Elsevier Academic Press, pp. 61-82 (2004).
Sharpe, M.J. et al., Somatic hypermutation of immunoglobulin kappa may depend on sequences 3' of C kappa and occurs on passenger transgenes, EMBO J., 10(8):2139-2145 (1991).
Shih, H.H., Discovery Process for Antibody-Based Therapeutics, Development of Antibody-Based Therapeutics 426, Eds. Tabrizi, M.A. et al., Springer New York, pp. 9-32 (2012).
Simon, T. and Rajewsky, K., Antibody domain mutants demonstrate autonomy of the antigen binding site, EMBO J., 9(4):1051-6 (1990).
Sirac, C. et al., Light chain inclusion permits terminal B cell differentiation and does not necessarily result in autoreactivity, Proc. Natl. Acad. Sci, U S A, 103(20):7747-52 (2006), and Supplemental information, 4 pages, retrieved Jul. 7, 2016: <http://www.pnas.org/content/103/20/7747.long?tab=ds#F6>.
Sirac, C. et al., Role of the monoclonal kappa chain V domain and reversibility of renal damage in a transgenic model of acquired Fanconi syndrome, Blood, 108(2):536-543 (2006).
Sirac, C. et al., Toward understanding renal Fanconi syndrome: step by step advances through experimental models, Contrib. Nephrol., 169:247-61 (2011).
Smith, B. et al., The unique and immunoglobulin-like regions of surrogate light chain component lambda5 differentially interrogate immunoglobulin heavy-chain structure, Molecular Immunology, 47:1195-1206 (2010).
Smith, E.J. et al., A novel, native-format bispecific antibody triggering T-cell killing of B-cells is robustly active in mouse tumor models and cynomolgus monkeys, Sci. Rep., 5:17943 (2015).
Soriano, P., Generalized lacZ expression with the ROSA26 Cre reporter strain, Nat. Genet., 21(1):70-1 (1999).
Statement of Facts and Arguments in Support of Opposition for EP2147594, 57 pages (Aug. 11, 2014).
Steipe, B., et al. Sequence statistics reliably predict stabilizing mutations in a protein domain, J. Mol. Biol., 240(3):188-92 (1994).
Stevens et al., Human Antibody Discovery, VelocImmune—A novel platform, Pharma Focus Asia, Issue 8: 72-74 (2008).
Stevens, S. et al., Velocimmune: Humanization of Immunoglobulin Loc Using Velocigene Technology, First International MUGEN Conference of Animal Models for Human Immunological Disease, Sep. 10-13, 2006—Athens, Greece, Abstract 4 and Poster, 2 pages (2006).
Storb, U. et al., Transgenic Mice with μ and κ Genes Encoding Antiphosphorycholine Antibodies, J. Exp Med, 164:627-41 (1986).
Su, Q. et al., A DNA transposon-based approach to validate oncogenic mutations in the mouse, Proc. Natl. Acad. Sci. USA, 105(50):19904-9 (2008).
Summary of Opponent's Submissions for AU2009263082, 35 pages (Aug. 30, 2016).
Summons to Attend Oral Proceedings Arranged in Connection with EP2147594 (Mar. 6, 2013).
Summons to attend oral proceedings dated Jan. 19, 2016, in EP Application 09075279.1, 20 pages.
Tada, H. et al., Expression and characterization of a chimeric bispecific antibody against fibrin and against urokinase-type plasminogen activator, Journal of Biotechnology, 33:157-174 (1994).
Taki, S. et al., Targeted insertion of a variable region gene into the immunoglobulin heavy chain locus, Science, 262(5137):1268-71 (1993).
Tanha, J. et al., Optimal design features of camelized human single-domain antibody libraries, J. Biol. Chem., 276(27):24774-80 (2001).
Taylor L.D. et al., Human immunoglobulin transgenes undergo rearrangement, somatic mutation and class switching in mice that lack endogenous IgM, Int Immunol. 6(4):579-91 (1994).
Taylor, L.D. et al., A Transgenic Mouse that Expresses a Diversity of Human Sequence Heavy and Light Chain Immunoglobulins, Nucleic Acid Research, 20(23):6287-6295 (1992).
Third Party Observation dated Apr. 8, 2014, In CA Application No. 2729095, 16 pages.
Third Party Observation dated Apr. 25, 2012, in EP Application No. 09075279.1, 145 pages.
Third Party Observation dated Feb. 28, 2013, in EP Application No. 11703799.4, 43 pages.
Third Party Observation dated Jul. 1, 2013, in EP Application No. 09075279.1, 6 pages.
Third Party Observation dated Jun. 24, 2013, in EP Application No. 09075279.1, 15 pages.
Third Party Observation dated May 16, 2013, in EP Application No. 09075279.1, 82 pages.
Third Party Observation dated Nov. 18, 2014, in EP Application No. 11703799.4, 132 pages.
Third Party Observation dated Nov. 3, 2014, in EP Application No. 12173456.0, 274 pages.
Third Party Observation dated Oct. 3, 2013, in EP Application No. 09075279.1, 3 pages.
Third Party Observation dated Oct. 21, 2013, in AU Application No. 2009263082, 24 pages.
Third Party Observation dated Oct. 25, 2012, in EP Application No. 09075279.1, 27 pages.
Third Party Observation dated Sep. 12, 2013, in EP Application No. 09075279.1, 5 pages.
Third Party Observation dated Sep. 16, 2015, in CA Application No. 2729095, 15 pages.

(56) References Cited

OTHER PUBLICATIONS

Third Party Observation dated Sep. 5, 2013, in EP Application No. 09075279.1, 11 pages.
Third Party Observation dated Sep. 7, 2015, in EP Application No. 12173456.0, 68 pages.
Third Party Observation pursuant to Article 115 EPC for EP 14170196.1, 6 pages (Jul. 1, 2015).
Third Party Observations on EP2501817 (Feb. 28, 2013).
Third Party Observations pursuant to Art. 115 EPC and R. 114 EPC against EP Application No. 12717033.0, 11 pages (May 4, 2015).
Third Party Observations pursuant to Article 115 EPC and R. 114 EPC against European Application No. 11703799.4, 5 pages (Apr. 10, 2015).
Third Party Observations Under Article 115 EPC against European Application No. 09075279.1 in the name of Merus BV, 12 pages (Oct. 25, 2012).
Third Party Observations under Article 115 EPC for EP 12 173 456.0, 8 pages (Nov. 3, 2014).
Third Party Submission dated Feb. 18, 2013, in U.S. Appl. No. 13/093,156, 179 pages.
Third Party Submission dated Feb. 19, 2014, in U.S. Appl. No. 13/750,753, 282 pages.
Third Party Submission dated Feb. 24, 2014, in U.S. Appl. No. 13/750,753, 97 pages.
Third Party Submission dated Feb. 27, 2014, in U.S. Appl. No. 13/948,818, 10 pages.
Third Party Submission dated Jan. 28, 2013, in U.S. Appl. No. 12/589,181, 13 pages.
Third Party Submission dated Jun. 12, 2013, in U.S. Appl. No. 13/750,753, 100 pages.
Third Party Submission filed in U.S. Appl. No. 13/795,637, 117 pages (Mar. 18, 2014).
Tiegs, S. et al., Receptor Editing in Self-reactive Bone Marrow B Cells, The Journal of Experimental Medicine, 177:1009-1020 (1993).
Tomizuka, K. et al., Double trans-chromosomic mice: maintenance of two individual human chromosome fragments containing Ig heavy and kappa loci and expression of fully human antibodies, Proc. Natl. Acad. Sci. U S A., 97(2):722-7 (2000).
Tonegawa, S., Somatic generation of antibody diversity, Nature, 302(5909):575-581 (1983).
Torres and Kuhn, Laboratory Protocols for Conditional Gene Targeting, 42-53 (1997).
Tsubata, T. and Reth, M., The Products of the Pre-B Cell-specific Genes(Lambda5 and VpreB) and the Immunoglobulin mu Chain Form a Comples that is Transported onto the Cell Surface, Journal of Experimental Medicine, 172:973-976 (1990).
UniProt Entry Q5QGZ9, retrieved Jan. 21, 2015 from <http://www.uniprot.org/uniprot/Q5QGZ9> (16 pages).
Van Spriel, A.B. et al., Immunotherapeutic perspective for bispecific antibodies, Immunol. Today, 21(8):391-7 (2000).
Vasquez, K.M. et al., Manipulating the mammalian genome by homologous recombination, Proc. Natl. Acad. Sci. U S A., 98(15):8403-10 (2001).
Vaughan, T.J. et al., Human antibodies with sub-nanomolar affinities isolated from a large non-immunized phage display library, Nat. Biotechnol., 14(3):309-14 (1996).
Verma, R. et al., Antibody engineering: Comparison of bacterial, yeast, insect and mammalian expression systems, Journal of Immunological Methods, 216:165-181 (1998).
Vieira, P. and Rajewsky, K., The half-lives of serum immunoglobulins in adult mice,; Eur. J. Immunol., 18(2):313-316 (1988).
Wang, X. et al., Ab-origin: an enhanced tool to identify the sourcing gene segments in germline for rearranged antibodies. BMC Bioinformatics, 9(Suppl 12), 9 pages (2008).
Waterfield, M.D. et al., Restricted Structural Heterogeneity in Antibodies: Might Different Heavy Chains have a Common Light Chain? Nature New Biology, vol. 240:215-217 (1972).
Wilmut, I. and Clark, A.J., Basic techniques for transgenesis, J. Reprod. Fertil. Suppl., 43:265-75 (1991).
Wilmut, I. et al., Viable offspring derived from fetal and adult mammalian cells, Nature, 385(6619):810-3 (1997).
Winter, D.B. et al., Insertion of 2 kb of bacteriophage DNA between an immunoglobulin promoter and leader exon stops somatic hypermutation in a kappa transgene, Mol. Immunol., 34(5):359-66 (1997).
Written Opinion for PCT/US2011/023971, 6 pages (Apr. 11, 2011).
Written Opinion for PCT/US2012/034737, 8 pages (Dec. 6, 2012).
Written Opinion for PCT/US2012/049600, 8 pages (Nov. 23, 2012).
Written Opinion for PCT/US2013/029125, 5 pages (Jun. 20, 2013).
Written Opinion for PCT/US2013/044257, 5 pages (Sep. 4, 2013).
Written Opinion for PCT/US2014/025982, 7 pages (Jul. 22, 2014).
Written Opinion for PCT/US2014/026040, 8 pages (Jul. 29, 2014).
Wu, H. et al., Double replacement: strategy for efficient introduction of subtle mutations into the murine Col1a-1 gene by homologous recombination in embryonic stem cells, Proc. Natl. Acad. Sci. U S A., 91(7):2819-23 (1994).
Xu, J. and Davis, M. Diversity in the CDR3 Region of VH Is Sufficient for Most Antibody Specificities, Immunity, 13:37-45 (2000).
Xu, L. et al., Combinatorial surrobody libraries, Proceedings of the National Academy of Sciences (USA), 105(31):10756-10761 (2008).
Yang, X.W. et al., Homologous recombination based modification in *Escherichia coli* and germline transmission in transgenic mice of a bacterial artificial chromosome, Nat. Biotechnol. 15(9):859-65 (1997).
Zemlin, M. et al., Expressed Murine and Human CDR-H3 Intervals of Equal Length Exhibit Distinct Repertoires that Differ in their Amino Acid Composition and Predicted Range of Structures, JMB, 334:733-749 (2003).
Zheng, J. et al., Immunoglobulin gene transcripts have distinct VHDJH recombination characteristics in human epithelial cancer cells, J. Biol. Chem., 284(20):13610-9 (2009).
Zou, Y.R. et al., Cre-loxP-mediated gene replacement: a mouse strain producing humanized antibodies, Curr. Biol., 4(12):1099-103 (1994).

* cited by examiner

Monospecific
Parent-2 Ab Binding

Monospecific
Parent-1 Ab Binding

Bispecific Ab Binding

SEQUENCE LISTING

<160> NUMBER OF SEQ ID NOS: 49

<210> SEQ ID NO 1
<211> LENGTH: 3155
<212> TYPE: DNA
<213> ORGANISM: Artificial Sequence
<220> FEATURE:
<223> OTHER INFORMATION: Synthetic

<400> SEQUENCE: 1

```
ggcgcgccgt agctttgaat tttaaacatc tatttgacaa gaaatgcata gttccttctc     60
tttaaaataa tgtaatgttt ctttcaagaa taagcttggt ttgatgcctc tctccccaac    120
atgatagaag tgtagcataa atctatgaaa aattccattt ccctgtgcct acaacaacta    180
cctgggattg aaaacttctt cccttgctct agtcctttct tctacaccta cttccacatc    240
atctgtgact caaaacaata cttgtcagga aagatcccgg aaagagcaaa aaagacttcc    300
ttagaggtgt cagagattcc tatgccacta tctgtcatct ctagaagggg ttgtgagtat    360
gaggaagagc agagcttgta aattttctac ttgctttgac ttccactgta tttcctaaca    420
acaacaacca cagcaacacc cataacatca caggacaaac ttctagtact tccaaggctt    480
tagtctcagt aaatcttctc tacctccatc acagcagcta gaaggtttga tactcataca    540
aatagtactg tagctttctg ttcataattg gaaaaataga caagacccaa tgtaatacag    600
gctttccttc agccagttag cgttcagttt ttggatcacc attgcacaca tatacccagc    660
atatgtctaa tatatatgta gaaatccgtg aagcaagagt tataatagct tgtgttttct    720
attgtattgt attttcctct tatatcatct tcttcttcgt tcattaaaaa aaaaccgttc    780
aagtaggtct aaattaatta ttggatcata agtagataaa atattttatt tcataacaca    840
ttgacccgat gaatatgttt ctttgccaga catagtcctc atttccaagg taacaagcct    900
gaaaaaatta tactggagca agtcaacagg taatgatggt agcttttcct tattgtcctg    960
gggcaagaat aagacaaaag ataacagggt agaataaaga ttgtgtaaga aagaaggaca   1020
gcaacaggac atgggaacct tttatagagt aacattttga taatggatga tgagaattaa   1080
tgagttagac agggatgggt gggaatgatt gaaggtgtga gtactttagc acagattaag   1140
accaaatcat taggatttaa agagttgtgt agagttagtg aaggaaaagc cttagaatta   1200
aatttggctg cggataaaac attcttggat tagactgaag actcttttct gtgctaagta   1260
agtatattta tgataatgat gatgactgta gtgctgaata tttaataaat aaaaacaaaa   1320
ttaattgccg catacataat gtcctgaata ctattgtaaa tgttttatct tatttccttt   1380
aaactgtcta cagcactata aggtaggtac cagtattgtc acagttacac agatatggaa   1440
accgagacac agggaagtta agttacttga tcaatttcaa gcaatcggca agccatggag   1500
catctatgtc agggctgcca ggacatgtga ctgtaaacag aagtttttca ctttttaact   1560
caaagagggt atgtggctgg gttaatggaa agcttcagga ccctcagaaa acattactaa   1620
caagcaaatg aaaggtgtat ctggaagatt aagttttaac agactcttca tttccatcga   1680
tccaataatg cacttaggga gatgactggg catattgagg ataggaagag agaagtgaaa   1740
acacagcttt ttatattgtt cttaacaggc ttgtgccaaa catcttctgg gtggatttag   1800
gtgattgagg agaagaaaga cacaggagcg aaattctctg agcacaaggg aggagttcta   1860
cactcagact gagccaacag acttttctgg cctgacaacc agggcggcgc aggatgctca   1920
gtgcagagag gaagaagcag gtggtctttg cagctgaaag ctcagctgat ttgcatatgg   1980
agtcattata caacatccca gaattcttta agggcagctg ccaggaagct aagaagcatc   2040
```

```
ctctcttcta gctctcagag atggagacag acacactcct gctatgggtg ctgctgctct   2100

gggttccagg tgagggtaca gataagtgtt atgagcaacc tctgtggcca ttatgatgct   2160

ccatgcctct ctgttcttga tcactataat tagggcattt gtcactggtt ttaagtttcc   2220

ccagtcccct gaattttcca ttttctcaga gtgatgtcca aaattattct taaaaattta   2280

aatgaaaagg tcctctgctg tgaaggcttt taaagatata taaaaataat ctttgtgttt   2340

atcattccag gtgccagatg tgacatccag atgacccagt ctccatcctc cctgtctgca   2400

tctgtaggag acagagtcac catcacttgc cgggcaagtc agagcattag cagctattta   2460

aattggtatc agcagaaacc agggaaagcc cctaagctcc tgatctatgc tgcatccagt   2520

ttgcaaagtg gggtcccatc aaggttcagt ggcagtggat ctgggacaga tttcactctc   2580

accatcagca gtctgcaacc tgaagatttt gcaacttact actgtcaaca gagttacagt   2640

acccctccga tcaccttcgg ccaagggaca cgactggaga ttaaacgtaa gtaatttttc   2700

actattgtct tctgaaattt gggtctgatg gccagtattg acttttagag gcttaaatag   2760

gagtttggta aagattggta aatgagggca tttaagattt gccatgggtt gcaaaagtta   2820

aactcagctt caaaaatgga tttggagaaa aaaagattaa attgctctaa actgaatgac   2880

acaaagtaaa aaaaaaaagt gtaactaaaa aggaaccctt gtatttctaa ggagcaaaag   2940

taaatttatt tttgttcact cttgccaaat attgtattgg ttgttgctga ttatgcatga   3000

tacagaaaag tggaaaaata cattttttag tctttctccc ttttgtttga taaattattt   3060

tgtcagacaa caataaaaat caatagcacg ccctaagatc tagatgcatg ctcgagtgcc   3120

atttcattac ctctttctcc gcacccgaca tagat                              3155


<210> SEQ ID NO 2
<211> LENGTH: 28
<212> TYPE: DNA
<213> ORGANISM: Artificial Sequence
<220> FEATURE:
<223> OTHER INFORMATION: Synthetic

<400> SEQUENCE: 2

aggtgagggt acagataagt gttatgag                                        28


<210> SEQ ID NO 3
<211> LENGTH: 27
<212> TYPE: DNA
<213> ORGANISM: Artificial Sequence
<220> FEATURE:
<223> OTHER INFORMATION: Synthetic

<400> SEQUENCE: 3

tgacaaatgc cctaattata gtgatca                                         27


<210> SEQ ID NO 4
<211> LENGTH: 21
<212> TYPE: DNA
<213> ORGANISM: Artificial Sequence
<220> FEATURE:
<223> OTHER INFORMATION: Synthetic

<400> SEQUENCE: 4

gggcaagtca gagcattagc a                                               21


<210> SEQ ID NO 5
<211> LENGTH: 21
<212> TYPE: DNA
```

<213> ORGANISM: Artificial Sequence
<220> FEATURE:
<223> OTHER INFORMATION: Synthetic

<400> SEQUENCE: 5
tgcaaactgg atgcagcata g 21

<210> SEQ ID NO 6
<211> LENGTH: 19
<212> TYPE: DNA
<213> ORGANISM: Artificial Sequence
<220> FEATURE:
<223> OTHER INFORMATION: Synthetic

<400> SEQUENCE: 6
ggtggagagg ctattcggc 19

<210> SEQ ID NO 7
<211> LENGTH: 17
<212> TYPE: DNA
<213> ORGANISM: Artificial Sequence
<220> FEATURE:
<223> OTHER INFORMATION: Synthetic

<400> SEQUENCE: 7
gaacacggcg gcatcag 17

<210> SEQ ID NO 8
<211> LENGTH: 23
<212> TYPE: DNA
<213> ORGANISM: Artificial Sequence
<220> FEATURE:
<223> OTHER INFORMATION: Synthetic

<400> SEQUENCE: 8
tgggcacaac agacaatcgg ctg 23

<210> SEQ ID NO 9
<211> LENGTH: 29
<212> TYPE: DNA
<213> ORGANISM: Artificial Sequence
<220> FEATURE:
<223> OTHER INFORMATION: Synthetic

<400> SEQUENCE: 9
ccattatgat gctccatgcc tctctgttc 29

<210> SEQ ID NO 10
<211> LENGTH: 26
<212> TYPE: DNA
<213> ORGANISM: Artificial Sequence
<220> FEATURE:
<223> OTHER INFORMATION: Synthetic

<400> SEQUENCE: 10
atcagcagaa accagggaaa gcccct 26

<210> SEQ ID NO 11
<211> LENGTH: 3166
<212> TYPE: DNA
<213> ORGANISM: Artificial Sequence
<220> FEATURE:
<223> OTHER INFORMATION: Synthetic

<400> SEQUENCE: 11
ggcgcgccgt agctttgaat tttaaacatc tatttgacaa gaaatgcata gttccttctc 60

```
tttaaaataa tgtaatgttt ctttcaagaa taagcttggt ttgatgcctc tctccccaac    120
atgatagaag tgtagcataa atctatgaaa aattccattt ccctgtgcct acaacaacta    180
cctgggattg aaaacttctt cccttgctct agtcctttct tctacaccta cttccacatc    240
atctgtgact caaaacaata cttgtcagga aagatcccgg aaagagcaaa aaagacttcc    300
ttagaggtgt cagagattcc tatgccacta tctgtcatct ctagaagggg ttgtgagtat    360
gaggaagagc agagcttgta aattttctac ttgctttgac ttccactgta tttcctaaca    420
acaacaacca cagcaacacc cataacatca caggacaaac ttctagtact tccaaggctt    480
tagtctcagt aaatcttctc tacctccatc acagcagcta gaaggtttga tactcataca    540
aatagtactg tagctttctg ttcataattg gaaaaataga caagacccaa tgtaatacag    600
gctttccttc agccagttag cgttcagttt ttggatcacc attgcacaca tatacccagc    660
atatgtctaa tatatatgta gaaatccgtg aagcaagagt tataatagct tgtgttttct    720
attgtattgt attttcctct tatatcatct tcttcttcgt tcattaaaaa aaaaccgttc    780
aagtaggtct aaattaatta ttggatcata agtagataaa atattttatt tcataacaca    840
ttgacccgat gaatatgttt ctttgccaga catagtcctc atttccaagg taacaagcct    900
gaaaaaatta tactggagca agtcaacagg taatgatggt agcttttcct tattgtcctg    960
gggcaagaat aagacaaaag ataacagggt agaataaaga ttgtgtaaga aagaaggaca   1020
gcaacaggac atgggaacct tttatagagt aacattttga taatggatga tgagaattaa   1080
tgagttagac agggatgggt gggaatgatt gaaggtgtga gtactttagc acagattaag   1140
accaaatcat taggatttaa agagttgtgt agagttagtg aaggaaaagc cttagaatta   1200
aatttggctg cggataaaac attcttggat tagactgaag actcttttct gtgctaagta   1260
agtatattta tgataatgat gatgactgta gtgctgaata tttaataaat aaaaacaaaa   1320
ttaattgccg catacataat gtcctgaata ctattgtaaa tgttttatct tatttccttt   1380
aaactgtcta cagcactata aggtaggtac cagtattgtc acagttacac agatatggaa   1440
accgagacac agggaagtta agttacttga tcaatttcaa gcaatcggca agccatggag   1500
catctatgtc agggctgcca ggacatgtga ctgtaaacag aagtttttca ctttttaact   1560
caaagagggt atgtggctgg gttaatggaa agcttcagga ccctcagaaa acattactaa   1620
caagcaaatg aaaggtgtat ctggaagatt aagttttaac agactcttca tttccatcga   1680
tccaataatg cacttaggga gatgactggg catattgagg ataggaagag agaagtgaaa   1740
acacagcttt ttatattgtt cttaacaggc ttgtgccaaa catcttctgg gtggatttag   1800
gtgattgagg agaagaaaga cacaggagcg aaattctctg agcacaaggg aggagttcta   1860
cactcagact gagccaacag acttttctgg cctgacaacc agggcggcgc aggatgctca   1920
gtgcagagag gaagaagcag gtggtctttg cagctgaaag ctcagctgat ttgcatatgg   1980
agtcattata caacatccca gaattcttta agggcagctg ccaggaagct aagaagcatc   2040
ctctcttcta gctctcagag atggagacag acacactcct gctatgggtg ctgctgctct   2100
gggttccagg tgagggtaca gataagtgtt atgagcaacc tctgtggcca ttatgatgct   2160
ccatgcctct ctgttcttga tcactataat tagggcattt gtcactggtt ttaagtttcc   2220
ccagtcccct gaattttcca ttttctcaga gtgatgtcca aaattattct taaaaattta   2280
aatgaaaagg tcctctgctg tgaaggcttt taaagatata taaaaataat ctttgtgttt   2340
atcattccag gtgccagatg tataccaccg gagaaattgt gttgacgcag tctccaggca   2400
```

```
ccctgtcttt gtctccaggg gaaagagcca ccctctcctg cagggccagt cagagtgtta   2460

gcagcagcta cttagcctgg taccagcaga aacctggcca ggctcccagg ctcctcatct   2520

atggtgcatc cagcagggcc actggcatcc cagacaggtt cagtggcagt gggtctggga   2580

cagacttcac tctcaccatc agcagactgg agcctgaaga ttttgcagtg tattactgtc   2640

agcagtatgg tagctcacct tggacgttcg gccaagggac caaggtggaa atcaaacgta   2700

agtaattttt cactattgtc ttctgaaatt tgggtctgat ggccagtatt gacttttaga   2760

ggcttaaata ggagtttggt aaagattggt aaatgagggc atttaagatt tgccatgggt   2820

tgcaaaagtt aaactcagct tcaaaaatgg atttggagaa aaaaagatta aattgctcta   2880

aactgaatga cacaaagtaa aaaaaaaaag tgtaactaaa aaggaaccct tgtatttcta   2940

aggagcaaaa gtaaatttat ttttgttcac tcttgccaaa tattgtattg gttgttgctg   3000

attatgcatg atacagaaaa gtggaaaaat acatttttta gtctttctcc cttttgtttg   3060

ataaattatt ttgtcagaca acaataaaaa tcaatagcac gccctaagat ctagatgcat   3120

gctcgagtgc catttcatta cctctttctc cgcacccgac atagat                  3166


<210> SEQ ID NO 12
<211> LENGTH: 19
<212> TYPE: DNA
<213> ORGANISM: Artificial Sequence
<220> FEATURE:
<223> OTHER INFORMATION: Synthetic

<400> SEQUENCE: 12

tccaggcacc ctgtctttg                                                  19


<210> SEQ ID NO 13
<211> LENGTH: 26
<212> TYPE: DNA
<213> ORGANISM: Artificial Sequence
<220> FEATURE:
<223> OTHER INFORMATION: Synthetic

<400> SEQUENCE: 13

aagtagctgc tgctaacact ctgact                                          26


<210> SEQ ID NO 14
<211> LENGTH: 24
<212> TYPE: DNA
<213> ORGANISM: Artificial Sequence
<220> FEATURE:
<223> OTHER INFORMATION: Synthetic

<400> SEQUENCE: 14

aaagagccac cctctcctgc aggg                                            24


<210> SEQ ID NO 15
<211> LENGTH: 3187
<212> TYPE: DNA
<213> ORGANISM: Artificial Sequence
<220> FEATURE:
<223> OTHER INFORMATION: Synthetic

<400> SEQUENCE: 15

ggcgcgccgt agctttgaat tttaaacatc tatttgacaa gaaatgcata gttccttctc     60

tttaaaataa tgtaatgttt ctttcaagaa taagcttggt ttgatgcctc tctccccaac    120

atgatagaag tgtagcataa atctatgaaa aattccattt ccctgtgcct acaacaacta    180

cctgggattg aaaacttctt cccttgctct agtcctttct tctacaccta cttccacatc    240
```

```
atctgtgact caaaacaata cttgtcagga aagatcccgg aaagagcaaa aaagacttcc    300
ttagaggtgt cagagattcc tatgccacta tctgtcatct ctagaagggg ttgtgagtat    360
gaggaagagc agagcttgta aattttctac ttgctttgac ttccactgta tttcctaaca    420
acaacaacca cagcaacacc cataacatca caggacaaac ttctagtact tccaaggctt    480
tagtctcagt aaatcttctc tacctccatc acagcagcta gaaggtttga tactcataca    540
aatagtactg tagctttctg ttcataattg gaaaaataga caagacccaa tgtaatacag    600
gctttccttc agccagttag cgttcagttt ttggatcacc attgcacaca tatacccagc    660
atatgtctaa tatatatgta gaaatccgtg aagcaagagt tataatagct tgtgttttct    720
attgtattgt attttcctct tatatcatct tcttcttcgt tcattaaaaa aaaaccgttc    780
aagtaggtct aaattaatta ttggatcata agtagataaa atattttatt tcataacaca    840
ttgacccgat gaatatgttt ctttgccaga catagtcctc atttccaagg taacaagcct    900
gaaaaaatta tactggagca agtcaacagg taatgatggt agcttttcct tattgtcctg    960
gggcaagaat aagacaaaag ataacagggt agaataaaga ttgtgtaaga aagaaggaca   1020
gcaacaggac atgggaacct tttatagagt aacattttga taatggatga tgagaattaa   1080
tgagttagac agggatgggt gggaatgatt gaaggtgtga gtactttagc acagattaag   1140
accaaatcat taggatttaa agagttgtgt agagttagtg aaggaaaagc cttagaatta   1200
aatttggctg cggataaaac attcttggat tagactgaag actcttttct gtgctaagta   1260
agtatattta tgataatgat gatgactgta gtgctgaata tttaataaat aaaaacaaaa   1320
ttaattgccg catacataat gtcctgaata ctattgtaaa tgttttatct tatttccttt   1380
aaactgtcta cagcactata aggtaggtac cagtattgtc acagttacac agatatggaa   1440
accgagacac agggaagtta agttacttga tcaatttcaa gcaatcggca agccatggag   1500
catctatgtc agggctgcca ggacatgtga ctgtaaacag aagtttttca ctttttaact   1560
caaagagggt atgtggctgg gttaatggaa agcttcagga ccctcagaaa acattactaa   1620
caagcaaatg aaaggtgtat ctggaagatt aagttttaac agactcttca tttccatcga   1680
tccaataatg cacttaggga gatgactggg catattgagg ataggaagag agaagtgaaa   1740
acacagcttt ttatattgtt cttaacaggc ttgtgccaaa catcttctgg gtggatttag   1800
gtgattgagg agaagaaaga cacaggagcg aaattctctg agcacaaggg aggagttcta   1860
cactcagact gagccaacag acttttctgg cctgacaacc agggcggcgc aggatgctca   1920
gtgcagagag gaagaagcag gtggtctttg cagctgaaag ctcagctgat ttgcatatgg   1980
agtcattata caacatccca gaattcttta agggcagctg ccaggaagct aagaagcatc   2040
ctctcttcta gctctcagag atggagacag acacactcct gctatgggtg ctgctgctct   2100
gggttccagg tgagggtaca gataagtgtt atgagcaacc tctgtggcca ttatgatgct   2160
ccatgcctct ctgttcttga tcactataat tagggcattt gtcactggtt ttaagtttcc   2220
ccagtcccct gaattttcca ttttctcaga gtgatgtcca aaattattct taaaaattta   2280
aatgaaaagg tcctctgctg tgaaggcttt taaagatata taaaaataat ctttgtgttt   2340
atcattccag gtgccagatg tgttgtggtc ctcagccggt gctgcatcag ccgccggcca   2400
tgtcctcggc ccttggaacc acaatccgcc tcacctgcac cctgaggaac gaccatgaca   2460
tcggtgtgta cagcgtctac tggtaccagc agaggccggg ccaccctccc aggttcctgc   2520
tgagatattt ctcacaatca gacaagagcc agggccccca ggtcccccct cgcttctctg   2580
```

```
gatccaaaga tgtggccagg aacagggggt atttgagcat ctctgagctg cagcctgagg   2640

acgaggctat gtattactgt gctatgcata actcagtgac gcatgtgttt ggcagcggga   2700

cccagctcac cgttttaagt aagtaatttt tcactattgt cttctgaaat ttgggtctga   2760

tggccagtat tgacttttag aggcttaaat aggagtttgg taaagattgg taaatgaggg   2820

catttaagat ttgccatggg ttgcaaaagt taaactcagc ttcaaaaatg gatttggaga   2880

aaaaaagatt aaattgctct aaactgaatg acacaaagta aaaaaaaaaa gtgtaactaa   2940

aaaggaaccc ttgtatttct aaggagcaaa agtaaattta tttttgttca ctcttgccaa   3000

atattgtatt ggttgttgct gattatgcat gatacagaaa agtggaaaaa tacatttttt   3060

agtctttctc ccttttgttt gataaattat tttgtcagac aacaataaaa atcaatagca   3120

cgccctaaga tctagatgca tgctcgagtg ccatttcatt acctctttct ccgcacccga   3180

catagat                                                             3187


<210> SEQ ID NO 16
<211> LENGTH: 17
<212> TYPE: DNA
<213> ORGANISM: Artificial Sequence
<220> FEATURE:
<223> OTHER INFORMATION: Synthetic

<400> SEQUENCE: 16

tgtcctcggc ccttgga                                                    17


<210> SEQ ID NO 17
<211> LENGTH: 20
<212> TYPE: DNA
<213> ORGANISM: Artificial Sequence
<220> FEATURE:
<223> OTHER INFORMATION: Synthetic

<400> SEQUENCE: 17

ccgatgtcat ggtcgttcct                                                 20


<210> SEQ ID NO 18
<211> LENGTH: 23
<212> TYPE: DNA
<213> ORGANISM: Artificial Sequence
<220> FEATURE:
<223> OTHER INFORMATION: Synthetic

<400> SEQUENCE: 18

acaatccgcc tcacctgcac cct                                             23


<210> SEQ ID NO 19
<211> LENGTH: 23
<212> TYPE: DNA
<213> ORGANISM: Artificial Sequence
<220> FEATURE:
<223> OTHER INFORMATION: synthetic

<400> SEQUENCE: 19

agcagtctgc aacctgaaga ttt                                             23


<210> SEQ ID NO 20
<211> LENGTH: 24
<212> TYPE: DNA
<213> ORGANISM: Artificial Sequence
<220> FEATURE:
<223> OTHER INFORMATION: synthetic

<400> SEQUENCE: 20
```

```
gtttaatctc cagtcgtgtc cctt                                            24


<210> SEQ ID NO 21
<211> LENGTH: 15
<212> TYPE: DNA
<213> ORGANISM: Artificial Sequence
<220> FEATURE:
<223> OTHER INFORMATION: synthetic

<400> SEQUENCE: 21

cctccgatca ccttc                                                      15


<210> SEQ ID NO 22
<211> LENGTH: 20
<212> TYPE: DNA
<213> ORGANISM: Artificial Sequence
<220> FEATURE:
<223> OTHER INFORMATION: synthetic

<400> SEQUENCE: 22

aaaccaggga aagcccctaa                                                 20


<210> SEQ ID NO 23
<211> LENGTH: 18
<212> TYPE: DNA
<213> ORGANISM: Artificial Sequence
<220> FEATURE:
<223> OTHER INFORMATION: synthetic

<400> SEQUENCE: 23

atgggacccc actttgca                                                   18


<210> SEQ ID NO 24
<211> LENGTH: 19
<212> TYPE: DNA
<213> ORGANISM: Artificial Sequence
<220> FEATURE:
<223> OTHER INFORMATION: synthetic

<400> SEQUENCE: 24

ctcctgatct atgctgcat                                                  19


<210> SEQ ID NO 25
<211> LENGTH: 21
<212> TYPE: DNA
<213> ORGANISM: Artificial Sequence
<220> FEATURE:
<223> OTHER INFORMATION: synthetic

<400> SEQUENCE: 25

cagcagactg gagcctgaag a                                               21


<210> SEQ ID NO 26
<211> LENGTH: 21
<212> TYPE: DNA
<213> ORGANISM: Artificial Sequence
<220> FEATURE:
<223> OTHER INFORMATION: synthetic

<400> SEQUENCE: 26

tgatttccac cttggtccct t                                               21


<210> SEQ ID NO 27
<211> LENGTH: 18
<212> TYPE: DNA
```

<213> ORGANISM: Artificial Sequence
<220> FEATURE:
<223> OTHER INFORMATION: synthetic

<400> SEQUENCE: 27
tagctcacct tggacgtt 18

<210> SEQ ID NO 28
<211> LENGTH: 22
<212> TYPE: DNA
<213> ORGANISM: Artificial Sequence
<220> FEATURE:
<223> OTHER INFORMATION: synthetic

<400> SEQUENCE: 28
ctcctcatct atggtgcatc ca 22

<210> SEQ ID NO 29
<211> LENGTH: 20
<212> TYPE: DNA
<213> ORGANISM: Artificial Sequence
<220> FEATURE:
<223> OTHER INFORMATION: synthetic

<400> SEQUENCE: 29
gacccactgc cactgaacct 20

<210> SEQ ID NO 30
<211> LENGTH: 13
<212> TYPE: DNA
<213> ORGANISM: Artificial Sequence
<220> FEATURE:
<223> OTHER INFORMATION: synthetic

<400> SEQUENCE: 30
ccactggcat ccc 13

<210> SEQ ID NO 31
<211> LENGTH: 19
<212> TYPE: DNA
<213> ORGANISM: Artificial Sequence
<220> FEATURE:
<223> OTHER INFORMATION: synthetic

<400> SEQUENCE: 31
tgagcagcac cctcacgtt 19

<210> SEQ ID NO 32
<211> LENGTH: 23
<212> TYPE: DNA
<213> ORGANISM: Artificial Sequence
<220> FEATURE:
<223> OTHER INFORMATION: synthetic

<400> SEQUENCE: 32
gtggcctcac aggtatagct gtt 23

<210> SEQ ID NO 33
<211> LENGTH: 18
<212> TYPE: DNA
<213> ORGANISM: Artificial Sequence
<220> FEATURE:
<223> OTHER INFORMATION: synthetic

<400> SEQUENCE: 33
accaaggacg agtatgaa 18

<210> SEQ ID NO 34
<211> LENGTH: 22
<212> TYPE: DNA
<213> ORGANISM: Artificial Sequence
<220> FEATURE:
<223> OTHER INFORMATION: synthetic

<400> SEQUENCE: 34
aagaagcaca cgactgaggc ac 22

<210> SEQ ID NO 35
<211> LENGTH: 24
<212> TYPE: DNA
<213> ORGANISM: Artificial Sequence
<220> FEATURE:
<223> OTHER INFORMATION: synthetic

<400> SEQUENCE: 35
ctcactggat ggtgggaaga tgga 24

<210> SEQ ID NO 36
<211> LENGTH: 16
<212> TYPE: DNA
<213> ORGANISM: Artificial Sequence
<220> FEATURE:
<223> OTHER INFORMATION: synthetic

<400> SEQUENCE: 36
gtaaaacgac ggccag 16

<210> SEQ ID NO 37
<211> LENGTH: 17
<212> TYPE: DNA
<213> ORGANISM: Artificial Sequence
<220> FEATURE:
<223> OTHER INFORMATION: synthetic

<400> SEQUENCE: 37
caggaaacag ctatgac 17

<210> SEQ ID NO 38
<211> LENGTH: 123
<212> TYPE: PRT
<213> ORGANISM: Artificial Sequence
<220> FEATURE:
<223> OTHER INFORMATION: synthetic

<400> SEQUENCE: 38

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Ser Thr Pro Tyr
                85                  90                  95

Thr Phe Gly Gln Gly Thr Lys Leu Glu Ile Lys Arg Ala Asp Ala Ala
            100                 105                 110
```

```
Pro Thr Val Ser Ile Phe Pro Pro Ser Ser Glu
        115                 120


<210> SEQ ID NO 39
<211> LENGTH: 123
<212> TYPE: PRT
<213> ORGANISM: Artificial Sequence
<220> FEATURE:
<223> OTHER INFORMATION: synthetic

<400> SEQUENCE: 39

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Ser Thr Pro Phe
                85                  90                  95

Thr Phe Gly Pro Gly Thr Lys Val Asp Ile Lys Arg Ala Asp Ala Ala
            100                 105                 110

Pro Thr Val Ser Ile Phe Pro Pro Ser Ser Glu
        115                 120


<210> SEQ ID NO 40
<211> LENGTH: 124
<212> TYPE: PRT
<213> ORGANISM: Artificial Sequence
<220> FEATURE:
<223> OTHER INFORMATION: synthetic

<400> SEQUENCE: 40

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Ser
            20                  25                  30

Tyr Leu Ala Trp Tyr Gln Gln Lys Pro Gly Gln Ala Pro Arg Leu Leu
        35                  40                  45

Ile Tyr Gly Ala Ser Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Gly Ser Ser Pro
                85                  90                  95

Arg Thr Phe Gly Gln Gly Thr Lys Val Glu Ile Lys Arg Ala Asp Ala
            100                 105                 110

Ala Pro Thr Val Ser Ile Phe Pro Pro Ser Ser Glu
        115                 120


<210> SEQ ID NO 41
<211> LENGTH: 123
<212> TYPE: PRT
<213> ORGANISM: Artificial Sequence
<220> FEATURE:
<223> OTHER INFORMATION: synthetic
```

<400> SEQUENCE: 41

```
Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Ser
            20                  25                  30

Tyr Leu Ala Trp Tyr Gln Gln Lys Pro Gly Gln Ala Pro Arg Leu Leu
        35                  40                  45

Ile Tyr Gly Ala Ser Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Gly Ser Ser Arg
                85                  90                  95

Thr Phe Gly Gln Gly Thr Lys Val Glu Ile Lys Arg Ala Asp Ala Ala
            100                 105                 110

Pro Thr Val Ser Ile Phe Pro Pro Ser Ser Glu
        115                 120
```

<210> SEQ ID NO 42
<211> LENGTH: 124
<212> TYPE: PRT
<213> ORGANISM: Artificial Sequence
<220> FEATURE:
<223> OTHER INFORMATION: synthetic

<400> SEQUENCE: 42

```
Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Ser
            20                  25                  30

Tyr Leu Ala Trp Tyr Gln Gln Lys Pro Gly Gln Ala Pro Arg Leu Leu
        35                  40                  45

Ile Tyr Gly Ala Ser Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Gly Ser Ser Pro
                85                  90                  95

Trp Thr Phe Gly Gln Gly Thr Lys Val Glu Ile Lys Arg Ala Asp Ala
            100                 105                 110

Ala Pro Thr Val Ser Ile Phe Pro Pro Ser Ser Glu
        115                 120
```

<210> SEQ ID NO 43
<211> LENGTH: 124
<212> TYPE: PRT
<213> ORGANISM: Artificial Sequence
<220> FEATURE:
<223> OTHER INFORMATION: synthetic

<400> SEQUENCE: 43

```
Glu Ile Val Leu Thr Gln Ser Pro Gly Thr Leu Phe Leu Ser Pro Gly
1               5                   10                  15

Glu Arg Ala Thr Leu Ser Cys Arg Ala Ser Gln Ser Val Ser Ser Ser
            20                  25                  30

Tyr Leu Ala Trp Tyr Gln Gln Lys Pro Gly Gln Ala Pro Arg Leu Leu
        35                  40                  45
```

```
Ile Tyr Gly Ala Ser Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Gly Ser Ser Pro
                85                  90                  95

Trp Thr Phe Gly Gln Gly Thr Lys Val Glu Ile Lys Arg Ala Asp Ala
            100                 105                 110

Ala Pro Thr Val Ser Ile Phe Pro Pro Ser Ser Glu
        115                 120
```

<210> SEQ ID NO 44
<211> LENGTH: 124
<212> TYPE: PRT
<213> ORGANISM: Artificial Sequence
<220> FEATURE:
<223> OTHER INFORMATION: synthetic

<400> SEQUENCE: 44

```
Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Ser
            20                  25                  30

Tyr Leu Ala Trp Tyr Gln Gln Lys Pro Gly Gln Ala Pro Arg His Leu
        35                  40                  45

Ile Tyr Gly Ala Ser Ser Arg Ala Thr Gly Ile Pro Asp Arg Phe Ser
    50                  55                  60

Gly Ser Gly Ser Gly Thr Asp Phe Thr Leu Thr Ile Ser Arg Leu Asp
65                  70                  75                  80

Pro Glu Asp Phe Ala Val Tyr Tyr Cys Gln Gln Tyr Gly Ser Ser Pro
                85                  90                  95

Arg Thr Phe Gly Gln Gly Thr Lys Val Glu Ile Lys Arg Ala Asp Ala
            100                 105                 110

Ala Pro Thr Val Ser Ile Phe Pro Pro Ser Ser Glu
        115                 120
```

<210> SEQ ID NO 45
<211> LENGTH: 118
<212> TYPE: PRT
<213> ORGANISM: Artificial Sequence
<220> FEATURE:
<223> OTHER INFORMATION: synthetic

<400> SEQUENCE: 45

```
Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Ser
            20                  25                  30

Tyr Leu Ala Trp Tyr Gln Gln Lys Pro Gly Gln Ala Pro Arg Leu Leu
        35                  40                  45

Ile Tyr Gly Ala Ser Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Gly Ser Ser Pro
                85                  90                  95

Arg Thr Phe Gly Gln Gly Thr Lys Val Glu Ile Lys Arg Ala Asp Ala
```

```
            100                 105                 110

Ala Pro Thr Val Ser Ile
        115


<210> SEQ ID NO 46
<211> LENGTH: 124
<212> TYPE: PRT
<213> ORGANISM: Artificial Sequence
<220> FEATURE:
<223> OTHER INFORMATION: synthetic

<400> SEQUENCE: 46

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Ser
            20                  25                  30

Tyr Leu Ala Trp Tyr Gln Gln Lys Pro Gly Gln Ala Pro Arg Leu Leu
        35                  40                  45

Ile Tyr Gly Ala Ser Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Gly Ser Ser Pro
                85                  90                  95

Trp Thr Phe Gly Gln Gly Thr Lys Val Glu Ile Lys Arg Ala Asp Ala
            100                 105                 110

Ala Pro Thr Val Ser Ile Phe Pro Pro Ser Ser Glu
        115                 120


<210> SEQ ID NO 47
<211> LENGTH: 124
<212> TYPE: PRT
<213> ORGANISM: Artificial Sequence
<220> FEATURE:
<223> OTHER INFORMATION: synthetic

<400> SEQUENCE: 47

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Ser
            20                  25                  30

His Leu Ala Trp Tyr Gln Gln Lys Pro Gly Gln Ala Pro Arg Leu Leu
        35                  40                  45

Ile Tyr Gly Ala Ser Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Gly Ser Ser Pro
                85                  90                  95

Pro Thr Phe Gly Gln Gly Thr Lys Val Glu Ile Lys Arg Ala Asp Ala
            100                 105                 110

Ala Pro Thr Val Ser Ile Phe Pro Pro Ser Ser Glu
        115                 120


<210> SEQ ID NO 48
<211> LENGTH: 124
<212> TYPE: PRT
<213> ORGANISM: Artificial Sequence
<220> FEATURE:
```

```
<223> OTHER INFORMATION: synthetic

<400> SEQUENCE: 48

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Ser
            20                  25                  30

Tyr Leu Ala Trp Tyr Gln Gln Lys Pro Gly Gln Ala Pro Arg Leu Leu
        35                  40                  45

Ile Tyr Gly Ala Ser Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Gly Ser Ser Pro
                85                  90                  95

Tyr Thr Phe Gly Gln Gly Thr Lys Leu Glu Ile Lys Arg Ala Asp Ala
            100                 105                 110

Ala Pro Thr Val Ser Ile Phe Pro Pro Ser Ser Glu
        115                 120


<210> SEQ ID NO 49
<211> LENGTH: 124
<212> TYPE: PRT
<213> ORGANISM: Artificial Sequence
<220> FEATURE:
<223> OTHER INFORMATION: synthetic

<400> SEQUENCE: 49

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Ser
            20                  25                  30

Tyr Leu Ala Trp Tyr Gln Gln Lys Pro Gly Gln Ala Pro Arg Leu Leu
        35                  40                  45

Ile Tyr Gly Ala Ser Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Gly Ser Ser Ile
                85                  90                  95

Phe Thr Phe Gly Pro Gly Thr Lys Val Asp Ile Lys Arg Ala Asp Ala
            100                 105                 110

Ala Pro Thr Val Ser Ile Phe Pro Pro Ser Ser Glu
        115                 120
```

MICE EXPRESSING A LIMITED IMMUNOGLOBULIN LIGHT CHAIN REPERTOIRE

CROSS-REFERENCE TO RELATED APPLICATIONS

This application is a continuation of U.S. Ser. No. 16/530,030 filed Aug. 2, 2019, which continuation of U.S. Ser. No. 16/128,360 filed Sep. 11, 2018, which is a continuation of U.S. Ser. No. 15/700,973 filed Sep. 11, 2017, which is a continuation of U.S. Ser. No. 13/798,455 filed Mar. 13, 2013, which is a continuation-in-part of U.S. Ser. No. 13/488,628 filed Jun. 5, 2012, which is a continuation-in-part of U.S. Ser. No. 13/412,936 filed Mar. 6, 2012, which is a continuation-in-part of U.S. Ser. No. 13/093,156 filed Apr. 25, 2011, which is a continuation-in-part of U.S. Ser. No. 13/022,759 filed Feb. 8, 2011, which is a nonprovisional application of U.S. Provisional Application Ser. No. 61/302,282, filed Feb. 8, 2010; which applications are hereby incorporated by reference in their entirety.

FIELD

A genetically modified mouse is provided that expresses antibodies having a common human variable/mouse constant light chain associated with diverse human variable/mouse constant heavy chains. A method for making a human bispecific antibody from human variable region gene sequences of B cells of the mouse is provided.

BACKGROUND

Antibodies typically comprise a homodimeric heavy chain component, wherein each heavy chain monomer is associated with an identical light chain. Antibodies having a heterodimeric heavy chain component (e.g., bispecific antibodies) are desirable as therapeutic antibodies. But making bispecific antibodies having a suitable light chain component that can satisfactorily associate with each of the heavy chains of a bispecific antibody has proved problematic.

In one approach, a light chain might be selected by surveying usage statistics for all light chain variable domains, identifying the most frequently employed light chain in human antibodies, and pairing that light chain in vitro with the two heavy chains of differing specificity.

In another approach, a light chain might be selected by observing light chain sequences in a phage display library (e.g., a phage display library comprising human light chain variable region sequences, e.g., a human scFv library) and selecting the most commonly used light chain variable region from the library. The light chain can then be tested on the two different heavy chains of interest.

In another approach, a light chain might be selected by assaying a phage display library of light chain variable sequences using the heavy chain variable sequences of both heavy chains of interest as probes. A light chain that associates with both heavy chain variable sequences might be selected as a light chain for the heavy chains.

In another approach, a candidate light chain might be aligned with the heavy chains' cognate light chains, and modifications are made in the light chain to more closely match sequence characteristics common to the cognate light chains of both heavy chains. If the chances of immunogenicity need to be minimized, the modifications preferably result in sequences that are present in known human light chain sequences, such that proteolytic processing is unlikely to generate a T cell epitope based on parameters and methods known in the art for assessing the likelihood of immunogenicity (i.e., in silico as well as wet assays).

All of the above approaches rely on in vitro methods that subsume a number of a priori restraints, e.g., sequence identity, ability to associate with specific pre-selected heavy chains, etc. There is a need in the art for compositions and methods that do not rely on manipulating in vitro conditions, but that instead employ more biologically sensible approaches to making human epitope-binding proteins that include a common light chain.

SUMMARY

Genetically modified mice that express human immunoglobulin heavy and light chain variable domains, wherein the mice have a limited light chain variable repertoire, are provided. A biological system for generating a human light chain variable domain that associates and expresses with a diverse repertoire of affinity-matured human heavy chain variable domains is provided. Methods for making binding proteins comprising immunoglobulin variable domains are provided, comprising immunizing mice that have a limited immunoglobulin light chain repertoire with an antigen of interest, and employing an immunoglobulin variable region gene sequence of the mouse in a binding protein that specifically binds the antigen of interest. Methods include methods for making human immunoglobulin heavy chain variable domains suitable for use in making multi-specific antigen-binding proteins.

Genetically engineered mice are provided that select suitable affinity-matured human immunoglobulin heavy chain variable domains derived from a repertoire of unrearranged human heavy chain variable region gene segments, wherein the affinity-matured human heavy chain variable domains associate and express with a single human light chain variable domain derived from one human light chain variable region gene segment. Genetically engineered mice that present a choice of two human light chain variable region gene segments are also provided. In various aspects, the one or two gene segments include human Vκ1-39 and/or human Vκ3-20.

Genetically engineered mice are provided that express a limited repertoire of human light chain variable domains, or a single human light chain variable domain, from a limited repertoire of human light chain variable region gene segments. In some embodiments, provided mice are genetically engineered to include a single unrearranged human light chain variable region gene segment (or two human light chain variable region gene segments) that rearranges to form a rearranged human light chain variable region gene (or two rearranged light chain variable region genes) that expresses a single light chain (or that express either or both of two light chains). The rearranged human light chain variable domains are capable of pairing with a plurality of affinity-matured human heavy chains selected by the mice, wherein the heavy chain variable regions specifically bind different epitopes.

Genetically engineered mice are provided that express a limited repertoire of human light chain variable domains, or a single human light chain variable domain, from a limited repertoire of human light chain variable region sequences. In some embodiments, provided mice are genetically engineered to include a single V/J human light chain sequence (or two V/J sequences) that express a variable region of a single light chain (or that express either or both of two variable regions). A light chain comprising the variable sequence is capable of pairing with a plurality of affinity-matured human heavy chains clonally selected by the mice, wherein the heavy chain variable regions specifically bind different epitopes.

In one aspect, a genetically modified mouse is provided that comprises a single human immunoglobulin light chain variable ($V_L$) region gene segment that is capable of rearranging with a human J gene segment (selected from one or a plurality of $J_L$ segments) and encoding a human $V_L$ domain of an immunoglobulin light chain. In another aspect, a genetically modified mouse is provided that comprises no more than two human $V_L$ gene segments, each of which is capable of rearranging with a human J gene segment (selected from one or a plurality of $J_L$ segments) and encoding a human $V_L$ domain of an immunoglobulin light chain. In some embodiments, the two human $V_L$ gene segments are juxtaposed in the genome of the mouse. In some embodiments, the two human $V_L$ gene segments are at different loci (e.g., a heterozygote, comprising a first human $V_L$ segment at a first light chain allele, and a second human $V_L$ segment at a second light chain allele, wherein the first and the second human $V_L$ segments are not identical) in the genome of the mouse. In some embodiments, the two human $V_L$ gene segments are a human Vκ1-39 gene segment and a human Vκ3-20 gene segment. In one embodiment, the human $J_L$ gene segment is selected from the group consisting of Jκ1, Jκ2, Jκ3, Jκ4, Jκ5, and pairwise combinations thereof. In various embodiments, a provided genetically engineered mouse is incapable of expressing an immunoglobulin light chain that contains an endogenous $V_L$ gene segment. For example, in some embodiments, a provided genetically engineered mouse contains a genetic modification that inactivates and/or removes part or all of an endogenous $V_L$ gene segment.

In one embodiment, the single human $V_L$ gene segment is operably linked to a human $J_L$ gene segment selected from Jκ1, Jκ2, Jκ3, Jκ4, and Jκ5, wherein the single human $V_L$ gene segment is capable of rearranging to form a sequence encoding a light chain variable region gene with any of the one or more human $J_L$ gene segments.

In one embodiment, a provided genetically modified mouse comprises an immunoglobulin light chain locus that does not comprise an endogenous mouse $V_L$ gene segment that is capable of rearranging to form an immunoglobulin light chain gene, wherein the $V_L$ locus contains a single human $V_L$ gene segment that is capable of rearranging to encode a $V_L$ region of a light chain gene. In specific embodiments, the human $V_L$ gene segment is a human Vκ1-39Jκ5 gene segment or a human Vκ3-20Jκ1 gene segment. In some embodiments, a provided genetically modified mouse comprises a $V_L$ locus that does not comprise an endogenous mouse $V_L$ gene segment that is capable of rearranging to form an immunoglobulin light chain gene, wherein the $V_L$ locus comprises no more than two human $V_L$ gene segments that are capable of rearranging to encode a $V_L$ region of a light chain gene. In some certain embodiments, the no more than two human $V_L$ gene segments are selected from the group consisting of a human Vκ1-39 gene segment, a human Vκ3-20 gene segment, and a combination thereof. In some certain embodiments, the no more than two human $V_L$ gene segments are a human Vκ1-39Jκ5 gene segment and a human Vκ3-20Jκ1 gene segment.

In one aspect, a genetically modified mouse is provided that comprises a single rearranged (V/J) human immunoglobulin light chain variable ($V_L$) region (i.e., a $V_L/J_L$ region) that encodes a human $V_L$ domain of an immunoglobulin light chain. In another aspect, the mouse comprises no more than two rearranged human $V_L$ regions that are capable of encoding a human $V_L$ domain of an immunoglobulin light chain.

In one embodiment, the $V_L$ region is a rearranged human Vκ1-39/J sequence or a rearranged human Vκ3-20/J sequence. In one embodiment, the human $J_L$ segment of the rearranged $V_L/J_L$ sequence is selected from Jκ1, Jκ2, Jκ3, Jκ4, and Jκ5. In a specific embodiment, the $V_L$ region is a human Vκ1-39Jκ5 sequence or a human Vκ3-20Jκ1 sequence. In a specific embodiment, the mouse has both a human Vκ1-39Jκ5 sequence and a human Vκ3-20Jκ1 sequence.

In one embodiment, the human $V_L$ gene segment is operably linked to a human or mouse leader sequence. In one embodiment, the leader sequence is a mouse leader sequence. In a specific embodiment, the mouse leader sequence is a mouse Vκ3-7 leader sequence. In a specific embodiment, the leader sequence is operably linked to an unrearranged human $V_L$ gene segment. In a specific embodiment, the leader sequence is operably linked to a rearranged human $V_L/J_L$ sequence.

In one embodiment, the $V_L$ gene segment is operably linked to an immunoglobulin promoter sequence. In one embodiment, the promoter sequence is a human promoter sequence. In a specific embodiment, the human immunoglobulin promoter is a human Vκ3-15 promoter. In a specific embodiment, the promoter is operably linked to an unrearranged human $V_L$ gene segment. In a specific embodiment, the promoter is operably linked to a rearranged human $V_L/J_L$ sequence.

In one embodiment, the light chain locus comprises a leader sequence flanked 5' (with respect to transcriptional direction of a $V_L$ gene segment) with a human immunoglobulin promoter and flanked 3' with a human $V_L$ gene segment that rearranges with a human J segment and encodes a $V_L$ domain of a reverse chimeric light chain comprising an endogenous mouse light chain constant region ($C_L$). In a specific embodiment, the $V_L$ gene segment is at the mouse Vκ locus, and the mouse $C_L$ is a mouse Cκ.

In one embodiment, the light chain locus comprises a leader sequence flanked 5' (with respect to transcriptional direction of a $V_L$ gene segment) with a human immunoglobulin promoter and flanked 3' with a rearranged human $V_L$ region ($V_L/J_L$ sequence) and encodes a $V_L$ domain of a reverse chimeric light chain comprising an endogenous mouse light chain constant region ($C_L$). In a specific embodiment, the rearranged human $V_L/J_L$ sequence is at the mouse kappa (κ) locus, and the mouse $C_L$ is a mouse Cκ.

In one embodiment, the $V_L$ locus of the modified mouse is a κ light chain locus, and the κ light chain locus comprises a mouse κ intronic enhancer, a mouse κ3' enhancer, or both an intronic enhancer and a 3' enhancer.

In one embodiment, the mouse comprises a nonfunctional immunoglobulin lambda (λ) light chain locus. In a specific embodiment, the λ light chain locus comprises a deletion of one or more sequences of the locus, wherein the one or more deletions renders the λ light chain locus incapable of rearranging to form a light chain gene. In another embodiment, all or substantially all of the $V_L$ gene segments of the λ light chain locus are deleted.

In one embodiment, mouse makes a light chain that comprises a somatically mutated $V_L$ domain derived from a human $V_L$ gene segment. In one embodiment, the light chain comprises a somatically mutated $V_L$ domain derived from a human $V_L$ gene segment, and a mouse Cκ region. In one embodiment, the mouse does not express a λ light chain.

In one embodiment, the genetically modified mouse is capable of somatically hypermutating the human $V_L$ region sequence. In a specific embodiment, the mouse comprises a cell that comprises a rearranged immunoglobulin light chain gene derived from a human $V_L$ gene segment that is capable of rearranging and encoding a $V_L$ domain, and the rearranged immunoglobulin light chain gene comprises a somatically mutated $V_L$ domain.

In one embodiment, the mouse comprises a cell that expresses a light chain comprising a somatically mutated human $V_L$ domain linked to a mouse Cκ, wherein the light chain associates with a heavy chain comprising a somatically mutated $V_H$ domain derived from a human $V_H$ gene segment and wherein the heavy chain comprises a mouse heavy chain constant region ($C_H$). In a specific embodiment, the heavy chain comprises a mouse $C_H1$, a mouse hinge, a mouse $C_H2$, and a mouse $C_H3$. In a specific embodiment, the heavy chain comprises a human $C_H1$, a hinge, a mouse $C_H2$, and a mouse $C_H3$.

In one embodiment, the mouse comprises a replacement of endogenous mouse $V_H$ gene segments with one or more human $V_H$ gene segments, wherein the human $V_H$ gene segments are operably linked to a mouse $C_H$ region gene, such that the mouse rearranges the human $V_H$ gene segments and expresses a reverse chimeric immunoglobulin heavy chain that comprises a human $V_H$ domain and a mouse $C_H$. In one embodiment, 90-100% of unrearranged mouse $V_H$ gene segments are replaced with at least one unrearranged human $V_H$ gene segment. In a specific embodiment, all or substantially all of the endogenous mouse $V_H$ gene segments are replaced with at least one unrearranged human $V_H$ gene segment. In one embodiment, the replacement is with at least 19, at least 39, or at least 80 or 81 unrearranged human $V_H$ gene segments. In one embodiment, the replacement is with at least 12 functional unrearranged human $V_H$ gene segments, at least 25 functional unrearranged human $V_H$ gene segments, or at least 43 functional unrearranged human $V_H$ gene segments. In one embodiment, the mouse comprises a replacement of all mouse $D_H$ and $J_H$ segments with at least one unrearranged human $D_H$ segment and at least one unrearranged human $J_H$ segment. In one embodiment, the at least one unrearranged human $D_H$ segment is selected from 1-1, D1-7, 1-26, 2-8, 2-15, 3-3, 3-10, 3-16, 3-22, 5-5, 5-12, 6-6, 6-13, 7-27, and a combination thereof. In one embodiment, the at least one unrearranged human $J_H$ segment is selected from 1, 2, 3, 4, 5, 6, and a combination thereof. In a specific embodiment, the one or more human $V_H$ gene segment is selected from a 1-2, 1-8, 1-24, 1-69, 2-5, 3-7, 3-9, 3-11, 3-13, 3-15, 3-20, 3-23, 3-30, 3-33, 3-48, 3-53, 4-31, 4-39, 4-59, 5-51, a 6-1 human $V_H$ gene segment, and a combination thereof.

In one embodiment, the mouse comprises a B cell that expresses a binding protein that specifically binds an antigen of interest, wherein the binding protein comprises a light chain derived from a human Vκ1-39/Jκ5 rearrangement or a human Vκ3-20/Jκ1 rearrangement, and wherein the cell comprises a rearranged immunoglobulin heavy chain gene derived from a rearrangement of human $V_H$ gene segments selected from a 1-69, 2-5, 3-13, 3-23, 3-30, 3-33, 3-53, 4-39, 4-59, and 5-51 gene segment. In one embodiment, the one or more human $V_H$ gene segments are rearranged with a human heavy chain $J_H$ gene segment selected from 1, 2, 3, 4, 5, and 6. In one embodiment, the one or more human $V_H$ and $J_H$ gene segments are rearranged with a human $D_H$ gene segment selected from 1-1, 1-7, 1-26, 2-8, 2-15, 3-3, 3-10, 3-16, 3-22, 5-5, 5-12, 6-6, 6-13, and 7-27. In a specific embodiment, the light chain gene has 1, 2, 3, 4, or 5 or more somatic hypermutations.

In one embodiment, the mouse comprises a B cell that comprises a rearranged immunoglobulin heavy chain variable region gene sequence comprising a $V_H/D_H/J_H$ region selected from 2-5/6-6/1, 2-5/3-22/1, 3-13/6-6/5, 3-23/2-8/4, 3-23/3-3/4, 3-23/3-10/4, 3-23/6-6/4, 3-23/7-27/4, 3-30/1-1/4, 3-30/1-7/4, 3-30/3-3/3, 3-30/3-3/4, 3-30/3-22/5, 3-30/5-5/2, 3-30/5-12/4, 3-30/6-6/1, 3-30/6-6/3, 3-30/6-6/4, 3-30/6-6/5, 3-30/6-13/4, 3-30/7-27/4, 3-30/7-27/5, 3-30/7-27/6, 3-33/1-7/4, 3-33/2-15/4, 4-39/1-26/3, 4-59/3-16/3, 4-59/3-16/4, 4-59/3-22/3, 5-51/3-16/6, 5-51/5-5/3, 5-51/6-13/5, 3-53/1-1/4, 1-69/6-6/5, and 1-69/6-13/4. In a specific embodiment, the B cell expresses a binding protein comprising a human immunoglobulin heavy chain variable region fused with a mouse heavy chain constant region, and a human immunoglobulin light chain variable region fused with a mouse light chain constant region.

In one embodiment, the rearranged human $V_L$ region is a human Vκ1-39Jκ5 sequence, and the mouse expresses a reverse chimeric light chain comprising (i) a $V_L$ domain derived from the human $V_L/J_L$ sequence and (ii) a mouse $C_L$; wherein the light chain is associated with a reverse chimeric heavy chain comprising (i) a mouse $C_H$ and (ii) a somatically mutated human $V_H$ domain derived from a human $V_H$ gene segment selected from a 1-2, 1-8, 1-24, 1-69, 2-5, 3-7, 3-9, 3-11, 3-13, 3-15, 3-20, 3-23, 3-30, 3-33, 3-48, 3-53, 4-31, 4-39, 4-59, 5-51, a 6-1 human $V_H$ gene segment, and a combination thereof. In one embodiment, the mouse expresses a light chain that is somatically mutated. In one embodiment the $C_L$ is a mouse Cκ. In a specific embodiment, the human $V_H$ gene segment is selected from a 2-5, 3-13, 3-23, 3-30, 4-59, 5-51, and 1-69 gene segment. In a specific embodiment, the somatically mutated human $V_H$ domain comprises a sequence derived from a $D_H$ segment selected from 1-1, 1-7, 2-8, 3-3, 3-10, 3-16, 3-22, 5-5, 5-12, 6-6, 6-13, and 7-27. In a specific embodiment, the somatically mutated human $V_H$ domain comprises a sequence derived from a $J_H$ segment selected from 1, 2, 3, 4, 5, and 6. In a specific embodiment, the somatically mutated human $V_H$ domain is encoded by a rearranged human $V_H/D_H/J_H$ sequence selected from 2-5/6-6/1, 2-5/3-22/1, 3-13/6-6/5, 3-23/2-8/4, 3-23/3-3/4, 3-23/3-10/4, 3-23/6-6/4, 3-23/7-27/4, 3-30/1-1/4, 3-30/1-7/4, 3-30/3-3/4, 3-30/3-22/5, 3-30/5-5/2, 3-30/5-12/4, 3-30/6-6/1, 3-30/6-6/3, 3-30/6-6/4, 3-30/6-6/5, 3-30/6-13/4, 3-30/7-27/4, 3-30/7-27/5, 3-30/7-27/6, 4-59/3-16/3, 4-59/3-16/4, 4-59/3-22/3, 5-51/5-5/3, 1-69/6-6/5, and 1-69/6-13/4.

In one embodiment, the rearranged human $V_L$ region is a human Vκ3-20Jκ1 sequence, and the mouse expresses a reverse chimeric light chain comprising (i) a $V_L$ domain derived from the rearranged human $V_L/J_L$ sequence, and (ii) a mouse $C_L$; wherein the light chain is associated with a reverse chimeric heavy chain comprising (i) a mouse $C_H$, and (ii) a somatically mutated human $V_H$ derived from a human $V_H$ gene segment selected from a 1-2, 1-8, 1-24, 1-69, 2-5, 3-7, 3-9, 3-11, 3-13, 3-15, 3-20, 3-23, 3-30, 3-33, 3-48, 3-53, 4-31, 4-39, 4-59, 5-51, a 6-1 human $V_H$ gene segment, and a combination thereof. In one embodiment, the mouse expresses a light chain that is somatically mutated. In one embodiment the $C_L$ is a mouse Cκ. In a specific embodiment, the human $V_H$ gene segment is selected from a 3-30, 3-33, 3-53, 4-39, and 5-51 gene segment. In a specific embodiment, the somatically mutated human $V_H$ domain comprises a sequence derived from a $D_H$ segment selected from 1-1, 1-7, 1-26, 2-15, 3-3, 3-16, and 6-13. In a specific embodiment, the somatically mutated human $V_H$ domain comprises a sequence derived from a $J_H$ segment selected from 3, 4, 5, and 6. In a specific embodiment, the somatically mutated human $V_H$ domain is encoded by a rearranged human $V_H/D_H/J_H$ sequence selected from 3-30/1-1/4, 3-30/3-3/3, 3-33/1-7/4, 3-33/2-15/4, 4-39/1-26/3, 5-51/3-16/6, 5-51/6-13/5, and 3-53/1-1/4.

In one embodiment, the mouse comprises both a rearranged human Vκ1-39Jκ5 sequence and a rearranged human Vκ3-20Jκ1 sequence, and the mouse expresses a reverse chimeric light chain comprising (i) a $V_L$ domain derived from the human Vκ1-39Jκ5 sequence or the human Vκ3-20Jκ1 sequence, and (ii) a mouse $C_L$; wherein the light chain is associated with a reverse chimeric heavy chain comprising (i) a mouse $C_H$, and (ii) a somatically mutated human $V_H$ derived from a human $V_H$ gene segment selected from a 1-2, 1-8, 1-24, 1-69, 2-5, 3-7, 3-9, 3-11, 3-13, 3-15, 3-20, 3-23, 3-30, 3-33, 3-48, 3-53, 4-31, 4-39, 4-59, 5-51, a 6-1 human $V_H$ gene segment, and a combination thereof. In one embodiment, the mouse expresses a light chain that is somatically mutated. In one embodiment the $C_L$ is a mouse Cκ.

In one embodiment, 90-100% of the endogenous unrearranged mouse $V_H$ gene segments are replaced with at least one unrearranged human $V_H$ gene segment. In a specific embodiment, all or substantially all of the endogenous unrearranged mouse $V_H$ gene segments are replaced with at least one unrearranged human $V_H$ gene segment. In one embodiment, the replacement is with at least 18, at least 39, at least 80, or 81 unrearranged human $V_H$ gene segments. In one embodiment, the replacement is with at least 12 functional unrearranged human $V_H$ gene segments, at least 25 functional unrearranged human $V_H$ gene segments, or at least 43 unrearranged human $V_H$ gene segments.

In one embodiment, the genetically modified mouse is a C57BL strain, in a specific embodiment selected from C57BL/JA, C57BL/JAn, C57BL/GrFa, C57BL/KaLwN, C57BL/6, C57BL/J6J, C57BL/6ByJ, C57BL/J6NJ, C57BL/10, C57BL/J10ScSn, C57BL/10Cr, and C57BL/Ola. In a specific embodiment, the genetically modified mouse is a mix of an aforementioned 129 strain and an aforementioned C57BL/J6 strain. In another specific embodiment, the mouse is a mix of aforementioned 129 strains, or a mix of aforementioned BL/6 strains. In a specific embodiment, the 129 strain of the mix is a 129S6 (129/SvEvTac) strain.

In one embodiment, the mouse expresses a reverse chimeric antibody comprising a light chain that comprises a mouse Cκ and a somatically mutated human $V_L$ domain derived from a rearranged human Vκ1-39Jκ5 sequence or a rearranged human Vκ3-20Jκ1 sequence, and a heavy chain that comprises a mouse $C_H$ and a somatically mutated human $V_H$ domain derived from a human $V_H$ gene segment selected from a 1-2, 1-8, 1-24, 1-69, 2-5, 3-7, 3-9, 3-11, 3-13, 3-15, 3-20, 3-23, 3-30, 3-33, 3-48, 3-53, 4-31, 4-39, 4-59, 5-51, and a 6-1 human $V_H$ gene segment, wherein the mouse does not express a fully mouse antibody and does not express a fully human antibody. In one embodiment the mouse comprises a κ light chain locus that comprises a replacement of endogenous mouse κ light chain gene segments with the rearranged human Vκ1-39Jκ5 sequence or the rearranged human Vκ3-20Jκ1 sequence, and comprises a replacement of all or substantially all endogenous mouse $V_H$ gene segments with a complete or substantially complete repertoire of human $V_H$ gene segments.

In one aspect, a population of antigen-specific antibodies derived from a mouse as described herein is provided, wherein the antibodies comprise a light chain gene derived from a human Vκ1-39/Jκ5 rearrangement or a human Vκ3-20/Jκ1 rearrangement, and wherein the antibodies comprise a rearranged immunoglobulin heavy chain gene derived from a rearrangement of a human $V_H$ gene segment selected from a 1-2, 1-3, 1-8, 1-18, 1-24, 1-46, 1-58, 1-69, 2-5, 2-26, 2-70, 3-7, 3-9, 3-11, 3-13, 3-15, 3-16, 3-20, 3-21, 3-23, 3-30, 3-33, 3-43, 3-48, 3-53, 3-64, 3-72, 3-73, 4-31, 4-34, 4-39, 4-59, 5-51, and a 6-1 human $V_H$ gene segment. In one embodiment, the one or more human $V_H$ gene segments are rearranged with a human heavy chain $J_H$ gene segment selected from 1, 2, 3, 4, 5, and 6. In a specific embodiment, the light chain has 1, 2, 3, 4, or 5 or more somatic hypermutations.

In one embodiment, the light chain has 1, 2, 3, or 4 somatic hypermutations. In one embodiment, the light chain gene has 1 or 2 mutations. In various embodiments, the light chain gene is capable of incurring multiple mutations along its sequence.

In one embodiment, the light chain is derived from a human Vκ1-39/Jκ5 rearrangement and the light chain has at least one or no more than four somatic hypermutations. In one embodiment, the light chain comprises at least two somatic hypermutations. In one embodiment, the light chain comprises at least three somatic hypermutations. In one embodiment, the light chain comprises at least four somatic hypermutations. In a specific embodiment, at least one such somatic hypermutation is present in one or more framework regions (FWs) of the light chain. In a specific embodiment, at least one such somatic hypermutation is present in one or more complementarity determining regions (CDRs) of the light chain. In a specific embodiment, at least one such somatic hypermutation is present in one or more FWs and/or one or more CDRs of the light chain. In various embodiments, the framework regions are selected from framework 1 (FW1), framework 2 (FW2), framework 3 (FW3), and/or a combination thereof. In various embodiments, the CDRs are selected from CDR1, CDR2, CDR3, and/or a combination thereof.

In one embodiment, the heavy chain comprises at least one mutation in one or more FWs or one or more CDRs. In one embodiment, the heavy chain comprises at least one mutation in one or more FWs and one or more CDRs. In one embodiment, the heavy chain comprises at least two mutations in one or more FWs and one or more CDRs. In one embodiment, the heavy chain comprises at least three mutations in one or more FWs and one or more CDRs. In one embodiment, the heavy chain comprises at least four mutations in one or more FWs and one or more CDRs. In one embodiment, the heavy chain comprises at least five or more than five mutations in one or more FWs and one or more CDRs; in a specific embodiment, the heavy chain comprises at least five or more than five mutations in two FWs; in a specific embodiment, the heavy chain comprises at least five or more than five mutations in one FW and one CDR.

In one embodiment, the light chain is derived from a human Vκ1-39/Jκ5 rearrangement and about 9% of the Vκ1-39/Jκ5-derived light chains have at least one mutation present in FW1; in one embodiment, at least 9% of the light chains comprise one mutation present in FW1. In one embodiment, the light chain is derived from a human Vκ1-39/Jκ5 rearrangement and about 25% of the Vκ1-39/Jκ5-derived light chains have at least one or no more than two mutations present in CDR1; in one embodiment, at least 19% of the light chains have one mutation present in CDR1; in one embodiment, at least 5% of the light chains have two mutations present in CDR1.

In one embodiment, the light chain is derived from a human Vκ1-39/Jκ5 rearrangement and about 20% of the Vκ1-39/Jκ5-derived light chains have at least one or no more than three mutations present in FW2; in one embodiment, at least 17% of the light chains have one mutation present in FW2; in one embodiment, at least 1% of the light chains have two mutations present in FW2; in one embodiment, at least 1% of the light chains have three mutations present in FW2.

In one embodiment, the light chain is derived from a human Vκ1-39/Jκ5 rearrangement and about 10% of the Vκ1-39/Jκ5-derived light chains have at least one or no more than two mutations present in CDR2; in one embodiment, at least 10% of the light chains have one mutation present in CDR2; in one embodiment, at least 1% of the light chains have two mutations present in CDR2.

In one embodiment, the light chain is derived from a human Vκ1-39/Jκ5 rearrangement and about 29% of the Vκ1-39/Jκ5-derived light chains have at least one or no more than four mutations present in FW3; in one embodiment, at least 21% of the light chains have one mutation present in FW3; in one embodiment, at least 5% of the light chains have two mutations present in FW3; in one embodiment, at least 2% of the light chains have three mutations present in FW3; in one embodiment, at least 2% of the light chains have four mutations present in FW3.

In one embodiment, the light chain is derived from a human Vκ1-39/Jκ5 rearrangement and about 37% of the Vκ1-39/Jκ5-derived light chains have at least one or no more than four mutations present in CDR3; in one embodiment, at least 27% of the light chains have one mutation present in CDR3; in one embodiment, at least 8% of the light chains have two mutations present in CDR3; in one embodiment, at least 1% of the light chains have three mutations present in CDR3; in one embodiment, at least 1% of the light chains have four mutations present in CDR3.

In one embodiment, a population of antigen-specific antibodies derived from a mouse as described herein is provided, wherein the antibodies comprise a light chain derived from a human Vκ1-39/Jκ5 rearrangement and about 9% of the Vκ1-39/Jκ5-derived light chains have one or more mutations present in FW1, about 25% of the Vκ1-39/Jκ5-derived light chains have one or more mutations present in CDR1, about 20% of the Vκ1-39/Jκ5-derived light chains have one or more mutations present in FW2, about 10% of the Vκ1-39/Jκ5-derived light chains have one or more mutations present in CDR2, about 29% of the Vκ1-39/Jκ5-derived light chains have one or more mutations present in FW3, and about 37% of the Vκ1-39/Jκ5-derived light chains have one or more mutations present in CDR3.

In one embodiment, the light chain is derived from a human Vκ1-39/Jκ5 rearrangement and about 35% of the heavy chains have at least one mutation present in FW1; in one embodiment, at least 25% of the heavy chains have one mutation present in FW1; in one embodiment, at least 9% of the heavy chains have two mutations present in FW1; in one embodiment, at least 1% of the heavy chains have three mutations present in FW1; in one embodiment, at least 1% of the heavy chains have more than five mutations present in FW1.

In one embodiment, the light chain is derived from a human Vκ1-39/Jκ5 rearrangement and about 92% of the heavy chains have at least one or no more than four mutations present in CDR1; in one embodiment, at least 92% of the heavy chains have at least one, at least two, at least three, or at least four mutations present in CDR1; in one embodiment, at least 26% of the heavy chains have one mutation present in CDR1; in one embodiment, at least 44% of the heavy chains have two mutations present in CDR1; in one embodiment, at least 19% of the heavy chains have three mutations present in CDR1; in one embodiment, at least 3% of the heavy chains have four mutations present in CDR1.

In one embodiment, the light chain is derived from a human Vκ1-39/Jκ5 rearrangement and about 66% of the heavy chains have at least one or no more than three mutations present in FW2; in one embodiment, at least 66% of the heavy chains have at least one, at least two, or at least three mutations present in FW2; in one embodiment, at least 35% of the heavy chains have one mutation present in FW2; in one embodiment, at least 23% of the heavy chains have two mutations present in FW2; in one embodiment, at least 8% of the heavy chains have three mutations present in FW2.

In one embodiment, the light chain is derived from a human Vκ1-39/Jκ5 rearrangement and about 70% of the heavy chains have at least one or no more than four mutations present in CDR2; in one embodiment, at least 70% of the heavy chains have at least two, at least three, or at least four mutations present in CDR2; in one embodiment, at least 34% have one mutation present in CDR2; in one embodiment, at least 20% of the heavy chains have two mutations present in CDR2; in one embodiment, at least 12% of the heavy chains have three mutations present in CDR2; in one embodiment, at least 5% of the heavy chains have four mutations present in CDR2.

In one embodiment, the light chain is derived from a human Vκ1-39/Jκ5 rearrangement and about 91% of the heavy chains have at least one or up to five or more mutations present in FW3; in one embodiment, at least 91% of the heavy chains have at least two, at least three, at least four, or at least five or more mutations present in FW3; in one embodiment, at least 19% of the heavy chains have one mutation present in FW3; in one embodiment, at least 33% of the heavy chains have two mutations present in FW3; in one embodiment, at least 22% of the heavy chains have three mutations present in FW3; in one embodiment, at least 11% of the heavy chains have four mutations present in FW3; in one embodiment, at least 7% of the heavy chains have five or more mutations present in FW3.

In one embodiment, the light chain is derived from a human Vκ1-39/Jκ5 rearrangement and about 63% of the heavy chains have at least one or no more than two mutations present in CDR3; in one embodiment, at least 63% of the heavy chains have at one mutation present in CDR3; in one embodiment, at least 54% of the heavy chains have one mutation present in CDR3; in one embodiment, at least 9% of the heavy chains have two mutations present in CDR3.

In one embodiment, a population of antigen-specific antibodies derived from a mouse as described herein is provided, wherein the antibodies comprise a light chain derived from a human Vκ1-39/Jκ5 rearrangement and at least 35% of the heavy chains have one or more mutations present in FW1, about 92% of the heavy chains have one or more mutations present in CDR1, about 66% of the heavy chains have one or more mutations present in FW2, about 70% of the heavy chains have one or more mutations present in CDR2, about 91% of the heavy chains have one or more mutations present in FW3, and about 63% of the heavy chains have one or more mutations present in CDR3.

In one embodiment, the light chain is derived from a human Vκ3-20/Jκ1 rearrangement and the light chain gene has at least one or no more than two somatic hypermutations; in one embodiment, the light chain gene has at least two, at least three, at least four or more somatic hypermutations. In a specific embodiment, the mutations are present in one or more framework regions of the light chain. In a specific embodiment, the mutations are present in one or more CDR regions of the light chain. In a specific embodiment, the mutations are present in one or more framework regions and/or one or more CDR regions of the light chain. In various embodiments, the framework regions are selected from framework 1 (FW1), framework 2 (FW2), framework 3 (FW3), and/or a combination thereof.

In one embodiment, the light chain is derived from a human Vκ3-20/Jκ1 rearrangement and about 10% of the Vκ3-20/Jκ1-derived light chains have at least one mutation present in FW1; in one embodiment, at least 10% of the light chains have one mutation in FW1.

In one embodiment, the light chain is derived from a human Vκ3-20/Jκ1 rearrangement and about 53% of the Vκ3-20/Jκ1-derived light chains have at least one or no more than two mutations present in CDR1; in one embodiment, at least 27% of the light chains have one or more mutations in CDR1; in one embodiment, about 54% of the light chains have one or two mutations present in CDR1.

In one embodiment, the light chain is derived from a human Vκ3-20/Jκ1 rearrangement and about 6% of the Vκ3-20/Jκ1-derived light chains have at least one or no more than two mutations present in FW2; in one embodiment, at least 6% of light chains have at least one mutation present in FW2; in one embodiment, at least 3% of the light chains have one mutation present in FW2; in one embodiment, at least 3% of the light chains have two mutations present in FW2.

In one embodiment, the light chain is derived from a human Vκ3-20/Jκ1 rearrangement and at least about 3% of the Vκ3-20/Jκ1-derived light chains have at least one mutation present in CDR2; in one embodiment, at least 3% of the light chains have one mutation in CDR2.

In one embodiment, the light chain is derived from a human Vκ3-20/Jκ1 rearrangement and about 17% or more of the Vκ3-20/Jκ1-derived light chains have at least one or no more than two mutations present in FW3; in one embodiment, at least 20% of the light chain have one mutation present in FW3; in one embodiment, at least 17% of the light chains have two mutations present in FW3.

In one embodiment, the light chain is derived from a human Vκ3-20/Jκ1 rearrangement and at least 43% of the Vκ3-20/Jκ1-derived light chains have at least one mutation present in CDR3; in one embodiment, at least 43% of the light chains have one mutation in CDR3.

In one embodiment, a population of antigen-specific antibodies derived from a mouse as described herein is provided, wherein the antibodies comprise a light chain derived from a human Vκ3-20/Jκ1 rearrangement and about 10% of the Vκ3-20/Jκ1-derived light chains have one or more mutations present in at least, about 53% of the Vκ3-20/Jκ1-derived light chains have one or more mutations present in CDR1, about 6% of the Vκ3-20/Jκ1-derived light chains have one or more mutations present in FW2, about 3% of the Vκ3-20/Jκ1-derived light chains have one or more mutations present in CDR2, about 37% of the Vκ3-20/Jκ1-derived light chains have one or more mutations present in FW3, and about 43% of the Vκ3-20/Jκ1-derived light chains have one or more mutations present in CDR3.

In one embodiment, the light chain is derived from a human Vκ3-20/Jκ1 rearrangement and about 43% of the heavy chains have at least one or no more than two mutations present in FW1; in one embodiment, at least 41% of the heavy chains have at least one mutation present in FW1; in one embodiment, about 41% of the heavy chains have one mutation present in FW1; in one embodiment, about 2% of the heavy chains have two mutations present in FW1.

In one embodiment, the light chain is derived from a human Vκ3-20/Jκ1 rearrangement and about 92% of the heavy chains have at least one or no more than four mutations present in CDR1; in one embodiment, at least 43% of heavy chains have at least one mutation present in CDR1; in one embodiment, at least 25% of heavy chains have at least two mutations present in CDR1; in one embodiment, at least 15% of heavy chains have at least 3 mutations present in CDR1; in one embodiment, at least 10% of heavy chains have 4 or more mutations present in CDR1.

In one embodiment, the light chain is derived from a human Vκ3-20/Jκ1 rearrangement and about 46% of the heavy chains have at least one or no more than three mutations present in FW2; in one embodiment, at least 34% of heavy chains have at least one mutation present in FW2; in one embodiment, at least 10% of heavy chains have two or more mutations present in FW2; in one embodiment, at least 2% of heavy chains have three or more mutations present in FW2.

In one embodiment, the light chain is derived from a human Vκ3-20/Jκ1 rearrangement and about 84% of the heavy chains have at least one or up to five or more than five mutations present in CDR2; in one embodiment, at least 39% of the heavy chains have one or more mutations present in CDR2; in one embodiment, at least 18% of the heavy chains have two or more mutations present in CDR2; in one embodiment, at least 21% of the heavy chains have three or more mutations present in CDR2; in one embodiment, at least 3% of the heavy chains have four or more mutations present in CDR2; in one embodiment, at least 2% of the heavy chains have five or more mutations present in CDR2.

In one embodiment, the light chain is derived from a human Vκ3-20/Jκ1 rearrangement and about 92% of the heavy chains have at least one or up to five or more than five mutations present in FW3; in one embodiment, at least 21% of the light chains have at least one mutation present in FW3; in one embodiment, at least 20% of heavy chains have at least two mutations present in FW3; in one embodiment, at least 13% of the heavy chains have at least three mutations present in FW3; in one embodiment, at least 20% of the heavy chains have at least four mutations in FW3; in one embodiment, at least 18% of the heavy chains have at least 5 mutations in FW3.

In one embodiment, the light chain is derived from a human Vκ3-20/Jκ1 rearrangement and about 7% of the heavy chains have at least one mutation present in CDR3; in one embodiment, about 7% of the heavy chains have one mutation in CDR3.

In one embodiment, a population of antigen-specific antibodies derived from a mouse as described herein is provided, wherein the antibodies comprise a light chain derived from a human Vκ3-20/Jκ1 rearrangement and about 43% of the heavy chains have one or more mutations present in FW1, about 92% of the heavy chains have one or more mutations present in CDR1, about 46% of the heavy chains have one or more mutations present in FW2, about 84% of the heavy chains have one or more mutations present in CDR2, about 92% of the heavy chains have one or more mutations present in FW3, and about 7% of the heavy chains have one or more mutations present in CDR3.

In one aspect, a mouse that expresses an immunoglobulin light chain from a rearranged immunoglobulin light chain sequence is provided, wherein the rearranged immunoglobulin light chain sequence is present in the germline of the mouse, wherein the immunoglobulin light chain comprises a human variable sequence. In one embodiment, the germline of the mouse comprises a rearranged immunoglobulin light chain sequence that is derived from the same V segment and the same J segment as all non-surrogate light chain sequences present in every B cell of the mouse that comprises a rearranged light chain sequence.

In one embodiment, the germline of the mouse lacks a functional unrearranged immunoglobulin light chain V gene segment. In one embodiment, the germline of the mouse lacks a functional unrearranged immunoglobulin light chain J gene segment.

In one embodiment, the germline of the mouse comprises no more than one, no more than two, or no more than three rearranged (V/J) light chain sequences.

In one embodiment, the rearranged V/J sequence comprises a κ light chain sequence. In a specific embodiment, the κ light chain sequence is a human κ light chain sequence. In a specific embodiment, the κ light chain sequence is selected from a human Vκ1-39/J sequence, a human Vκ3-20/J sequence, and a combination thereof. In a specific embodiment, the κ light chain sequence is a human Vκ1-39/Jκ5 sequence. In a specific embodiment, the κ light chain sequence is a human Vκ3-20/Jκ1 sequence.

In one embodiment, the mouse further comprises in its germline a sequence selected from a mouse κ intronic enhancer 5' with respect to the rearranged immunoglobulin light chain sequence, a mouse κ3' enhancer, and a combination thereof.

In one embodiment, the mouse comprises an unrearranged human $V_H$ gene segment, an unrearranged human $D_H$ gene segment, and an unrearranged human $J_H$ gene segment, wherein said $V_H$, $D_H$, and $J_H$ gene segments are capable of rearranging to form an immunoglobulin heavy chain variable gene sequence operably linked to a heavy chain constant gene sequence. In one embodiment, the mouse comprises a plurality of human $V_H$, $D_H$, and $J_H$ gene segments. In a specific embodiment, the human $V_H$, $D_H$, and $J_H$ gene segments replace endogenous mouse $V_H$, $D_H$, and $J_H$ gene segments at the endogenous mouse immunoglobulin heavy chain locus. In a specific embodiment, the mouse comprises a replacement of all or substantially all functional mouse $V_H$, $D_H$, and $J_H$ gene segments with all or substantially all functional human $V_H$, $D_H$, and $J_H$ gene segments.

In one embodiment, the mouse expresses an immunoglobulin light chain that comprises a mouse constant sequence. In one embodiment, the mouse expresses an immunoglobulin light chain that comprises a human constant sequence.

In one embodiment, the mouse expresses an immunoglobulin heavy chain that comprises a mouse sequence selected from a $C_H1$ sequence, a hinge sequence, a $C_H2$ sequence, a $C_H3$ sequence, and a combination thereof.

In one embodiment, the mouse expresses an immunoglobulin heavy chain that comprises a human sequence selected from a $C_H1$ sequence, a hinge sequence, a $C_H2$ sequence, a $C_H3$ sequence, and a combination thereof.

In one embodiment, the rearranged immunoglobulin light chain sequence in the germline of the mouse is at an endogenous mouse immunoglobulin light chain locus. In a specific embodiment, the rearranged immunoglobulin light chain sequence in the germline of the mouse replaces all or substantially all mouse light chain V and J sequences at the endogenous mouse immunoglobulin light chain locus.

In one aspect, a mouse is provided that comprises a B cell population characterized by each B cell that comprises a non-surrogate light chain sequence, which sequence comprises a rearranged light chain gene that is generated from a single human V gene segment and a single human J gene segment, wherein the only light chain variable sequence in the germline of the mouse is a rearranged sequence generated from the single human V segment and the single human J segment, and wherein each B cell that comprises the rearranged light chain gene further comprises a gene encoding a cognate human heavy chain variable domain, and wherein the rearranged light chain gene comprises at least one, at least two, at least three, or at least four somatic hypermutations.

In some embodiments, a mouse is provided whose mature B cell population is characterized in that each mature B cell comprises a non-surrogate light chain sequence on its surface, which sequence comprises a rearranged light chain gene that is generated through rearrangement of one of two human $V_L$ gene segments and one of no more than five human $J_L$ gene segments, wherein the only light chain variable sequence ($V_LJ_L$ sequence) in the germline of the mouse is a rearranged sequence that is generated through rearrangement of one of the two human $V_L$ gene segments and one of the no more than five human $J_L$ gene segments, and wherein each B cell that comprises the rearranged light chain gene further comprises a gene encoding a cognate human heavy chain variable domain, and wherein the rearranged light chain gene comprises at least one, at least two, at least three, at least four, or five or more somatic hypermutations. In some embodiments, a rearranged light chain gene comprises one, two, three, four, or five somatic hypermutations. In some embodiments, mice as described herein have been immunized with an antigen of interest, and, in some embodiments, a mature B cell population is enriched with B cells that bind the antigen of interest.

In some embodiments, a mouse is provided whose mature B cell population is characterized in that each mature B cell comprises a non-surrogate light chain sequence on its surface, which sequence comprises a rearranged light chain gene that is generated through rearrangement of one of two human $V_L$ gene segments and one of two or more (e.g., 2, 3, 4, or 5) human $J_L$ gene segments, wherein the $V_L$ gene segments consist essentially of two $V_L$ gene segments that are not identical and the $V_L$ locus comprises two or more (e.g., 2, 3, 4, or 5) human $J_L$ gene segments, and wherein each B cell that comprises the rearranged light chain gene further comprises a gene encoding a cognate human heavy chain variable domain, and wherein the rearranged light chain gene comprises at least one, at least two, at least three, at least four, or five or more somatic hypermutations. In some embodiments, a rearranged light chain gene comprises one, two, three, four, or five somatic hypermutations. In some embodiments, mice as described herein have been immunized with an antigen of interest, and in some embodiments, a mature B cell population is enriched with B cells that bind the antigen of interest.

In one aspect, a pluripotent, induced pluripotent, or totipotent cell derived from a mouse as described herein is provided. In a specific embodiment, the cell is a mouse embryonic stem (ES) cell.

In one aspect, a tissue derived from a mouse as described herein is provided. In one embodiment, the tissue is derived from spleen, lymph node or bone marrow of a mouse as described herein.

In one aspect, a nucleus derived from a mouse as described herein is provided. In one embodiment, the nucleus is from a diploid cell that is not a B cell.

In one aspect, a mouse cell is provided that is isolated from a mouse as described herein. In one embodiment, the cell is an ES cell. In one embodiment, the cell is a lymphocyte. In one embodiment, the lymphocyte is a B cell. In one embodiment, the B cell expresses a chimeric heavy chain comprising a variable domain derived from a human gene segment; and a light chain derived from a rearranged human Vκ1-39/J sequence, rearranged human Vκ3-20/J sequence, or a combination thereof; wherein the heavy chain variable domain is fused to a mouse constant region and the light chain variable domain is fused to a mouse or a human constant region.

In one aspect, a hybridoma is provided, wherein the hybridoma is made with a B cell of a mouse as described herein. In a specific embodiment, the B cell is from a mouse as described herein that has been immunized with an immunogen comprising an epitope of interest, and the B cell expresses a binding protein that binds the epitope of interest, the binding protein has a somatically mutated human $V_H$ domain and a mouse $C_H$, and has a human $V_L$ domain derived from a rearranged human Vκ1-39Jκ5 or a rearranged human Vκ3-20Jκ1 and a mouse $C_L$.

In one aspect, a mouse embryo is provided, wherein the embryo comprises a donor ES cell that is derived from a mouse as described herein.

In one aspect, a targeting vector is provided, comprising, from 5' to 3' in transcriptional direction with reference to the sequences of the 5' and 3' mouse homology arms of the vector, a 5' mouse homology arm, a human or mouse immunoglobulin promoter, a human or mouse leader sequence, and a human $V_L$ region selected from a rearranged human Vκ1-39Jκ5 or a rearranged human Vκ3-20Jκ1, and a 3' mouse homology arm. In one embodiment, the 5' and 3' homology arms target the vector to a sequence 5' with respect to an enhancer sequence that is present 5' and proximal to the mouse Cκ gene. In one embodiment, the promoter is a human immunoglobulin variable region gene segment promoter. In a specific embodiment, the promoter is a human Vκ3-15 promoter. In one embodiment, the leader sequence is a mouse leader sequence. In a specific embodiment, the mouse leader sequence is a mouse Vκ3-7 leader sequence.

In one aspect, a targeting vector is provided as described above, but in place of the 5' mouse homology arm the human or mouse promoter is flanked 5' with a site-specific recombinase recognition site (SRRS), and in place of the 3' mouse homology arm the human $V_L$ region is flanked 3' with an SRRS.

In one aspect, a reverse chimeric antibody made by a mouse as described herein, wherein the reverse chimeric antibody comprises a light chain comprising a human $V_L$ and a mouse $C_L$, and a heavy chain comprising a human $V_H$ and a mouse $C_H$.

In one aspect, a method for making an antibody is provided, comprising expressing in a single cell (a) a first $V_H$ gene sequence of an immunized mouse as described herein fused with a human $C_H$ gene sequence; (b) a $V_L$ gene sequence of an immunized mouse as described herein fused with a human $C_L$ gene sequence; and, (c) maintaining the cell under conditions sufficient to express a fully human antibody, and isolating the antibody. In one embodiment, the cell comprises a second $V_H$ gene sequence of a second immunized mouse as described herein fused with a human $C_H$ gene sequence, the first $V_H$ gene sequence encodes a $V_H$ domain that recognizes a first epitope, and the second $V_H$ gene sequence encodes a $V_H$ domain that recognizes a second epitope, wherein the first epitope and the second epitope are not identical.

In one aspect, a method for making an epitope-binding protein is provided, comprising exposing a mouse as described herein with an immunogen that comprises an epitope of interest, maintaining the mouse under conditions sufficient for the mouse to generate an immunoglobulin molecule that specifically binds the epitope of interest, and isolating the immunoglobulin molecule that specifically binds the epitope of interest; wherein the epitope-binding protein comprises a heavy chain that comprises a somatically mutated human $V_H$ and a mouse $C_H$, associated with a light chain comprising a mouse $C_L$ and a human $V_L$ derived from a rearranged human Vκ1-39Jκ5 or a rearranged human Vκ3-20Jκ1.

In one aspect, a cell that expresses an epitope-binding protein is provided, wherein the cell comprises: (a) a human nucleotide sequence encoding a human $V_L$ domain that is derived from a rearranged human Vκ1-39Jκ5 or a rearranged human Vκ3-20Jκ1, wherein the human nucleotide sequence is fused (directly or through a linker) to a human immunoglobulin light chain constant domain cDNA sequence (e.g., a human κ constant domain DNA sequence); and, (b) a first human $V_H$ nucleotide sequence encoding a human $V_H$ domain derived from a first human $V_H$ nucleotide sequence, wherein the first human $V_H$ nucleotide sequence is fused (directly or through a linker) to a human immunoglobulin heavy chain constant domain cDNA sequence; wherein the epitope-binding protein recognizes a first epitope. In one embodiment, the epitope-binding protein binds the first epitope with a dissociation constant of lower than $10^{-6}$ M, lower than $10^{-8}$M, lower than $10^{-9}$ M, lower than $10^{-10}$ M, lower than $10^{-11}$ M, or lower than $10^{-12}$ M.

In one embodiment, the cell comprises a second human nucleotide sequence encoding a second human $V_H$ domain, wherein the second human sequence is fused (directly or through a linker) to a human immunoglobulin heavy chain constant domain cDNA sequence, and wherein the second human $V_H$ domain does not specifically recognize the first epitope (e.g., displays a dissociation constant of, e.g., $10^{-6}$ M, $10^{-5}$ M, $10^{-4}$ M, or higher), and wherein the epitope-binding protein recognizes the first epitope and the second epitope, and wherein the first and the second immunoglobulin heavy chains each associate with an identical light chain of (a).

In one embodiment, the second $V_H$ domain binds the second epitope with a dissociation constant that is lower than $10^{-6}$ M, lower than $10^{-7}$M, lower than $10^{-8}$ M, lower than $10^{-9}$ M, lower than $10^{-10}$ M, lower than $10^{-11}$ M, or lower than $10^{-12}$ M.

In one embodiment, the epitope-binding protein comprises a first immunoglobulin heavy chain and a second immunoglobulin heavy chain, each associated with an identical light chain derived from a rearranged human $V_L$ region selected from a human Vκ1-39Jκ5 or a human Vκ3-20Jκ1, wherein the first immunoglobulin heavy chain binds a first epitope with a dissociation constant in the nanomolar to picomolar range, the second immunoglobulin heavy chain binds a second epitope with a dissociation constant in the nanomolar to picomolar range, the first epitope and the second epitope are not identical, the first immunoglobulin heavy chain does not bind the second epitope or binds the second epitope with a dissociation constant weaker than the micromolar range (e.g., the millimolar range), the second immunoglobulin heavy chain does not bind the first epitope or binds the first epitope with a dissociation constant weaker than the micromolar range (e.g., the millimolar range), and one or more of the $V_L$, the $V_H$ of the first immunoglobulin heavy chain, and the $V_H$ of the second immunoglobulin heavy chain, are somatically mutated.

In one embodiment, the first immunoglobulin heavy chain comprises a protein A-binding residue, and the second immunoglobulin heavy chain lacks the protein A-binding residue.

In one embodiment, the cell is selected from CHO, COS, 293, HeLa, and a retinal cell expressing a viral nucleic acid sequence (e.g., a PERC.6™ cell).

In one aspect, a reverse chimeric antibody is provided, comprising a human $V_H$ and a mouse heavy chain constant domain, a human $V_L$ and a mouse light chain constant domain, wherein the antibody is made by a process that comprises immunizing a mouse as described herein with an immunogen comprising an epitope, and the antibody specifically binds the epitope of the immunogen with which the mouse was immunized. In one embodiment, the $V_L$ domain is somatically mutated. In one embodiment the $V_H$ domain is somatically mutated. In one embodiment, both the $V_L$ domain and the $V_H$ domain are somatically mutated. In one embodiment, the $V_L$ is linked to a mouse Cκ domain.

In one aspect, a mouse is provided, comprising human $V_H$ gene segments replacing all or substantially all mouse $V_H$ gene segments at the endogenous mouse heavy chain locus; no more than one or two rearranged human light chain $V_L/J_L$ sequences selected from a rearranged Vκ1-39/J and a rearranged Vκ3-20/J or a combination thereof, replacing all mouse light chain gene segments; wherein the human heavy chain variable gene segments are linked to a mouse constant gene, and the rearranged human light chain sequences are linked to a human or mouse constant gene.

In some embodiments, a mouse is provided, comprising human immunoglobulin $V_H$ gene segments replacing all or substantially all mouse immunoglobulin $V_H$ gene segments at the endogenous mouse immunoglobulin heavy chain locus; no more than two unrearranged human immunoglobulin $V_L$ gene segments and two or more (e.g., 2, 3, 4 or 5) unrearranged human immunoglobulin $J_L$ gene segments or five human immunoglobulin $J_L$ gene segments, replacing all mouse immunoglobulin light chain gene segments; wherein the human immunoglobulin $V_H$ gene segments are linked to a mouse immunoglobulin constant gene, and the unrearranged human immunoglobulin $V_L$ and $J_L$ gene segments are linked to a human or non-human immunoglobulin constant gene. In some embodiments, a non-human constant gene is a mouse immunoglobulin constant gene. In some embodiments, a non-human immunoglobulin constant gene is a rat immunoglobulin constant gene.

In one aspect, a mouse ES cell comprising a replacement of all or substantially all mouse heavy chain variable gene segments with human heavy chain variable gene segments, and no more than one or two rearranged human light chain $V_L/J_L$ sequences, wherein the human heavy chain variable gene segments are linked to a mouse immunoglobulin heavy chain constant gene, and the rearranged human light chain $V_L/J_L$ sequences are linked to a mouse or human immunoglobulin light chain constant gene. In a specific embodiment, the light chain constant gene is a mouse constant gene.

In some embodiments, a mouse ES cell is provided, comprising a replacement of all or substantially all mouse immunoglobulin $V_H$ gene segments with human immunoglobulin $V_H$ gene segments and no more than two unrearranged human immunoglobulin $V_L$ gene segments and two or more (e.g., 2, 3, 4, or 5) unrearranged human immunoglobulin $J_L$ gene segments, wherein the human immunoglobulin $V_H$ gene segments are linked to a mouse immunoglobulin heavy chain constant gene, and the unrearranged human immunoglobulin $V_L$ and $J_L$ gene segments are linked to a non-human or human immunoglobulin light chain constant gene. In some certain embodiments, the non-human immunoglobulin light chain constant gene is a mouse immunoglobulin constant gene. In some certain embodiments, the mouse comprises five unrearranged immunoglobulin $J_L$ gene segments.

In some embodiments, a mouse is provided, comprising a light chain locus whose structure is different from that of the reference structure of FIG. 19 in that at least one, and in some embodiments all, mouse $V_L$ gene segments are replaced by one human $V_L$ gene segment or no more than two human $V_L$ gene segments. In some embodiments, human $V_L$ gene segments of a mouse are capable of rearranging to one of two or more human $J_L$ gene segments to encode an immunoglobulin $V_L$ domain of an antibody. In some embodiments, human $V_L$ gene segment(s) of a light chain locus of a mouse as described herein is/are operably linked to two or more (e.g., two, three, four, or five) human $J_L$ gene segments.

In some embodiments, a mouse is provided, comprising a light chain locus whose structure is different from that of the reference structure of FIG. 19 in that it does not contain a nucleotide sequence before rearrangement that encodes an endogenous $V_L$ gene segment. In some embodiments, a mouse is provided, comprising a light chain locus whose structure is different from that of the reference structure of FIG. 19 in that it does not contain a nucleotide sequence before rearrangement that encodes an endogenous $J_L$ gene segment. In some embodiments, a mouse is provided, comprising a light chain locus whose structure is different from that of the reference structure of FIG. 19 in that it does not contain a nucleotide before rearrangement that encodes endogenous $V_L$ and $J_L$ gene segments.

In some embodiments, a mouse is provided, comprising a light chain locus whose structure is different from that of the reference structure of FIG. 19 in that it does not contain a nucleotide sequence after rearrangement that encodes an endogenous $V_L$ gene segment. In some embodiments, a mouse is provided, comprising a light chain locus whose structure is different from that of the reference structure of FIG. 19 in that it does not contain a nucleotide sequence after rearrangement that encodes an endogenous $J_L$ gene segment. In some embodiments, a mouse is provided, comprising a light chain locus whose structure is different from that of the reference structure of FIG. 19 in that it does not contain a nucleotide sequence after rearrangement that encodes endogenous $V_L$ and $J_L$ gene segments.

In some embodiments, a mouse is provided, comprising a light chain locus whose structure is different from that of the reference structure of FIG. 19 in that it contains no more than two human $V_L$ gene segments and two or more (e.g., two, three, four, or five) human $J_L$ gene segments before rearrangement. In some embodiments, a mouse is provided, comprising a light chain locus whose structure is different from that of the reference structure of FIG. 19 in that it contains no more than two human $V_L$ gene segments and five human $J_L$ gene segments before rearrangement.

In some embodiments, a mouse is provided, comprising a light chain locus whose structure is different from that of the reference structure of FIG. 19 in that it contains no more than two human $V_L$ gene segments and five or less (e.g., 5, 4, 3, 2, or 1) human $J_L$ gene segments after rearrangement. In some embodiments, a mouse is provided, comprising a light chain locus whose structure is different from that of the reference structure of FIG. 19 in that it contains no more than two human $V_L$ gene segments and one, two, three, four, or five human $J_L$ gene segments after rearrangement.

In some embodiments, a mouse is provided, comprising a light chain locus whose structure is different from that of the reference structure of FIG. 19 in that it contains one human $V_L$ gene segment and five or less (e.g., 5, 4, 3, 2, or 1) human $J_L$ gene segments after rearrangement. In some embodiments, a mouse is provided, comprising a light chain locus whose structure is different from that of the reference structure of FIG. 19 in that it contains one human $V_L$ gene segment and one, two, three, four, or five human $J_L$ gene segments after rearrangement.

In various embodiments, human $V_L$ and $J_L$ gene segments are human Vκ and Jκ gene segments. In various embodiments, human Vκ segments are selected from a human Vκ1-39 gene segment and a human Vκ3-20 gene segment. In some embodiments, human Vκ segments are human Vκ1-39 and human Vκ3-20. In some embodiments, human Jκ segments are selected from a Jκ1, Jκ2, Jκ3, Jκ4, Jκ5 gene segment, and a combination thereof. In some embodiments, human Jκ gene segments are human Jκ1, Jκ2, Jκ3, Jκ4, and Jκ5.

In some embodiments, a mouse is provided, comprising a light chain locus whose structure is different from that of the reference structure of FIG. 19 in that it contains a structure that is substantially the same as that of the structure of FIG. 1, FIG. 2, FIG. 3, or FIG. 9 before rearrangement. In some embodiments, a mouse is provided, comprising a light chain locus whose structure is identical to the structure of FIG. 1, FIG. 2, FIG. 3 or FIG. 9 before rearrangement.

In one aspect, an antigen-binding protein made by a mouse as described herein is provided. In a specific embodiment, the antigen-binding protein comprises a human immunoglobulin heavy chain variable region fused with a mouse constant region, and a human immunoglobulin light chain variable region derived from a Vκ1-39 gene segment or a Vκ3-20 gene segment, wherein the light chain constant region is a mouse constant region.

In one aspect, a fully human antigen-binding protein made from an immunoglobulin variable region gene sequence from a mouse as described herein is provided, wherein the antigen-binding protein comprises a fully human heavy chain comprising a human variable region derived from a sequence of a mouse as described herein, and a fully human light chain comprising a Vκ1-39 or a Vκ3-20. In one embodiment, the light chain variable region comprises one to five somatic mutations. In one embodiment, the light chain variable region is a cognate light chain variable region that is paired in a B cell of the mouse with the heavy chain variable region.

In one embodiment, the fully human antigen-binding protein comprises a first heavy chain and a second heavy chain, wherein the first heavy chain and the second heavy chain comprise non-identical variable regions independently derived from a mouse as described herein, and wherein each of the first and second heavy chains express from a host cell associated with a human light chain derived from a Vκ1-39 gene segment or a Vκ3-20 gene segment. In one embodiment, the first heavy chain comprises a first heavy chain variable region that specifically binds a first epitope of a first antigen, and the second heavy chain comprises a second heavy chain variable region that specifically binds a second epitope of a second antigen. In a specific embodiment, the first antigen and the second antigen are different. In a specific embodiment, the first antigen and the second antigen are the same, and the first epitope and the second epitope are not identical; in a specific embodiment, binding of the first epitope by a first molecule of the binding protein does not block binding of the second epitope by a second molecule of the binding protein.

In one aspect, a fully human binding protein derived from a human immunoglobulin sequence of a mouse as described herein comprises a first immunoglobulin heavy chain and a second immunoglobulin heavy chain, wherein the first immunoglobulin heavy chain comprises a first variable region that is not identical to a variable region of the second immunoglobulin heavy chain, and wherein the first immunoglobulin heavy chain comprises a wild type protein A binding determinant, and the second heavy chain lacks a wild type protein A binding determinant. In one embodiment, the first immunoglobulin heavy chain binds protein A under isolation conditions, and the second immunoglobulin heavy chain does not bind protein A or binds protein A at least 10-fold, a hundred-fold, or a thousand-fold weaker than the first immunoglobulin heavy chain binds protein A under isolation conditions. In a specific embodiment, the first and the second heavy chains are IgG1 isotypes, wherein the second heavy chain comprises a modification selected from 95R (EU 435R), 96F (EU 436F), and a combination thereof, and wherein the first heavy chain lacks such modification.

In one aspect, a method for making a bispecific antigen-binding protein is provided, comprising exposing a first mouse as described herein to a first antigen of interest that comprises a first epitope, exposing a second mouse as described herein to a second antigen of interest that comprises a second epitope, allowing the first and the second mouse to each mount immune responses to the antigens of interest, identifying in the first mouse a first human heavy chain variable region that binds the first epitope of the first antigen of interest, identifying in the second mouse a second human heavy chain variable region that binds the second epitope of the second antigen of interest, making a first fully human heavy chain gene that encodes a first heavy chain that binds the first epitope of the first antigen of interest, making a second fully human heavy chain gene that encodes a second heavy chain that binds the second epitope of the second antigen of interest, expressing the first heavy chain and the second heavy chain in a cell that expresses a single fully human light chain derived from a human Vκ1-39 or a human Vκ3-20 gene segment to form a bispecific antigen-binding protein, and isolating the bispecific antigen-binding protein.

In one embodiment, the first antigen and the second antigen are not identical.

In one embodiment, the first antigen and the second antigen are identical, and the first epitope and the second epitope are not identical. In one embodiment, binding of the first heavy chain variable region to the first epitope does not block binding of the second heavy chain variable region to the second epitope.

In one embodiment, the human light chain when paired with the first heavy chain specifically binds the first epitope of the first antigen and when paired the second heavy chain specifically binds the second epitope of the second antigen.

In one embodiment, the first antigen is selected from a soluble antigen and a cell surface antigen (e.g., a tumor antigen), and the second antigen comprises a cell surface receptor. In a specific embodiment, the cell surface receptor is an immunoglobulin receptor. In a specific embodiment, the immunoglobulin receptor is an Fc receptor. In one embodiment, the first antigen and the second antigen are the same cell surface receptor, and binding of the first heavy chain to the first epitope does not block binding of the second heavy chain to the second epitope.

In one embodiment, the light chain variable domain of the light chain comprises 2 to 5 somatic mutations. In one embodiment, the light chain variable domain is a somatically mutated cognate light chain expressed in a B cell of the first or the second immunized mouse with either the first or the second heavy chain variable domain. In one embodiment, the light chain of the cell comprises a germline sequence.

In one embodiment, the first fully human heavy chain bears an amino acid modification that reduces its affinity to protein A, and the second fully human heavy chain does not comprise a modification that reduces its affinity to protein A.

In one aspect, a method of preparing a bispecific antibody that specifically binds to a first and a second antigen is provided, wherein the method comprises (a) identifying a first nucleic acid sequence that encodes a first human heavy chain variable ($V_H$) domain that is specific for the first antigen; (b) identifying a second nucleic acid sequence that encodes a second human heavy chain variable ($V_H$) domain that is specific for the second antigen; (c) providing a third nucleic acid sequence that encodes a human light chain variable ($V_L$) region which, when paired with the $V_H$ region of (a) specifically binds the first antigen, and when paired with the $V_H$ region of (b) specifically binds to the second antigen; (d) culturing a host cell comprising the first, second, and third nucleic acid sequences to allow expression of the first and second human $V_H$ regions and the human $V_L$ region to form the bispecific antibody; and (d) recovering said bispecific antibody. In various aspects, the first and second antigens are different from one another. In various aspects the first and second nucleic acid sequences are isolated from an immunized mouse that expresses a human immunoglobulin $V_L$ region from a rearranged immunoglobulin light chain sequence, wherein the rearranged immunoglobulin sequence is in the germline of the mouse.

In one embodiment, the human $V_L$ region is derived from a rearranged human light chain sequence comprising a human Vκ1-39 gene segment or a human Vκ3-20 gene segment. In a specific embodiment, the rearranged human light chain sequence is a germline sequence (i.e., does not comprise a somatic hypermutation within the V gene segment sequence).

In one embodiment, the third nucleic acid sequence is isolated from a mouse that expresses a human immunoglobulin $V_L$ region from a rearranged immunoglobulin light chain sequence in the germline of the mouse. In one embodiment, the rearranged immunoglobulin light chain sequence comprises a human Vκ1-39 or human Vκ3-20 gene segment. In a specific embodiment, the rearranged immunoglobulin light chain sequence comprises a human Vκ1-39 gene segment. In one embodiment, the human immunoglobulin $V_L$ region is expressed from a modified endogenous immunoglobulin light chain locus.

In one embodiment, the first and second antigens are present on one molecule. In one embodiment, the first and second antigens are present on different molecules. In various embodiments, the first or second nucleic acid sequence comprises a modification that reduces the affinity of the encoded heavy chain to protein A.

In one embodiment, the first or second nucleic acid sequences comprise a rearranged human heavy chain variable region sequence comprising a human heavy chain gene segment selected from $V_H$1-2, $V_H$1-3, $V_H$1-8, $V_H$1-18, $V_H$1-24, $V_H$1-46, $V_H$1-58, $V_H$1-69, $V_H$2-5, $V_H$2-26, $V_H$2-70, $V_H$3-7, $V_H$3-9, $V_H$3-11, $V_H$3-13, $V_H$3-15, $V_H$3-20, $V_H$3-21, $V_H$3-23, $V_H$3-30, $V_H$3-33, $V_H$3-43, $V_H$3-48, $V_H$3-53, $V_H$3-64, $V_H$3-72, $V_H$3-73, $V_H$4-31, $V_H$4-34, $V_H$4-39, $V_H$4-59, $V_H$5-51, and $V_H$6-1. In a specific embodiment, the heavy chain gene segment is $V_H$2-5, $V_H$3-23 or $V_H$3-30.

In one aspect, a method of preparing a bispecific antibody that specifically binds to a first and a second antigen is provided, wherein the method comprises (a) identifying a first nucleic acid sequence that encodes a first human heavy chain variable ($V_H$) domain that is specific for the first antigen; (b) identifying a second nucleic acid sequence that encodes a second human heavy chain variable ($V_H$) domain that is specific for the second antigen; (c) providing a third nucleic acid sequence that encodes a human light chain variable ($V_L$) region derived from a human Vκ1-39 or human Vκ3-20 gene segment which, when paired with the $V_H$ region of (a) specifically binds the first antigen, and when paired with the $V_H$ region of (b) specifically binds to the second antigen; (d) culturing a host cell comprising the first, second, and third nucleic acid sequences to allow expression of the first and second human $V_H$ regions and the human $V_L$ region to form the bispecific antibody; and (d) recovering said bispecific antibody. In various aspects, the first and second antigens are different from one another. In various aspects, the first and second nucleic acid sequences are isolated from an immunized mouse that expresses a human immunoglobulin $V_L$ region from a rearranged immunoglobulin sequence that is derived from a human Vκ1-39 or human Vκ3-20 gene segment, wherein the rearranged human Vκ1-39 or Vκ3-30 gene segment is in the germline of the mouse.

In one embodiment, the third nucleic acid sequence is a germline sequence (i.e., does not comprise a somatic hypermutation within the V gene segment sequence). In one embodiment, the third nucleic acid sequence is isolated from the mouse that expresses a human immunoglobulin $V_L$ region derived from a human Vκ1-39 or human Vκ3-20 gene segment from a rearranged immunoglobulin light chain sequence in the germline of the mouse. In a specific embodiment, the third nucleic acid sequence comprises two to five somatic hypermutations in a complementary determining region (CDR) and/or a framework region (FWR). In one embodiment, the human immunoglobulin $V_L$ region is expressed from a modified endogenous immunoglobulin light chain locus.

In one embodiment, the first and second antigens are present on one molecule. In one embodiment, the first and second antigens are present on different molecules. In one embodiment, the first or second nucleic acid sequence comprises a modification that reduces the affinity of the encoded heavy chain to protein A.

In one embodiment, the first or second nucleic acid sequences comprise a rearranged human heavy chain variable region sequence comprising a human heavy chain gene segment selected from $V_H$1-2, $V_H$1-3, $V_H$1-8, $V_H$1-18, $V_H$1-24, $V_H$1-46, $V_H$1-58, $V_H$1-69, $V_H$2-5, $V_H$2-26, $V_H$2-70, $V_H$3-7, $V_H$3-9, $V_H$3-11, $V_H$3-13, $V_H$3-15, $V_H$3-20, $V_H$3-21, $V_H$3-23, $V_H$3-30, $V_H$3-33, $V_H$3-43, $V_H$3-48, $V_H$3-53, $V_H$3-64, $V_H$3-72, $V_H$3-73, $V_H$4-31, $V_H$4-34, $V_H$4-39, $V_H$4-59, $V_H$5-51, and $V_H$6-1. In a specific embodiment, the heavy chain gene segment is $V_H$2-5, $V_H$3-23 or $V_H$3-30.

In one aspect, a method for making a bispecific antibody is provided, comprising exposing a mouse as described herein to an antigen of interest, allowing the mouse to mount an immune response to the antigen of interest, identifying a first human heavy chain variable region that binds a first epitope of the antigen of interest, identifying a second human heavy chain variable region that binds a second epitope of the antigen of interest, making a first fully human heavy chain gene that encodes the first heavy chain that binds the first epitope of the antigen of interest, making a second fully human heavy chain gene that encodes a second heavy chain that binds the second epitope of the antigen of interest, expressing the first heavy chain and the second heavy chain in a cell that expresses a single fully human light chain derived from a human Vκ1-39 or a human Vκ3-20 gene segment to form a bispecific antibody, and isolating the bispecific antigen-binding protein.

In one embodiment, the first epitope and the second epitope are not identical. In one embodiment, binding of the first heavy chain variable region to the first epitope does not block binding of the second heavy chain variable region to the second epitope. In one embodiment, the first and second heavy chains are capable of binding the first and second epitopes simultaneously.

In one embodiment, the bispecific antibody binds the first and second epitopes simultaneously. In one embodiment, the bispecific antibody binds the first epitope and second epitope independently.

In one embodiment, the binding response of the bispecific antibody to the antigen is about 2-fold higher than the binding response of the first heavy chain variable region to the antigen. In one embodiment, the binding response of the bispecific antibody to the antigen is about 2-fold higher than the binding response of the second heavy chain variable region to the antigen. In one embodiment, the binding response of the bispecific antibody to the antigen is about the same as, or about equal to, the binding response of the first heavy chain variable region and or the second heavy chain variable region to the antigen.

In one embodiment, the antigen is selected from a soluble antigen, a cell surface antigen (e.g., a tumor antigen) and a cell surface receptor. In a specific embodiment, the cell surface receptor is an immunoglobulin receptor. In a specific embodiment, the immunoglobulin receptor is an Fc receptor.

In one embodiment, the light chain variable domain of the light chain comprises 2 to 5 somatic mutations. In one embodiment, the light chain variable domain is a somatically mutated cognate light chain expressed in a B cell of the immunized mouse with either the first or the second heavy chain variable domain.

In one embodiment, the first fully human heavy chain bears an amino acid modification that reduces its affinity to protein A, and the second fully human heavy chain does not comprise a modification that reduces its affinity to protein A.

In various embodiments, methods for making bispecific antibodies are enhanced by employing a common light chain to pair with each heavy chain variable regions of the bispecific antibodies. In various embodiments, employing a common light chain as described herein reduces the number of inappropriate species of immunoglobulins lacking bispecificity as compared to employing original cognate light chains. In various embodiments, the heavy chain variable regions of the bispecific antibodies are identified from monospecific antibodies comprising a common light chain. In various embodiments, the heavy chain variable regions of the bispecific antibodies comprise human heavy chain variable gene segments that are rearranged in vivo within mouse B cells that have been previously engineered to express a limited human light chain repertoire, or a single human light chain, cognate with human heavy chains and, in response to exposure with an antigen of interest, generate a chimeric antibody repertoire containing a plurality of human heavy chain variable regions that are cognate with one or one of two possible human light chain variable regions, wherein the chimeric antibodies are specific for the antigen of interest.

In various aspects, a method of preparing a bispecific antibody is provided, the bispecific antibody comprising 1) a first polypeptide and a second polypeptide, wherein the first and second polypeptides each include a multimerization domain (e.g., an immunoglobulin Fc domain) allowing the first and second polypeptides to form a dimer, and the multimerization domains promote stable interaction between first and second polypeptides, and wherein one of the multimerization domains bears an amino acid modification that reduces its affinity to protein A and the other multimerization domain lacks the modification, 2) a binding domain in each of the first and second polypeptide, each binding domain comprising a variable heavy chain and a variable light chain, wherein the variable light chain of the first polypeptide and the variable light chain of the second polypeptide have a common amino acid sequence, which common sequence has an amino acid sequence identity to an original light chain of each of the polypeptides of at least 80%, of at least 85%, preferably at least 90%, more preferably at least 95% and most preferably 100% sequence identity. In various embodiments, the variable light chain is derived from a human Vκ1-39 or a human Vκ3-20 gene segment. In various embodiments, the variable light chain is a rearranged human light chain sequence. In various embodiments, the variable light chain is isolated from a mouse as described herein.

In various embodiments, the method comprises the steps of (i) culturing a host cell comprising a nucleic acid encoding the first polypeptide, the second polypeptide, and the common light chain, wherein the nucleic acid is expressed; and (ii) recovering the bispecific antibody from the host cell culture; in one embodiment, the nucleic acid encoding the first polypeptide or the nucleic acid encoding the second polypeptide, bears an amino acid modification that reduces its affinity to protein A. In one embodiment, the nucleic acid encoding the first polypeptide, the second polypeptide, and the common light chain is present in a single vector or in separate vectors. In one embodiment, the host cell is used to make a bispecific antibody according to the preceding paragraph.

In one aspect, a method of preparing a bispecific antibody is provided, comprising (a) selecting a first nucleic acid encoding a first human heavy chain variable region isolated from a mouse as described herein; (b) selecting a second nucleic acid encoding a second human heavy chain variable region isolated from the same or separate mouse as described herein; (c) providing a third nucleic acid encoding a human light chain variable region isolated from a mouse as described herein or derived from a rearranged human light chain variable region as described herein; (c) introducing into a host cell the first, second and third nucleic acids and culturing the host cell so that expression of the first, second and third nucleic acid occurs; and (d) recovering the bispecific antibody formed from the cell culture.

In one embodiment, the first and second human heavy chain variable regions are somatically mutated. In a specific embodiment, the first and second human heavy chain variable regions are independently derived from a rearranged human $V_H$ gene segment selected from 1-2, 1-3, 1-8, 1-18, 1-24, 1-46, 1-58, 1-69, 2-5, 2-26, 2-70, 3-7, 3-9, 3-11, 3-13, 3-15, 3-16, 3-20, 3-21, 3-23, 3-30, 3-33, 3-43, 3-48, 3-53, 3-64, 3-72, 3-73, 4-31, 4-34, 4-39, 4-59, 5-51, and a 6-1 human $V_H$ gene segment. In one embodiment, the first and second human heavy chain variable regions are independently derived from a rearranged human $V_H$ gene segment selected from 2-5, 3-30 and 3-23. In one embodiment, the first human heavy chain variable region is derived from a human $V_H$2-5 gene segment and the second human heavy chain variable region is derived from a human $V_H$3-30 gene segment. In one embodiment, the first human heavy chain variable region is derived from a human $V_H$3-30 gene segment and the second human heavy chain variable region is derived from a human $V_H$3-23 gene segment. In one embodiment, the first human heavy chain variable region is derived from a human $V_H$3-23 gene segment and the second human heavy chain variable region is derived from a human $V_H$3-30 gene segment.

In one embodiment, the first or second nucleic acid is modified prior to step (c), wherein the first or second nucleic acid is modified such that it has a reduced affinity to protein A.

In one embodiment, the third nucleic acid is isolated from a mouse as described herein. In one embodiment, the third nucleic acid comprises 2 to 5 somatic mutations. In one embodiment, the third nucleic acid encodes a human light chain variable region derived from a human Vκ1-39 gene segment. In one embodiment, the third nucleic acid encodes a human light chain variable region derived from a human Vκ3-20 gene segment.

In one embodiment, the third nucleic acid is derived from a rearranged human light chain variable region. In one embodiment, the rearranged human light chain variable region comprises a sequence derived from a human Vκ1-39 gene segment or a human Vκ3-20 gene segment. In one embodiment, the rearranged human light chain variable region comprises a germline human Vκ1-39 sequence (i.e., does not comprise a somatic hypermutation within the V gene segment sequence). In one embodiment, the rearranged human light chain variable region comprises a germline human Vκ3-20 sequence.

In various embodiments, a method of preparing a bispecific antibody that incorporates a first human heavy chain comprising a variable domain derived from a modified mouse that lacks a rearranged human light chain sequence in its germline is provided, wherein the first human heavy chain is paired with a cognate human light chain that comprises a rearranged human light chain variable region derived from a human Vκ1-39 or a human Vκ3-20 gene segment. In various embodiments, a second human heavy chain with a different specificity from the first human heavy chain is identified from an immunized mouse as described herein. Nucleic acids encoding the two heavy chains and the common light chain are introduced into a host cell as described in the preceding paragraphs so that expression of all three chains occurs and the bispecific antibody is recovered from the cell culture.

In one embodiment, the mouse is immunized with the same antigen used to generate the first human heavy chain variable domain. In one embodiment, the mouse is immunized with a different antigen used to generate the first human heavy chain variable domain.

In one aspect, a method of selecting human heavy chains that can pair with a single human light chain to make a bispecific antibody is provided, including nucleic acids that encode the bispecific antibody and a host cell comprising the nucleic acids.

In one aspect, a method of increasing the amount of a desired bispecific antibody in a cell culture over undesired products such as monospecific antibodies is provided, wherein one of the heavy chains of the bispecific antibody is modified to reduce its affinity to protein A.

In one aspect, an isolated host cell is provided, wherein the host cell comprises (a) a first nucleic acid sequence encoding a first human heavy chain variable region that binds a first antigen, wherein the first nucleic acid sequence is isolated from a mouse immunized with the first antigen that expresses a human immunoglobulin $V_L$ region from a rearranged immunoglobulin light chain sequence in the germline of the mouse; (b) a second nucleic acid sequence encoding a second human heavy chain variable region that binds a second antigen, wherein the second nucleic acid sequence is isolated from a mouse immunized with the second antigen that expresses a human immunoglobulin $V_L$ region from a rearranged immunoglobulin light chain sequence in the germline of the mouse; (c) a third nucleic acid sequence encoding a human light chain variable region which, when paired with the heavy chain variable region of (a) specifically binds the first antigen, and when paired with the heavy chain variable region of (b) specifically binds to the second antigen.

In various aspects, the first and second antigens are different from one another. In various aspects, the expression of the first, second and third nucleic acid sequences leads to the formation of a bispecific antibody that specifically binds to the first and second antigens.

In one embodiment, the human $V_L$ region is derived from a rearranged human light chain sequence comprising a human Vκ1-39 gene segment or a human Vκ3-20 gene segment. In a specific embodiment, the rearranged human light chain sequence is a germline sequence (i.e., does not comprise a somatic hypermutation within the variable domain). In one embodiment, the third nucleic acid sequence is isolated from a mouse that expresses a human immunoglobulin $V_L$ region from a rearranged immunoglobulin light chain sequence, wherein the rearranged human light chain sequence is present in the germline of the mouse. In one embodiment, the rearranged immunoglobulin light chain sequence comprises a human Vκ1-39 gene segment or a human Vκ3-20 gene segment. In a specific embodiment, the human Vκ1-39 gene segment or human Vκ3-20 gene segment comprises at least one somatic hypermutation in a complementary determining region (CDR) or framework region (FWR). In a specific embodiment, the first, second and third nucleic acid sequences are isolated from a mouse that expresses a human immunoglobulin $V_L$ region derived from a human Vκ1-39 or human Vκ3-20 gene segment from a rearranged immunoglobulin light chain sequence, wherein the rearranged immunoglobulin light chain sequence is present in the germline of the mouse.

In various embodiments, the mouse does not contain an endogenous light chain variable region gene segment that is capable of rearranging to form an immunoglobulin light chain.

In one embodiment, the human immunoglobulin $V_L$ region is expressed from a modified endogenous immunoglobulin light chain locus. In one embodiment, the first and second antigens are present on one molecule. In one embodiment, the first and second antigens are present on different molecules. In one embodiment, the first or second nucleic acid sequence comprises a modification that reduces the affinity of the encoded heavy chain to protein A.

In one embodiment, the first or second nucleic acid sequences comprise a rearranged human heavy chain variable region sequence comprising a human heavy chain gene segment selected from $V_H$1-2, $V_H$1-3, $V_H$1-8, $V_H$1-18, $V_H$1-24, $V_H$1-46, $V_H$1-58, $V_H$1-69, $V_H$2-5, $V_H$2-26, $V_H$2-70, $V_H$3-7, $V_H$3-9, $V_H$3-11, $V_H$3-13, $V_H$3-15, $V_H$3-20, $V_H$3-21, $V_H$3-23, $V_H$3-30, $V_H$3-33, $V_H$3-43, $V_H$3-48, $V_H$3-53, $V_H$3-64, $V_H$3-72, $V_H$3-73, $V_H$4-31, $V_H$4-34, $V_H$4-39, $V_H$4-59, $V_H$5-51, and $V_H$6-1. In a specific embodiment, the heavy chain gene segment is $V_H$2-5, $V_H$3-23 or $V_H$3-30.

In one aspect, an antibody or a bispecific antibody comprising a human heavy chain variable domain made in accordance with the invention is provided. In another aspect, use of a mouse as described herein to make a fully human antibody or a fully human bispecific antibody is provided.

In one aspect, a genetically modified mouse, embryo, or cell described herein comprises a κ light chain locus that retains endogenous regulatory or control elements, e.g., a mouse κ intronic enhancer, a mouse κ3' enhancer, or both an intronic enhancer and a 3' enhancer, wherein the regulatory or control elements facilitate somatic mutation and affinity maturation of an expressed sequence of the κ light chain locus.

In one aspect, a mouse is provided that comprises a B cell population characterized by having immunoglobulin light chains derived from no more than one, or no more than two, rearranged or unrearranged immunoglobulin light chain V and J gene segments, wherein the mouse exhibits a κ:λ light chain ratio that is about the same as a mouse that comprises a wild type complement of immunoglobulin light chain V and J gene segments.

In one embodiment, the immunoglobulin light chains are derived from no more than one, or no more than two, rearranged immunoglobulin light chain V and J gene segments. In a specific embodiment, the light chains are derived from no more than one rearranged immunoglobulin light chain V and J gene segments. In one embodiment, the immunoglobulin light chains are generated from one of two unrearranged immunoglobulin $V_L$ gene segments and one of 1, 2, 3, 4, or 5 immunoglobulin $J_L$ gene segments. In one embodiment, the immunoglobulin light chains are generated from one of two unrearranged immunoglobulin $V_L$ gene segments and one immunoglobulin $J_L$ gene segment.

In one aspect, a mouse as described herein is provided that expresses an immunoglobulin light chain derived from no more than one, or no more than two, human Vκ/Jκ sequences, wherein the mouse comprises a replacement of all or substantially all endogenous mouse heavy chain variable region gene segments with one or more human heavy chain variable region gene segments, and the mouse exhibits a ratio of (a) $CD19^+$ B cells that express an immunoglobulin having a λ light chain, to (b) $CD19^+$ B cells that express an immunoglobulin having a κ light chain, of about 1 to about 20.

In one embodiment, the mouse expresses a single κ light chain derived from a human Vκ1-39Jκ5 sequence, and the ratio of $CD19^+$ B cells that express an immunoglobulin having a λ light chain to $CD19^+$ B cells that express an immunoglobulin having a κ light chain is about 1 to about 20; in one embodiment, the ratio is about 1 to at least about 66; in a specific embodiment, the ratio is about 1 to 66.

In one embodiment, the mouse expresses a single κ light chain derived from a human Vκ3-20Jκ5 sequence, and the ratio of $CD19^+$ B cells that express an immunoglobulin having a λ light chain to $CD19^+$ B cells that express an immunoglobulin having a κ light chain is about 1 to about 20; in one embodiment, the ratio is about 1 to about 21. In specific embodiments, the ratio is 1 to 20, or 1 to 21.

In some embodiments, the present invention provides a mouse that expresses an immunoglobulin light chain whose sequence is identical to that achieved by rearrangement of one of two human Vκ gene segments with 1, 2, 3, 4, or 5 human Jκ gene segments.

In some embodiments, a mouse is provided that expresses an immunoglobulin light chain generated from a rearrangement of one of two human Vκ gene segments and one of 1, 2, 3, 4, or 5 human Jκ gene segments, wherein the mouse comprises a replacement of all or substantially all endogenous immunoglobulin $V_H$ gene segments with one or more human immunoglobulin $V_H$, one or more $D_H$, and one or more $J_H$ gene segments, and the mouse exhibits a ratio of (a) B cells in the bone marrow that express an immunoglobulin having a λ light chain, to (b) B cells in the bone marrow that express an immunoglobulin having a κ light chain, of about 1 to about 15. In some embodiments, the rearrangement includes a human Vκ1-39 gene segment. In some embodiments, the rearrangement includes a human Vκ3-20 gene segment. In some embodiments, the replacement of the endogenous immunoglobulin $V_H$ gene segments is at an endogenous immunoglobulin $V_H$ locus. In some embodiments, the two human Vκ gene segments is at an endogenous immunoglobulin Vκ locus, and, in some embodiments, the two human Vκ gene segments replace all or substantially all mouse immunoglobulin Vκ gene segments. In some embodiments, the two human Vκ gene segments are at an endogenous immunoglobulin Vκ locus, and, in some embodiments, the two human Vκ gene segments replace all or substantially all mouse immunoglobulin Vκ and Jκ gene segments. In various embodiments, the two human Vκ gene segments are operably linked to two or more (e.g., 2, 3, 4, 5) human Jκ gene segments.

In some embodiments, a mouse of the present invention expresses a light chain generated through a rearrangement of a human Vκ1-39 gene segment or a human Vκ3-20 gene segment and one of two or more (e.g., 2, 3, 4, or 5) human Jκ gene segments, and the ratio of immature B cells in the bone marrow that express an immunoglobulin having a λ light chain to immature B cells that express an immunoglobulin having a κ light chain is about 1 to about 13.

In some embodiments, a mouse of the present invention expresses a light chain generated through a rearrangement of a human Vκ1-39 gene segment or a human Vκ3-20 gene segment and one of two or more (e.g., 2, 3, 4, or 5) human Jκ gene segments, and the ratio of mature B cells in the bone marrow that express an immunoglobulin having a λ light chain to immature B cells that express an immunoglobulin having a κ light chain is about 1 to about 7.

In some embodiments, a mouse of the present invention expresses a light chain generated through a rearrangement of a human Vκ1-39 gene segment or a human Vκ3-20 gene segment and one of two or more (e.g., 2, 3, 4, or 5) human Jκ gene segments, and has a pro B cell population in the bone marrow within in the range of about $2.5\times10^4$ to about $1.5\times10^5$ cells, inclusive, for example about $2.5\times10^4$, $3.0\times10^4$, $3.5\times10^4$, $4.0\times10^4$, $4.5\times10^4$, $5.0\times10^4$, $5.5\times10^4$, $6.0\times10^4$, $6.5\times10^4$, $7.0\times10^4$, $7.5\times10^4$, $8.0\times10^4$, $8.5\times10^4$, $9.0\times10^4$, $9.5\times10^4$, $1.0\times10^5$, or $1.5\times10^5$ cells; in some embodiments, a mouse of the present invention comprises a pro B cell population in the bone marrow of about $2.88\times10^4$ cells; in some embodiments, a mouse of the present invention comprises a pro B cell population in the bone marrow of about $6.42\times10^4$ cells; in some embodiments, a mouse of the present invention comprises a pro B cell population in the bone marrow of about $9.16\times10^4$ cells; in some embodiments, a mouse of the present invention comprises a pro B cell population in the bone marrow of about $1.19\times10^5$ cells. Exemplary pro B cells in the bone marrow of genetically modified mice as described herein are characterized by expression of CD19, CD43, c-kit and/or a combination thereof (e.g., $CD19^+$, $CD43^+$, c-$kit^+$).

In some embodiments, a mouse of the present invention expresses a light chain generated through a rearrangement of a human Vκ1-39 gene segment or a human Vκ3-20 gene segment and one of two or more (e.g., 2, 3, 4, or 5) human Jκ gene segments, and has a pre B cell population in the bone marrow within in the range of about $1\times10^6$ to about $2\times10^6$ cells, inclusive, for example, about $1.0\times10^6$, $1.1\times10^6$, $1.2\times10^6$, $1.3\times10^6$, $1.4\times10^6$, $1.5\times10^6$, $1.6\times10^6$, $1.7\times10^6$, $1.8\times10^6$, $1.9\times10^6$, or $2.0\times10^6$ cells; in some embodiments, a mouse of the present invention comprises a pre B cell population in the bone marrow of about $1.25\times10^6$ cells; in some embodiments, a mouse of the present invention comprises a pre B cell population in the bone marrow of about $1.46\times10^6$ cells; in some embodiments, a mouse of the present invention comprises a pre B cell population in the bone marrow of about $1.64\times10^6$ cells; in some embodiments, a mouse of the present invention comprises a pre B cell population in the bone marrow of about $2.03\times10^6$ cells. Exemplary pre B cells in the bone marrow of genetically modified mice as described herein are characterized by expression of CD19, CD43, c-kit and/or a combination thereof (e.g., $CD19^+$, $CD43^-$, c-kit).

In some embodiments, a mouse of the present invention expresses a light chain generated through a rearrangement of a human Vκ1-39 gene segment or a human Vκ3-20 gene segment and one of two or more (e.g., 2, 3, 4, or 5) human Jκ gene segments, and has an immature B cell population in the bone marrow within the range of about $5\times10^5$ to about $7\times10^5$ cells, inclusive, for example, about 5.0×105, 5.1×105, $5.2\times10^5$, $5.3\times10^5$, $5.4\times10^5$, $5.5\times10^5$, $5.6\times10^5$, $5.7\times10^5$, $5.8\times10^5$, $5.9\times10^5$, $6.0\times10^5$, $6.1\times10^5$, $6.2\times10^5$, $6.3\times10^5$, $6.4\times10^5$, $6.5\times10^5$, $6.6\times10^5$, $6.7\times10^5$, $6.8\times10^5$, $6.9\times10^5$, or $7.0\times10^5$ cells; in some embodiments, a mouse of the present invention comprises an immature B cell population in the bone marrow of about $5.33\times10^5$ cells; in some embodiments, a mouse of the present invention comprises an immature B cell population in the bone marrow of about $5.80\times10^5$ cells; in some embodiments, a mouse of the present invention comprises an immature B cell population in the bone marrow of about $5.92\times10^5$ cells; in some embodiments, the mouse comprises an immature B cell population in the bone marrow of about $6.67\times10^5$ cells. Exemplary immature B cells in the bone marrow of genetically modified mice as described herein are characterized by expression of IgM, B220 and/or a combination thereof (e.g., $IgM^+$, $B220^{int}$).

In some embodiments, a mouse of the present invention expresses a light chain generated through a rearrangement of a human Vκ1-39 gene segment or a human Vκ3-20 gene segment and one of two or more (e.g., 2, 3, 4, or 5) human Jκ gene segments, and has a mature B cell population in the bone marrow within the range of about $3\times10^4$ to about $1.5\times10^5$ cells, inclusive, for example about $3.0\times10^4$, $3.5\times10^4$, $4.0\times10^4$, $4.5\times10^4$, $5.0\times10^4$, $5.5\times10^4$, $6.0\times10^4$, $6.5\times10^4$, $7.0\times10^4$, $7.5\times10^4$, $8.0\times10^4$, $8.5\times10^4$, $9.0\times10^4$, $9.5\times10^4$, $1.0\times10^5$, or $1.5\times10^5$ cells; in some embodiments, a mouse of the present invention comprises a mature B cell population in the bone marrow of about $3.11\times10^4$ cells; in some embodiments, a mouse of the present invention comprise a mature B cell population in the bone marrow of about $1.09\times10^5$ cells; in some embodiments, a mouse of the present invention comprises a mature B cell population in the bone marrow of about $1.16\times10^5$ cells; in some embodiments, a mouse of the present invention comprises a mature B cell population in the bone marrow of about $1.44\times10^5$ cells. Exemplary mature B cells in the bone marrow of genetically modified mice as described herein are characterized by expression of IgM, B220 and/or a combination thereof (e.g., $IgM^+$, $B220^{hi}$).

In some embodiments, a mouse of the present invention expresses a light chain generated through a rearrangement of a human Vκ1-39 gene segment or a human Vκ3-20 gene segment and one of two or more (e.g., 2, 3, 4, or 5) human Jκ gene segments, and has a total B cell population in the bone marrow within the range of about $1\times10^6$ to about $3\times10^6$ cells, inclusive, for example about $1.0\times10^6$, $1.1\times10^6$, $1.2\times10^6$, $1.3\times10^6$, $1.4\times10^6$, $1.5\times10^6$, $1.6\times10^6$, $1.7\times10^6$, $1.8\times10^6$, $1.9\times10^6$, $2.0\times10^6$, $2.1\times10^6$, $2.2\times10^6$, $2.3\times10^6$, $2.4\times10^6$, $2.5\times10^6$, $2.6\times10^6$, $2.7\times10^6$, $2.8\times10^6$, $2.9\times10^6$ or $2.0\times10^6$ cells; in some embodiments, a mouse of the present invention comprises a total B cell population in the bone marrow of about $1.59\times10^6$ cells; in some embodiments, a mouse of the present invention comprises a total B cell population in the bone marrow of about $1.75\times10^6$ cells; in some embodiments, a mouse of the present invention comprises a total B cell population in the bone marrow of about $2.13\times10^6$ cells; in some embodiments, a mouse of the present invention comprises a total B cell population in the bone marrow of about $2.55\times10^6$ cells. An exemplary total B cells in the bone marrow of genetically modified mice as described herein are characterized by expression CD19, CD20 and/or a combination thereof (e.g., $CD19^+$).

In one aspect, a genetically modified mouse is provided that expresses a single rearranged κ light chain, wherein the mouse comprises a functional λ light chain locus, and wherein the mouse expresses a B cell population that comprises $Ig\kappa^+$ cells that express a κ light chain derived from the same single rearranged κ light chain. In one embodiment, the percent of $Ig\kappa^+Ig\lambda^+$ B cells in the mouse is about the same as in a wild type mouse. In a specific embodiment, the percent of $Ig\kappa^+Ig\lambda^+$ B cells in the mouse is about 2 to about 6 percent. In a specific embodiment, the percent of $Ig\kappa^+Ig\lambda^+$ B cells in a mouse wherein the single rearranged κ light chain is derived from a Vκ1-39Jκ5 sequence is about 2 to about 3; in a specific embodiment, the percent is about 2.6. In a specific embodiment, the percent of $Ig\kappa^+Ig\lambda^+$ B cells in a mouse wherein the single rearranged κ light chain is derived from a Vκ3-20Jκ1 sequence is about 4 to about 8; in a specific embodiment, the percent is about 6.

In some embodiments, a genetically modified mouse is provided that expresses an immunoglobulin light chain comprising a rearranged human immunoglobulin Vic/Jκ sequence, wherein the mouse comprises a functional immunoglobulin λ light chain locus, and wherein the mouse comprises a splenic B cell population that comprises a ratio of $Ig\lambda^+$ B cells to $Ig\kappa^+$ B cells that is about 1 to about 8; in some embodiments, about 1 to about 5. In some embodiments, the rearranged human immunoglobulin Vic/Jκ sequence is generated through a rearrangement of one of two human immunoglobulin Vκ gene segments and one of 1, 2, 3, 4, or 5 human immunoglobulin Jκ gene segments. In some embodiments, the rearranged human immunoglobulin Vκ/Jκ sequence is generated through a rearrangement of a human immunoglobulin Vκ1-39 gene segment and a human immunoglobulin Jκ gene segment selected from Jκ1, Jκ2, Jκ3, Jκ4, Jκ5, and a combination thereof. In some embodiments, the rearranged human immunoglobulin Vκ/Jκ sequence is generated through a rearrangement of a human immunoglobulin Vκ3-20 gene segment and a human immunoglobulin Jκ gene segment selected from Jκ1, Jκ2, Jκ3, Jκ4, Jκ5, and a combination thereof.

In some embodiments, a mouse of the present invention comprises a $CD19^+$ splenic B cell population within the range of about $2\times10^6$ to about $7\times10^6$ cells, inclusive, for example about $2.0\times10^6$, $2.5\times10^6$, $3.0\times10^6$, $3.5\times10^6$, $4.0\times10^6$, $4.5\times10^6$, $5.0\times10^6$, $5.5\times10^6$, $6.0\times10^6$, $6.5\times10^6$, or $7.0\times10^6$ cells; in some embodiments, a mouse of the present invention comprises a $CD19^+$ splenic B cell population of about $2.74\times10^6$ cells; some embodiments, a mouse of the present invention comprises a $CD19^+$ splenic B cell population of about $4.30\times10^6$ cells; in some embodiments, a mouse of the present invention comprises a $CD19^+$ splenic B cell population of about $5.53\times10^6$ cells; in some embodiments, a mouse of the present invention comprises a $CD19^+$ splenic B cell population of about $6.18\times10^6$ cells.

In some embodiments, a mouse of the present invention comprises a $CD19^+$, $IgD^{hi}$, $IgM^{lo}$ splenic B cell population within the range of about $1\times10^6$ to about $4\times10^6$ cells, inclusive, for example about $1.0\times10^6$, $1.5\times10^6$, $2.0\times10^6$, $2.5\times10^6$, $3.0\times10^6$, $3.5\times10^6$, $4.0\times10^6$ cells; in some embodiments, a mouse of the present invention comprises a $CD19^+$, $IgD^{hi}$, $IgM^{lo}$ splenic B cell population of about $1.30\times10^6$; in some embodiments, a mouse of the present invention comprises a $CD19^+$, $IgD^{hi}$, $IgM^{lo}$ splenic B cell population of about $2.13\times10^6$ cells; in some embodiments, a mouse of the present invention comprises $CD19^+$, $IgD^{hi}$, $IgM^{lo}$ splenic B cell population of about $3.15\times10^6$ cells; in some embodiments, a mouse of the present invention comprises a $CD19^+$, $IgD^{hi}$, $IgM^{lo}$ splenic B cell population of about $3.93\times10^6$ cells.

In some embodiment, a mouse of the present invention comprises a $CD19^+$, $IgD^{hi}$, splenic B cell population within the range of about $9\times10^5$ to about $2\times10^6$ cells, inclusive, for example about $9.0\times10^5$, $9.25\times10^5$, $9.5\times10^5$, $9.75\times10^5$, $1.0\times10^6$, $1.25\times10^6$, $1.50\times10^6$, $1.75\times10^6$, $2.0\times10^6$ cells; in some embodiments, a mouse of the present invention comprises a $CD19^+$, $IgD^{lo}$, $IgM^{hi}$ splenic B cell population of about $9.52\times10^5$; in some embodiments, a mouse of the present invention comprises a $CD19^+$, $IgD^{lo}$, $IgM^{hi}$ splenic B cell population of about $1.23\times10^6$ cells; in some embodiments, a mouse of the present invention comprises $CD19^+$, $IgD^{lo}$, $IgM^{hi}$ splenic B cell population of about $1.40\times10^6$ cells; in some embodiments, a mouse of the present invention comprises a $CD19^+$, $IgD^{lo}$, $IgM^{hi}$ splenic B cell population of about $1.42\times10^6$ cells.

In some embodiments, a genetically modified mouse is provided, wherein the mouse comprises an immunoglobulin κ light chain locus that comprises two unrearranged human immunoglobulin Vκ gene segments and two or more (e.g., 2, 3, 4, or 5) unrearranged human Jκ gene segments, and wherein the mouse comprises a peripheral splenic B cell population comprising transitional (e.g., T1, T2 and T3) B cell populations that are about the same as a mouse that comprises a wild type complement of immunoglobulin κ light chain V and J gene segments. Exemplary transitional B cell populations (e.g., T1, T2 and T3) in the spleen of a genetically modified mouse as described herein are characterized by expression of IgM, CD23, CD93, B220 and/or a combination thereof.

In some embodiments, a mouse of the present invention comprises a T1 B cell population in the spleen (e.g., $CD93^+$, $B220^+$, $IgM^{hi}$, $CD23^-$) within the range of about $2\times10^6$ to about $7\times10^6$ cells, inclusive, for example about $2.0\times10^6$, $2.5\times10^6$, $3.0\times10^6$, $3.5\times10^6$, $4.0\times10^6$, $4.5\times10^6$, $5.0\times10^6$, $5.5\times10^6$, $6.0\times10^6$, $6.5\times10^6$, or $7.0\times10^6$ cells; in some embodiments, a mouse of the present invention comprises a T1 B cell population in the spleen of about $2.16\times10^6$ cells; in some embodiments, a mouse of the present invention comprises a T1 B cell population in the spleen of about $3.63\times10^6$ cells; in some embodiments, a mouse of the present invention comprises a T1 B cell population in the spleen of about $3.91\times10^6$; in some embodiments, a mouse of the present invention comprises a T1 B cell population in the spleen of about $6.83\times10^6$ cells.

In some embodiments, a mouse of the present invention comprises a T2 B cell population in the spleen (e.g., $CD93^+$, $B220^+$, $IgM^{hi}$, $CD23^+$) within the range of about $1\times10^6$ to about $7\times10^6$ cells, inclusive, for example about $1.0\times10^6$, $1.5\times10^6$, $2.0\times10^6$, $2.5\times10^6$, $3.0\times10^6$, $3.5\times10^6$, $4.0\times10^6$, $4.5\times10^6$, $5.0\times10^6$, $5.5\times10^6$, $6.0\times10^6$, $6.5\times10^6$, or $7.0\times10^6$ cells; in some embodiments, a mouse of the present invention mouse comprises a T2 B cell population in the spleen of about $1.30\times10^6$ cells; in some embodiments, a mouse of the present invention comprises a T2 B cell population in the spleen of about $2.46\times10^6$ cells; in some embodiments, a mouse of the present invention comprises a T2 B cell population in the spleen of about $3.24\times10^6$; in some embodiments, a mouse of the present invention comprises a T2 B cell population in the spleen of about $6.52\times10^6$ cells.

In some embodiments, a mouse of the present invention comprises a T3 B cell population in the spleen (e.g., $CD93^+$, $B220^+$, $IgM^{hi}$, $CD23^+$) within the range of about $1\times10^6$ to about $4\times10^6$ cells, inclusive, for example about $1.0\times10^6$, $1.5\times10^6$, $2.0\times10^6$, $2.5\times10^6$, $3.0\times10^6$, $3.5\times10^6$, or $4.0\times10^6$ cells; in some embodiments, a mouse of the present invention comprises a T3 B cell population in the spleen of about $1.08\times10^6$ cells; in some embodiments, a mouse of the present invention comprises a T3 B cell population in the spleen of about $1.35\times10^6$ cells; in some embodiments, a mouse of the present invention comprises a T3 B cell population in the spleen of about $3.37\times10^6$; in some embodiments, a mouse of the present invention comprises a T1 B cell population in the spleen of about $3.63\times10^6$ cells.

In some embodiments, a genetically modified mouse is provided, wherein the mouse comprises an immunoglobulin κ light chain locus that comprises two unrearranged human immunoglobulin Vκ gene segments and 1, 2, 3, 4, or 5 unrearranged human immunoglobulin Jκ gene segments, and wherein the mouse comprises a peripheral splenic B cell population comprising marginal zone and marginal zone precursor B cell populations that are about the same as a mouse that comprises a wild type complement of immunoglobulin Vκ and Jκ gene segments. Exemplary marginal zone B cell populations in the spleen of a genetically modified mouse as described herein are characterized by expression of IgM, CD21/35, CD23, CD93, B220 and/or a combination thereof.

In some embodiments, a mouse of the present invention comprises marginal zone B cell population in the spleen (e.g., $CD93^-$, $B220^+$, $IgM^{hi}$, $CD21/35^{hi}$, $CD23^-$) within the range of about $1\times10^6$ to about $3\times10^6$ cells, inclusive, for example, about $1.0\times10^6$, $1.5\times10^6$, $2.0\times10^6$, $2.5\times10^6$, or $3.0\times10^6$ cells; in some embodiments, a mouse of the present invention comprises a marginal zone B cell population in the spleen of about $1.47\times10^6$ cells; in some embodiments, a mouse of the present invention comprises a marginal zone B cell population in the spleen of about $1.49\times10^6$ cells; in some embodiments, a mouse of the present invention comprises a marginal zone B cell population in the spleen of about $2.26\times10^6$ cells; in some embodiments, a mouse of the present invention comprises a marginal zone B cell population in the spleen of about $2.33\times10^6$ cells.

In some embodiments, a genetically modified mouse is provided, wherein the mouse comprises an immunoglobulin κ light chain locus that comprises two unrearranged human immunoglobulin Vκ gene segments and 1, 2, 3, 4, or 5 unrearranged human immunoglobulin Jκ gene segments, and wherein the mouse comprises a peripheral splenic B cell population comprising follicular (e.g., FO-I and FO-II) B cell population(s) that are about the same as a mouse that comprises a wild type complement of immunoglobulin Vκ and Jκ gene segments. Exemplary follicular B cell populations (e.g., FO-I and FO-II) in the spleen of a genetically modified mouse as described herein are characterized by expression of IgM, IgD, CD21/35, CD93, B220 and/or a combination thereof.

In some embodiments, a mouse of the present invention comprises a follicular type 1 B cell population in the spleen (e.g., $CD93^-$, $B220^+$, $CD21/35^{int}$, $IgM^{lo}$, $IgD^{hi}$) within the range of about $3\times10^6$ to about $1.5\times10^7$ cells, inclusive, for example about $3.0\times10^6$, $3.5\times10^6$, $4.0\times10^6$, $4.5\times10^6$, $5.0\times10^6$, $5.5\times10^6$, $6.0\times10^6$, $6.5\times10^6$, $7.0\times10^6$, $7.5\times10^6$, $8.0\times10^6$, $8.5\times10^6$, $9.0\times10^6$, $9.5\times10^6$, $1.0\times10^7$, or $1.5\times10^7$ cells; in some embodiments, a mouse of the present invention comprises a follicular type 1 B cell population in the spleen of about $3.57\times10^6$ cells; in some embodiments, a mouse of the present invention comprises a follicular type 1 B cell population in the spleen of about $6.31\times10^6$ cells; in some embodiments, a mouse of the present invention comprises a follicular type 1 B cell population in the spleen of about $9.42\times10^6$ cells; in some embodiments, a mouse of the present invention comprise a follicular type 1 B cell population in the spleen of about $1.14\times10^7$ cells.

In some embodiments, a mouse of the present invention comprises a follicular type 2 B cell population in the spleen (e.g., $CD93^-$, $B220^+$, $CD21/35^{int}$, $IgM^{int}$, $IgD^{hi}$) within the range of about $1\times10^6$ to about $2\times10^6$ cells, inclusive, for example, $1.0\times10^6$, $1.25\times10^6$, $1.5\times10^6$, $1.75\times10^6$, or $2.0\times10^6$ cells; in some embodiments, a mouse of the present invention comprises a follicular type 2 B cell population in the spleen of about $1.14\times10^6$ cells; in some embodiments, a mouse of the present invention comprises a follicular type 2 B cell population in the spleen of about $1.45\times10^6$ cells; in some embodiments, a mouse of the present invention comprises a follicular type 2 B cell population in the spleen of about $1.80\times10^6$; in some embodiments, a mouse of the present invention comprise a follicular type 2 B cell population in the spleen of about $2.06\times10^6$ cells.

In one aspect, a genetically modified mouse is provided, wherein the mouse expresses a single rearranged κ light chain derived from a human Vκ and Jκ gene segment, wherein the mouse expresses a B cell population that comprises a single κ light chain derived from the single rearranged κ light chain sequence, wherein the genetically modified mouse has not been rendered resistant to somatic hypermutations. In one embodiment, at least 90% of the κ light chains expressed on a B cell of the mouse exhibit from at least one to about five somatic hypermutations.

In one aspect, a genetically modified mouse is provided that is modified to express a single κ light chain derived from no more than one, or no more than two, rearranged κ light chain sequences, wherein the mouse exhibits a κ light chain usage that is about two-fold or more, at least about three-fold or more, or at least about four-fold or more greater than the κ light chain usage exhibited by a wild type mouse, or greater than the κ light chain usage exhibited by a mouse of the same strain that comprises a wild type repertoire of κ light chain gene segments. In a specific embodiment, the mouse expresses the single κ light chain from no more than one rearranged κ light chain sequence. In a more specific embodiment, the rearranged κ light chain sequence is selected from a Vκ1-39Jκ5 and Vκ3-20Jκ1 sequence. In one embodiment, the rearranged κ light chain sequence is a Vκ1-39Jκ5 sequence. In one embodiment, the rearranged κ light chain sequence is a Vκ3-20Jκ1 sequence.

In one aspect, a genetically modified mouse is provided that expresses a single κ light chain derived from no more than one, or no more than two, rearranged κ light chain sequences, wherein the mouse exhibits a κ light chain usage that is about 100-fold or more, at least about 200-fold or more, at least about 300-fold or more, at least about 400-fold or more, at least about 500-fold or more, at least about 600-fold or more, at least about 700-fold or more, at least about 800-fold or more, at least about 900-fold or more, at least about 1000-fold or more greater than the same κ light chain usage exhibited by a mouse bearing a complete or substantially complete human κ light chain locus. In a specific embodiment, the mouse bearing a complete or substantially complete human κ light chain locus lacks a functional unrearranged mouse κ light chain sequence. In a specific embodiment, the mouse expresses the single κ light chain from no more than one rearranged κ light chain sequence. In one embodiment, the mouse comprises one copy of a rearranged κ light chain sequence (e.g., a heterozygote). In one embodiment, the mouse comprises two copies of a rearranged κ light chain sequence (e.g., a homozygote). In a more specific embodiment, the rearranged κ light chain sequence is selected from a Vκ1-39Jκ5 and Vκ3-20Jκ1 sequence. In one embodiment, the rearranged κ light chain sequence is a Vκ1-39Jκ5 sequence. In one embodiment, the rearranged κ light chain sequence is a Vκ3-20Jκ1 sequence.

In one aspect, a genetically modified mouse is provided that expresses a single light chain derived from no more than one, or no more than two, rearranged light chain sequences, wherein the light chain in the genetically modified mouse exhibits a level of expression that is at least 10-fold to about 1,000-fold, 100-fold to about 1,000-fold, 200-fold to about 1,000-fold, 300-fold to about 1,000-fold, 400-fold to about 1,000-fold, 500-fold to about 1,000-fold, 600-fold to about 1,000-fold, 700-fold to about 1,000-fold, 800-fold to about 1,000-fold, or 900-fold to about 1,000-fold higher than expression of the same rearranged light chain exhibited by a mouse bearing a complete or substantially complete light chain locus. In one embodiment, the light chain comprises a human sequence. In a specific embodiment, the human sequence is a κ sequence. In one embodiment, the human sequence is a λ sequence. In one embodiment, the light chain is a fully human light chain.

In one embodiment, the level of expression is characterized by quantitating mRNA of transcribed light chain sequence, and comparing it to transcribed light chain sequence of a mouse bearing a complete or substantially complete light chain locus.

In one aspect, a genetically modified mouse is provided that expresses a single κ light chain derived from no more than one, or no more than two, rearranged κ light chain sequences, wherein the mouse, upon immunization with antigen, exhibits a serum titer that is comparable to a wild type mouse immunized with the same antigen. In a specific embodiment, the mouse expresses a single κ light chain from no more than one rearranged κ light chain sequence. In one embodiment, the serum titer is characterized as total immunoglobulin. In a specific embodiment, the serum titer is characterized as IgM specific titer. In a specific embodiment, the serum titer is characterized as IgG specific titer. In a more specific embodiment, the rearranged κ light chain sequence is selected from a Vκ1-39Jκ5 and Vκ3-20Jκ1 sequence. In one embodiment, the rearranged κ light chain sequence is a Vκ1-39Jκ5 sequence. In one embodiment, the rearranged κ light chain sequence is a Vκ3-20Jκ1 sequence.

In one aspect, a genetically modified mouse is provided that expresses a population of antigen-specific antibodies, wherein all of the immunoglobulin light chains of the population of antigen-specific antibodies comprise a human light chain variable ($V_L$) region derived from the same single human $V_L$ gene segment and the immunoglobulin heavy chains comprise a human heavy chain variable ($V_H$) region derived from one of a plurality of human $V_H$ gene segments.

In various embodiments, the human $V_H$ gene segments are selected from $V_H$1-2, $V_H$1-3, $V_H$1-8, $V_H$1-18, $V_H$1-24, $V_H$1-46, $V_H$1-58, $V_H$1-69, $V_H$2-5, $V_H$2-26, $V_H$2-70, $V_H$3- 7, $V_H$3-9, $V_H$3-11, $V_H$3-13, $V_H$3-15, $V_H$3-20, $V_H$3-21, $V_H$3-23, $V_H$3-30, $V_H$3-33, $V_H$3-43, $V_H$3-48, $V_H$3-53, $V_H$3-64, $V_H$3-72, $V_H$3-73, $V_H$4-31, $V_H$4-34, $V_H$4-39, $V_H$4-59, $V_H$5-51, and $V_H$6-1.

In various embodiments, same single human $V_L$ gene segment is selected from a human Vκ1-39 gene segment and a human Vκ3-20 gene segment. In various embodiments, all of the immunoglobulin light chains comprise a human light chain J ($J_L$) gene segment selected from a Jκ and a Jλ gene segment. In a specific embodiment, the human $J_L$ gene segment is selected from a human Jκ1 and a Jκ5 gene segment. In various embodiments, the mouse lacks a sequence selected from a mouse immunoglobulin $V_L$ gene segment, a mouse immunoglobulin $J_L$ gene segment, and a combination thereof. In various embodiments, the human $V_L$ region is operably linked to a human, mouse, or rat immunoglobulin light chain constant ($C_L$) region. In a specific embodiment, the human $V_L$ region is operably linked to a mouse Cκ region. In a specific embodiment, the human $V_L$ region is operably linked to a rat Cκ region.

In various embodiments, the human $V_L$ region is expressed from an endogenous immunoglobulin light chain locus. In various embodiments, the human $V_H$ region is operably linked to a human, mouse, or rat immunoglobulin heavy chain constant ($C_H$) region. In various embodiments the ($C_H$) region comprises a human sequence selected from a $C_H$1, a hinge, a $C_H$2, a $C_H$3, a $C_H$4, and/or a combination thereof. In various embodiments, the human $V_H$ region is expressed from an endogenous immunoglobulin heavy chain locus.

In one aspect, a genetically modified mouse is provided that expresses a plurality of immunoglobulin heavy chains associated with a single light chain. In one embodiment, the heavy chain comprises a human sequence. In various embodiments, the human sequence is selected from a variable sequence, a $C_H$1, a hinge, a $C_H$2, a $C_H$3, and a combination thereof. In one embodiment, the single light chain comprises a human sequence. In various embodiments, the human sequence is selected from a variable sequence, a constant sequence, and a combination thereof. In one embodiment, the mouse comprises a disabled endogenous immunoglobulin locus and expresses the heavy chain and/or the light chain from a transgene or extrachromosomal episome. In one embodiment, the mouse comprises a replacement at an endogenous mouse locus of some or all endogenous mouse heavy chain gene segments (i.e., V, D, J), and/or some or all endogenous mouse heavy chain constant sequences (e.g., $C_H$1, hinge, $C_H$2, $C_H$3, or a combination thereof), and/or some or all endogenous mouse light chain sequences (e.g., V, J, constant, or a combination thereof), with one or more human immunoglobulin sequences.

In one aspect, a mouse suitable for making antibodies that have the same light chain is provided, wherein all or substantially all antibodies made in the mouse are expressed with the same light chain. In one embodiment, the light chain is expressed from an endogenous light chain locus.

In one aspect, a method for making a light chain for a human antibody is provided, comprising obtaining from a mouse as described herein a light chain sequence and a heavy chain sequence, and employing the light chain sequence and the heavy chain sequence in making a human antibody. In one embodiment, the human antibody is a bispecific antibody.

In one aspect, a method for identifying a human heavy chain variable domain that is capable of binding an antigen of interest with an engineered light chain as described herein is provided, wherein the method comprises providing a heavy chain variable domain derived from a first antibody that is capable of binding the antigen, repairing the heavy chain variable domain with a germline light chain sequence and transfecting a cell so that each are expressed to form a second antibody, exposing the second antibody to the antigen, and measuring binding of the second antibody to the antigen.

In one embodiment, the light chain of the first antibody comprises a human Vκ1-39 sequence. In one embodiment, the light chain of the first antibody comprises a human Vκ3-20 sequence. In one embodiment, the germline light chain sequence comprises a human Vκ1-39 or Vκ3-20 sequence. In various embodiments, binding of the second antibody to the antigen is determined by comparison of binding of the first antibody to the antigen.

Any of the embodiments and aspects described herein can be used in conjunction with one another, unless otherwise indicated or apparent from the context. Other embodiments will become apparent to those skilled in the art from a review of the ensuing description.

DETAILED DESCRIPTION

This invention is not limited to particular methods, and experimental conditions described, as such methods and conditions may vary. It is also to be understood that the terminology used herein is for the purpose of describing particular embodiments only, and is not intended to be limiting, since the scope of the present invention is defined by the claims.

Unless defined otherwise, all terms and phrases used herein include the meanings that the terms and phrases have attained in the art, unless the contrary is clearly indicated or clearly apparent from the context in which the term or phrase is used. Although any methods and materials similar or equivalent to those described herein can be used in the practice or testing of the present invention, particular methods and materials are now described. All publications mentioned are hereby incorporated by reference in their entirety.

The term "antibody", as used herein, includes immunoglobulin molecules comprising four polypeptide chains, two heavy (H) chains and two light (L) chains inter-connected by disulfide bonds. Each heavy chain comprises a heavy chain variable ($V_H$) region and a heavy chain constant region ($C_H$). The heavy chain constant region comprises three domains, $C_H1$, $C_H2$ and $C_H3$. Each light chain comprises a light chain variable ($V_L$) region and a light chain constant region ($C_L$). The $V_H$ and $V_L$ regions can be further subdivided into regions of hypervariability, termed complementarity determining regions (CDR), interspersed with regions that are more conserved, termed framework regions (FR). Each $V_H$ and $V_L$ comprises three CDRs and four FRs, arranged from amino-terminus to carboxy-terminus in the following order: FR1, CDR1, FR2, CDR2, FR3, CDR3, FR4 (heavy chain CDRs may be abbreviated as HCDR1, HCDR2 and HCDR3; light chain CDRs may be abbreviated as LCDR1, LCDR2 and LCDR3. The term "high affinity" antibody refers to an antibody that has a $K_D$ with respect to its target epitope about of $10^{-9}$ M or lower (e.g., about $1\times10^{-9}$ M, $1\times10^{-10}$ M, $1\times10^{-11}$ M, or about $1\times10^{-12}$ M). In one embodiment, $K_D$ is measured by surface plasmon resonance, e.g., BIACORE™; in another embodiment, $K_D$ is measured by ELISA.

Figure 7A:
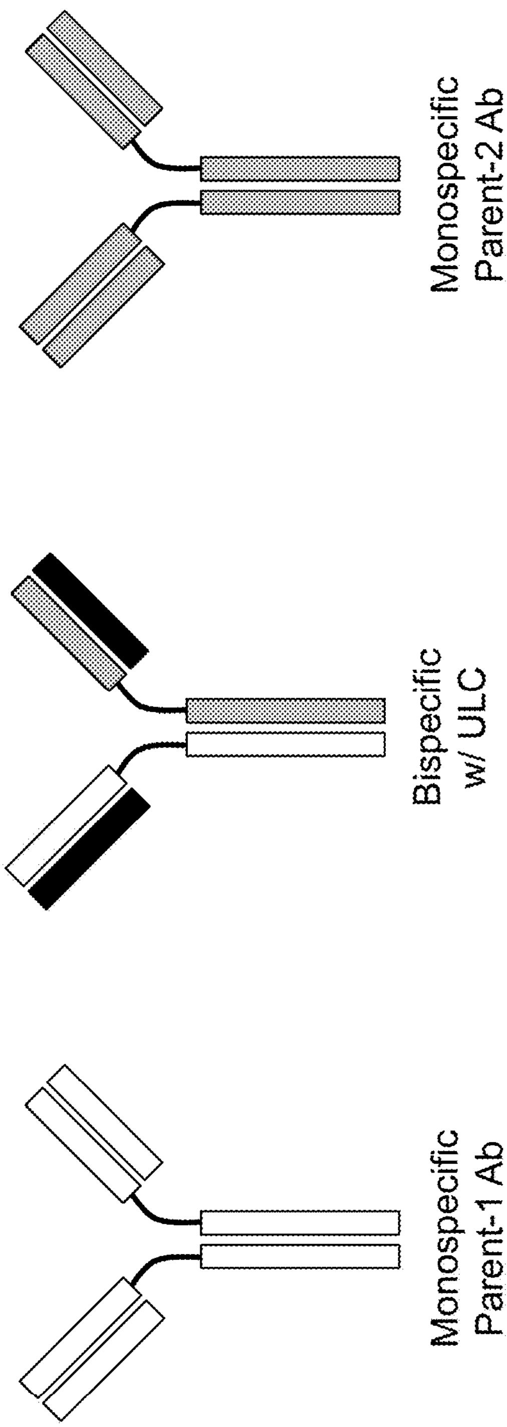
FIG. 7A shows a schematic of monospecific antibodies (Parent-1 and Parent-2) and a bispecific antibody (Bispecific) constructed from heavy chain variable regions from each parent monospecific antibody. A common light chain variable region (darkened) is indicated in the bispecific antibody.
Figure 7B:
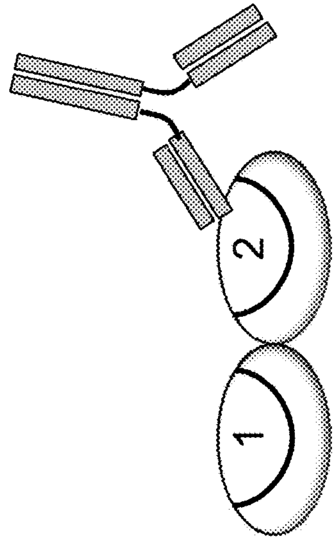
FIG. 7B shows a schematic for the binding characteristics of two parent monoclonal antibodies (Parent-1 and Parent-2) for an antigen of interest, as well as the binding characteristic of a bispecific antibody constructed from pairing the heavy chain variable regions from each monospecific parent antibody with a common light chain. The capability of the bispecific antibody to bind to two distinct epitopes of the antigen of interest either separately (bottom left) or simultaneously (bottom right) is indicated.
Figure 7B:
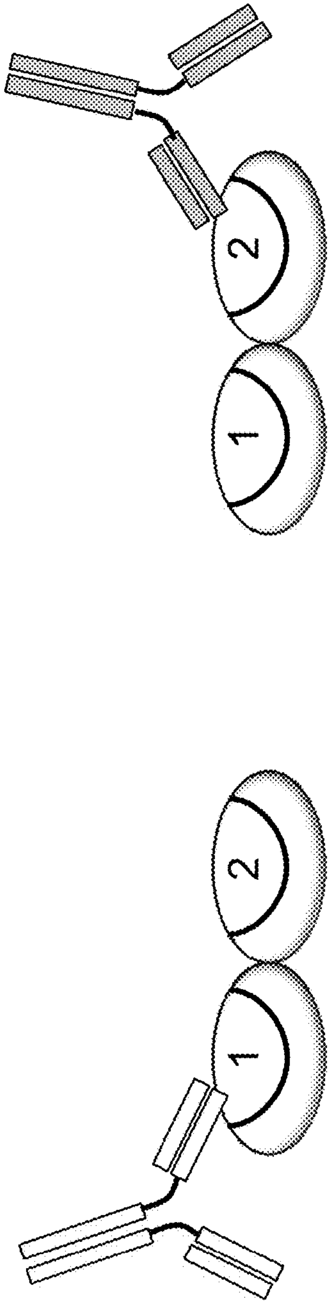
Figure 7B:
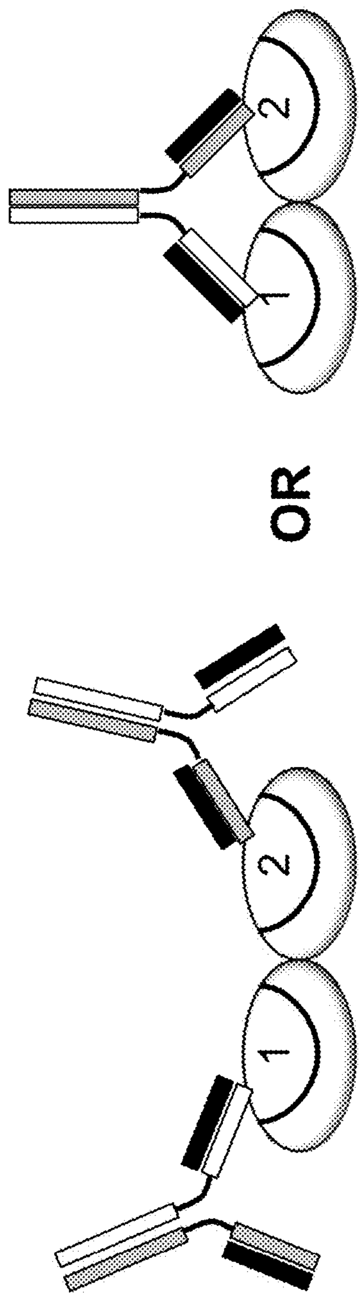

The phrase "bispecific antibody" refers to an antibody capable of selectively binding two or more epitopes. Bispecific antibodies include fragments of two different monoclonal antibodies (FIG. 7A) and generally comprise two nonidentical heavy chains derived from the two different monoclonal antibodies, with each heavy chain specifically binding a different epitope—either on two different molecules (e.g., different epitopes on two different immunogens; see FIG. 7B, bottom left) or on the same molecule (e.g., different epitopes on the same immunogen; see FIG. 7B, bottom right). If a bispecific antibody is capable of selectively binding two different epitopes (a first epitope and a second epitope), the affinity of the first heavy chain for the first epitope will generally be at least one to two or three or four or more orders of magnitude lower than the affinity of the first heavy chain for the second epitope, and vice versa. Epitopes specifically bound by the bispecific antibody can be on the same or a different target (e.g., on the same or a different protein; see FIG. 7B). Exemplary bispecific antibodies include those with a first heavy chain specific for a tumor antigen and a second heavy chain specific for a cytotoxic marker, e.g., an Fc receptor (e.g., FcγRI, FcγRII, FcγRIII, etc.) or a T cell marker (e.g., CD3, CD28, etc.). Further, the second heavy chain variable region can be substituted with a heavy chain variable region having a different desired specificity. For example, a bispecific antibody with a first heavy chain specific for a tumor antigen and a second heavy chain specific for a toxin can be paired so as to deliver a toxin (e.g., saporin, vinca alkaloid, etc.) to a tumor cell. Other exemplary bispecific antibodies include those with a first heavy chain specific for an activating receptor (e.g., B cell receptor, FcγRI, FcγRIIA, FcγRIIIA, FcαRI, T cell receptor, etc.) and a second heavy chain specific for an inhibitory receptor (e.g., FcγRIIB, CD5, CD22, CD72, CD300a, etc.). Such bispecific antibodies can be constructed for therapeutic conditions associated with cell activation (e.g. allergy and asthma). Bispecific antibodies can be made, for example, by combining heavy chains that recognize different epitopes of the same or different immunogen (FIG. 7B). For example, nucleic acid sequences encoding heavy chain variable sequences that recognize different epitopes of the same or different immunogen can be fused to nucleic acid sequences encoding the same or different heavy chain constant regions, and such sequences can be expressed in a cell that expresses an immunoglobulin light chain. A typical bispecific antibody has two heavy chains each having three heavy chain CDRs, followed by (N-terminal to C-terminal) a $C_H1$ domain, a hinge, a $C_H2$ domain, and a $C_H3$ domain, and an immunoglobulin light chain that either does not confer epitope-binding specificity but that can associate with each heavy chain, or that can associate with each heavy chain and that can bind one or more of the epitopes bound by the heavy chain epitope-binding regions, or that can associate with each heavy chain and enable binding or one or both of the heavy chains to one or both epitopes.

The term "cell" includes any cell that is suitable for expressing a recombinant nucleic acid sequence. Cells include those of prokaryotes and eukaryotes (single-cell or multiple-cell), bacterial cells (e.g., strains of *E. coli, Bacillus* spp., *Streptomyces* spp., etc.), mycobacteria cells, fungal cells, yeast cells (e.g., *S. cerevisiae, S. pombe, P. pastoris, P. methanolica*, etc.), plant cells, insect cells (e.g., SF-9, SF-21, baculovirus-infected insect cells, *Trichoplusia ni*, etc.), non-human animal cells, human cells, or cell fusions such as, for example, hybridomas or quadromas. In some embodiments, the cell is a human, monkey, ape, hamster, rat, or mouse cell. In some embodiments, the cell is eukaryotic and is selected from the following cells: CHO (e.g., CHO K1, DXB-11 CHO, Veggie-CHO), COS (e.g., COS-7), retinal cell, Vero, CV1, kidney (e.g., HEK293, 293 EBNA, MSR 293, MDCK, HaK, BHK), HeLa, HepG2, WI38, MRC 5, Colo205, HB 8065, HL-60, (e.g., BHK21), Jurkat, Daudi, A431 (epidermal), CV-1, U937, 3T3, L cell, C127 cell, SP2/0, NS-0, MMT 060562, Sertoli cell, BRL 3A cell, HT1080 cell, myeloma cell, tumor cell, and a cell line derived from an aforementioned cell. In some embodiments, the cell comprises one or more viral genes, e.g., a retinal cell that expresses a viral gene (e.g., a PER.C6™ cell).

The phrase "complementarity determining region," or the term "CDR," includes an amino acid sequence encoded by a nucleic acid sequence of an organism's immunoglobulin genes that normally (i.e., in a wild type animal) appears between two framework regions in a variable region of a light or a heavy chain of an immunoglobulin molecule (e.g., an antibody or a T cell receptor). A CDR can be encoded by, for example, a germline sequence or a rearranged or unrearranged sequence, and, for example, by a naive or a mature B cell or a T cell. A CDR can be somatically mutated (e.g., vary from a sequence encoded in an animal's germline), humanized, and/or modified with amino acid substitutions, additions, or deletions. In some circumstances (e.g., for a CDR3), CDRs can be encoded by two or more sequences (e.g., germline sequences) that are not contiguous (e.g., in an unrearranged nucleic acid sequence) but are contiguous in a B cell nucleic acid sequence, e.g., as the result of splicing or connecting the sequences (e.g., V-D-J recombination to form a heavy chain CDR3).

The term "conservative," when used to describe a conservative amino acid substitution, includes substitution of an amino acid residue by another amino acid residue having a side chain R group with similar chemical properties (e.g., charge or hydrophobicity). In general, a conservative amino acid substitution will not substantially change the functional properties of interest of a protein, for example, the ability of a variable region to specifically bind a target epitope with a desired affinity. Examples of groups of amino acids that have side chains with similar chemical properties include aliphatic side chains such as glycine, alanine, valine, leucine, and isoleucine; aliphatic-hydroxyl side chains such as serine and threonine; amide-containing side chains such as asparagine and glutamine; aromatic side chains such as phenylalanine, tyrosine, and tryptophan; basic side chains such as lysine, arginine, and histidine; acidic side chains such as aspartic acid and glutamic acid; and, sulfur-containing side chains such as cysteine and methionine. Conservative amino acids substitution groups include, for example, valine/leucine/isoleucine, phenylalanine/tyrosine, lysine/arginine, alanine/valine, glutamate/aspartate, and asparagine/glutamine. In some embodiments, a conservative amino acid substitution can be substitution of any native residue in a protein with alanine, as used in, for example, alanine scanning mutagenesis. In some embodiments, a conservative substitution is made that has a positive value in the PAM250 log-likelihood matrix disclosed in Gonnet et al. (1992) Exhaustive Matching of the Entire Protein Sequence Database, Science 256:1443-45, hereby incorporated by reference. In some embodiments, the substitution is a moderately conservative substitution wherein the substitution has a nonnegative value in the PAM250 log-likelihood matrix.

In some embodiments, residue positions in an immunoglobulin light chain or heavy chain differ by one or more conservative amino acid substitutions. In some embodiments, residue positions in an immunoglobulin light chain or functional fragment thereof (e.g., a fragment that allows expression and secretion from, e.g., a B cell) are not identical to a light chain whose amino acid sequence is listed herein, but differs by one or more conservative amino acid substitutions.

The phrase "epitope-binding protein" includes a protein having at least one CDR and that is capable of selectively recognizing an epitope, e.g., is capable of binding an epitope with a $K_D$ that is at about one micromolar or lower (e.g., a $K_D$ that is about $1\times10^{-6}$ M, $1\times10^{-7}$ M, $1\times10^{-9}$ M, $1\times10^{-9}$ M, $1\times10^{-10}$ M, $1\times10^{-11}$ M, or about $1\times10^{-12}$ M). Therapeutic epitope-binding proteins (e.g., therapeutic antibodies) frequently require a $K_D$ that is in the nanomolar or the picomolar range.

The phrase "functional fragment" includes fragments of epitope-binding proteins that can be expressed, secreted, and specifically bind to an epitope with a $K_D$ in the micromolar, nanomolar, or picomolar range. Specific recognition includes having a $K_D$ that is at least in the micromolar range, the nanomolar range, or the picomolar range.

The term "germline" includes reference to an immunoglobulin nucleic acid sequence in a non-somatically mutated cell, e.g., a non-somatically mutated B cell or pre-B cell or hematopoietic cell.

The phrase "heavy chain," or "immunoglobulin heavy chain" includes an immunoglobulin heavy chain constant region sequence from any organism. Heavy chain variable domains include three heavy chain CDRs and four FR regions, unless otherwise specified. Fragments of heavy chains include CDRs, CDRs and FRs, and combinations thereof. A typical heavy chain has, following the variable domain (from N-terminal to C-terminal), a $C_H1$ domain, a hinge, a $C_H2$ domain, and a $C_H3$ domain. A functional fragment of a heavy chain includes a fragment that is capable of specifically recognizing an epitope (e.g., recognizing the epitope with a $K_D$ in the micromolar, nanomolar, or picomolar range), that is capable of expressing and secreting from a cell, and that comprises at least one CDR.

The term "identity" when used in connection with sequence includes identity as determined by a number of different algorithms known in the art that can be used to measure nucleotide and/or amino acid sequence identity. In some embodiments described herein, identities are determined using a ClustalW v. 1.83 (slow) alignment employing an open gap penalty of 10.0, an extend gap penalty of 0.1, and using a Gonnet similarity matrix (MACVECTOR™ 10.0.2, MacVector Inc., 2008). The length of the sequences compared with respect to identity of sequences will depend upon the particular sequences, but in the case of a light chain constant domain, the length should contain sequence of sufficient length to fold into a light chain constant domain that is capable of self-association to form a canonical light chain constant domain, e.g., capable of forming two beta sheets comprising beta strands and capable of interacting with at least one $C_H1$ domain of a human or a mouse. In the case of a $C_H1$ domain, the length of sequence should contain sequence of sufficient length to fold into a $C_H1$ domain that is capable of forming two beta sheets comprising beta strands and capable of interacting with at least one light chain constant domain of a mouse or a human.

The phrase "immunoglobulin molecule" includes two immunoglobulin heavy chains and two immunoglobulin light chains. The heavy chains may be identical or different, and the light chains may be identical or different.

The phrase "light chain" includes an immunoglobulin light chain sequence from any organism, and unless otherwise specified includes human κ and λ light chains and a VpreB, as well as surrogate light chains. Light chain variable ($V_L$) domains typically include three light chain CDRs and four framework (FR) regions, unless otherwise specified. Generally, a full-length light chain includes, from amino terminus to carboxyl terminus, a $V_L$ domain that includes FR1-CDR1-FR2-CDR2-FR3-CDR3-FR4, and a light chain constant domain. Light chains include those, e.g., that do not selectively bind either a first or a second epitope selectively bound by the epitope-binding protein in which they appear. Light chains also include those that bind and recognize, or assist the heavy chain with binding and recognizing, one or more epitopes selectively bound by the epitope-binding protein in which they appear. Common light chains are those derived from a rearranged human Vκ1-39Jκ5 sequence or a rearranged human Vκ3-20Jκ1 sequence, and include somatically mutated (e.g., affinity matured) versions.

The phrase "micromolar range" is intended to mean 1-999 micromolar; the phrase "nanomolar range" is intended to mean 1-999 nanomolar; the phrase "picomolar range" is intended to mean 1-999 picomolar.

The phrase "somatically mutated" includes reference to a nucleic acid sequence from a B cell that has undergone class-switching, wherein the nucleic acid sequence of an immunoglobulin variable region (e.g., a heavy chain variable domain or including a heavy chain CDR or FR sequence) in the class-switched B cell is not identical to the nucleic acid sequence in the B cell prior to class-switching, such as, for example, a difference in a CDR or framework nucleic acid sequence between a B cell that has not undergone class-switching and a B cell that has undergone class-switching. "Somatically mutated" includes reference to nucleic acid sequences from affinity-matured B cells that are not identical to corresponding immunoglobulin variable region sequences in B cells that are not affinity-matured (i.e., sequences in the genome of germline cells). The phrase "somatically mutated" also includes reference to an immunoglobulin variable region nucleic acid sequence from a B cell after exposure of the B cell to an epitope of interest, wherein the nucleic acid sequence differs from the corresponding nucleic acid sequence prior to exposure of the B cell to the epitope of interest. The phrase "somatically mutated" refers to sequences from antibodies that have been generated in an animal, e.g., a mouse having human immunoglobulin variable region nucleic acid sequences, in response to an immunogen challenge, and that result from the selection processes inherently operative in such an animal.

The term "unrearranged," with reference to a nucleic acid sequence, includes nucleic acid sequences that exist in the germline of an animal cell.

The phrase "variable domain" includes an amino acid sequence of an immunoglobulin light or heavy chain (modified as desired) that comprises the following amino acid regions, in sequence from N-terminal to C-terminal (unless otherwise indicated): FR1, CDR1, FR2, CDR2, FR3, CDR3, FR4.

Universal Light Chain

Prior efforts to make useful multispecific epitope-binding proteins, e.g., bispecific antibodies, have been hindered by variety of problems that frequently share a common paradigm: in vitro selection or manipulation of sequences to rationally engineer, or to engineer through trial-and-error, a suitable format for pairing a heterodimeric bispecific human immunoglobulin. Unfortunately, most if not all of the in vitro engineering approaches provide largely ad hoc fixes that are suitable, if at all, for individual molecules. On the other hand, in vivo methods for employing complex organisms to select appropriate pairings that are capable of leading to human therapeutics have not been realized.

Mice containing human immunoglobulin loci, variable and constant regions randomly inserted into the mouse genome, are known in the art. Initial strains of such mice contained a limited number of human immunoglobulin gene segments. Specifically, a handful of strains containing human immunoglobulin light chain gene segments contained either one, three or four human immunoglobulin $V_L$ gene segments and five human immunoglobulin $J_L$ gene segments (Taylor et al. 1992, Nucleic Acids Research 20(23): 6287-6295; Fishwild et al. 1996, Nature Biotechnology 14: 845-851; Lonberg et al. 1994, Nature 368: 856-859; Green et al. 1994, Nature Genetics 7:13-21; Green and Jakobovits 1998, J. Exp. Med. 188(3): 483-495; Green 1999, J. Immunol. Methods 231: 11-23). These mice that contained only a few human immunoglobulin $V_L$ gene segments as part of fully human transgenes randomly inserted into the mouse genome demonstrated compromised B cell numbers, impaired B cell development and other immune deficiencies. Expression of the human immunoglobulin $V_L$ genes, as detected by surface expression of human Cκ on B cells, was lower than the endogenous κ light chain as compared to wild type. Surprisingly, the present invention provides mice whose B cell numbers and development is nearly wild-type in respects when mice are engineered at the endogenous immunoglobulin κ light chain loci to contain either one or two human immunoglobulin Vκ gene segments (e.g., Examples 2 and 14, Tables 3, 25 and 26, and FIGS. 4, 10A-18). Further, in some embodiments, mice provided by the present invention, are able to generate several high-affinity reverse chimeric antibodies containing human $V_H$ and $V_L$ domains in response to antigen, wherein the $V_L$ domains each contain one of two possible human $V_L$ gene segments and one of five possible human $J_L$ gene segments (e.g., see Examples 5-10, 12, and 14). Thus, in contrast to preliminary strains of mice engineered with human immunoglobulin light chain miniloci (i.e., a limited number of human immunoglobulin gene segments), presently provided engineered mice that contain a limited number of human immunoglobulin $V_L$ gene segments (either one or two) and, in some embodiments, two or more (e.g., 2, 3, 4, or 5) human immunoglobulin $J_L$ gene segments, surprisingly exhibit normal B cell numbers, normal immunoglobulin light chain expression, and normal B cell development. Further, such provided mice also show no reduced or impaired ability to mount robust immune responses to multiple antigens as a result of a limited immunoglobulin light chain repertoire. Accordingly, mice are 00249 provided that comprise a humanized $V_L$ locus comprising no more than two unrearranged human immunoglobulin $V_L$ gene segments and two or more (e.g., 2, 3, 4, or 5) human immunoglobulin $J_L$ gene segments—or no more than two rearranged human $V_LJ_L$ segments—and that exhibit wild-type B cell populations in number, and exhibit wild-type B cell development.

Generally, native mouse sequences are frequently not a good source for human therapeutic sequences. For at least that reason, generating mouse heavy chain immunoglobulin variable regions that pair with a common human light chain is of limited practical utility. More in vitro engineering efforts would be expended in a trial-and-error process to try to humanize the mouse heavy chain variable sequences while hoping to retain epitope specificity and affinity while maintaining the ability to couple with the common human light chain, with uncertain outcome. At the end of such a process, the final product may maintain some of the specificity and affinity, and associate with the common light chain, but ultimately immunogenicity in a human would likely remain a profound risk.

Therefore, a suitable mouse for making human therapeutics would include a suitably large repertoire of human heavy chain variable region gene segments in place of endogenous mouse heavy chain variable region gene segments. The human heavy chain variable region gene segments should be able to rearrange and recombine with an endogenous mouse heavy chain constant domain to form a reverse chimeric heavy chain (i.e., a heavy chain comprising a human variable domain and a mouse constant region). The heavy chain should be capable of class switching and somatic hypermutation so that a suitably large repertoire of heavy chain variable domains are available for the mouse to select one that can associate with the limited repertoire of human light chain variable regions.

A mouse that selects a common light chain for a plurality of heavy chains has a practical utility. In various embodiments, antibodies that express in a mouse that can only express a common light chain will have heavy chains that can associate and express with an identical or substantially identical light chain. This is particularly useful in making bispecific antibodies. For example, such a mouse can be immunized with a first immunogen to generate a B cell that expresses an antibody that specifically binds a first epitope. The mouse (or a mouse genetically the same) can be immunized with a second immunogen to generate a B cell that expresses an antibody that specifically binds the second epitope. Variable heavy chain regions can be cloned from the B cells and expressed with the same heavy chain constant region, and the same variable light chain region (e.g., a common light chain) in a cell to make a bispecific antibody, wherein the variable heavy chain component of the bispecific antibody has been selected by a mouse to associate and express with the variable light chain (or common light chain) component.

The inventors have engineered a mouse for generating immunoglobulin light chains that will suitably pair with a rather diverse family of heavy chains, including heavy chains whose variable regions depart from germline sequences, e.g., affinity matured or somatically mutated variable regions. In various embodiments, the mouse is devised to pair human light chain variable domains with human heavy chain variable domains that comprise somatic mutations, thus enabling a route to high affinity binding proteins suitable for use as human therapeutics.

The genetically engineered mouse, through the long and complex process of antibody selection within an organism, makes biologically appropriate choices in pairing a diverse collection of human heavy chain variable domains with a limited number of human light chain options. In order to achieve this, the mouse is engineered to present a limited number of human light chain variable domain options in conjunction with a wide diversity of human heavy chain variable domain options. Upon challenge with an immunogen, the mouse maximizes the number of solutions in its repertoire to develop an antibody to the immunogen, limited largely or solely by the number or light chain options in its repertoire. In various embodiments, this includes allowing the mouse to achieve suitable and compatible somatic mutations of the light chain variable domain that will nonetheless be compatible with a relatively large variety of human heavy chain variable domains, including in particular somatically mutated human heavy chain variable domains.

To achieve a limited repertoire of light chain options, the mouse is engineered to render nonfunctional or substantially nonfunctional its ability to make, or rearrange, a native mouse light chain variable domain. This can be achieved, e.g., by deleting the mouse's light chain variable region gene segments. The endogenous mouse locus can then be modified by an exogenous suitable human light chain variable region gene segment of choice, operably linked to the endogenous mouse light chain constant domain, in a manner such that the exogenous human variable region gene segments can combine with the endogenous mouse light chain constant region gene and form a rearranged reverse chimeric light chain gene (human variable, mouse constant). In various embodiments, the light chain variable region is capable of being somatically mutated. In various embodiments, to maximize ability of the light chain variable region to acquire somatic mutations, the appropriate enhancer(s) is retained in the mouse. For example, in modifying a mouse κ light chain locus to replace endogenous mouse κ light chain gene segments with human κ light chain gene segments, the mouse κ intronic enhancer and mouse κ3' enhancer are functionally maintained, or undisrupted.

A genetically engineered mouse is provided that expresses a limited repertoire of reverse chimeric (human variable, mouse constant) light chains associated with a diversity of reverse chimeric (human variable, mouse constant) heavy chains. In various embodiments, the endogenous mouse κ light chain gene segments are deleted and replaced with a single (or two) rearranged human light chain region, operably linked to the endogenous mouse Cκ gene. In embodiments for maximizing somatic hypermutation of the rearranged human light chain region, the mouse κ intronic enhancer and the mouse κ3' enhancer are maintained. In various embodiments, the mouse also comprises a nonfunctional λ light chain locus, or a deletion thereof or a deletion that renders the locus unable to make a λ light chain.

A genetically engineered mouse is provided that, in various embodiments, comprises a light chain variable region locus lacking endogenous mouse light chain $V_L$ and $J_L$ gene segments and comprising a rearranged human light chain variable region, in one embodiment a rearranged human $V_L/J_L$ sequence, operably linked to a mouse constant region, wherein the locus is capable of undergoing somatic hypermutation, and wherein the locus expresses a light chain comprising the human $V_L/J_L$ sequence linked to a mouse constant region. Thus, in various embodiments, the locus comprises a mouse κ3' enhancer, which is correlated with a normal, or wild type, level of somatic hypermutation.

The genetically engineered mouse in various embodiments when immunized with an antigen of interest generates B cells that exhibit a diversity of rearrangements of human immunoglobulin heavy chain variable regions that express and function with one or with two rearranged light chains, including embodiments where the one or two light chains comprise human light chain variable regions that comprise, e.g., 1 to 5 somatic mutations. In various embodiments, the human light chains so expressed are capable of associating and expressing with any human immunoglobulin heavy chain variable region expressed in the mouse.

In addition to genetically engineered mice comprising restricted immunoglobulin light chain repertoire (e.g., a single human $V_L$ gene segment or no more than two human $V_L$ gene segments and, one human $J_L$ gene segment or, optionally, two or more human $J_L$ gene segments) as described herein, also provided herein are other genetically modified non-human animals that comprise a single hum $V_L$ gene segment or no more than two human $V_L$ gene segments. In some embodiments, such non-human animals comprise a single rearranged human $V_L$ region composed of a rearranged human $V_LJ_L$ sequence. In some embodiments, such non-human animals comprise no more than two human $V_L$ gene segments and two or more (e.g., 2, 3, 4, or 5 human $J_L$ gene segments. In various embodiments, human gene segments are operably linked to a non-human light chain constant region, e.g., a mouse a rat light chain constant region.

Such non-human animals may be selected from a group consisting of a mouse, rat, rabbit, pig, bovine (e.g., cow, bull, buffalo), deer, sheep, goat, chicken, cat, dog, ferret, primate (e.g., marmoset, rhesus monkey). For the non-human animals where suitable genetically modifiable ES cells are not readily available, other methods are employed to make a non-human animal comprising genetic modifications as described herein. Such methods include, e.g., modifying a non-ES cell genome (e.g., a fibroblast or an induced pluripotent cell) and employing nuclear transfer to transfer the modified genome to a suitable cell, e.g., an oocyte, and gestating the modified cell (e.g., the modified oocyte) in a non-human animal under suitable conditions to form an embryo.

In some embodiments, a non-human animal of the present invention is a mammal. In some embodiments, a non-human animal of the present invention is a small mammal, e.g., of the superfamily Dipodoidea or Muroidea. In some embodiments, a genetically modified animal of the present invention is a rodent. In some embodiments, a rodent of the present invention is selected from a mouse, a rat, and a hamster. In some embodiments, a rodent of the present invention is selected from the superfamily Muroidea. In some embodiments, a genetically modified animal of the present invention is from a family selected from Calomyscidae (e.g., mouse-like hamsters), Cricetidae (e.g., hamster, New World rats and mice, voles), Muridae (true mice and rats, gerbils, spiny mice, crested rats), Nesomyidae (climbing mice, rock mice, with-tailed rats, Malagasy rats and mice), Platacanthomyidae (e.g., spiny dormice), and Spalacidae (e.g., mole rates, bamboo rats, and zokors). In some certain embodiments, a genetically modified rodent of the present invention is selected from a true mouse or rat (family Muridae), a gerbil, a spiny mouse, and a crested rat. In some certain embodiments, a genetically modified mouse of the present invention is from a member of the family Muridae. In some embodiment, an non-human animal of the present invention is a rodent. In some certain embodiments, a rodent of the present invention is selected from a mouse and a rat. In some embodiments, a non-human animal of the present invention is a mouse.

In some embodiments, a non-human animal of the present invention is a rodent that is a mouse of a C57BL strain selected from C57BL/A, C57BL/An, C57BL/GrFa, C57BL/KaLwN, C57BL/6, C57BL/6J, C57BL/6ByJ, C57BL/6NJ, C57BL/10, C57BL/10ScSn, C57BL/10Cr, and C57BL/Ola. In some certain embodiments, a mouse of the present invention is a 129 strain selected from the group consisting of a strain that is 129P1, 129P2, 129P3,129X1, 129S1 (e.g., 129S1/SV, 129S1/SvIm), 129S2, 129S4, 129S5, 129S9/SvEvH, 129S6 (129/SvEvTac), 129S7, 129S8, 129T1, 129T2 (see, e.g., Festing et al., 1999, Mammalian Genome 10:836; Auerbach et al., 2000, Biotechniques 29(5):1024-1028, 1030, 1032). In some certain embodiments, a genetically modified mouse of the present invention is a mix of an aforementioned 129 strain and an aforementioned C57BL/6 strain. In some certain embodiments, a mouse of the present invention is a mix of aforementioned 129 strains, or a mix of aforementioned BL/6 strains. In some certain embodiments, a 129 strain of the mix as described herein is a 129S6 (129/SvEvTac) strain. In some embodiment, a mouse of the present invention is a BALB strain, e.g., BALB/c strain. In some embodiments, a mouse of the present invention is a mix of a BALB strain and another aforementioned strain.

In some embodiments, a non-human animal of the present invention is a rat. In some certain embodiments, a rat of the present invention is selected from a Wistar rat, an LEA strain, a Sprague Dawley strain, a Fischer strain, F344, F6, and Dark Agouti. In some certain embodiments, a rat strain as described herein is a mix of two or more strains selected from the group consisting of Wistar, LEA, Sprague Dawley, Fischer, F344, F6, and Dark Agouti.

Epitope-Binding Proteins Binding More Than One Epitope

Compositions and methods described herein can be used to make binding proteins that bind more than one epitope with high affinity, e.g., bispecific antibodies. Advantages of the invention include the ability to select suitably high binding (e.g., affinity matured) heavy chain immunoglobulin chains each of which will associate with a single light chain.

Several techniques for making bispecific antibody fragments from recombinant cell culture have been reported. However, synthesis and expression of bispecific binding proteins has been problematic, in part due to issues associated with identifying a suitable light chain that can associate and express with two different heavy chains, and in part due to isolation issues. In various embodiments, compositions and methods described herein provide the advantage of full length bispecific antibodies that do not require special modification(s) to maintain traditional immunoglobulin structure by increasing stability/interaction of the components (FIG. 7A). In various embodiments, such modification(s) has proven cumbersome and served as an obstacle to development of bispecific antibody technology and their potential use in treating for human disease. Thus, in various embodiments, through providing a natural immunoglobulin structure (i.e., full length) having the added property of multiple specificities, full length bispecific antibodies maintain their critical effector functions that previous bispecific fragments lack, and further provide therapeutics that demonstrate the important pharmacokinetic parameter of a longer half-life.

Methods and compositions described herein allow for a genetically modified mouse to select, through otherwise natural processes, a suitable light chain that can associate and express with more than one heavy chain, including heavy chains that are somatically mutated (e.g., affinity matured). Human $V_L$ and $V_H$ sequences from suitable B cells of immunized mice as described herein that express affinity matured antibodies having reverse chimeric heavy chains (i.e., human variable and mouse constant) can be identified and cloned in frame in an expression vector with a suitable human constant region gene sequence (e.g., a human IgG1). Two such constructs can be prepared, wherein each construct encodes a human heavy chain variable domain that binds a different epitope. One of the human $V_L$s (e.g., human Vκ1-39Jκ5 or human Vκ3-20Jκ1), in germline sequence or from a B cell wherein the sequence has been somatically mutated, can be fused in frame to a suitable human constant region gene (e.g., a human κ constant gene). These three fully human heavy and light constructs can be placed in a suitable cell for expression. The cell will express two major species: a homodimeric heavy chain with the identical light chain, and a heterodimeric heavy chain with the identical light chain. To allow for a facile separation of these major species, one of the heavy chains is modified to omit a Protein A-binding determinant, resulting in a differential affinity of a homodimeric binding protein from a heterodimeric binding protein. Compositions and methods that address this issue are described in U.S. Ser. No. 12/832,838, filed 25 Jun. 2010, entitled "Readily Isolated Bispecific Antibodies with Native Immunoglobulin Format," published as US 2010/0331527A1, hereby incorporated by reference.

In one aspect, an epitope-binding protein as described herein is provided, wherein human $V_L$ and $V_H$ sequences are derived from mice described herein that have been immunized with an antigen comprising an epitope of interest.

In one embodiment, an epitope-binding protein is provided that comprises a first and a second polypeptide, the first polypeptide comprising, from N-terminal to C-terminal, a first epitope-binding region that selectively binds a first epitope, followed by a constant region that comprises a first $C_H3$ region of a human IgG selected from IgG1, IgG2, IgG4, and a combination thereof; and, a second polypeptide comprising, from N-terminal to C-terminal, a second epitope-binding region that selectively binds a second epitope, followed by a constant region that comprises a second $C_H3$ region of a human IgG selected from IgG1, IgG2, IgG4, and a combination thereof, wherein the second $C_H3$ region comprises a modification that reduces or eliminates binding of the second $C_H3$ domain to protein A.

In one embodiment, the second $C_H3$ region comprises an H95R modification (by IMGT exon numbering; H435R by EU numbering). In another embodiment, the second $C_H3$ region further comprises a Y96F modification (IMGT; Y436F by EU).

In one embodiment, the second $C_H3$ region is from a modified human IgG1, and further comprises a modification selected from the group consisting of D16E, L18M, N44S, K52N, V57M, and V82I (IMGT; D356E, L358M, N384S, K392N, V397M, and V422I by EU).

In one embodiment, the second $C_H3$ region is from a modified human IgG2, and further comprises a modification selected from the group consisting of N44S, K52N, and V82I (IMGT; N384S, K392N, and V422I by EU).

In one embodiment, the second $C_H3$ region is from a modified human IgG4, and further comprises a modification selected from the group consisting of Q15R, N44S, K52N, V57M, R69K, E79Q, and V82I (IMGT; Q355R, N384S, K392N, V397M, R409K, E419Q, and V422I by EU).

One method for making an epitope-binding protein that binds more than one epitope is to immunize a first mouse in accordance with the invention with an antigen that comprises a first epitope of interest, wherein the mouse comprises an endogenous immunoglobulin light chain variable region locus that does not contain an endogenous mouse $V_L$ that is capable of rearranging and forming a light chain, wherein at the endogenous mouse immunoglobulin light chain variable region locus is a single rearranged human $V_L$ region operably linked to the mouse endogenous light chain constant region gene, and the rearranged human $V_L$ region is selected from a human Vκ1-39Jκ5 and a human Vκ3-20Jκ1, and the endogenous mouse $V_H$ gene segments have been replaced in whole or in part with human $V_H$ gene segments, such that immunoglobulin heavy chains made by the mouse are solely or substantially heavy chains that comprise human variable domains and mouse constant domains. When immunized, such a mouse will make a reverse chimeric antibody, comprising only one of two human light chain variable domains (e.g., one of human Vκ1-39Jκ5 or human Vκ3-20Jκ1). Once a B cell is identified that encodes a $V_H$ that binds the epitope of interest, the nucleotide sequence of the $V_H$ (and, optionally, the $V_L$) can be retrieved (e.g., by PCR) and cloned into an expression construct in frame with a suitable human immunoglobulin constant domain. This process can be repeated to identify a second $V_H$ domain that binds a second epitope, and a second $V_H$ gene sequence can be retrieved and cloned into an expression vector in frame to a second suitable immunoglobulin constant domain. The first and the second immunoglobulin constant domains can the same or different isotype, and one of the immunoglobulin constant domains (but not the other) can be modified as described herein or in US 2010/0331527A1, and epitope-binding protein can be expressed in a suitable cell and isolated based on its differential affinity for Protein A as compared to a homodimeric epitope-binding protein, e.g., as described in US 2010/0331527A1.

In one embodiment, a method for making a bispecific epitope-binding protein is provided, comprising identifying a first affinity-matured (e.g., comprising one or more somatic hypermutations) human $V_H$ nucleotide sequence ($V_H1$) from a mouse as described herein, identifying a second affinity-matured (e.g., comprising one or more somatic hypermutations) human $V_H$ nucleotide sequence ($V_H2$) from a mouse as described herein, cloning $V_H1$ in frame with a human heavy chain lacking a Protein A-determinant modification as described in US 2010/0331527A1 for form heavy chain 1 (HC1), cloning $V_H2$ in frame with a human heavy chain comprising a Protein A-determinant as described in US 2010/0331527A1 to form heavy chain 2 (HC2), introducing an expression vector comprising HC1 and the same or a different expression vector comprising HC2 into a cell, wherein the cell also expresses a human immunoglobulin light chain that comprises a human Vκ1-39/human Jκ5 or a human Vκ3-20/human Jκ1 fused to a human light chain constant domain, allowing the cell to express a bispecific epitope-binding protein comprising a $V_H$ domain encoded by $V_H1$ and a $V_H$ domain encoded by $V_H2$, and isolating the bispecific epitope-binding protein based on its differential ability to bind Protein A as compared with a monospecific homodimeric epitope-binding protein. In a specific embodiment, HC1 is an IgG1, and HC2 is an IgG1 that comprises the modification H95R (IMGT; H435R by EU) and further comprises the modification Y96F (IMGT; Y436F by EU). In one embodiment, the $V_H$ domain encoded by $V_H1$, the $V_H$ domain encoded by $V_H2$, or both, are somatically mutated.

Human $V_H$ Genes that Express with a Common Human $V_L$

A variety of human variable regions from affinity-matured antibodies raised against four different antigens were expressed with either their cognate light chain, or at least one of a human light chain selected from human Vκ1-39/Jκ5, human Vκ3-20/Jκ1, or human VpreB/JX5 (see Example 1). For antibodies to each of the antigens, somatically mutated high affinity heavy chains from different gene families paired successfully with rearranged human germline Vκ1-39Jκ5 and Vκ3-20Jκ1 regions and were secreted from cells expressing the heavy and light chains. For Vκ1-39Jκ5 and Vκ3-20Jκ1, $V_H$ domains derived from the following human $V_H$ gene families expressed favorably: 1-2, 1-8, 1-24, 2-5, 3-7, 3-9, 3-11, 3-13, 3-15, 3-20, 3-23, 3-30, 3-33, 3-48, 4-31, 4-39, 4-59, 5-51, and 6-1. Thus, a mouse that is engineered to express a limited repertoire of human $V_L$ domains from one or both of Vκ1-39Jκ5 and Vκ3-20Jκ1 will generate a diverse population of somatically mutated human $V_H$ domains from a $V_H$ locus modified to replace mouse $V_H$ gene segments with human $V_H$ gene segments.

Mice genetically engineered to express reverse chimeric (human variable, mouse constant) immunoglobulin heavy chains associated with a single rearranged light chain (e.g., a Vκ1-39/J or a Vκ3-20/J), when immunized with an antigen of interest, generated B cells that comprised a diversity of human $V_H$ rearrangements and expressed a diversity of high-affinity antigen-specific antibodies with diverse properties with respect to their ability to block binding of the antigen to its ligand, and with respect to their ability to bind variants of the antigen (see Examples 5 through 10).

Thus, the mice and methods described herein are useful in making and selecting human immunoglobulin heavy chain variable domains, including somatically mutated human heavy chain variable domains, that result from a diversity of rearrangements, that exhibit a wide variety of affinities (including exhibiting a $K_D$ of about a nanomolar or less), a wide variety of specificities (including binding to different epitopes of the same antigen), and that associate and express with the same or substantially the same human immunoglobulin light chain variable region.

Fully Human Bispecific Antibodies Having a Common Light Chain

As a first step in various embodiments, the first and second nucleic acid sequences that each encode human heavy chain variable domains (and any additional nucleic acid sequences forming the bispecific antibody) are selected from parent monoclonal antibodies having desired characteristics such as, for example, capable of binding different epitopes (see FIGS. 7A and 7B), having different affinities, etc. Normally, the nucleic acid sequences encoding the human heavy chain variable domains are isolated from immunized mice, as described herein, to allow for fusing with human heavy chain constant regions to be suitable for human administration. Further modifications to the sequence(s) can be made by introducing mutations that add additional functionality to the bispecific antibody can be achieved, which include, for example, increasing serum half-life (e.g., see U.S. Pat. No. 7,217,797) and/or increasing antibody-dependent cell-mediated cytotoxicity (e.g., see U.S. Pat. No. 6,737,056). Introducing mutations into the constant regions of antibodies is known in the art. Additionally, part of the bispecific antibody can be made recombinantly in cell culture and other part(s) of the molecule can be made by those techniques mentioned above.

Several techniques for the producing antibodies have been described. For example, in various embodiments chimeric antibodies are produced in mice as described herein. Antibodies can be isolated directly from B cells of an immunized mouse (e.g., see U.S. 2007/0280945A1) and/or the B cells of the immunized mouse can be used to make hybridomas (Kohler and Milstein, 1975, *Nature* 256:495-497). DNA encoding the antibodies (human heavy and/or light chains) from mice as described herein is readily isolated and sequenced using conventional techniques. Hybridoma and/or B cells of derived from mice as described herein serve as a preferred source of such DNA. Once isolated, the DNA may be placed into expression vectors, which are then transfected into host cells that do not otherwise produce immunoglobulin protein, to obtain the synthesis of monoclonal antibodies in the recombinant host cells. The DNA also may be modified, for example, by substituting the coding sequence for human heavy and light chain constant domains in place of the murine sequences.

In various embodiments, following isolation of the DNA and selection of the first and second nucleic acid sequences that encode the first and second human heavy chain variable domains having the desired specificities/affinities, and a third nucleic acid sequence that encodes a human light chain domain (a germline rearranged sequence or a light chain sequence isolated from a mouse as described herein), the three nucleic acids sequences encoding the molecules are expressed to form the bispecific antibody using recombinant techniques which are widely available in the art. Often, the expression system of choice will involve a mammalian cell expression vector and host so that the bispecific antibody is appropriately glycosylated (e.g., in the case of bispecific antibodies comprising antibody domains which are glycosylated). However, the molecules can also be produced in the prokaryotic expression systems. Normally, the host cell will be transformed with DNA encoding both the first human heavy chain variable domain, the second human heavy chain variable domain, the human light chain domain on a single vector or independent vectors. However, it is possible to express the first human heavy chain variable domain, second human heavy chain variable domain, and human light chain domain (the bispecific antibody components) in independent expression systems and couple the expressed polypeptides in vitro. In various embodiments, the human light chain domain comprises a germline sequence. In various embodiments, the human light chain domain comprises no more than one, no more than two, no more than three, no more than four, or no more than five somatic hypermutations with the light chain variable sequence of the light chain domain.

In various embodiments, the nucleic acid(s) (e.g., cDNA or genomic DNA) encoding the two heavy chains and single human light chain is inserted into a replicable vector for further cloning (amplification of the DNA) and/or for expression. Many vectors are available, and generally include, but are not limited to, one or more of the following: a signal sequence, an origin of replication, one or more marker genes, an enhancer element, a promoter, and a transcription termination sequence. Each component may be selected individually or based on a host cell choice or other criteria determined experimentally. Several examples of each component are known in the art.

Expression and cloning vectors usually contain a promoter that is recognized by the host organism and is operably linked to the nucleic acid sequences that encode each or all the components of the bispecific antibody. A large number of promoters recognized by a variety of potential host cells are well known. These promoters are operably linked to bispecific antibody-encoding DNA by removing the promoter from the source DNA by restriction enzyme digestion and inserting the isolated promoter sequence into the vector.

Expression vectors used in eukaryotic host cells (yeast, fungi, insect, plant, animal, human, or nucleated cells from other multicellular organisms) may also contain sequences necessary for the termination of transcription and for stabilizing the mRNA. Such sequences are commonly available from the 5' and, occasionally 3', untranslated regions of eukaryotic or viral DNAs or cDNAs. These regions contain nucleotide segments transcribed as polyadenylated fragments in the untranslated portion of the mRNA encoding the bispecific antibody components. Suitable expression vectors for various embodiments include those that provide for the transient expression in mammalian cells of DNA encoding the bispecific antibody. In general, transient expression involves the use of an expression vector that is able to replicate efficiently in a host cell, such that the host cell accumulates many copies of the expression vector and, in turn, synthesizes high levels of a desired polypeptide encoded by the expression vector. Transient expression systems, comprising a suitable expression vector and a host cell, allow for the convenient positive identification of polypeptides encoded by cloned DNAs, as well as for the rapid screening of bispecific antibodies having desired binding specificities/affinities or the desired gel migration characteristics relative to the parental antibodies having homodimers of the first or second human heavy chain variable domains.

In various embodiments, once the DNA encoding the components of the bispecific antibody are assembled into the desired vector(s) as described above, they are introduced into a suitable host cell for expression and recovery. Transfecting host cells can be accomplished using standard techniques known in the art appropriate to the host cell selected (e.g., electroporation, nuclear microinjection, bacterial protoplast fusion with intact cells, or polycations, e.g., polybrene, polyornithine, etc.).

A host cell is chosen, in various embodiments, that best suits the expression vector containing the components and allows for the most efficient and favorable production of the bispecific antibody species. Exemplary host cells for expression include those of prokaryotes and eukaryotes (single-cell or multiple-cell), bacterial cells (e.g., strains of *E. coli, Bacillus* spp., *Streptomyces* spp., etc.), mycobacteria cells, fungal cells, yeast cells (e.g., *S. cerevisiae, S. pombe, P. pastoris, P. methanolica*, etc.), plant cells, insect cells (e.g., SF-9, SF-21, baculovirus-infected insect cells, *Trichoplusia ni*, etc.), non-human animal cells, human cells, or cell fusions such as, for example, hybridomas or quadromas. In various embodiments, the cell is a human, monkey, ape, hamster, rat, or mouse cell. In various embodiments, the cell is eukaryotic cell selected from CHO (e.g., CHO K1, DXB-11 CHO, Veggie-CHO), COS (e.g., COS-7), retinal cell, Vero, CV1, kidney (e.g., HEK293, 293 EBNA, MSR 293, MDCK, HaK, BHK), HeLa, HepG2, WI38, MRC 5, Colo205, HB 8065, HL-60, (e.g., BHK21), Jurkat, Daudi, A431 (epidermal), CV-1, U937, 3T3, L cell, C127 cell, SP2/0, NS-0, MMT 060562, Sertoli cell, BRL 3A cell, HT1080 cell, myeloma cell, tumor cell, and a cell line derived from an aforementioned cell. In various embodiments, the cell comprises one or more viral genes, e.g. a retinal cell that expresses a viral gene (e.g., a PER.C6™ cell).

Mammalian host cells used to produce the bispecific antibody may be cultured in a variety of media. Commercially available media such as Ham's F10 (Sigma), Minimal Essential Medium ((MEM), Sigma), RPMI-1640 (Sigma), and Dulbeccols Modified Eagle's Medium ((DMEM), Sigma) are suitable for culturing the host cells. Media may be supplemented as necessary with hormones and/or other growth factors (such as insulin, transferrin, or epidermal growth factor), salts (such as sodium chloride, calcium, magnesium, and phosphate), buffers (such as HEPES), nucleosides (such as adenosine and thymidine), antibiotics (such as GENTAMYCIN™), trace elements (defined as inorganic compounds usually present at final concentrations in the micromolar range), and glucose or an equivalent energy source. Any other supplements may also be included at appropriate concentrations as known to those skilled in the art. The culture conditions, such as temperature, pH, and the like, are, in various embodiments, those previously used with the host cell selected for expression, and will be apparent to those skilled in the art.

The bispecific antibody is in various embodiments recovered from the culture medium as a secreted polypeptide, although it also may be recovered from host cell lysate when directly produced without a secretory signal. If the bispecific antibody is membrane-bound, it can be released from the membrane using a suitable detergent solution (e.g., Triton-X 100). Preferably, the bispecific antibodies described herein involves the use of a first immunoglobulin $C_H3$ domain and a second immunoglobulin $C_H3$ domain, wherein the first and second immunoglobulin $C_H3$ domains differ from one another by at least one amino acid, and wherein at least one amino acid difference reduces binding of the bispecific antibody to Protein A as compared to a bi-specific antibody lacking the amino acid difference (see U.S. 2010/0331527A1; herein incorporated by reference). In one embodiment, the first immunoglobulin $C_H3$ domain binds Protein A and the second immunoglobulin $C_H3$ domain contains a mutation that reduces or abolishes Protein A binding such as an H95R modification (by IMGT exon numbering; H435R by EU numbering). The second $C_H3$ may further comprise a Y96F modification (by IMGT; Y436F by EU). Further modifications that may be found within the second $C_H3$ include: D16E, L18M, N44S, K52N, V57M, and V821 (by IMGT; D356E, L358M, N384S, K392N, V397M, and V422I by EU) in the case of IgG1 antibodies; N44S, K52N, and V821 (IMGT; N384S, K392N, and V422I by EU) in the case of IgG2 antibodies; and Q15R, N44S, K52N, V57M, R69K, E79Q, and V821 (by IMGT; Q355R, N384S, K392N, V397M, R409K, E419Q, and V422I by EU) in the case of IgG4 antibodies. Variations on the bi-specific antibody format described above are contemplated within the scope of the present invention.

Because of the dual nature of bispecific antibodies (i.e., may be specific for different epitopes of one polypeptide or may contain antigen-binding domains specific for more than one target polypeptide, see FIG. 7B; see also, e.g., Tutt et al., 1991, *J. Immunol.* 147:60-69; Kufer et al., 2004, Trends Biotechnol. 22:238-244), they offer many useful advantages for therapeutic application. For example, the bispecific antibodies can be used for redirected cytotoxicity (e.g., to kill tumor cells), as a vaccine adjuvant, for delivering thrombolytic agents to clots, for converting enzyme activated prodrugs at a target site (e.g., a tumor), for treating infectious diseases, targeting immune complexes to cell surface receptors, or for delivering immunotoxins to tumor cells.

The bispecific antibodies described herein can also be used in several therapeutic and non-therapeutic and/or diagnostic assay methods, such as, enzyme immunoassays, two-site immunoassays, in vitro or in vivo immunodiagnosis of various diseases (e.g., cancer), competitive binding assays, direct and indirect sandwich assays, and immunoprecipitation assays. Other uses for the bispecific antibodies will be apparent to those skilled in the art.

The following examples are provided so as to describe to those of ordinary skill in the art how to make and use methods and compositions of the invention, and are not intended to limit the scope of what the inventors regard as their invention. Efforts have been made to ensure accuracy with respect to numbers used (e.g., amounts, temperature, etc.) but some experimental errors and deviations should be accounted for. Unless indicated otherwise, parts are parts by weight, molecular weight is average molecular weight, temperature is indicated in Celsius, and pressure is at or near atmospheric.

EXAMPLES

The following examples are provided so as to describe to those of ordinary skill in the art how to make and use methods and compositions of the invention, and are not intended to limit the scope of what the inventors regard as their invention. Efforts have been made to ensure accuracy with respect to numbers used (e.g., amounts, temperature, etc.) but some experimental errors and deviations should be accounted for. Unless indicated otherwise, temperature is indicated in Celsius, pressure is at or near atmospheric, parts are by parts by weight, and molecular weight is average molecular weight.

Example 1. Identification of Human $V_H$ Regions that Associate with Selected Human $V_L$ Regions An in vitro expression system was constructed to determine if a single rearranged human germline light chain could be co-expressed with human heavy chains from antigen specific human antibodies.

Methods for generating human antibodies in genetically modified mice are known (see e.g., U.S. Pat. No. 6,596,541, Regeneron Pharmaceuticals, VELOCIMMUNE®). The VELOCIMMUNE® technology involves generation of a genetically modified mouse having a genome comprising human heavy and light chain variable regions operably linked to endogenous mouse constant region loci such that the mouse produces an antibody comprising a human variable region and a mouse constant region in response to antigenic stimulation. The DNA encoding the variable regions of the heavy and light chains of the antibodies produced from a VELOCIMMUNE® mouse are fully human. Initially, high affinity chimeric antibodies are isolated having a human variable region and a mouse constant region. As described below, the antibodies are characterized and selected for desirable characteristics, including affinity, selectivity, epitope, etc. The mouse constant regions are replaced with a desired human constant region to generate a fully human antibody containing a non-IgM isotype, for example, wild type or modified IgG1, IgG2, IgG3 or IgG4. While the constant region selected may vary according to specific use, high affinity antigen-binding and target specificity characteristics reside in the variable region.

A VELOCIMMUNE® mouse was immunized with a growth factor that promotes angiogenesis (Antigen C) and antigen-specific human antibodies were isolated and sequenced for V gene usage using standard techniques recognized in the art. Selected antibodies were cloned onto human heavy and light chain constant regions and 69 heavy chains were selected for pairing with one of three human light chains: (1) the cognate κ light chain linked to a human κ constant region, (2) a rearranged human germline Vκ1-39Jκ5 linked to a human κ constant region, or (3) a rearranged human germline Vκ3-20Jκ1 linked to a human κ constant region. Each heavy chain and light chain pair was co-transfected in CHO-K1 cells using standard techniques. Presence of antibody in the supernatant was detected by anti-human IgG in an ELISA assay. Antibody titer (ng/ml) was determined for each heavy chain/light chain pair and titers with the different rearranged germline light chains were compared to the titers obtained with the parental antibody molecule (i.e., heavy chain paired with cognate light chain) and percent of native titer was calculated (Table 1). $V_H$: Heavy chain variable gene. ND: no expression detected under current experimental conditions.

TABLE 1

| | Antibody Titer (ng/mL) | | | Percent of Native Titer | |
|---|---|---|---|---|---|
| $V_H$ | Cognate LC | Vκ1-39Jκ5 | Vκ3-20Jκ1 | Vκ1-39Jκ5 | Vκ3-20Jκ1 |
| 3-15 | 63 | 23 | 11 | 36.2 | 17.5 |
| 1-2 | 103 | 53 | ND | 51.1 | — |
| 3-23 | 83 | 60 | 23 | 72.0 | 27.5 |
| 3-33 | 15 | 77 | ND | 499.4 | — |
| 4-31 | 22 | 69 | 17 | 309.4 | 76.7 |
| 3-7 | 53 | 35 | 28 | 65.2 | 53.1 |
| — | 22 | 32 | 19 | 148.8 | 89.3 |
| 1-24 | 3 | 13 | ND | 455.2 | — |
| 3-33 | 1 | 47 | ND | 5266.7 | — |
| 3-33 | 58 | 37 | ND | 63.1 | — |
| — | 110 | 67 | 18 | 60.6 | 16.5 |
| 3-23 | 127 | 123 | 21 | 96.5 | 16.3 |
| 3-33 | 28 | 16 | 2 | 57.7 | 7.1 |
| 3-23 | 32 | 50 | 38 | 157.1 | 119.4 |
| — | 18 | 45 | 18 | 254.3 | 101.7 |
| 3-9 | 1 | 30 | 23 | 2508.3 | 1900.0 |
| 3-11 | 12 | 26 | 6 | 225.9 | 48.3 |
| 1-8 | 16 | ND | 13 | — | 81.8 |
| 3-33 | 54 | 81 | 10 | 150.7 | 19.1 |
| — | 34 | 9 | ND | 25.9 | — |
| 3-20 | 7 | 14 | 54 | 203.0 | 809.0 |
| 3-33 | 19 | 38 | ND | 200.5 | — |
| 3-11 | 48 | ND | 203 | — | 423.6 |
| — | 11 | 23 | 8 | 212.7 | 74.5 |
| 3-33 | 168 | 138 | 182 | 82.0 | 108.2 |
| 3-20 | 117 | 67 | 100 | 57.5 | 86.1 |
| 3-23 | 86 | 61 | 132 | 70.7 | 154.1 |
| 3-33 | 20 | 12 | 33 | 60.9 | 165.3 |
| 4-31 | 69 | 92 | 52 | 133.8 | 75.0 |
| 3-23 | 87 | 78 | 62 | 89.5 | 71.2 |
| 1-2 | 31 | 82 | 51 | 263.0 | 164.6 |
| 3-23 | 53 | 93 | 151 | 175.4 | 285.4 |
| — | 11 | 8 | 17 | 75.7 | 151.4 |
| 3-33 | 114 | 36 | 27 | 31.6 | 23.4 |
| 3-15 | 73 | 39 | 44 | 53.7 | 59.6 |
| 3-33 | 1 | 34 | 16 | 5600.0 | 2683.3 |
| 3-9 | 58 | 112 | 57 | 192.9 | 97.6 |
| 3-33 | 67 | 20 | 105 | 30.1 | 157.0 |
| 3-33 | 34 | 21 | 24 | 62.7 | 70.4 |

TABLE 1-continued

| | Antibody Titer (ng/mL) | | | Percent of Native Titer | |
|---|---|---|---|---|---|
| $V_H$ | Cognate LC | Vκ1-39Jκ5 | Vκ3-20Jκ1 | Vκ1-39Jκ5 | Vκ3-20Jκ1 |
| 3-20 | 10 | 49 | 91 | 478.4 | 888.2 |
| 3-33 | 66 | 32 | 25 | 48.6 | 38.2 |
| 3-23 | 17 | 59 | 56 | 342.7 | 329.8 |
| — | 58 | 108 | 19 | 184.4 | 32.9 |
| — | 68 | 54 | 20 | 79.4 | 29.9 |
| 3-33 | 42 | 35 | 32 | 83.3 | 75.4 |
| — | 29 | 19 | 13 | 67.1 | 43.9 |
| 3-9 | 24 | 34 | 29 | 137.3 | 118.4 |
| 3-30/33 | 17 | 33 | 7 | 195.2 | 43.1 |
| 3-7 | 25 | 70 | 74 | 284.6 | 301.6 |
| 3-33 | 87 | 127 | ND | 145.1 | — |
| 6-1 | 28 | 56 | ND | 201.8 | — |
| 3-33 | 56 | 39 | 20 | 69.9 | 36.1 |
| 3-33 | 10 | 53 | 1 | 520.6 | 6.9 |
| 3-33 | 20 | 67 | 10 | 337.2 | 52.3 |
| 3-33 | 11 | 36 | 18 | 316.8 | 158.4 |
| 3-23 | 12 | 42 | 32 | 356.8 | 272.9 |
| 3-33 | 66 | 95 | 15 | 143.6 | 22.5 |
| 3-15 | 55 | 68 | ND | 123.1 | — |
| — | 32 | 68 | 3 | 210.9 | 10.6 |
| 1-8 | 28 | 48 | ND | 170.9 | — |
| 3-33 | 124 | 192 | 21 | 154.3 | 17.0 |
| 3-33 | 0 | 113 | ND | 56550.0 | — |
| 3-33 | 10 | 157 | 1 | 1505.8 | 12.5 |
| 3-33 | 6 | 86 | 15 | 1385.5 | 243.5 |
| 3-23 | 70 | 115 | 22 | 163.5 | 31.0 |
| 3-7 | 71 | 117 | 21 | 164.6 | 29.6 |
| 3-33 | 82 | 100 | 47 | 122.7 | 57.1 |
| 3-7 | 124 | 161 | 41 | 130.0 | 33.5 |

In a similar experiment, VELOCIMMUNE® mice were immunized with several different antigens and selected heavy chains of antigen specific human antibodies were tested for their ability to pair with different rearranged human germline light chains (as described above). The antigens used in this experiment included an enzyme involved in cholesterol homeostasis (Antigen A), a serum hormone involved in regulating glucose homeostasis (Antigen B), a growth factor that promotes angiogenesis (Antigen C) and a cell-surface receptor (Antigen D). Antigen specific antibodies were isolated from mice of each immunization group and the heavy chain and light chain variable regions were cloned and sequenced. From the sequence of the heavy and light chains, V gene usage was determined and selected heavy chains were paired with either their cognate light chain or a rearranged human germline Vκ1-39Jκ5 region. Each heavy/light chain pair was co-transfected in CHO-K1 cells and the presence of antibody in the supernatant was detected by anti-human IgG in an ELISA assay. Antibody titer (μg/ml) was determined for each heavy chain/light chain pairing and titers with the different rearranged human germline light chains were compared to the titers obtained with the parental antibody molecule (i.e., heavy chain paired with cognate light chain) and percent of native titer was calculated (Table 2). $V_H$: Heavy chain variable gene. Vκ: κ light chain variable gene. ND: no expression detected under current experimental conditions.

TABLE 2

| | | | | Titer (μg/ml) | | | |
|---|---|---|---|---|---|---|---|
| Antigen | Anti-body | $V_H$ | Vκ | $V_H$ Alone | $V_H$ + Vκ | $V_H$ + Vκ1-39Jκ5 | Percent of Native Titer |
| A | 320 | 1-18 | 2-30 | 0.3 | 3.1 | 2.0 | 66 |
| | 321 | 2-5 | 2-28 | 0.4 | 0.4 | 1.9 | 448 |
| | 334 | 2-5 | 2-28 | 0.4 | 2.7 | 2.0 | 73 |
| | 313 | 3-13 | 3-15 | 0.5 | 0.7 | 4.5 | 670 |
| | 316 | 3-23 | 4-1 | 0.3 | 0.2 | 4.1 | 2174 |
| | 315 | 3-30 | 4-1 | 0.3 | 0.2 | 3.2 | 1327 |
| | 318 | 4-59 | 1-17 | 0.3 | 4.6 | 4.0 | 86 |
| B | 257 | 3-13 | 1-5 | 0.4 | 3.1 | 3.2 | 104 |
| | 283 | 3-13 | 1-5 | 0.4 | 5.4 | 3.7 | 69 |
| | 637 | 3-13 | 1-5 | 0.4 | 4.3 | 3.0 | 70 |
| | 638 | 3-13 | 1-5 | 0.4 | 4.1 | 3.3 | 82 |
| | 624 | 3-23 | 1-17 | 0.3 | 5.0 | 3.9 | 79 |
| | 284 | 3-30 | 1-17 | 0.3 | 4.6 | 3.4 | 75 |
| | 653 | 3-33 | 1-17 | 0.3 | 4.3 | 0.3 | 7 |
| | 268 | 4-34 | 1-27 | 0.3 | 5.5 | 3.8 | 69 |
| | 633 | 4-34 | 1-27 | 0.6 | 6.9 | 3.0 | 44 |
| C | 730 | 3-7 | 1-5 | 0.3 | 1.1 | 2.8 | 249 |
| | 728 | 3-7 | 1-5 | 0.3 | 2.0 | 3.2 | 157 |
| | 691 | 3-9 | 3-20 | 0.3 | 2.8 | 3.1 | 109 |
| | 749 | 3-33 | 3-15 | 0.3 | 3.8 | 2.3 | 62 |
| | 750 | 3-33 | 1-16 | 0.3 | 3.0 | 2.8 | 92 |
| | 724 | 3-33 | 1-17 | 0.3 | 2.3 | 3.4 | 151 |
| | 706 | 3-33 | 1-16 | 0.3 | 3.6 | 3.0 | 84 |
| | 744 | 1-18 | 1-12 | 0.4 | 5.1 | 3.0 | 59 |
| | 696 | 3-11 | 1-16 | 0.4 | 3.0 | 2.9 | 97 |
| | 685 | 3-13 | 3-20 | 0.3 | 0.5 | 3.4 | 734 |
| | 732 | 3-15 | 1-17 | 0.3 | 4.5 | 3.2 | 72 |
| | 694 | 3-15 | 1-5 | 0.4 | 5.2 | 2.9 | 55 |
| | 743 | 3-23 | 1-12 | 0.3 | 3.2 | 0.3 | 10 |
| | 742 | 3-23 | 2-28 | 0.4 | 4.2 | 3.1 | 74 |
| | 693 | 3-23 | 1-12 | 0.5 | 4.2 | 4.0 | 94 |
| D | 136 | 3-23 | 2-28 | 0.4 | 5.0 | 2.7 | 55 |
| | 155 | 3-30 | 1-16 | 0.4 | 1.0 | 2.2 | 221 |
| | 163 | 3-30 | 1-16 | 0.3 | 0.6 | 3.0 | 506 |
| | 171 | 3-30 | 1-16 | 0.3 | 1.0 | 2.8 | 295 |
| | 145 | 3-43 | 1-5 | 0.4 | 4.4 | 2.9 | 65 |
| | 49 | 3-48 | 3-11 | 0.3 | 1.7 | 2.6 | 155 |
| | 51 | 3-48 | 1-39 | 0.1 | 1.9 | 0.1 | 4 |
| | 159 | 3-7 | 6-21 | 0.4 | 3.9 | 3.6 | 92 |
| | 169 | 3-7 | 6-21 | 0.3 | 1.3 | 3.1 | 235 |
| | 134 | 3-9 | 1-5 | 0.4 | 5.0 | 2.9 | 58 |
| | 141 | 4-31 | 1-33 | 2.4 | 4.2 | 2.6 | 63 |
| | 142 | 4-31 | 1-33 | 0.4 | 4.2 | 2.8 | 67 |

The results obtained from these experiments demonstrate that somatically mutated, high affinity heavy chains from different gene families are able to pair with rearranged human germline Vκ1-39Jκ5 and Vκ3-20Jκ1 regions and be secreted from the cell as a normal antibody molecule. As shown in Table 1, antibody titer was increased for about 61% (42 of 69) heavy chains when paired with the rearranged human Vκ1-39Jκ5 light chain and about 29% (20 of 69) heavy chains when paired with the rearranged human Vκ3-20Jκ1 light chain as compared to the cognate light chain of the parental antibody. For about 20% (14 of 69) of the heavy chains, both rearranged human germline light chains conferred an increase in expression as compared to the cognate light chain of the parental antibody. As shown in Table 2, the rearranged human germline Vκ1-39Jκ5 region conferred an increase in expression of several heavy chains specific for a range of different classes of antigens as compared to the cognate light chain for the parental antibodies. Antibody titer was increased by more than two-fold for about 35% (15/43) of the heavy chains as compared to the cognate light chain of the parental antibodies. For two heavy chains (315 and 316), the increase was greater than ten-fold as compared to the parental antibody. Within all the heavy chains that showed increase expression relative to the cognate light chain of the parental antibody, family three ($V_H$3) heavy chains are over represented in comparison to other heavy chain variable region gene families. This demonstrates a favorable relationship of human $V_H3$ heavy chains to pair with rearranged human germline Vκ1-39Jκ5 and Vκ3-20Jκ1 light chains.

Example 2. Generation of a Rearranged Human Germline Light Chain Locus

Various rearranged human germline light chain targeting vectors were made using VELOCIGENE® technology (see, e.g., U.S. Pat. No. 6,586,251 and Valenzuela et al. (2003) High-throughput engineering of the mouse genome coupled with high-resolution expression analysis, Nature Biotech. 21(6): 652-659) to modify mouse genomic Bacterial Artificial Chromosome (BAC) clones 302g12 and 254m04 (Invitrogen). Using these two BAC clones, genomic constructs were engineered to contain a single rearranged human germline light chain region and inserted into an endogenous κ light chain locus that was previously modified to delete the endogenous κ variable and joining gene segments.

Construction of Rearranged Human Germline Light Chain Targeting Vectors. Three different rearranged human germline light chain regions were made using standard molecular biology techniques recognized in the art. The human variable gene segments used for constructing these three regions included rearranged human Vκ1-39Jκ5 sequence, a rearranged human Vκ3-20Jκ1 sequence and a rearranged human VpreBJX5 sequence.

A DNA segment containing exon 1 (encoding the leader peptide) and intron 1 of the mouse Vκ3-7 gene was made by de novo DNA synthesis (Integrated DNA Technologies). Part of the 5' untranslated region up to a naturally occurring BlpI restriction enzyme site was included. Exons of human Vκ1-39 and Vκ3-20 genes were PCR amplified from human genomic BAC libraries. The forward primers had a 5' extension containing the splice acceptor site of intron 1 of the mouse Vκ3-7 gene. The reverse primer used for PCR of the human Vκ1-39 sequence included an extension encoding human Jκ S, whereas the reverse primer used for PCR of the human Vκ3-20 sequence included an extension encoding human Jκ1. The human VpreBJX5 sequence was made by de novo DNA synthesis (Integrated DNA Technologies). A portion of the human Jκ-Cκ intron including the splice donor site was PCR amplified from plasmid pBS-296-HA18-PIScel. The forward PCR primer included an extension encoding part of either a human Jκ S, Jκ1, or JXS sequence. The reverse primer included a PI-Scel site, which was previously engineered into the intron.

The mouse Vκ3-7 exon1/intron 1, human variable light chain exons, and human Jκ-Cκ intron fragments were sewn together by overlap extension PCR, digested with BlpI and PI-Scel, and ligated into plasmid pBS-296-HA18-PIScel, which contained the promoter from the human Vκ3-15 variable gene segment. A loxed hygromycin cassette within plasmid pBS-296-HA18-PIScel was replaced with a FRTed hygromycin cassette flanked by NotI and AscI sites. The NotI/PI-Scel fragment of this plasmid was ligated into modified mouse BAC 254m04, which contained part of the mouse Jκ-Cκ intron, the mouse Cκ exon, and about 75 kb of genomic sequence downstream of the mouse κ locus, which provided a 3' homology arm for homologous recombination in mouse ES cells. The NotI/AscI fragment of this BAC was then ligated into modified mouse BAC 302g12, which contained a FRTed neomycin cassette and about 23 kb of genomic sequence upstream of the endogenous κ locus for homologous recombination in mouse ES cells.

Figure 1:
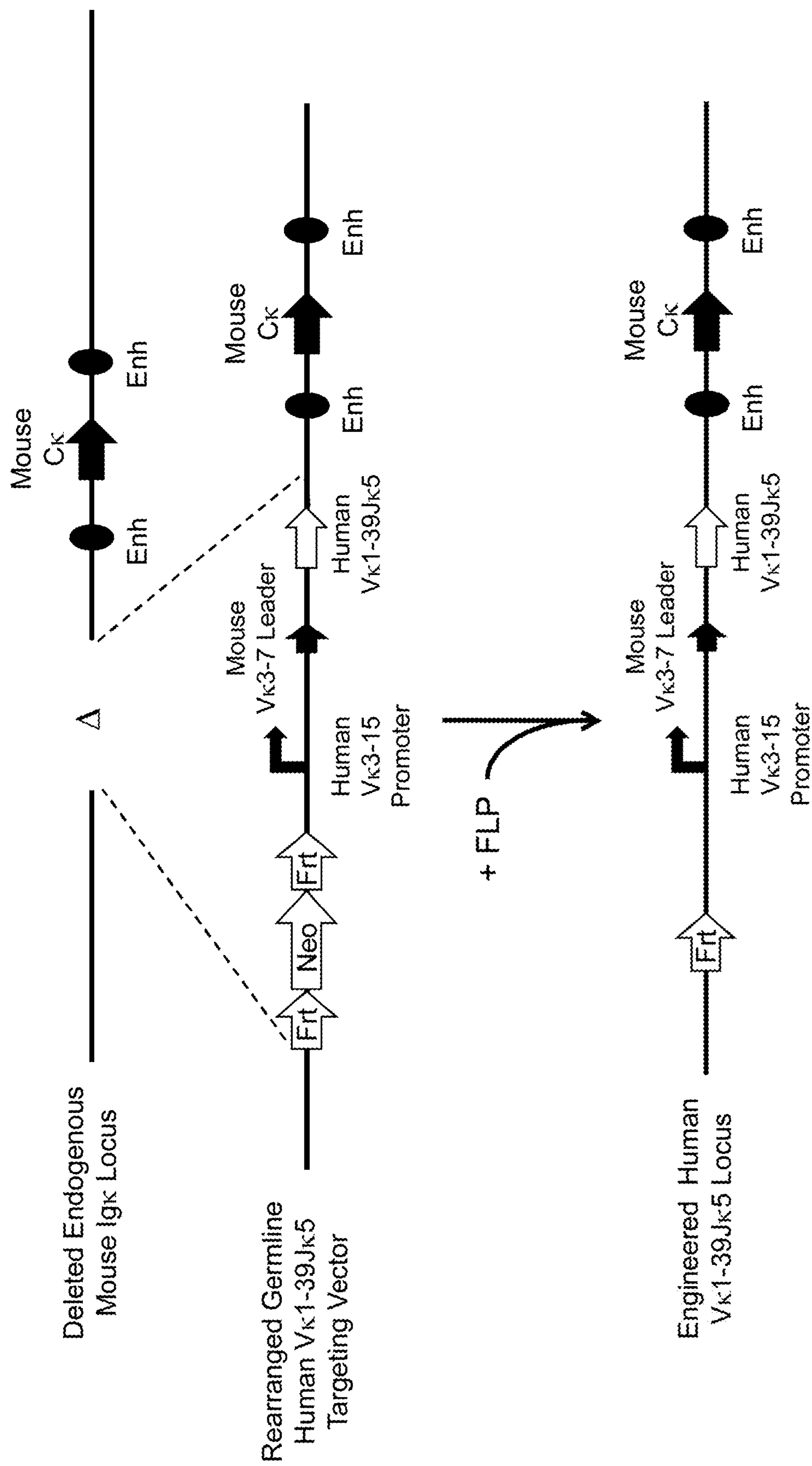
FIG. 1 illustrates a targeting strategy for replacing endogenous mouse immunoglobulin light chain variable region gene segments with a human Vκ1-39Jκ5 gene region.

Rearranged Human Germline Vic1-39,1K5 Targeting Vector (FIG. 1). Restriction enzyme sites were introduced at the 5' and 3' ends of an engineered light chain insert for cloning into a targeting vector: an AscI site at the 5' end and a PI-Scel site at the 3' end. Within the 5' AscI site and the 3' PI-Scel site the targeting construct from 5' to 3' included a 5' homology arm containing sequence 5' to the endogenous mouse κ light chain locus obtained from mouse BAC clone 302g12, a FRTed neomycin resistance gene, an genomic sequence including the human Vκ3-15 promoter, a leader sequence of the mouse Vκ3-7 variable gene segment, a intron sequence of the mouse Vκ3-7 variable gene segment, an open reading frame of a rearranged human germline Vκ1-39Jκ5 region, a genomic sequence containing a portion of the human Jκ-Cκ intron, and a 3' homology arm containing sequence 3' of the endogenous mouse Jκ5 gene segment obtained from mouse BAC clone 254m04 (FIG. 1, middle). Genes and/or sequences upstream of the endogenous mouse κ light chain locus and downstream of the most 3' Jκ gene segment (e.g., the endogenous 3' enhancer) were unmodified by the targeting construct (see FIG. 1). The sequence of the engineered human Vκ1-39Jκ5 locus is shown in SEQ ID NO: 1.

Targeted insertion of the rearranged human germline Vκ1-39Jκ5 region into BAC DNA was confirmed by polymerase chain reaction (PCR) using primers located at sequences within the rearranged human germline light chain region. Briefly, the intron sequence 3' to the mouse Vκ3-7 leader sequence was confirmed with primers ULC-m1F (AGGTGAGGGT ACAGATAAGT GTTATGAG; SEQ ID NO: 2) and ULC-ml R (TGACAAATGC CCTAATTATA GTGATCA; SEQ ID NO: 3). The open reading frame of the rearranged human germline Vκ1-39Jκ5 region was confirmed with primers 1633-h2F (GGGCAAGTCA GAGCATTAGC A; SEQ ID NO: 4) and 1633-h2R (TGCAAACTGG ATGCAGCATA G; SEQ ID NO: 5). The neomycin cassette was confirmed with primers neoF (GGTGGAGAGG CTATTCGGC; SEQ ID NO: 6) and neoR (GAACACGGCG GCATCAG; SEQ ID NO: 7). Targeted BAC DNA was then used to electroporate mouse ES cells to created modified ES cells for generating chimeric mice that express a rearranged human germline Vκ1-39Jκ5 region.

Positive ES cell clones were confirmed by TAQMAN™ screening and karyotyping using probes specific for the engineered Vκ1-39Jκ5 light chain region inserted into the endogenous locus. Briefly, probe neoP (TGGGCACAAC AGACAATCGG CTG; SEQ ID NO: 8) which binds within the neomycin marker gene, probe ULC-m1P (CCATTATGAT GCTCCATGCC TCTCTGTTC; SEQ ID NO: 9) which binds within the intron sequence 3' to the mouse Vκ3-7 leader sequence, and probe 1633h2P (ATCAGCAGAA ACCAGGGAAA GCCCCT; SEQ ID NO: 10) which binds within the rearranged human germline Vκ1-39Jκ5 open reading frame. Positive ES cell clones were then used to implant female mice to give rise to a litter of pups expressing the germline Vκ1-39Jκ5 light chain region.

Alternatively, ES cells bearing the rearranged human germline Vκ1-39Jκ5 light chain region are transfected with a construct that expresses FLP in order to remove the FRTed neomycin cassette introduced by the targeting construct. Optionally, the neomycin cassette is removed by breeding to mice that express FLP recombinase (e.g., U.S. Pat. No. 6,774,279). Optionally, the neomycin cassette is retained in the mice.

Figure 2:
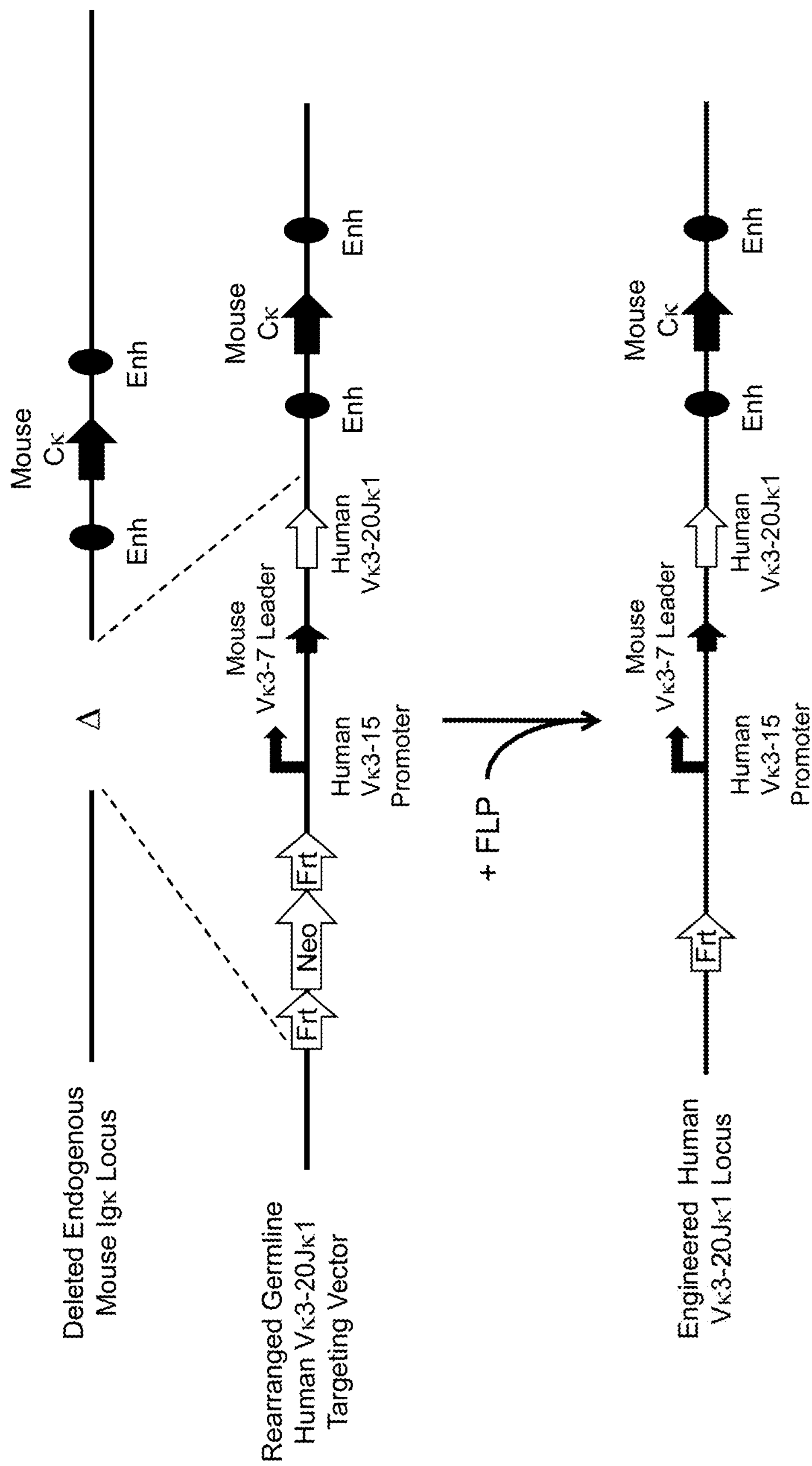
FIG. 2 illustrates a targeting strategy for replacing endogenous mouse immunoglobulin light chain variable region gene segments with a human Vκ3-20Jκ1 gene region.

Rearranged Human Germline W3-20,10 Targeting Vector (FIG. 2). In a similar fashion, an engineered light chain locus expressing a rearranged human germline Vκ3-20Jκ1 region was made using a targeting construct including, from 5' to 3', a 5' homology arm containing sequence 5' to the endogenous mouse κ light chain locus obtained from mouse BAC clone 302g12, a FRTed neomycin resistance gene, a genomic sequence including the human Vκ3-15 promoter, a leader sequence of the mouse Vκ3-7 variable gene segment, an intron sequence of the mouse Vκ3-7 variable gene segment, an open reading frame of a rearranged human germline Vκ3-20Jκ1 region, a genomic sequence containing a portion of the human Jκ-Cκ intron, and a 3' homology arm containing sequence 3' of the endogenous mouse Jκ5 gene segment obtained from mouse BAC clone 254m04 (FIG. 2, middle). The sequence of the engineered human Vκ3-20Jκ1 locus is shown in SEQ ID NO: 11.

Targeted insertion of the rearranged human germline Vκ3-20Jκ1 region into BAC DNA was confirmed by polymerase chain reaction (PCR) using primers located at sequences within the rearranged human germline Vκ3-20Jκ1 light chain region. Briefly, the intron sequence 3' to the mouse Vκ3-7 leader sequence was confirmed with primers ULC-ml F (SEQ ID NO: 2) and ULC-m1R (SEQ ID NO: 3). The open reading frame of the rearranged human germline Vκ3-20Jκ1 region was confirmed with primers 1635-h2F (TCCAGGCACC CTGTCTTTG; SEQ ID NO: 12) and 1635-h2R (AAGTAGCTGC TGCTAACACT CTGACT; SEQ ID NO: 13). The neomycin cassette was confirmed with primers neoF (SEQ ID NO: 6) and neoR (SEQ ID NO: 7). Targeted BAC DNA was then used to electroporate mouse ES cells to created modified ES cells for generating chimeric mice that express the rearranged human germline Vκ3-20Jκ1 light chain.

Positive ES cell clones were confirmed by TAQMAN™ screening and karyotyping using probes specific for the engineered Vκ3-20Jκ1 light chain region inserted into the endogenous κ light chain locus. Briefly, probe neoP (SEQ ID NO: 8) which binds within the neomycin marker gene, probe ULC-ml P (SEQ ID NO: 9) which binds within the mouse Vκ3-7 leader sequence, and probe 1635h2P (AAAGAGCCAC CCTCTCCTGC AGGG; SEQ ID NO: 14) which binds within the human Vκ3-20Jκ1 open reading frame. Positive ES cell clones were then used to implant female mice. A litter of pups expressing the human germline Vκ3-20Jκ1 light chain region.

Alternatively, ES cells bearing human germline Vκ3-20Jκ1 light chain region can be transfected with a construct that expresses FLP in order to remove the FRTed neomycin cassette introduced by the targeting construct. Optionally, the neomycin cassette may be removed by breeding to mice that express FLP recombinase (e.g., U.S. Pat. No. 6,774,279). Optionally, the neomycin cassette is retained in the mice.

Figure 3:
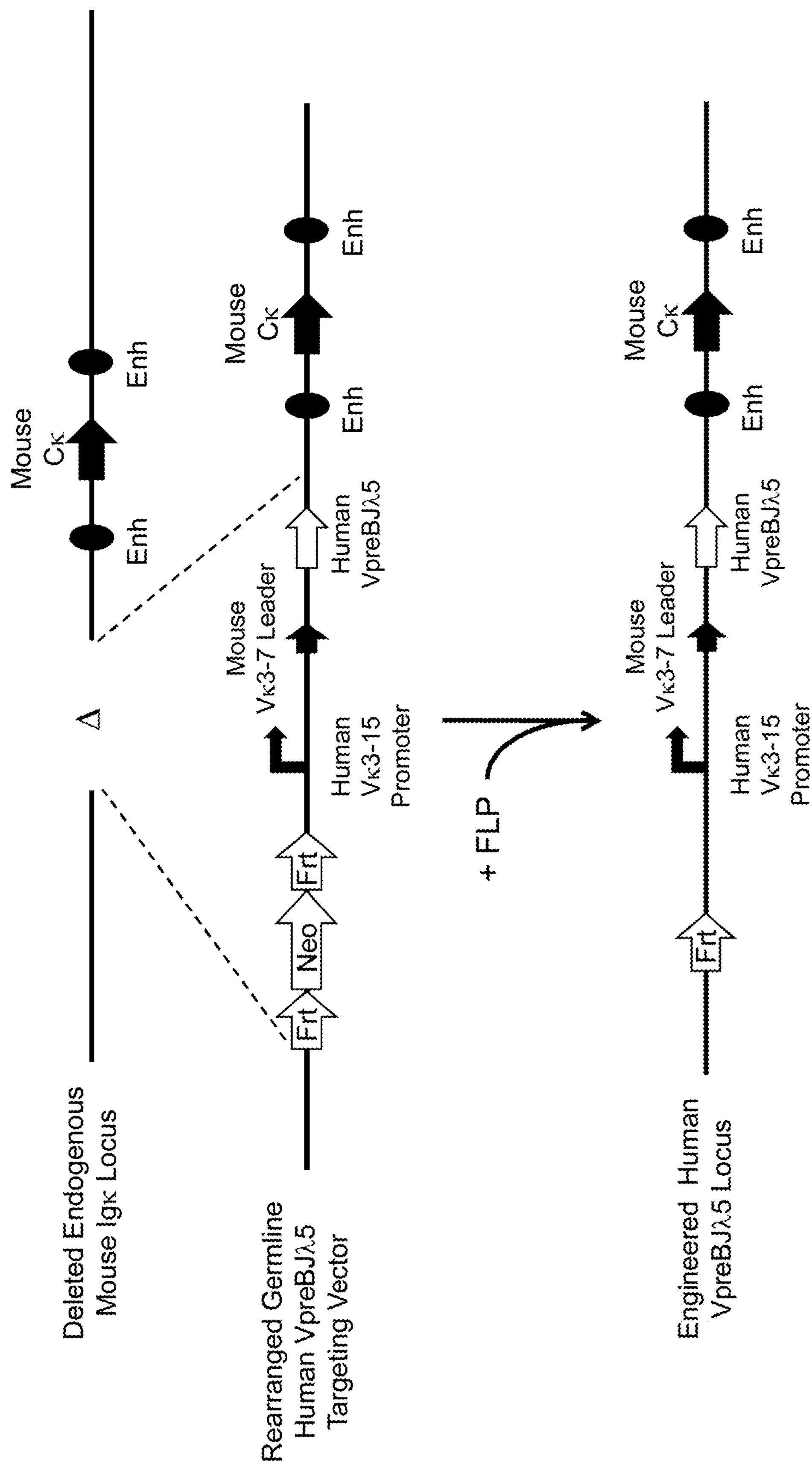
FIG. 3 illustrates a targeting strategy for replacing endogenous mouse immunoglobulin light chain variable region gene segments with a human VpreB/Jλ5 gene region.

Rearranged Human Germline VpreBA5 Targeting Vector (FIG. 3). In a similar fashion, an engineered light chain locus expressing a rearranged human germline VpreBJX5 region was made using a targeting construct including, from 5' to 3', a 5' homology arm containing sequence 5' to the endogenous mouse κ light chain locus obtained from mouse BAC clone 302g12, a FRTed neomycin resistance gene, an genomic sequence including the human Vκ3-15 promoter, a leader sequence of the mouse Vκ3-7 variable gene segment, an intron sequence of the mouse Vκ3-7 variable gene segment, an open reading frame of a rearranged human germline VpreBJX5 region, a genomic sequence containing a portion of the human Jκ-Cκ intron, and a 3' homology arm containing sequence 3' of the endogenous mouse Jκ5 gene segment obtained from mouse BAC clone 254m04 (FIG. 3, middle). The sequence of the engineered human VpreBJX5 locus is shown in SEQ ID NO: 15.

Targeted insertion of the rearranged human germline VpreBJX5 region into BAC DNA was confirmed by polymerase chain reaction (PCR) using primers located at sequences within the rearranged human germline VpreBJX5 region light chain region. Briefly, the intron sequence 3' to the mouse Vκ3-7 leader sequence was confirmed with primers ULC-ml F (SEQ ID NO: 2) and ULC-m1R (SEQ ID NO: 3). The open reading frame of the rearranged human germline VpreBJX5 region was confirmed with primers 1616-h1F (TGTCCTCGGC CCTTGGA; SEQ ID NO: 16) and 1616-h1R (CCGATGTCAT GGTCGTTCCT; SEQ ID NO: 17). The neomycin cassette was confirmed with primers neoF (SEQ ID NO: 6) and neoR (SEQ ID NO: 7). Targeted BAC DNA was then used to electroporate mouse ES cells to created modified ES cells for generating chimeric mice that express the rearranged human germline VpreBJX5 light chain.

Positive ES cell clones are confirmed by TAQMAN™ screening and karyotyping using probes specific for the engineered VpreBJX5 light chain region inserted into the endogenous κ light chain locus. Briefly, probe neoP (SEQ ID NO:8), which binds within the neomycin marker gene, probe ULC-m1P (SEQ ID NO: 9), which binds within the mouse IgVκ3-7 leader sequence, and probe 1616h1P (ACAATCCGCC TCACCTGCAC CCT; SEQ ID NO: 18) which binds within the human VpreBJX5 open reading frame. Positive ES cell clones are then used to implant female mice to give rise to a litter of pups expressing a germline light chain region.

Alternatively, ES cells bearing the rearranged human germline VpreBJX5 light chain region are transfected with a construct that expresses FLP in order to remove the FRTed neomycin cassette introduced by the targeting construct. Optionally, the neomycin cassette is removed by breeding to mice that express FLP recombinase (e.g., U.S. Pat. No. 6,774,279). Optionally, the neomycin cassette is retained in the mice.

Example 3. Generation of Mice Expressing a Single Rearranged Human Light Chain Targeted ES cells described above were used as donor ES cells and introduced into an 8-cell stage mouse embryo by the VELOCIMOUSE® method (see, e.g., U.S. Pat. No. 7,294,754 and Poueymirou et al. (2007) FO generation mice that are essentially fully derived from the donor gene-targeted ES cells allowing immediate phenotypic analyses Nature Biotech. 25(1): 91-99. VELOCIMICE® independently bearing an engineered human germline Vκ1-39Jκ5 light chain region, a Vκ3-20Jκ1 light chain region or a VpreBJX5 light chain region are identified by genotyping using a modification of allele assay (Valenzuela et al., supra) that detects the presence of the unique rearranged human germline light chain region.

Pups are genotyped and a pup heterozygous or homozygous for the unique rearranged human germline light chain region are selected for characterizing expression of the rearranged human germline light chain region.

Flow Cytometry. Expression of the rearranged human light chain region in the normal antibody repertoire of common light chain mice was validated by analysis of immunoglobulin κ and λ expression in splenocytes and peripheral blood of common light chain mice. Cell suspensions from harvested spleens and peripheral blood of wild type (n=5), Vκ1-39Jκ5 common light chain heterozygote (n=3), Vκ1-39Jκ5 common light chain homozygote (n=3), Vκ3-20Jκ1 common light chain heterozygote (n=2), and Vκ3-20Jκ1 common light chain homozygote (n=2) mice were made using standard methods and stained with $CD19^+$, $Ig\lambda^+$ and $Ig\kappa^+$ using fluorescently labeled antibodies (BD Pharmigen).

Figure 4:
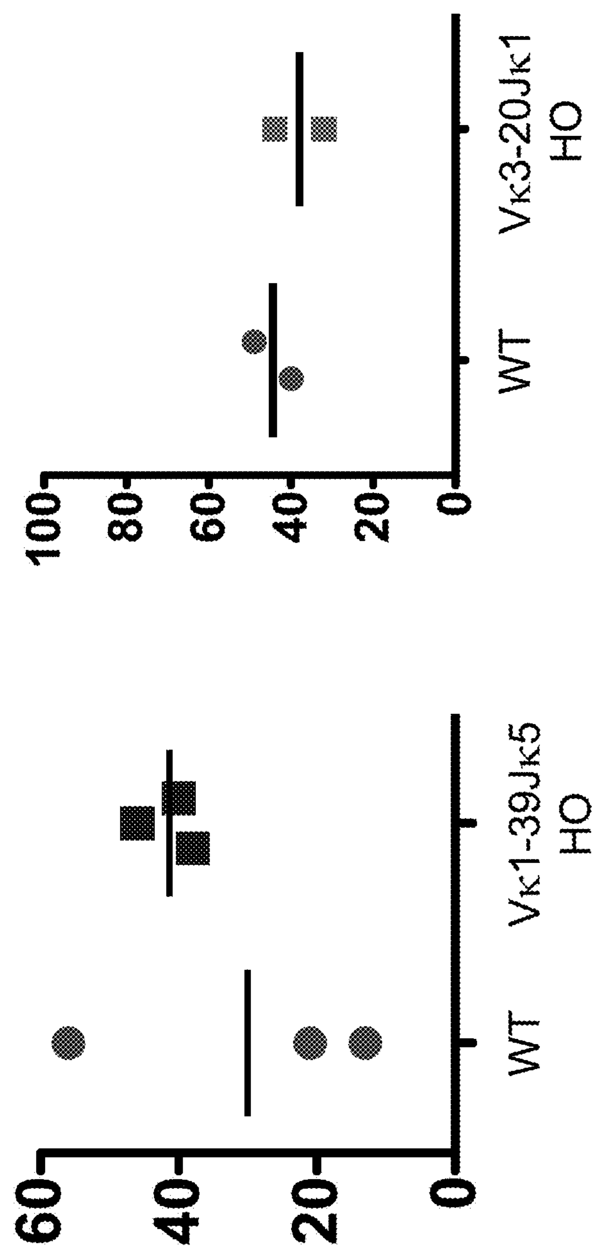
FIG. 4 shows the percent of $CD19^+$ B cells (y-axis) from peripheral blood for wild type mice (WT), mice homozygous for an engineered human rearranged Vκ1-39Jκ5 light chain region (Vκ1-39Jκ5 HO) and mice homozygous for an engineered human rearranged Vκ3-20Jκ1 light chain region (Vκ3-20Jκ1 HO).

Briefly, $1\times10^6$ cells were incubated with anti-mouse CD16/CD32 (clone 2.4G2, BD Pharmigen) on ice for 10 minutes, followed by labeling with the following antibody cocktail for 30 minutes on ice: APC conjugated anti-mouse CD19 (clone 1D3, BD Pharmigen), PerCP-Cy5.5 conjugated anti-mouse CD3 (clone 17A2, BioLegend), FITC conjugated anti-mouse Igκ(clone 187.1, BD Pharmigen), PE conjugated anti-mouse Igλ(clone RML-42, BioLegend). Following staining, cells were washed and fixed in 2% formaldehyde. Data acquisition was performed on an LSRII flow cytometer and analyzed with FlowJo. Gating: total B cells ($CD19^+CD3$), $Ig\kappa^+$ B cells ($Ig\kappa^+Ig\lambda^-CD19^+CD3^-$), $Ig\lambda^+$ B cells ($Ig\kappa^-Ig\lambda^+CD19^+CD3^-$). Data gathered from blood and splenocyte samples demonstrated similar results. Table 3 sets forth the percent positive $CD19^+$ B cells from peripheral blood of one representative mouse from each group that are $Ig\lambda^+$, $Ig\kappa^+$, or $Ig\lambda^+Ig\kappa^+$. Percent of $CD19^+$ B cells in peripheral blood from wild type (WT) and mice homozygous for either the Vκ1-39Jκ5 or Vκ3-20Jκ1 common light chain are shown in FIG. 4.

TABLE 3

| | CD19⁺ B cells | | |
|---|---|---|---|
| Mouse | $Ig\lambda^+$ | $Ig\kappa^+$ | $Ig\lambda^+Ig\kappa^+$ |
| Wild type | 4.8 | 93 | 0.53 |
| Vκ1-39Jκ5 | 1.4 | 93 | 2.6 |
| Vκ3-20Jκ1 | 4.2 | 88 | 6 |

Common Light Chain Expression. Expression of each common light chain (Vκ1-39Jκ5 and Vκ3-20Jκ1) was analyzed in heterozygous and homozygous mice using a quantitative PCR assay (e.g. TAQMAN™).

Figure 5A:
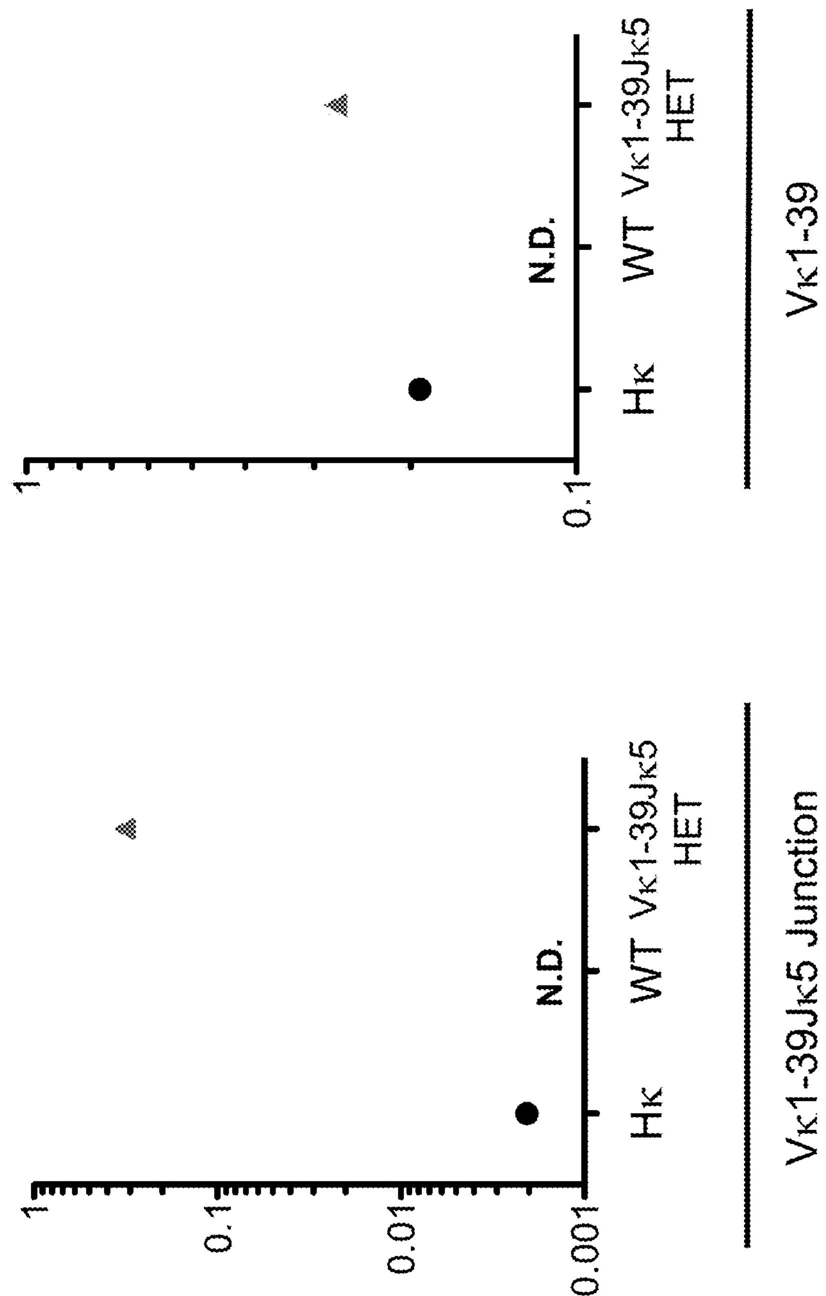
FIG. 5A shows the relative mRNA expression (y-axis) of a Vκ1-39-derived light chain in a quantitative PCR assay using probes specific for the junction of an engineered human rearranged Vκ1-39Jκ5 light chain region (Vκ1-39Jκ5 Junction Probe) and the human Vκ1-39 gene segment (Vκ1-39 Probe) in a mouse homozygous for a replacement of the endogenous Vκ and Jκ gene segments with human Vκ and Jκ gene segments (Hκ), a wild type mouse (WT), and a mouse heterozygous for an engineered human rearranged Vκ1-39Jκ5 light chain region (Vκ1-39Jκ5 HET). Signals are normalized to expression of mouse Cκ. N.D.: not detected.
Figure 5B:
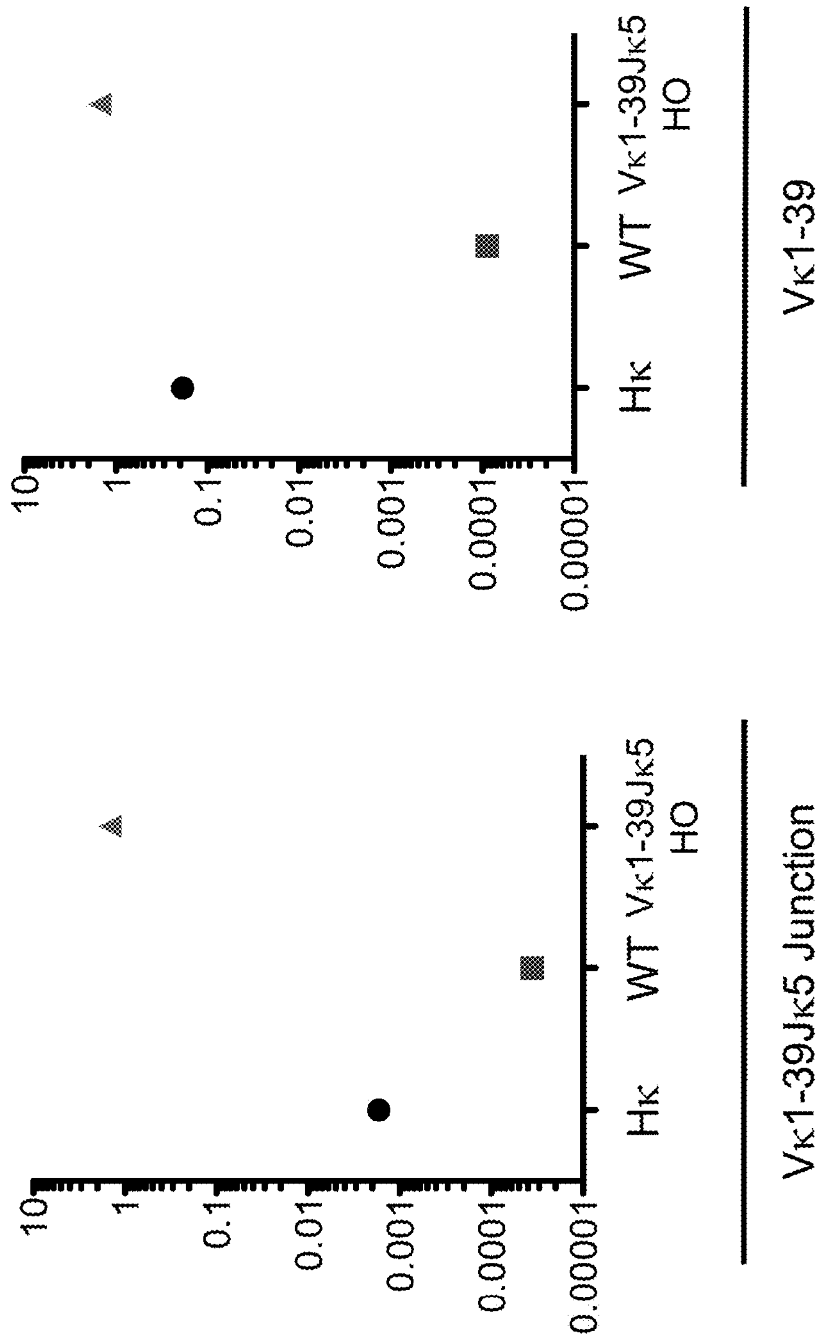
FIG. 5B shows the relative mRNA expression (y-axis) of a Vκ1-39-derived light chain in a quantitative PCR assay using probes specific for the junction of an engineered human rearranged Vκ1-39Jκ5 light chain region (Vκ1-39Jκ5 Junction Probe) and the human Vκ1-39 gene segment (Vκ1-39 Probe) in a mouse homozygous for a replacement of the endogenous Vκ and Jκ gene segments with human Vκ and Jκ gene segments (Hκ), a wild type mouse (WT), and a mouse homozygous for an engineered human rearranged Vκ1-39Jκ5 light chain region (Vκ1-39Jκ5 HO). Signals are normalized to expression of mouse Cκ.
Figure 5C:
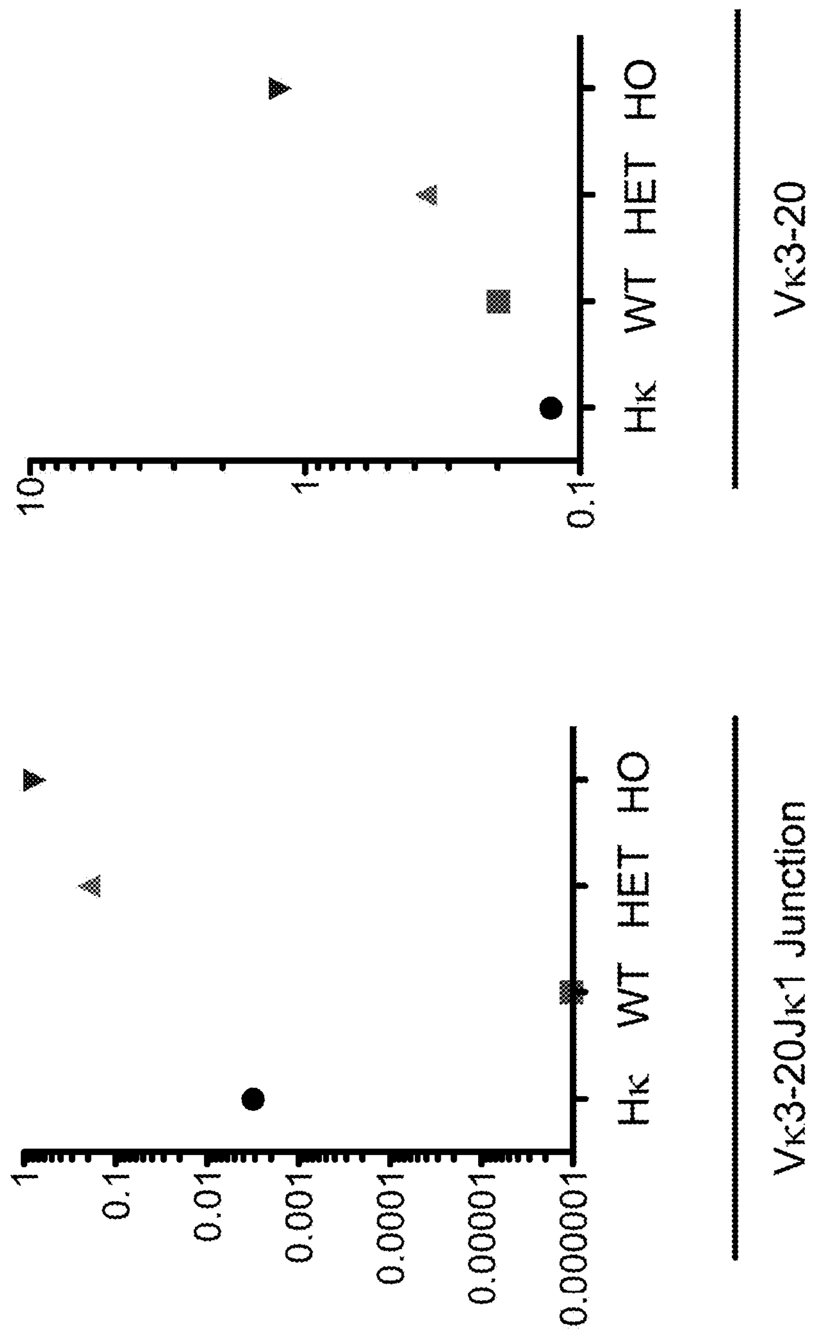
FIG. 5C shows the relative mRNA expression (y-axis) of a Vκ3-20-derived light chain in a quantitative PCR assay using probes specific for the junction of an engineered human rearranged Vκ3-20Jκ1 light chain region (Vκ3-20Jκ1 Junction Probe) and the human Vκ3-20 gene segment (Vκ3-20 Probe) in a mouse homozygous for a replacement of the endogenous Vκ and Jκ gene segments with human Vκ and Jκ gene segments (Hκ), a wild type mouse (WT), and a mouse heterozygous (HET) and homozygous (HO) for an engineered human rearranged Vκ3-20Jκ1 light chain region. Signals are normalized to expression of mouse Cκ.

Briefly, $CD19^+$ B cells were purified from the spleens of wild type, mice homozygous for a replacement of the mouse heavy chain and κ light chain variable region loci with corresponding human heavy chain and κ light chain variable region loci (Hκ), as well as mice homozygous and heterozygous for each rearranged human light chain region (Vκ1-39Jκ5 or Vκ3-20Jκ1) using mouse CD19 Microbeads (Miltenyi Biotec) according to manufacturer's specifications. Total RNA was purified from $CD19^+$ B cells using RNeasy Mini kit (Qiagen) according to manufacturer's specifications and genomic RNA was removed using an RNase-free DNase on-column treatment (Qiagen). 200 ng mRNA was reverse-transcribed into cDNA using the First Stand cDNA Synthesis kit (Invitrogen) and the resulting cDNA was amplified with the Taqman Universal PCR Master Mix (Applied Biosystems). All reactions were performed using the ABI 7900 Sequence Detection System (Applied Biosystems) using primers and Taqman MGB probes spanning (1) the Vκ-Jκ junction for both common light chains, (2) the Vκ gene alone (i.e. Vκ1-39 and Vκ3-20), and (3) the mouse Cκ region. Table 4 sets forth the sequences of the primers and probes employed for this assay. Relative expression was normalized to expression of the mouse Cκ region. Results are shown in FIGS. 5A, 5B and 5C.

TABLE 4

| Region | Primer/Probe Description (5'-3') | | SEQ ID NOs: |
|---|---|---|---|
| Vκ1-39Jκ5 Junction | (Sense) | AGCAGTCTGC AACCTGAAGA TTT | 19 |
| | (Anti-sense) | GTTTAATCTC CAGTCGTGTC CCTT | 20 |
| | (Probe) | CCTCCGATCA CCTTC | 21 |
| Vκ1-39 | (Sense) | AAACCAGGGA AAGCCCCTAA | 22 |
| | (Anti-sense) | ATGGGACCCC ACTTTGCA | 23 |
| | (Probe) | CTCCTGATCT ATGCTGCAT | 24 |
| Vκ3-20Jκ1 Junction | (Sense) | CAGCAGACTG GAGCCTGAAG A | 25 |
| | (Anti-sense) | TGATTTCCAC CTTGGTCCCT T | 26 |
| | (Probe) | TAGCTCACCT TGGACGTT | 27 |
| Vκ3-20 | (Sense) | CTCCTCATCT ATGGTGCATC CA | 28 |
| | (Anti-sense) | GACCCACTGC CACTGAACCT | 29 |
| | (Probe) | CCACTGGCAT CCC | 30 |
| Mouse Cκ | (Sense) | TGAGCAGCAC CCTCACGTT | 31 |
| | (Anti-sense) | GTGGCCTCAC AGGTATAGCT GTT | 32 |
| | (Probe) | ACCAAGGACG AGTATGA | 33 |

Antigen Specific Common Light Chain Antibodies. Common light chain mice bearing either a Vκ1-39Jκ5 or Vκ3-20Jκ1 common light chain at the endogenous mouse κ light chain locus were immunized with β-galactosidase and antibody titer was measured.

Figure 6A:
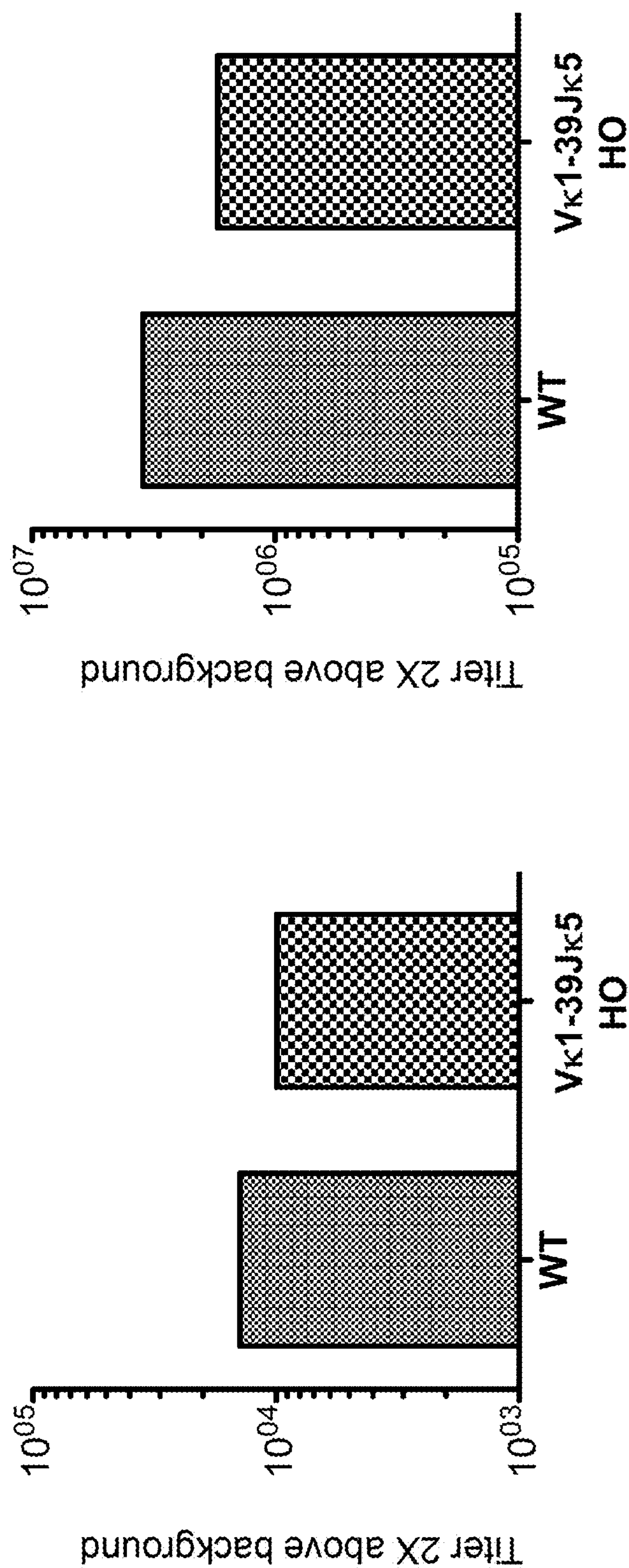
FIG. 6A shows IgM (left) and IgG (right) titer in wild type (WT; N=2) and mice homozygous for an engineered human rearranged Vκ1-39Jκ5 light chain region (Vκ1-39Jκ5 HO; N=2) immunized with β-galatosidase.
Figure 6B:
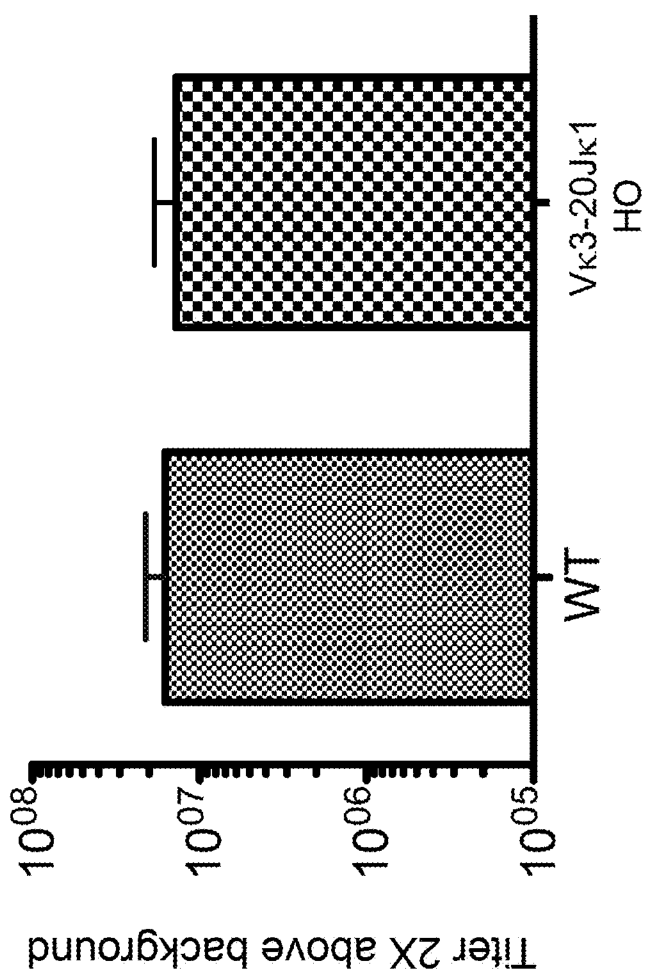
FIG. 6B shows total immunoglobulin (IgM, IgG, IgA) titer in wild type (WT; N=5) and mice homozygous for an engineered human rearranged Vκ3-20Jκ1 light chain region (Vκ3-20Jκ1 HO; N=5) immunized with β-galatosidase.

Briefly, β-galactosidase (Sigma) was emulsified in titermax adjuvant (Sigma), as per manufacturer's directions. Wild type (n=7), Vκ1-39Jκ5 common light chain homozygotes (n=2) and Vκ3-20Jκ1 common light chain homozygotes (n=5) were immunized by subcutaneous injection with 100 μg β-galactosidase/Titermax. Mice were boosted by subcutaneous injection two times, 3 weeks apart, with 50 μg β-galactosidase/Titermax. After the second boost, blood was collected from anaesthetized mice using a retro-orbital bleed into serum separator tubes (BD Biosciences) as per manufacturer's directions. To measure anti-β-galactosidase IgM or IgG antibodies, ELISA plates (Nunc) were coated with 1 μg/mL β-galactosidase overnight at 4° C. Excess antigen was washed off before blocking with PBS with 1% BSA for one hour at room temperature. Serial dilutions of serum were added to the plates and incubated for one hour at room temperature before washing. Plates were then incubated with HRP conjugated anti-IgM (Southern Biotech) or anti- IgG (Southern Biotech) for one hour at room temperature. Following another wash, plates were developed with TMB substrate (BD Biosciences). Reactions were stopped with 1N sulfuric acid and $OD_{450}$ was read using a Victor X5 Plate Reader (Perkin Elmer). Data was analyzed with GraphPad Prism and signal was calculated as the dilution of serum that is two times above background. Results are shown in FIGS. 6A and 6B.

As shown in this Example, the ratio of κ/λ B cells in both the splenic and peripheral compartments of Vκ1-39Jκ5 and Vκ3-20Jκ1 common light chain mice demonstrated a near wild type pattern (Table 3 and FIG. 4). VpreBJX5 common light chain mice, however, demonstrated fewer peripheral B cells, of which about 1-2% express the engineered human light chain region (data not shown). The expression levels of the Vκ1-39Jκ5 and Vκ3-20Jκ1 rearranged human light chain regions from the endogenous κ light chain locus were elevated in comparison to an endogenous κ light chain locus containing a complete replacement of mouse Vκ and Jκ gene segments with human Vκ and Jκ gene segments (FIGS. 5A, 5B and 5C). The expression levels of the VpreBJX5 rearranged human light chain region demonstrated similar high expression from the endogenous κ light chain locus in both heterozygous and homozygous mice (data not shown). This demonstrates that in direct competition with the mouse λ, κ, or both endogenous light chain loci, a single rearranged human $V_L/J_L$ sequence can yield better than wild type level expression from the endogenous κ light chain locus and give rise to normal splenic and blood B cell frequency. Further, the presence of an engineered κ light chain locus having either a human Vκ1-39Jκ5 or human Vκ3-20Jκ1 sequence was well tolerated by the mice and appear to function in wild type fashion by representing a substantial portion of the light chain repertoire in the humoral component of the immune response (FIGS. 6A and 6B).

Example 4. Breeding of Mice Expressing a Single Rearranged Human Germline Light Chain This Example describes several other genetically modified mouse strains that can be bred to any one of the common light chain mice described herein to create multiple genetically modified mouse strains harboring multiple genetically modified immunoglobulin loci.

Endogenous Igλ Knockout (KO). To optimize the usage of the engineered light chain locus, mice bearing one of the rearranged human germline light chain regions are bred to another mouse containing a deletion in the endogenous λ light chain locus. In this manner, the progeny obtained will express, as their only light chain, the rearranged human germline light chain region as described in Example 2. Breeding is performed by standard techniques recognized in the art and, alternatively, by a commercial breeder (e.g., The Jackson Laboratory). Mouse strains bearing an engineered light chain locus and a deletion of the endogenous λ light chain locus are screened for presence of the unique light chain region and absence of endogenous mouse λ light chains.

Humanized Endogenous Heavy Chain Locus. Mice bearing an engineered human germline light chain locus are bred with mice that contain a replacement of the endogenous mouse heavy chain variable gene locus with the human heavy chain variable gene locus (see U.S. Pat. No. 6,596,541; the VELOCIMMUNE® mouse, Regeneron Pharmaceuticals, Inc.). The VELOCIMMUNE® mouse comprises a genome comprising human heavy chain variable regions operably linked to endogenous mouse constant region loci such that the mouse produces antibodies comprising a human heavy chain variable region and a mouse heavy chain constant region in response to antigenic stimulation. The DNA encoding the variable regions of the heavy chains of the antibodies is isolated and operably linked to DNA encoding the human heavy chain constant regions. The DNA is then expressed in a cell capable of expressing the fully human heavy chain of the antibody.

Mice bearing a replacement of the endogenous mouse $V_H$ locus with the human $V_H$ locus and a single rearranged human germline $V_L$ region at the endogenous κ light chain locus are obtained. Reverse chimeric antibodies containing somatically mutated heavy chains (human $V_H$ and mouse $C_H$) with a single human light chain (human $V_L$ and mouse $C_L$) are obtained upon immunization with an antigen of interest. $V_H$ and $V_L$ nucleotide sequences of B cells expressing the antibodies are identified and fully human antibodies are made by fusion the $V_H$ and $V_L$ nucleotide sequences to human $C_H$ and $C_L$ nucleotide sequences in a suitable expression system.

Example 5. Generation of Antibodies from Mice Expressing Human Heavy Chains and a Rearranged Human Germline Light Chain Region After breeding mice that contain the engineered human light chain region to various desired strains containing modifications and deletions of other endogenous Ig loci (as described in Example 4), selected mice can be immunized with an antigen of interest.

Generally, a VELOCIMMUNE® mouse containing one of the single rearranged human germline light chain regions is challenged with an antigen, and lymphatic cells (such as B-cells) are recovered from serum of the animals. The lymphatic cells are fused with a myeloma cell line to prepare immortal hybridoma cell lines, and such hybridoma cell lines are screened and selected to identify hybridoma cell lines that produce antibodies containing human heavy chain variables and a rearranged human germline light chains which are specific to the antigen used for immunization. DNA encoding the variable regions of the heavy chains and the light chain are isolated and linked to desirable isotypic constant regions of the heavy chain and light chain. Due to the presence of the endogenous mouse sequences and any additional cis-acting elements present in the endogenous locus, the single light chain of each antibody may be somatically mutated. This adds additional diversity to the antigen-specific repertoire comprising a single light chain and diverse heavy chain sequences. The resulting cloned antibody sequences are subsequently expressed in a cell, such as a CHO cell. Alternatively, DNA encoding the antigen-specific chimeric antibodies or the variable domains of the light and heavy chains is identified directly from antigen-specific lymphocytes.

Initially, high affinity chimeric antibodies are isolated having a human variable region and a mouse constant region. As described above, the antibodies are characterized and selected for desirable characteristics, including affinity, selectivity, epitope, etc. The mouse constant regions are replaced with a desired human constant region to generate the fully human antibody containing a somatically mutated human heavy chain and a single light chain derived from a rearranged human germline light chain region of the invention. Suitable human constant regions include, for example wild type or modified IgG1 or IgG4.

Separate cohorts of VELOCIMMUNE® mice containing a replacement of the endogenous mouse heavy chain locus with human $V_H$, $D_H$, and $J_H$ gene segments and a replacement of the endogenous mouse κ light chain locus with either the engineered germline Vκ1-39Jκ5 human light chain region or the engineered germline Vκ3-20Jκ1 human light chain region (described above) were immunized with a human cell-surface receptor protein (Antigen E). Antigen E is administered directly onto the hind footpad of mice with six consecutive injections every 3-4 days. Two to three micrograms of Antigen E are mixed with 10 μg of CpG oligonucleotide (Cat #tlrl-modn—ODN1826 oligonucleotide; InVivogen, San Diego, CA) and 25 μg of Adju-Phos (Aluminum phosphate gel adjuvant, Cat#H-71639-250; Brenntag Biosector, Frederikssund, Denmark) prior to injection. A total of six injections are given prior to the final antigen recall, which is given 3-5 days prior to sacrifice. Bleeds after the 4th and 6th injection are collected and the antibody immune response is monitored by a standard antigen-specific immunoassay.

When a desired immune response is achieved splenocytes are harvested and fused with mouse myeloma cells to preserve their viability and form hybridoma cell lines. The hybridoma cell lines are screened and selected to identify cell lines that produce Antigen E-specific common light chain antibodies. Using this technique several anti-Antigen E-specific common light chain antibodies (i.e., antibodies possessing human heavy chain variable domains, the same human light chain variable domain, and mouse constant domains) are obtained.

Alternatively, anti-Antigen E common light chain antibodies are isolated directly from antigen-positive B cells without fusion to myeloma cells, as described in U.S. 2007/0280945A1, herein specifically incorporated by reference in its entirety. Using this method, several fully human anti-Antigen E common light chain antibodies (i.e., antibodies possessing human heavy chain variable domains, either an engineered human Vκ1-39Jκ5 light chain or an engineered human Vκ3-20Jκ1 light chain region, and human constant domains) were obtained.

The biological properties of the exemplary anti-Antigen E common light chain antibodies generated in accordance with the methods of this Example are described in detail in the sections set forth below.

Example 6. Heavy Chain Gene Segment Usage in Antigen-Specific Common Light Chain Antibodies To analyze the structure of the human anti-Antigen E common light chain antibodies produced, nucleic acids encoding heavy chain antibody variable regions were cloned and sequenced. From the nucleic acid sequences and predicted amino acid sequences of the antibodies, gene usage was identified for the heavy chain variable region (HCVR) of selected common light chain antibodies obtained from immunized VELOCIMMUNE® mice containing either the engineered human Vκ1-39Jκ5 light chain or engineered human Vκ3-20Jκ1 light chain region. Results are shown in Tables 5 and 6, which demonstrate that mice according to the invention generate antigen-specific common light chain antibodies from a variety of human heavy chain gene segments, due to a variety of rearrangements, when employing either a mouse that expresses a light chain from only a human Vκ1-39- or a human Vκ3-20-derived light chain. Human $V_H$ gene segments of the 2, 3, 4, and 5 families rearranged with a variety of human $D_H$ segments and human $J_H$ segments to yield antigen-specific antibodies.

TABLE 5

Vκ1-39Jκ5 Common Light Chain Antibodies

| Antibody | HCVR $V_H$ | HCVR $D_H$ | HCVR $J_H$ |
|---|---|---|---|
| 2952 | 2-5 | 6-6 | 1 |
| 5978 | 2-5 | 6-6 | 1 |
| 5981 | 2-5 | 3-22 | 1 |
| 6027 | 3-13 | 6-6 | 5 |
| 3022 | 3-23 | 3-10 | 4 |
| 3028 | 3-23 | 3-3 | 4 |
| 5999 | 3-23 | 6-6 | 4 |
| 6009 | 3-23 | 2-8 | 4 |
| 6011 | 3-23 | 7-27 | 4 |
| 5980 | 3-30 | 1-1 | 4 |
| 3014 | 3-30 | 1-7 | 4 |
| 3015 | 3-30 | 1-7 | 4 |
| 3023 | 3-30 | 1-7 | 4 |
| 3024 | 3-30 | 1-7 | 4 |
| 3032 | 3-30 | 1-7 | 4 |
| 6024 | 3-30 | 1-7 | 4 |
| 6025 | 3-30 | 1-7 | 4 |
| 6031 | 3-30 | 1-7 | 4 |
| 6007 | 3-30 | 3-3 | 4 |
| 2982 | 3-30 | 3-22 | 5 |
| 6001 | 3-30 | 3-22 | 5 |
| 6005 | 3-30 | 3-22 | 5 |
| 6035 | 3-30 | 5-5 | 2 |
| 3013 | 3-30 | 5-12 | 4 |
| 3042 | 3-30 | 5-12 | 4 |
| 2955 | 3-30 | 6-6 | 1 |
| 3043 | 3-30 | 6-6 | 3 |
| 3018 | 3-30 | 6-6 | 4 |
| 2949 | 3-30 | 6-6 | 5 |
| 2950 | 3-30 | 6-6 | 5 |
| 2954 | 3-30 | 6-6 | 5 |
| 2978 | 3-30 | 6-6 | 5 |
| 3016 | 3-30 | 6-6 | 5 |
| 3017 | 3-30 | 6-6 | 5 |
| 3033 | 3-30 | 6-6 | 5 |
| 3041 | 3-30 | 6-6 | 5 |
| 5979 | 3-30 | 6-6 | 5 |
| 5998 | 3-30 | 6-6 | 5 |
| 6004 | 3-30 | 6-6 | 5 |
| 6010 | 3-30 | 6-6 | 5 |
| 6019 | 3-30 | 6-6 | 5 |
| 6021 | 3-30 | 6-6 | 5 |
| 6022 | 3-30 | 6-6 | 5 |
| 6023 | 3-30 | 6-6 | 5 |
| 6030 | 3-30 | 6-6 | 5 |
| 6032 | 3-30 | 6-6 | 5 |
| 2985 | 3-30 | 6-13 | 4 |
| 2997 | 3-30 | 6-13 | 4 |
| 3011 | 3-30 | 6-13 | 4 |
| 3047 | 3-30 | 6-13 | 4 |
| 5982 | 3-30 | 6-13 | 4 |
| 6002 | 3-30 | 6-13 | 4 |
| 6003 | 3-30 | 6-13 | 4 |
| 6012 | 3-30 | 6-13 | 4 |
| 6013 | 3-30 | 6-13 | 4 |
| 6014 | 3-30 | 6-13 | 4 |
| 6015 | 3-30 | 6-13 | 4 |
| 6016 | 3-30 | 6-13 | 4 |
| 6017 | 3-30 | 6-13 | 4 |
| 6020 | 3-30 | 6-13 | 4 |
| 6034 | 3-30 | 6-13 | 4 |
| 2948 | 3-30 | 7-27 | 4 |
| 2987 | 3-30 | 7-27 | 4 |
| 2996 | 3-30 | 7-27 | 4 |
| 3005 | 3-30 | 7-27 | 4 |
| 3012 | 3-30 | 7-27 | 4 |
| 3020 | 3-30 | 7-27 | 4 |
| 3021 | 3-30 | 7-27 | 4 |
| 3025 | 3-30 | 7-27 | 4 |
| 3030 | 3-30 | 7-27 | 4 |
| 3036 | 3-30 | 7-27 | 4 |
| 5997 | 3-30 | 7-27 | 4 |
| 6033 | 3-30 | 7-27 | 4 |

TABLE 5-continued

| Vκ1-39Jκ5 Common Light Chain Antibodies | | | |
|---|---|---|---|
| | HCVR | | |
| Antibody | $V_H$ | $D_H$ | $J_H$ |
| 3004 | 3-30 | 7-27 | 5 |
| 6028 | 3-30 | 7-27 | 6 |
| 3010 | 4-59 | 3-16 | 3 |
| 3019 | 4-59 | 3-16 | 3 |
| 6018 | 4-59 | 3-16 | 3 |
| 6026 | 4-59 | 3-16 | 3 |
| 6029 | 4-59 | 3-16 | 3 |
| 6036 | 4-59 | 3-16 | 3 |
| 6037 | 4-59 | 3-16 | 3 |
| 2964 | 4-59 | 3-22 | 3 |
| 3027 | 4-59 | 3-16 | 4 |
| 3046 | 5-51 | 5-5 | 3 |
| 6000 | 1-69 | 6-13 | 4 |
| 6006 | 1-69 | 6-6 | 5 |
| 6008 | 1-69 | 6-13 | 4 |

TABLE 6

| Vκ3-20Jκ1 Common Light Chain Antibodies | | | |
|---|---|---|---|
| | HCVR | | |
| Antibody | $V_H$ | $D_H$ | $J_H$ |
| 5989 | 3-30 | 3-3 | 3 |
| 5994 | 3-33 | 1-7 | 4 |
| 5985 | 3-33 | 2-15 | 4 |
| 5987 | 3-33 | 2-15 | 4 |
| 5995 | 3-33 | 2-15 | 4 |
| 2968 | 4-39 | 1-26 | 3 |
| 5988 | 4-39 | 1-26 | 3 |
| 5992 | 4-39 | 1-26 | 3 |
| 2975 | 5-51 | 6-13 | 5 |
| 2972 | 5-51 | 3-16 | 6 |
| 5986 | 5-51 | 3-16 | 6 |
| 5993 | 5-51 | 3-16 | 6 |
| 5996 | 5-51 | 3-16 | 6 |
| 5984 | 3-53 | 1-1 | 4 |

Example 7. Determination of Blocking Ability of Antigen-Specific Common Light Chain Antibodies by LUMINEX™ Assay Ninety-eight human common light chain antibodies raised against Antigen E were tested for their ability to block binding of Antigen E's natural ligand (Ligand Y) to Antigen E in a bead-based assay.

The extracellular domain (ECD) of Antigen E was conjugated to two myc epitope tags and a 6× histidine tag (Antigen E-mmH) and amine-coupled to carboxylated microspheres at a concentration of 20 μg/mL in MES buffer. The mixture was incubated for two hours at room temperature followed by bead deactivation with 1M Tris pH 8.0 followed by washing in PBS with 0.05% (v/v) Tween-20. The beads were then blocked with PBS (Irvine Scientific, Santa Ana, CA) containing 2% (w/v) BSA (Sigma-Aldrich Corp., St. Louis, MO). In a 96-well filter plate, supernatants containing Antigen E-specific common light chain antibodies were diluted 1:15 in buffer. A negative control containing a mock supernatant with the same media components as for the antibody supernatant was prepared. Antigen E-labeled beads were added to the supernatants and incubated overnight at 4° C. Biotinylated-Ligand Y protein was added to a final concentration of 0.06 nM and incubated for two hours at room temperature. Detection of biotinylated-Ligand Y bound to Antigen E-myc-myc-6His labeled beads was determined with R-Phycoerythrin conjugated to Streptavidin (Moss Inc, Pasadena, MD) followed by measurement in a LUMINEX™ flow cytometry-based analyzer. Background Mean Fluorescence Intensity (MFI) of a sample without Ligand Y was subtracted from all samples. Percent blocking was calculated by division of the background-subtracted MFI of each sample by the adjusted negative control value, multiplying by 100 and subtracting the resulting value from 100.

In a similar experiment, the same 98 human common light chain antibodies raised against Antigen E were tested for their ability to block binding of Antigen E to Ligand Y-labeled beads.

Briefly, Ligand Y was amine-coupled to carboxylated microspheres at a concentration of 20 μg/mL diluted in MES buffer. The mixture and incubated two hours at room temperature followed by deactivation of beads with 1M Tris pH 8 then washing in PBS with 0.05% (v/v) Tween-20. The beads were then blocked with PBS (Irvine Scientific, Santa Ana, CA) containing 2% (w/v) BSA (Sigma-Aldrich Corp., St. Louis, MO). In a 96-well filter plate, supernatants containing Antigen E-specific common light chain antibodies were diluted 1:15 in buffer. A negative control containing a mock supernatant with the same media components as for the antibody supernatant was prepared. A biotinylated-Antigen E-mmH was added to a final concentration of 0.42 nM and incubated overnight at 4° C. Ligand Y-labeled beads were then added to the antibody/Antigen E mixture and incubated for two hours at room temperature. Detection of biotinylated-Antigen E-mmH bound to Ligand Y-beads was determined with R-Phycoerythrin conjugated to Streptavidin (Moss Inc, Pasadena, MD) followed by measurement in a LUMINEX™ flow cytometry-based analyzer. Background Mean Fluorescence Intensity (MFI) of a sample without Antigen E was subtracted from all samples. Percent blocking was calculated by division of the background-subtracted MFI of each sample by the adjusted negative control value, multiplying by 100 and subtracting the resulting value from 100.

Tables 7 and 8 show the percent blocking for all 98 anti-Antigen E common light chain antibodies tested in both LUMINEX™ assays. ND: not determined under current experimental conditions.

TABLE 7

| Vκ1-39Jκ5 Common Light Chain Antibodies | | |
|---|---|---|
| Antibody | % Blocking of Antigen E-Labeled Beads | % Blocking of Antigen E In Solution |
| 2948 | 81.1 | 47.8 |
| 2948G | 38.6 | ND |
| 2949 | 97.6 | 78.8 |
| 2949G | 97.1 | 73.7 |
| 2950 | 96.2 | 81.9 |
| 2950G | 89.8 | 31.4 |
| 2952 | 96.1 | 74.3 |
| 2952G | 93.5 | 39.9 |
| 2954 | 93.7 | 70.1 |
| 2954G | 91.7 | 30.1 |
| 2955 | 75.8 | 30.0 |
| 2955G | 71.8 | ND |
| 2964 | 92.1 | 31.4 |
| 2964G | 94.6 | 43.0 |
| 2978 | 98.0 | 95.1 |

TABLE 7-continued

| Vκ1-39Jκ5 Common Light Chain Antibodies | | |
|---|---|---|
| Antibody | % Blocking of Antigen E-Labeled Beads | % Blocking of Antigen E In Solution |
| 2978G | 13.9 | 94.1 |
| 2982 | 92.8 | 78.5 |
| 2982G | 41.9 | 52.4 |
| 2985 | 39.5 | 31.2 |
| 2985G | 2.0 | 5.0 |
| 2987 | 81.7 | 67.8 |
| 2987G | 26.6 | 29.3 |
| 2996 | 87.3 | 55.3 |
| 2996G | 95.9 | 38.4 |
| 2997 | 93.4 | 70.6 |
| 2997G | 9.7 | 7.5 |
| 3004 | 79.0 | 48.4 |
| 3004G | 60.3 | 40.7 |
| 3005 | 97.4 | 93.5 |
| 3005G | 77.5 | 75.6 |
| 3010 | 98.0 | 82.6 |
| 3010G | 97.9 | 81.0 |
| 3011 | 87.4 | 42.8 |
| 3011G | 83.5 | 41.7 |
| 3012 | 91.0 | 60.8 |
| 3012G | 52.4 | 16.8 |
| 3013 | 80.3 | 65.8 |
| 3013G | 17.5 | 15.4 |
| 3014 | 63.4 | 20.7 |
| 3014G | 74.4 | 28.5 |
| 3015 | 89.1 | 55.7 |
| 3015G | 58.8 | 17.3 |
| 3016 | 97.1 | 81.6 |
| 3016G | 93.1 | 66.4 |
| 3017 | 94.8 | 70.2 |
| 3017G | 87.9 | 40.8 |
| 3018 | 85.4 | 54.0 |
| 3018G | 26.1 | 12.7 |
| 3019 | 99.3 | 92.4 |
| 3019G | 99.3 | 88.1 |
| 3020 | 96.7 | 90.3 |
| 3020G | 85.2 | 41.5 |
| 3021 | 74.5 | 26.1 |
| 3021G | 81.1 | 27.4 |
| 3022 | 65.2 | 17.6 |
| 3022G | 67.2 | 9.1 |
| 3023 | 71.4 | 28.5 |
| 3023G | 73.8 | 29.7 |
| 3024 | 73.9 | 32.6 |
| 3024G | 89.0 | 10.0 |
| 3025 | 70.7 | 15.6 |
| 3025G | 76.7 | 24.3 |
| 3027 | 96.2 | 61.6 |
| 3027G | 98.6 | 75.3 |
| 3028 | 92.4 | 29.0 |
| 3028G | 87.3 | 28.8 |
| 3030 | 6.0 | 10.6 |
| 3030G | 41.3 | 14.2 |
| 3032 | 76.5 | 31.4 |
| 3032G | 17.7 | 11.0 |
| 3033 | 98.2 | 86.1 |
| 3033G | 93.6 | 64.0 |
| 3036 | 74.7 | 32.7 |
| 3036G | 90.1 | 51.2 |
| 3041 | 95.3 | 75.9 |
| 3041G | 92.4 | 51.6 |
| 3042 | 88.1 | 73.3 |
| 3042G | 60.9 | 25.2 |
| 3043 | 90.8 | 65.8 |
| 3043G | 92.8 | 60.3 |

TABLE 8

| Vκ3-20Jκ1 Common Light Chain Antibodies | | |
|---|---|---|
| Antibody | % Blocking of Antigen E-Labeled Beads | % Blocking of Antigen E In Solution |
| 2968 | 97.1 | 73.3 |
| 2968G | 67.1 | 14.6 |
| 2969 | 51.7 | 20.3 |
| 2969G | 37.2 | 16.5 |
| 2970 | 92.2 | 34.2 |
| 2970G | 92.7 | 27.2 |
| 2971 | 23.4 | 11.6 |
| 2971G | 18.8 | 18.9 |
| 2972 | 67.1 | 38.8 |
| 2972G | 64.5 | 39.2 |
| 2973 | 77.7 | 27.0 |
| 2973G | 51.1 | 20.7 |
| 2974 | 57.8 | 12.4 |
| 2974G | 69.9 | 17.6 |
| 2975 | 49.4 | 18.2 |
| 2975G | 32.0 | 19.5 |
| 2976 | 1.0 | 1.0 |
| 2976G | 50.4 | 20.4 |

In the first LUMINEX™ experiment described above, 80 common light chain antibodies containing the Vκ1-39Jκ5 engineered light chain were tested for their ability to block Ligand Y binding to Antigen E-labeled beads. Of these 80 common light chain antibodies, 68 demonstrated >50% blocking, while 12 demonstrated <50% blocking (6 at 25-50% blocking and 6 at <25% blocking). For the 18 common light chain antibodies containing the Vκ3-20Jκ1 engineered light chain, 12 demonstrated >50% blocking, while 6 demonstrated <50% blocking (3 at 25-50% blocking and 3 at <25% blocking) of Ligand Y binding to Antigen E-labeled beads.

In the second LUMINEX™ experiment described above, the same 80 common light chain antibodies containing the Vκ1-39Jκ5 engineered light chain were tested for their ability to block binding of Antigen E to Ligand Y-labeled beads. Of these 80 common light chain antibodies, 36 demonstrated >50% blocking, while 44 demonstrated <50% blocking (27 at 25-50% blocking and 17 at <25% blocking). For the 18 common light chain antibodies containing the Vκ3-20Jκ1 engineered light chain, 1 demonstrated >50% blocking, while 17 demonstrated <50% blocking (5 at 25-50% blocking and 12 at <25% blocking) of Antigen E binding to Ligand Y-labeled beads.

The data of Tables 7 and 8 establish that the rearrangements described in Tables 5 and 6 generated anti-Antigen E-specific common light chain antibodies that blocked binding of Ligand Y to its cognate receptor Antigen E with varying degrees of efficacy, which is consistent with the anti-Antigen E common light chain antibodies of Tables 5 and 6 comprising antibodies with overlapping and non-overlapping epitope specificity with respect to Antigen E.

Example 8. Determination of Blocking Ability of Antigen-Specific Common Light Chain Antibodies by ELISA Human common light chain antibodies raised against Antigen E were tested for their ability to block Antigen E binding to a Ligand Y-coated surface in an ELISA assay.

Ligand Y was coated onto 96-well plates at a concentration of 2 μg/mL diluted in PBS and incubated overnight followed by washing four times in PBS with 0.05% Tween-20. The plate was then blocked with PBS (Irvine Scientific, Santa Ana, CA) containing 0.5% (w/v) BSA (Sigma-Aldrich Corp., St. Louis, MO) for one hour at room temperature. In a separate plate, supernatants containing anti-Antigen E common light chain antibodies were diluted 1:10 in buffer. A mock supernatant with the same components of the antibodies was used as a negative control. Antigen E-mmH (described above) was added to a final concentration of 0.150 nM and incubated for one hour at room temperature. The antibody/Antigen E-mmH mixture was then added to the plate containing Ligand Y and incubated for one hour at room temperature. Detection of Antigen E-mmH bound to Ligand Y was determined with Horse-Radish Peroxidase (HRP) conjugated to anti-Penta-His antibody (Qiagen, Valencia, CA) and developed by standard colorimetric response using tetramethylbenzidine (TMB) substrate (BD Biosciences, San Jose, CA) neutralized by sulfuric acid. Absorbance was read at OD450 for 0.1 sec. Background absorbance of a sample without Antigen E was subtracted from all samples. Percent blocking was calculated by division of the background-subtracted MFI of each sample by the adjusted negative control value, multiplying by 100 and subtracting the resulting value from 100.

Tables 9 and 10 show the percent blocking for all 98 anti-Antigen E common light chain antibodies tested in the ELISA assay. ND: not determined under current experimental conditions.

TABLE 9

| Vκ1-39Jκ5 Common Light Chain Antibodies | |
|---|---|
| Antibody | % Blocking of Antigen E In Solution |
| 2948 | 21.8 |
| 2948G | 22.9 |
| 2949 | 79.5 |
| 2949G | 71.5 |
| 2950 | 80.4 |
| 2950G | 30.9 |
| 2952 | 66.9 |
| 2952G | 47.3 |
| 2954 | 55.9 |
| 2954G | 44.7 |
| 2955 | 12.1 |
| 2955G | 25.6 |
| 2964 | 34.8 |
| 2964G | 47.7 |
| 2978 | 90.0 |
| 2978G | 90.2 |
| 2982 | 59.0 |
| 2982G | 20.4 |
| 2985 | 10.5 |
| 2985G | ND |
| 2987 | 31.4 |
| 2987G | ND |
| 2996 | 29.3 |
| 2996G | ND |
| 2997 | 48.7 |
| 2997G | ND |
| 3004 | 16.7 |
| 3004G | 3.5 |
| 3005 | 87.2 |
| 3005G | 54.3 |
| 3010 | 74.5 |
| 3010G | 84.6 |
| 3011 | 19.4 |
| 3011G | ND |
| 3012 | 45.0 |
| 3012G | 12.6 |
| 3013 | 39.0 |
| 3013G | 9.6 |
| 3014 | 5.2 |
| 3014G | 17.1 |
| 3015 | 23.7 |

TABLE 9-continued

| Vκ1-39Jκ5 Common Light Chain Antibodies | |
|---|---|
| Antibody | % Blocking of Antigen E In Solution |
| 3015G | 10.2 |
| 3016 | 78.1 |
| 3016G | 37.4 |
| 3017 | 61.6 |
| 3017G | 25.2 |
| 3018 | 40.6 |
| 3018G | 14.5 |
| 3019 | 94.6 |
| 3019G | 92.3 |
| 3020 | 80.8 |
| 3020G | ND |
| 3021 | 7.6 |
| 3021G | 20.7 |
| 3022 | 2.4 |
| 3022G | 15.0 |
| 3023 | 9.1 |
| 3023G | 19.2 |
| 3024 | 7.5 |
| 3024G | 15.2 |
| 3025 | ND |
| 3025G | 13.9 |
| 3027 | 61.4 |
| 3027G | 82.7 |
| 3028 | 40.3 |
| 3028G | 12.3 |
| 3030 | ND |
| 3030G | 9.5 |
| 3032 | ND |
| 3032G | 13.1 |
| 3033 | 77.1 |
| 3033G | 32.9 |
| 3036 | 17.6 |
| 3036G | 24.6 |
| 3041 | 59.3 |
| 3041G | 30.7 |
| 3042 | 39.9 |
| 3042G | 16.1 |
| 3043 | 57.4 |
| 3043G | 46.1 |

TABLE 10

| Vκ3-20Jκ1 Common Light Chain Antibodies | |
|---|---|
| Antibody | % Blocking of Antigen E In Solution |
| 2968 | 68.9 |
| 2968G | 15.2 |
| 2969 | 10.1 |
| 2969G | 23.6 |
| 2970 | 34.3 |
| 2970G | 41.3 |
| 2971 | 6.3 |
| 2971G | 27.1 |
| 2972 | 9.6 |
| 2972G | 35.7 |
| 2973 | 20.7 |
| 2973G | 23.1 |
| 2974 | ND |
| 2974G | 22.0 |
| 2975 | 8.7 |
| 2975G | 19.2 |
| 2976 | 4.6 |
| 2976G | 26.7 |

As described in this Example, of the 80 common light chain antibodies containing the Vκ1-39Jκ5 engineered light chain tested for their ability to block Antigen E binding to a Ligand Y-coated surface, 22 demonstrated >50% blocking, while 58 demonstrated <50% blocking (20 at 25-50% blocking and 38 at <25% blocking). For the 18 common light chain antibodies containing the Vκ3-20Jκ1 engineered light chain, one demonstrated >50% blocking, while 17 demonstrated <50% blocking (5 at 25-50% blocking and 12 at <25% blocking) of Antigen E binding to a Ligand Y-coated surface.

These results are also consistent with the Antigen E-specific common light chain antibody pool comprising antibodies with overlapping and non-overlapping epitope specificity with respect to Antigen E.

Example 9. BIACORE™ Affinity Determination for Antigen-Specific Common Light Chain Antibodies Equilibrium dissociation constants ($K_D$) for selected antibody supernatants were determined by SPR (Surface Plasmon Resonance) using a BIACORE™ T100 instrument (GE Healthcare). All data was obtained using HBS-EP (10 mM Hepes, 150 mM NaCl, 0.3 mM EDTA, 0.05% Surfactant P20, pH 7.4) as both the running and sample buffers, at 25° C. Antibodies were captured from crude supernatant samples on a CM5 sensor chip surface previously derivatized with a high density of anti-human Fc antibodies using standard amine coupling chemistry. During the capture step, supernatants were injected across the anti-human Fc surface at a flow rate of 3 μL/min, for a total of 3 minutes. The capture step was followed by an injection of either running buffer or analyte at a concentration of 100 nM for 2 minutes at a flow rate of 35 μL/min. Dissociation of antigen from the captured antibody was monitored for 6 minutes. The captured antibody was removed by a brief injection of 10 mM glycine, pH 1.5. All sensorgrams were double referenced by subtracting sensorgrams from buffer injections from the analyte sensorgrams, thereby removing artifacts caused by dissociation of the antibody from the capture surface. Binding data for each antibody was fit to a 1:1 binding model with mass transport using BIAcore T100 Evaluation software v2.1. Results are shown in Tables 11 and 12.

TABLE 11

Vκ1-39Jκ5 Common Light Chain Antibodies

| Antibody | 100 nM Antigen E $K_D$ (nM) | $T_{1/2}$ (min) |
|---|---|---|
| 2948 | 8.83 | 28 |
| 2948G | 95.0 | 1 |
| 2949 | 3.57 | 18 |
| 2949G | 6.37 | 9 |
| 2950 | 4.91 | 17 |
| 2950G | 13.6 | 5 |
| 2952 | 6.25 | 7 |
| 2952G | 7.16 | 4 |
| 2954 | 2.37 | 24 |
| 2954G | 5.30 | 9 |
| 2955 | 14.4 | 6 |
| 2955G | 12.0 | 4 |
| 2964 | 14.8 | 6 |
| 2964G | 13.0 | 9 |
| 2978 | 1.91 | 49 |
| 2978G | 1.80 | 58 |
| 2982 | 6.41 | 19 |
| 2982G | 16.3 | 9 |
| 2985 | 64.4 | 9 |
| 2985G | 2.44 | 8 |
| 2987 | 21.0 | 11 |
| 2987G | 37.6 | 4 |
| 2996 | 10.8 | 9 |
| 2996G | 24.0 | 2 |
| 2997 | 7.75 | 19 |

TABLE 11-continued

Vκ1-39Jκ5 Common Light Chain Antibodies

| Antibody | 100 nM Antigen E $K_D$ (nM) | $T_{1/2}$ (min) |
|---|---|---|
| 2997G | 151 | 1 |
| 3004 | 46.5 | 14 |
| 3004G | 1.93 | 91 |
| 3005 | 2.35 | 108 |
| 3005G | 6.96 | 27 |
| 3010 | 4.13 | 26 |
| 3010G | 2.10 | 49 |
| 3011 | 59.1 | 5 |
| 3011G | 41.7 | 5 |
| 3012 | 9.71 | 20 |
| 3012G | 89.9 | 2 |
| 3013 | 20.2 | 20 |
| 3013G | 13.2 | 4 |
| 3014 | 213 | 4 |
| 3014G | 36.8 | 3 |
| 3015 | 29.1 | 11 |
| 3015G | 65.9 | 0 |
| 3016 | 4.99 | 17 |
| 3016G | 18.9 | 4 |
| 3017 | 9.83 | 8 |
| 3017G | 55.4 | 2 |
| 3018 | 11.3 | 36 |
| 3018G | 32.5 | 3 |
| 3019 | 1.54 | 59 |
| 3019G | 2.29 | 42 |
| 3020 | 5.41 | 39 |
| 3020G | 41.9 | 6 |
| 3021 | 50.1 | 6 |
| 3021G | 26.8 | 4 |
| 3022 | 25.7 | 17 |
| 3022G | 20.8 | 12 |
| 3023 | 263 | 9 |
| 3023G | 103 | 5 |
| 3024 | 58.8 | 7 |
| 3024G | 7.09 | 10 |
| 3025 | 35.2 | 6 |
| 3025G | 42.5 | 8 |
| 3027 | 7.15 | 6 |
| 3027G | 4.24 | 18 |
| 3028 | 6.89 | 37 |
| 3028G | 7.23 | 22 |
| 3030 | 46.2 | 7 |
| 3030G | 128 | 3 |
| 3032 | 53.2 | 9 |
| 3032G | 13.0 | 1 |
| 3033 | 4.61 | 17 |
| 3033G | 12.0 | 5 |
| 3036 | 284 | 12 |
| 3036G | 18.2 | 10 |
| 3041 | 6.90 | 12 |
| 3041G | 22.9 | 2 |
| 3042 | 9.46 | 34 |
| 3042G | 85.5 | 3 |
| 3043 | 9.26 | 29 |
| 3043G | 13.1 | 22 |

TABLE 12

Vκ3-20Jκ1 Common Light Chain Antibodies

| Antibody | 100 nM Antigen E $K_D$ (nM) | $T_{1/2}$ (min) |
|---|---|---|
| 2968 | 5.50 | 8 |
| 2968G | 305 | 0 |
| 2969 | 34.9 | 2 |
| 2969G | 181 | 1 |
| 2970G | 12.3 | 3 |

TABLE 12-continued

| Vκ3-20Jκ1 Common Light Chain Antibodies | | |
|---|---|---|
| | 100 nM Antigen E | |
| Antibody | $K_D$ (nM) | $T_{1/2}$ (min) |
| 2971G | 32.8 | 22 |
| 2972 | 6.02 | 13 |
| 2972G | 74.6 | 26 |
| 2973 | 5.35 | 39 |
| 2973G | 11.0 | 44 |
| 2974 | 256 | 0 |
| 2974G | 138 | 0 |
| 2975 | 38.0 | 2 |
| 2975G | 134 | 1 |
| 2976 | 6.73 | 10 |
| 2976G | 656 | 8 |

The binding affinities of common light chain antibodies comprising the rearrangements shown in Tables 5 and 6 vary, with nearly all exhibiting a $K_D$ in the nanomolar range. The affinity data is consistent with the common light chain antibodies resulting from the combinatorial association of rearranged variable domains described in Tables 5 and 6 being high-affinity, clonally selected, and somatically mutated. Coupled with data previously shown, the common light chain antibodies described in Tables 5 and 6 comprise a collection of diverse, high-affinity antibodies that exhibit specificity for one or more epitopes on Antigen E.

Example 10. Determination of Binding Specificities of Antigen-Specific Common Light Chain Antibodies by LUMINEX™ Assay Selected anti-Antigen E common light chain antibodies were tested for their ability to bind to the ECD of Antigen E and Antigen E ECD variants, including the cynomolgous monkey ortholog (Mf Antigen E), which differs from the human protein in approximately 10% of its amino acid residues; a deletion mutant of Antigen E lacking the last 10 amino acids from the C-terminal end of the ECD (Antigen E-ACT); and two mutants containing an alanine substitution at suspected locations of interaction with Ligand Y (Antigen E-Ala1 and AntigenE-Ala2). The Antigen E proteins were produced in CHO cells and each contained a myc-myc-His C-terminal tag.

For the binding studies, Antigen E ECD protein or variant protein (described above) from 1 mL of culture medium was captured by incubation for 2 hr at room temperature with $1\times10^6$ microsphere (LUMINEX™) beads covalently coated with an anti-myc monoclonal antibody (MAb 9E10, hybridoma cell line CRL-1729™; ATCC, Manassas, VA). The beads were then washed with PBS before use. Supernatants containing anti-Antigen E common light chain antibodies were diluted 1:4 in buffer and added to 96-well filter plates. A mock supernatant with no antibody was used as negative control. The beads containing the captured Antigen E proteins were then added to the antibody samples (3000 beads per well) and incubated overnight at 4° C. The following day, the sample beads were washed and the bound common light chain antibody was detected with a R-phycoerythrin-conjugated anti-human IgG antibody. The fluorescence intensity of the beads (approximately 100 beads counted for each antibody sample binding to each Antigen E protein) was measured with a LUMINEX™ flow cytometry-based analyzer, and the median fluorescence intensity (MFI) for at least 100 counted beads per bead/antibody interaction was recorded. Results are shown in Tables 13 and 14.

TABLE 13

| Vκ1-39Jκ5 Common Light Chain Antibodies | | | | | |
|---|---|---|---|---|---|
| | Mean Fluorescence Intensity (MFI) | | | | |
| Antibody | Antigen E-ECD | Antigen E-ΔCT | Antigen E-Ala1 | Antigen E-Ala2 | Mf Antigen E |
| 2948 | 1503 | 2746 | 4953 | 3579 | 1648 |
| 2948G | 537 | 662 | 2581 | 2150 | 863 |
| 2949 | 3706 | 4345 | 8169 | 5678 | 5142 |
| 2949G | 3403 | 3318 | 7918 | 5826 | 5514 |
| 2950 | 3296 | 4292 | 7756 | 5171 | 4749 |
| 2950G | 2521 | 2408 | 7532 | 5079 | 3455 |
| 2952 | 3384 | 1619 | 1269 | 168 | 911 |
| 2952G | 3358 | 1001 | 108 | 55 | 244 |
| 2954 | 2808 | 3815 | 7114 | 5039 | 3396 |
| 2954G | 2643 | 2711 | 7620 | 5406 | 3499 |
| 2955 | 1310 | 2472 | 4738 | 3765 | 1637 |
| 2955G | 1324 | 1802 | 4910 | 3755 | 1623 |
| 2964 | 5108 | 1125 | 4185 | 346 | 44 |
| 2964G | 4999 | 729 | 4646 | 534 | 91 |
| 2978 | 6986 | 2800 | 14542 | 10674 | 8049 |
| 2978G | 5464 | 3295 | 11652 | 8026 | 6452 |
| 2982 | 4955 | 2388 | 13200 | 9490 | 6772 |
| 2982G | 3222 | 2013 | 8672 | 6509 | 4949 |
| 2985 | 1358 | 832 | 4986 | 3892 | 1669 |
| 2985G | 43 | 43 | 128 | 244 | 116 |
| 2987 | 3117 | 1674 | 7646 | 5944 | 2546 |
| 2987G | 3068 | 1537 | 9202 | 6004 | 4744 |
| 2996 | 4666 | 1917 | 12875 | 9046 | 6459 |
| 2996G | 2752 | 1736 | 8742 | 6150 | 4873 |
| 2997 | 5164 | 2159 | 12167 | 8361 | 5922 |
| 2997G | 658 | 356 | 3392 | 2325 | 1020 |
| 3004 | 2794 | 1397 | 8542 | 6268 | 3083 |
| 3004G | 2753 | 1508 | 8267 | 5808 | 4345 |
| 3005 | 5683 | 2221 | 12900 | 9864 | 5868 |
| 3005G | 4344 | 2732 | 10669 | 7125 | 5880 |
| 3010 | 4829 | 1617 | 2642 | 3887 | 44 |
| 3010G | 3685 | 1097 | 2540 | 3022 | 51 |
| 3011 | 2859 | 2015 | 7855 | 5513 | 3863 |
| 3011G | 2005 | 1072 | 6194 | 4041 | 3181 |
| 3012 | 3233 | 2221 | 8543 | 5637 | 3307 |
| 3012G | 968 | 378 | 3115 | 2261 | 1198 |
| 3013 | 2343 | 1791 | 6715 | 4810 | 2528 |
| 3013G | 327 | 144 | 1333 | 1225 | 370 |
| 3014 | 1225 | 1089 | 5436 | 3621 | 1718 |
| 3014G | 1585 | 851 | 5178 | 3705 | 2411 |
| 3015 | 3202 | 2068 | 8262 | 5554 | 3796 |
| 3015G | 1243 | 531 | 4246 | 2643 | 1611 |
| 3016 | 4220 | 2543 | 8920 | 5999 | 5666 |
| 3016G | 2519 | 1277 | 6344 | 4288 | 4091 |
| 3017 | 3545 | 2553 | 8700 | 5547 | 5098 |
| 3017G | 1972 | 1081 | 5763 | 3825 | 3038 |
| 3018 | 2339 | 1971 | 6140 | 4515 | 2293 |
| 3018G | 254 | 118 | 978 | 1020 | 345 |
| 3019 | 5235 | 1882 | 7108 | 4249 | 54 |
| 3019G | 4090 | 1270 | 4769 | 3474 | 214 |
| 3020 | 3883 | 3107 | 8591 | 6602 | 4420 |
| 3020G | 2165 | 1209 | 6489 | 4295 | 2912 |
| 3021 | 1961 | 1472 | 6872 | 4641 | 2742 |
| 3021G | 2091 | 1005 | 6430 | 3988 | 2935 |
| 3022 | 2418 | 793 | 7523 | 2679 | 36 |
| 3022G | 2189 | 831 | 6182 | 3051 | 132 |
| 3023 | 1692 | 1411 | 5788 | 3898 | 2054 |
| 3023G | 1770 | 825 | 5702 | 3677 | 2648 |
| 3024 | 1819 | 1467 | 6179 | 4557 | 2450 |
| 3024G | 100 | 87 | 268 | 433 | 131 |
| 3025 | 1853 | 1233 | 6413 | 4337 | 2581 |
| 3025G | 1782 | 791 | 5773 | 3871 | 2717 |
| 3027 | 4131 | 1018 | 582 | 2510 | 22 |
| 3027G | 3492 | 814 | 1933 | 2596 | 42 |
| 3028 | 4361 | 2545 | 9884 | 5639 | 975 |
| 3028G | 2835 | 1398 | 7124 | 3885 | 597 |
| 3030 | 463 | 277 | 1266 | 1130 | 391 |
| 3030G | 943 | 302 | 3420 | 2570 | 1186 |

TABLE 13-continued

| Vκ1-39Jκ5 Common Light Chain Antibodies | | | | | |
|---|---|---|---|---|---|
| | Mean Fluorescence Intensity (MFI) | | | | |
| Antibody | Antigen E-ECD | Antigen E-ΔCT | Antigen E-Ala1 | Antigen E-Ala2 | Mf Antigen E |
| 3032 | 2083 | 1496 | 6594 | 4402 | 2405 |
| 3032G | 295 | 106 | 814 | 902 | 292 |
| 3033 | 4409 | 2774 | 8971 | 6331 | 5825 |
| 3033G | 2499 | 1234 | 6745 | 4174 | 4210 |
| 3036 | 1755 | 1362 | 6137 | 4041 | 1987 |
| 3036G | 2313 | 1073 | 6387 | 4243 | 3173 |
| 3041 | 3674 | 2655 | 8629 | 5837 | 4082 |
| 3041G | 2519 | 1265 | 6468 | 4274 | 3320 |
| 3042 | 2653 | 2137 | 7277 | 5124 | 3325 |
| 3042G | 1117 | 463 | 4205 | 2762 | 1519 |
| 3043 | 3036 | 2128 | 7607 | 5532 | 3366 |
| 3043G | 2293 | 1319 | 6573 | 4403 | 3228 |

TABLE 14

| Vκ3-20Jκ1 Common Light Chain Antibodies | | | | | |
|---|---|---|---|---|---|
| | Mean Fluorescence Intensity (MFI) | | | | |
| Antibody | Antigen E-ECD | Antigen E-ΔCT | Antigen E-Ala1 | Antigen E-Ala2 | Mf Antigen E |
| 2968 | 6559 | 3454 | 14662 | 3388 | 29 |
| 2968G | 2149 | 375 | 9109 | 129 | 22 |
| 2969 | 2014 | 1857 | 7509 | 5671 | 3021 |
| 2969G | 1347 | 610 | 6133 | 4942 | 2513 |
| 2970 | 5518 | 1324 | 14214 | 607 | 32 |
| 2970G | 4683 | 599 | 12321 | 506 | 31 |
| 2971 | 501 | 490 | 2506 | 2017 | 754 |
| 2971G | 578 | 265 | 2457 | 2062 | 724 |
| 2972 | 2164 | 2158 | 8408 | 6409 | 3166 |
| 2972G | 1730 | 992 | 6364 | 4602 | 2146 |
| 2973 | 3527 | 1148 | 3967 | 44 | 84 |
| 2973G | 1294 | 276 | 1603 | 28 | 44 |
| 2974 | 1766 | 722 | 8821 | 241 | 19 |
| 2974G | 2036 | 228 | 8172 | 135 | 26 |
| 2975 | 1990 | 1476 | 8669 | 6134 | 2468 |
| 2975G | 890 | 315 | 4194 | 3987 | 1376 |
| 2976 | 147 | 140 | 996 | 1079 | 181 |
| 2976G | 1365 | 460 | 6024 | 3929 | 1625 |

The anti-Antigen E common light chain antibody supernatants exhibited high specific binding to the beads linked to Antigen E-ECD. For these beads, the negative control mock supernatant resulted in negligible signal (<10 MFI) when combined with the Antigen E-ECD bead sample, whereas the supernatants containing anti-Antigen E common light chain antibodies exhibited strong binding signal (average MFI of 2627 for 98 antibody supernatants; MFI >500 for 91/98 antibody samples).

As a measure of the ability of the selected anti-Antigen E common light chain antibodies to identify different epitopes on the ECD of Antigen E, the relative binding of the antibodies to the variants were determined. All four Antigen E variants were captured to the anti-myc LUMINEX™ beads as described above for the native Antigen E-ECD binding studies, and the relative binding ratios ($MFI_{variant}/MH_{Antigen\ E\text{-}ECD}$) were determined. For 98 tested common light chain antibody supernatants shown in Tables 12 and 13, the average ratios ($MFI_{variant}/MH_{Antigen\ E\text{-}ECD}$) differed for each variant, likely reflecting different capture amounts of proteins on the beads (average ratios of 0.61, 2.9, 2.0, and 1.0 for Antigen E-ΔCT, Antigen E-Ala1, Antigen E-Ala2, and Mf Antigen E, respectively). For each protein variant, the binding for a subset of the 98 tested common light chain antibodies showed greatly reduced binding, indicating sensitivity to the mutation that characterized a given variant. For example, 19 of the common light chain antibody samples bound to the Mf Antigen E with $MFI_{variant}/MH_{Antigen\ E\text{-}ECD}$ of <8%. Since many in this group include high or moderately high affinity antibodies (5 with $K_D$<5 nM, 15 with $K_D$<50 nM), it is likely that the lower signal for this group results from sensitivity to the sequence (epitope) differences between native Antigen E-ECD and a given variant rather than from lower affinities.

These data establish that the common light chain antibodies described in Tables 5 and 6 represent a diverse group of Antigen-E-specific common light chain antibodies that specifically recognize more than one epitope on Antigen E.

Example 11. Light Chain Shuffling in Common Light Chain Antibodies

Heavy chains of selected antigen-specific common light chain antibodies were tested for binding to Antigen E after repairing the heavy chains with either a germline Vκ1-39Jκ5 or a germline Vκ3-20Jκ1 engineered light chain (as described in Example 1).

Briefly, 247 heavy chains of Antigen E-specific common light chain antibodies (Vκ1-39Jκ5 and Vκ3-20Jκ1) were transfected with either a germline Vκ1-39 or a germline Vκ3-20 engineered light chain and rescreened for binding to Antigen E by a LUMINEX™ assay (as described in Example 7 and Example 10). Binding to Antigen E was confirmed by BIACORE™ (as described in Example 9). The results are shown in Table 15.

As shown in this Example, twenty-eight common light chain antibodies specific for Antigen E were capable of binding to Antigen E when repaired with a germline form of the light chain.

TABLE 15

| Original Light Chain | Repaired Light Chain | No. Tested | No. Confirmed Binders |
|---|---|---|---|
| 1-39 | 1-39 | 198 | 23 |
| 3-20 | 3-20 | 49 | 5 |

Example 12. Heavy Chain Gene Usage and Somatic Hypermutation Frequency in Common Light Chain Antibodies Heavy and light chain sequences (>6000) of antibodies raised in VELCOIMMUNE® mice (e.g., U.S. Pat. Nos. 6,596,541 and 7,105,348) were compiled with heavy and light chain sequences (>600) of common light chain antibodies obtained by a multi-antigen immunization scheme employing the engineered light chain mice (described above) to compare heavy chain gene segment usage and somatic hypermutation frequencies of the antibody chains.

Heavy Chain Gene Usage. Heavy and light chain sequences obtained from VELOCIMMUNE® mice containing a replacement of the endogenous mouse heavy chain locus with human $V_H$, $D_H$, and $J_H$ gene segments and a replacement of the endogenous mouse κ light chain locus with either the engineered germline Vκ1-39Jκ5 human light chain region or the engineered germline Vκ3-20Jκ1 human light chain region (as described in Example 2) immunized with a human cell-surface receptor (Antigen E), a heterodimer of two human cell-surface glycoproteins (Antigen F), a human cytokine receptor (Antigen G) and a human tumor differentiation antigen (Antigen H) were analyzed for heavy chain gene segment usage and $V_H$ and $J_H$ gene segments were recorded. Results are shown in Tables 16-18. Percentages in Tables 16-18 represent rounded values and in some cases may not equal 100% when added together.

Table 16 sets forth the percent heavy chain family usage for antibodies from VELCOIMMUNE® mice (VI), antibodies from VELCOIMMUNE® mice having a cognate Vκ1-39 light chain (VI-Vκ1-39), antibodies from Vκ1-39 engineered light chain mice (Vκ1-39), antibodies from VELCOIMMUNE® mice having a cognate Vκ3-20 light chain (VI-Vκ3-20), and antibodies from Vκ3-20 engineered light chain mice (Vκ3-20). Table 17 sets forth the percent $V_H$ and $J_H$ gene usage for antibodies from VELCOIMMUNE® mice (VI), antibodies from VELCOIMMUNE® mice having a cognate Vκ1-39 light chain (VI-Vκ1-39), antibodies from Vκ1-39 engineered light chain mice (Vκ1-39), antibodies from VELCOIMMUNE® mice having a cognate Vκ3-20 light chain (VI-Vκ3-20), and antibodies from Vκ3-20 engineered light chain mice (Vκ3-20). Table 18 sets forth the percent $V_H$ gene usage for antibodies from Vκ1-39 engineered light chain mice (Vκ1-39 Mice) from each immunization group (Antigens E, F, G and H) and the percent $V_H$ gene usage for antibodies from Vκ3-20 engineered light chain mice (Vκ3-20 Mice) from selected immunization groups (Antigens E and G).

As shown in this Example, heavy chain gene usage for antigens tested in Vκ1-39Jκ5-engineered light chain mice was characterized by a preponderance of $V_H$ family III subgroups ($V_H$3-7, $V_H$3-9, $V_H$3-11, $V_H$3-13, $V_H$3-20, $V_H$3-23, $V_H$3-30, $V_H$3-33 and $V_H$3-48). Notable usage of other $V_H$ family subgroups was characterized by usage of $V_H$1-18, $V_H$1-69, $V_H$2-5, $V_H$4-59 and $V_H$6-1. For antigens tested in Vκ3-20Jκ1 engineered light chain mice, heavy chain gene usage was characterized by a preponderance of $V_H$ family III, $V_H$ family IV and $V_H$ family V subgroups ($V_H$3-11, $V_H$3-30, $V_H$3-33, $V_H$4-39, $V_H$4-59 and $V_H$5-51). Notable usage of other $V_H$ family subgroups was characterized by usage of $V_H$1-18, $V_H$1-69, $V_H$2-70 and $V_H$6-1.

Somatic Hypermutation Frequency. Heavy and light chains from antibodies raised in VELCOIMMUNE® mice and the engineered light chain mice (described above) were aligned to germline sequences according to the heavy and light chain gene usage demonstrated for each heavy and/or light chain. Amino acid changes for each framework region (FW) and complementarity determining region (CDR) for both heavy and light chain of each sequence were calculated. Results are shown in Tables 19-22. Percentages in Tables 21-24 represent rounded values and in some cases may not equal 100% when added together.

Table 19 sets forth the number of amino acid (AA) changes observed in each FW and CDR region of heavy chains of antibodies from VELCOIMMUNE® mice, heavy chains of antibodies from Vκ1-39 engineered light chain mice (Vκ1-39 Mice) and heavy chains of antibodies from Vκ3-20 engineered light chain mice (Vκ3-20 Mice). Table 20 sets forth the number of amino acid (AA) changes observed in each FW and CDR region of light chains of antibodies from VELCOIMMUNE® mice, the light chain of antibodies from Vκ1-39 engineered mice (Vκ1-39 Mice) and the light chain of antibodies from Vκ3-20 engineered mice (Vκ3-20 Mice). Table 21 sets forth the number of amino acid (AA) changes observed in each FW and CDR region of heavy chains of antibodies from Vκ1-39 engineered light chain mice (Vκ1-39 Mice) for selected immunization groups (Antigens E, F and H). Table 22 sets forth the number of amino acid (AA) changes observed in each FW and CDR region of heavy chains of antibodies from Vκ3-20 engineered light chain mice (Vκ3-20 Mice) for selected immunization groups (Antigens E and G).

TABLE 16

| $V_H$ Family | VI | VI - Vκ1-39 | Vκ1-39 | VI - Vκ3-20 | Vκ3-20 |
|---|---|---|---|---|---|
| 1 | 9.0 | 14.8 | 3.3 | 7.1 | 4.9 |
| 2 | 2.2 | 1.8 | 4.6 | 0 | 1.6 |
| 3 | 77.8 | 69.8 | 77.3 | 61.4 | 29.5 |
| 4 | 8.4 | 8.3 | 11.2 | 27.1 | 39.3 |
| 5 | 0.9 | 0 | 0.7 | 4.3 | 23.0 |
| 6 | 1.7 | 5.3 | 3.0 | 0 | 1.6 |

TABLE 17

| | VI | VI - Vκ1-39 | Vκ1-39 | VI - Vκ3-20 | Vκ3-20 |
|---|---|---|---|---|---|
| $V_H$ Gene | | | | | |
| 1-2 | 3.9 | 8.3 | 0 | 2.9 | 0 |
| 1-3 | 0 | 0 | 0 | 0 | 0 |
| 1-8 | 1.3 | 0.6 | 0 | 1.4 | 0 |
| 1-18 | 3.0 | 0.6 | 1.3 | 2.1 | 1.6 |
| 1-24 | 0.4 | 3.6 | 0 | 0.7 | 0 |
| 1-46 | 0.1 | 0 | 0 | 0 | 0 |
| 1-58 | 0 | 0 | 0 | 0 | 0 |
| 1-69 | 0.3 | 1.8 | 2.0 | 0 | 3.3 |
| 2-5 | 1.9 | 0 | 4.6 | 0 | 0 |
| 2-26 | 0.2 | 1.8 | 0.0 | 0 | 0 |
| 2-70 | 0.1 | 0 | 0 | 0 | 1.6 |
| 3-7 | 3.0 | 14.8 | 0 | 1.4 | 0 |
| 3-9 | 8.5 | 3.6 | 29.6 | 16.4 | 0 |
| 3-11 | 5.4 | 10.7 | 0 | 7.1 | 1.6 |
| 3-13 | 3.2 | 1.8 | 0.7 | 2.1 | 0 |
| 3-15 | 4.0 | 4.7 | 0.3 | 0.7 | 0 |
| 3-20 | 1.0 | 0.6 | 0.3 | 5.0 | 0 |
| 3-21 | 0.8 | 0.6 | 0 | 2.1 | 0 |
| 3-23 | 20.4 | 8.9 | 3.3 | 8.6 | 0 |
| 3-30 | 17.6 | 4.1 | 35.2 | 12.9 | 1.6 |
| 3-33 | 12.6 | 14.8 | 0 | 5.0 | 26.2 |
| 3-43 | 0.2 | 0.6 | 0 | 0 | 0 |
| 3-48 | 0.8 | 1.2 | 7.2 | 0 | 0 |
| 3-53 | 0.3 | 3.6 | 0.3 | 0 | 0 |
| 3-64 | 0 | 0 | 0.3 | 0 | 0 |
| 3-72 | 0 | 0 | 0 | 0 | 0 |
| 3-73 | 0 | 0 | 0 | 0 | 0 |
| 4-31 | 2.7 | 0 | 0.7 | 8.6 | 0 |
| 4-34 | 1.8 | 0.6 | 0.3 | 14.3 | 0 |
| 4-39 | 1.6 | 0.6 | 3.0 | 2.1 | 14.8 |
| 4-59 | 2.3 | 7.1 | 7.2 | 2.1 | 24.6 |
| 5-51 | 0.9 | 0 | 0.7 | 4.3 | 23.0 |
| 6-1 | 1.7 | 5.3 | 3.0 | 0 | 1.6 |
| $J_H$ Gene | | | | | |
| 1 | 1.5 | 1.2 | 7.1 | 0 | 0 |
| 2 | 4.5 | 2.4 | 0.7 | 5.0 | 26.9 |
| 3 | 10.5 | 16.6 | 13.1 | 13.6 | 26.9 |
| 4 | 44.0 | 34.3 | 32.3 | 50.7 | 9.6 |
| 5 | 9.6 | 10.1 | 16.8 | 7.9 | 1.9 |
| 6 | 29.7 | 35.5 | 30.0 | 22.9 | 34.6 |

TABLE 18

| $V_H$ Gene | Vκ1-39 Mice Antigen E | Vκ1-39 Mice Antigen F | Vκ1-39 Mice Antigen G | Vκ1-39 Mice Antigen H | Vκ3-20 Mice Antigen E | Vκ3-20 Mice Antigen G |
|---|---|---|---|---|---|---|
| 1-2 | 0 | 0 | 0 | 0 | 0 | 0 |
| 1-3 | 0 | 0 | 0 | 0 | 0 | 0 |
| 1-8 | 0 | 0 | 0 | 0 | 0 | 0 |
| 1-18 | 0 | 0 | 0 | 8.3 | 0 | 3.1 |
| 1-24 | 0 | 0 | 0 | 0 | 0 | 0 |
| 1-46 | 0 | 0 | 0 | 0 | 0 | 0 |
| 1-58 | 0 | 0 | 0 | 0 | 0 | 0 |
| 1-69 | 2.9 | 0 | 25.0 | 0 | 0 | 6.3 |
| 2-5 | 8.2 | 0 | 0 | 0 | 0 | 0 |
| 2-26 | 0 | 0 | 0 | 0 | 0 | 0 |
| 2-70 | 0 | 0 | 0 | 0 | 0 | 3.1 |
| 3-7 | 0 | 0 | 0 | 0 | 0 | 0 |
| 3-9 | 1.2 | 98.8 | 0 | 14.6 | 0 | 0 |
| 3-11 | 0 | 0 | 0 | 0 | 0 | 3.1 |
| 3-13 | 0.6 | 0 | 25.0 | 0 | 0 | 0 |
| 3-15 | 0 | 1.2 | 0 | 0 | 0 | 0 |
| 3-20 | 0 | 0 | 25.0 | 0 | 0 | 0 |
| 3-21 | 0 | 0 | 0 | 0 | 0 | 0 |
| 3-23 | 4.1 | 0 | 25.0 | 4.2 | 0 | 0 |
| 3-30 | 62.9 | 0 | 0 | 0 | 3.4 | 0 |
| 3-33 | 0 | 0 | 0 | 0 | 13.8 | 37.5 |
| 3-43 | 0 | 0 | 0 | 0 | 0 | 0 |
| 3-48 | 0.6 | 0 | 0 | 43.8 | 0 | 0 |
| 3-53 | 1.6 | 0 | 0 | 0 | 0 | 0 |
| 3-64 | 1.6 | 0 | 0 | 0 | 0 | 0 |
| 3-72 | 0 | 0 | 0 | 0 | 0 | 0 |
| 3-73 | 0 | 0 | 0 | 0 | 0 | 0 |
| 4-31 | 0 | 0 | 0 | 4.2 | 0 | 0 |
| 4-34 | 0 | 0 | 0 | 2.1 | 0 | 0 |
| 4-39 | 5.3 | 0 | 0 | 0 | 31.0 | 0 |
| 4-59 | 11.8 | 0 | 0 | 4.2 | 3.4 | 43.8 |
| 5-51 | 1.2 | 0 | 0 | 0 | 48.3 | 0 |
| 6-1 | 0 | 0 | 0 | 18.8 | 0 | 3.1 |

TABLE 19

| # AA Changes | FW1 | CDR1 | FW2 | CDR2 | FW3 | CDR3 |
|---|---|---|---|---|---|---|
| | Heavy Chains of Antibodies from VELCOIMMUNE ® Mice | | | | | |
| 0 | 63 | 32 | 36 | 26 | 12 | 82 |
| 1 | 23 | 32 | 41 | 31 | 22 | 17 |
| 2 | 9 | 25 | 17 | 23 | 27 | 1 |
| 3 | 4 | 10 | 5 | 16 | 13 | 0 |
| 4 | 0 | 1 | 1 | 3 | 12 | 0 |
| >5 | 1 | 0 | 0 | 1 | 14 | 0 |
| | Heavy Chains of Antibodies from Vκ1-39 Mice | | | | | |
| 0 | 65 | 8 | 34 | 30 | 9 | 37 |
| 1 | 25 | 26 | 35 | 34 | 19 | 54 |
| 2 | 9 | 44 | 23 | 20 | 33 | 9 |
| 3 | 1 | 19 | 8 | 12 | 22 | 0 |
| 4 | 0 | 3 | 0 | 5 | 11 | 0 |
| >5 | 1 | 0 | 0 | 0 | 7 | 0 |
| | Heavy Chains of Antibodies from Vκ3-20 Mice | | | | | |
| 0 | 57 | 8 | 54 | 16 | 8 | 93 |
| 1 | 41 | 43 | 34 | 39 | 21 | 7 |
| 2 | 2 | 25 | 10 | 18 | 20 | 0 |
| 3 | 0 | 15 | 2 | 21 | 13 | 0 |
| 4 | 0 | 10 | 0 | 3 | 20 | 0 |
| >5 | 0 | 0 | 0 | 2 | 18 | 0 |

TABLE 20

| # AA Changes | FW1 | CDR1 | FW2 | CDR2 | FW3 | CDR3 |
|---|---|---|---|---|---|---|
| | Light Chains of Antibodies from VELCOIMMUNE ® Mice | | | | | |
| 0 | 65 | 24 | 49 | 60 | 33 | 23 |
| 1 | 24 | 20 | 34 | 31 | 27 | 38 |
| 2 | 9 | 27 | 16 | 9 | 18 | 28 |
| 3 | 1 | 20 | 1 | 0 | 14 | 7 |
| 4 | 0 | 7 | 0 | 0 | 4 | 3 |
| >5 | 1 | 1 | 0 | 0 | 3 | 0 |
| | Light Chains of Antibodies from Vκ1-39 Mice | | | | | |
| 0 | 91 | 75 | 80 | 90 | 71 | 63 |
| 1 | 9 | 19 | 17 | 10 | 21 | 27 |
| 2 | 0 | 5 | 1 | 1 | 5 | 8 |
| 3 | 0 | 0 | 1 | 0 | 2 | 1 |
| 4 | 0 | 0 | 0 | 0 | 2 | 1 |
| >5 | 0 | 0 | 0 | 0 | 0 | 0 |
| | Light Chains of Antibodies from Vκ3-20 Mice | | | | | |
| 0 | 90 | 47 | 93 | 97 | 63 | 57 |
| 1 | 10 | 27 | 3 | 3 | 20 | 43 |
| 2 | 0 | 27 | 3 | 0 | 17 | 0 |
| 3 | 0 | 0 | 0 | 0 | 0 | 0 |
| 4 | 0 | 0 | 0 | 0 | 0 | 0 |
| >5 | 0 | 0 | 0 | 0 | 0 | 0 |

TABLE 21

| # AA Changes | FW1 | CDR1 | FW2 | CDR2 | FW3 | CDR3 |
|---|---|---|---|---|---|---|
| | Heavy Chains of Anti-Antigen E Antibodies from Vκ1-39 Mice | | | | | |
| 0 | 75 | 8 | 49 | 41 | 14 | 36 |
| 1 | 21 | 25 | 33 | 35 | 25 | 52 |
| 2 | 4 | 43 | 14 | 18 | 28 | 12 |
| 3 | 0 | 20 | 4 | 5 | 16 | 0 |
| 4 | 0 | 5 | 0 | 1 | 12 | 0 |
| >5 | 1 | 0 | 0 | 0 | 5 | 0 |
| | Heavy Chains of Anti-Antigen F Antibodies from Vκ1-39 Mice | | | | | |
| 0 | 52 | 0 | 6 | 6 | 2 | 15 |
| 1 | 35 | 24 | 32 | 35 | 15 | 78 |
| 2 | 11 | 59 | 46 | 22 | 49 | 7 |
| 3 | 0 | 17 | 16 | 24 | 29 | 0 |
| 4 | 0 | 0 | 0 | 12 | 4 | 0 |
| >5 | 1 | 0 | 0 | 0 | 1 | 0 |
| | Heavy Chains of Anti-Antigen H Antibodies from Vκ1-39 Mice | | | | | |
| 0 | 54 | 21 | 29 | 33 | 4 | 77 |
| 1 | 17 | 35 | 50 | 27 | 6 | 23 |
| 2 | 23 | 21 | 15 | 21 | 25 | 0 |
| 3 | 6 | 21 | 4 | 15 | 27 | 0 |
| 4 | 0 | 2 | 2 | 2 | 15 | 0 |
| >5 | 0 | 0 | 0 | 2 | 23 | 0 |

TABLE 22

| # AA | Heavy Chains of Anti-Antigen E Antibodies from Vκ3-20 Mice |
|---|---|

TABLE 22-continued

| Changes | FW1 | CDR1 | FW2 | CDR2 | FW3 | CDR3 |
|---|---|---|---|---|---|---|
| 0 | 79 | 17 | 62 | 24 | 17 | 90 |
| 1 | 21 | 28 | 34 | 55 | 31 | 10 |
| 2 | 0 | 28 | 3 | 21 | 24 | 0 |
| 3 | 0 | 14 | 0 | 0 | 10 | 0 |
| 4 | 0 | 14 | 0 | 0 | 3 | 0 |
| >5 | 0 | 0 | 0 | 0 | 14 | 0 |

| # AA | Heavy Chains of Anti-Antigen G Antibodies from Vκ3-20 Mice | | | | | |
|---|---|---|---|---|---|---|
| Changes | FW1 | CDR1 | FW2 | CDR2 | FW3 | CDR3 |
| 0 | 38 | 0 | 47 | 9 | 0 | 97 |
| 1 | 59 | 56 | 34 | 25 | 13 | 3 |
| 2 | 3 | 22 | 16 | 16 | 16 | 0 |
| 3 | 0 | 16 | 3 | 41 | 16 | 0 |
| 4 | 0 | 6 | 0 | 6 | 34 | 0 |
| >5 | 0 | 0 | 0 | 3 | 22 | 0 |

Example 13. Binding Affinity of Bispecific Antibodies Having Universal Light Chains Fully human bispecific antibodies were constructed from cloned human heavy chain variable regions of selected monospecific anti-Antigen E common light chain antibodies (described in Example 5) using standard recombinant DNA techniques known in the art. Table 23 sets forth the pairing of human heavy chains (HC-1 and HC-2) from selected parental monospecific antibodies; each pair employed with a germline rearranged human Vκ1-39/Jκ1 light chain for construction of each bispecific antibody.

Binding of bispecific or parental monospecific anti-Antigen E antibodies to the extracellular domain (ECD) of Antigen E was determined using a real-time surface plasmon resonance biosensor assay on a BIACORE™ 2000 instrument (GE Healthcare). A CM5 BIACORE™ sensor surface derivatized with anti-c-myc-specific monoclonal antibody (Clone#9E10) using EDC-NHS chemistry was used to capture the C-terminal myc-myc-hexahistidine tagged ECD of Antigen E (AntigenE-mmh). Around 190 RUs of AntigenE-mmh was captured on the BIACORE™ sensor surface, followed by the injection of 300 nM and 50 nM concentrations of different bispecific or parental monospecific anti-Antigen E antibodies at a flow rate of 50 μl/min. The experiment was performed at 25° C. in HBST running buffer (0.01M HEPES pH 7.4, 0.15M NaCl, 3 mM EDTA, 0.05% v/v Surfactant P20). The amount of antibody binding to AntigenE-mmh surface at 300 nM concentration was recorded three seconds before the end of antibody injection and plotted.

Figure 8:
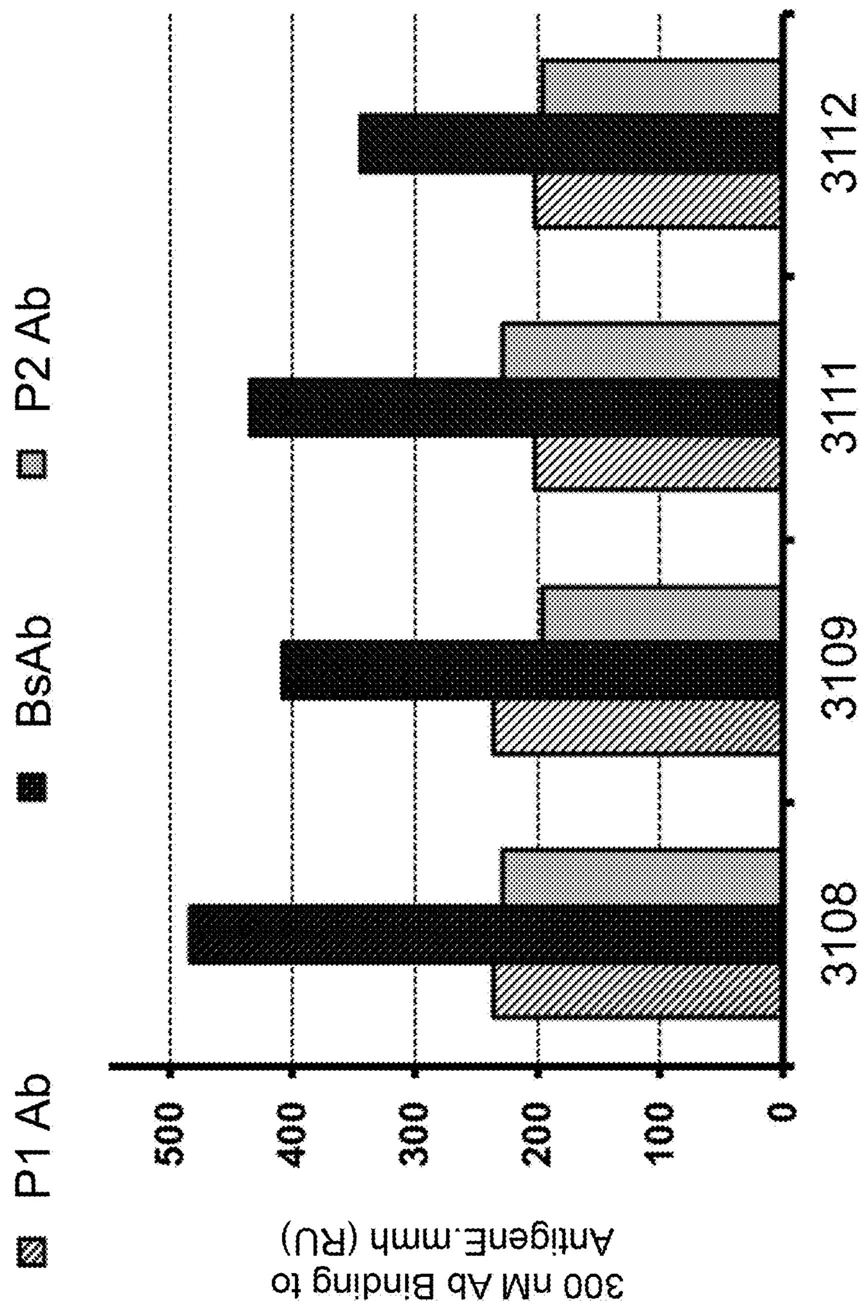
FIG. 8 shows a bar graph of the binding of 300 nM bispecific (darkened bars) and monospecific (striped and gray bars) antibodies to a captured monomeric Antigen E surface in BIACORE™ units (RU). Monoclonal parent-1 antibody (P1 Ab), monoclonal parent-2 (P2 Ab) and bispecific antibodies (BsAb) are indicated.

Table 24 and FIG. 8 set forth the binding responses (BIACORE™ units; RU) observed for each bispecific antibody (BsAb) and monospecific parental antibody (PAb-1, PAb-2). Since each antibody was injected under saturating conditions over an identical AntigenE-mmh surface, the binding response reflects the binding stoichiometry for each antibody binding to the antigen capture surface.

As shown in this Example, the observed binding response for each bispecific antibody was approximately 2-fold greater than the binding response for each parental monospecific antibody (Table 24 and FIG. 8), demonstrating functional construction of bispecific antibodies using heavy chains of antigen-specific monoclonal antibodies and a common light chain where each Fab arm in the bispecific antibody molecule binds simultaneously to distinct epitopes on the extracellular domain of a cell surface receptor (Antigen E; see FIG. 7B, bottom left).

TABLE 23

| Bispecific Antibody | Parent HC-1 | Parent HC-2 |
|---|---|---|
| 3108 | 2952 | 2978 |
| 3109 | 2978 | 3022 |
| 3111 | 2952 | 3005 |
| 3112 | 3022 | 3005 |

TABLE 24

| | Binding Response (RU) | | |
|---|---|---|---|
| Bispecific Antibody | PAb-1 | PAb-2 | BsAb |
| 3108 | 236 | 229 | 485 |
| 3109 | 236 | 197 | 408 |
| 3111 | 202 | 229 | 435 |
| 3112 | 202 | 197 | 345 |

Figure 9:
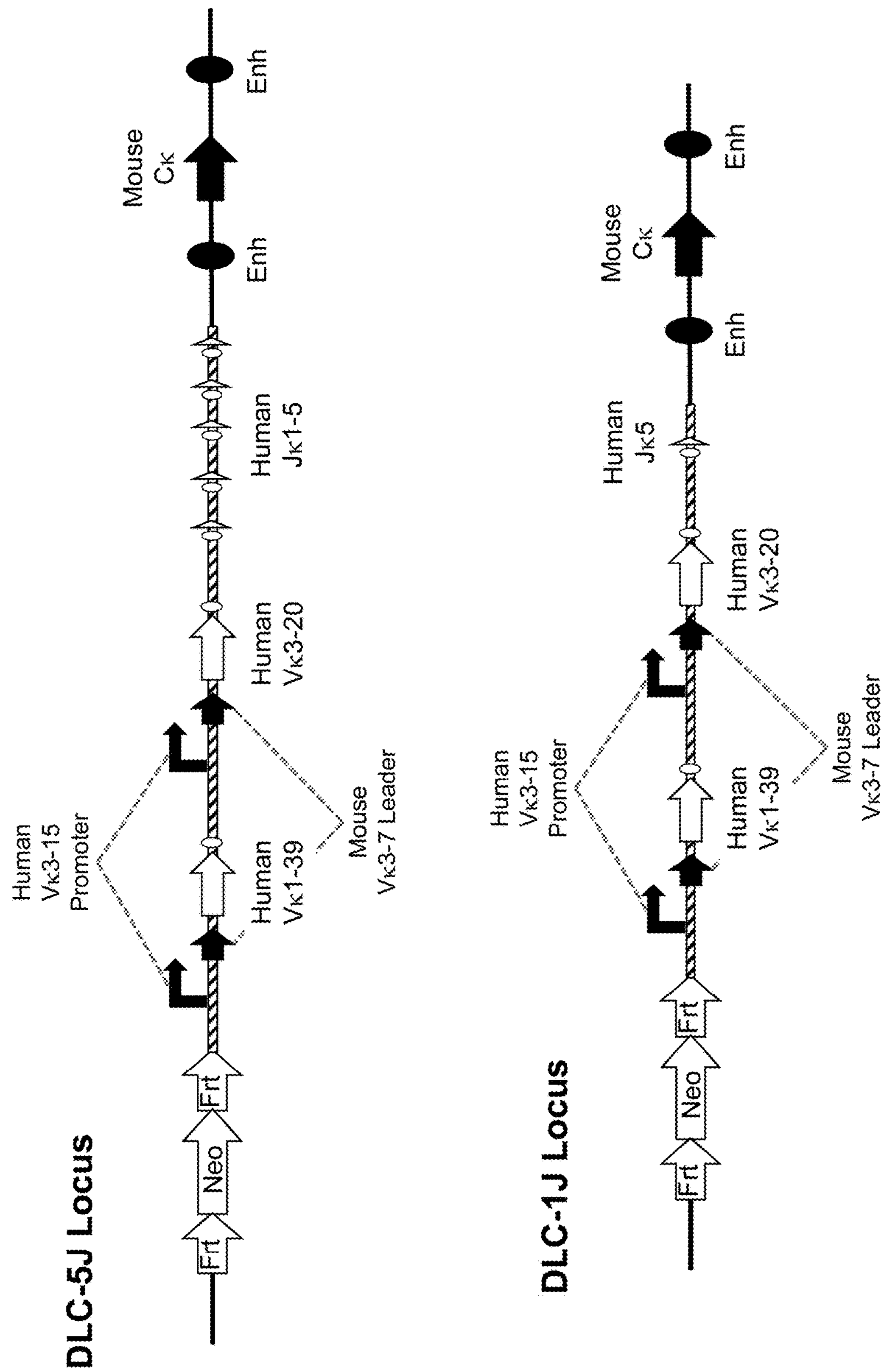
FIG. 9 shows two genetically modified endogenous immunoglobulin light chain (e.g., κ light chain) loci. The locus on the top (DLC-5J) contains an engineered human DNA fragment (striped line) containing two human Vκ gene segments and five human Jκ gene segments. The locus on the bottom (DLC-1J) contains an engineered human DNA fragment (striped line) containing two human Vκ gene segments and one human Jκ gene segment. Each locus is capable of rearranging to form a human Vκ region operably linked to an endogenous light chain constant region (e.g., a Cκ). Immunoglobulin promoters (arrow above locus), leader exons (closed arrows), and the two human Vκ gene segments (open arrows), all flanked upstream (5') by a neomycin cassette containing Frt recombination sites are shown. Recombination signal sequences engineered with each of the human gene segments (Vκ and Jκ) are indicated by open ovals juxtaposed with each gene segment.
Figure 10A:
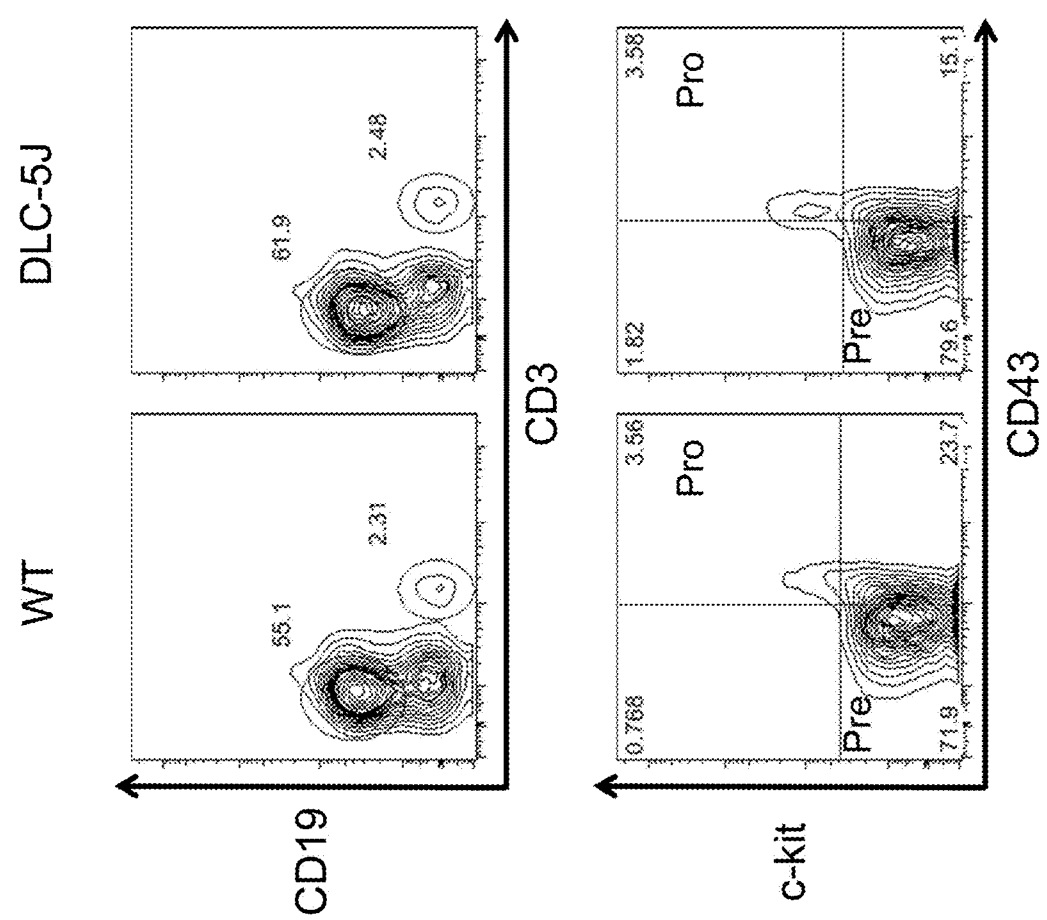
FIG. 10A, in the top panel, shows representative contour plots of bone marrow stained for B and T cells (CD19$^+$ and CD3$^+$, respectively) from a wild type mouse (WT) and a mouse homozygous for two human Vκ and five human Jκ gene segments (DLC-5J). The bottom panel shows representative contour plots of bone marrow gated on CD19$^+$ and stained for ckit$^+$ and CD43$^+$ from a wild type mouse (WT) and a mouse homozygous for two human Vκ and five human Jκ gene segments (DLC-5J). Pro and Pre B cells are noted on the contour plots of the bottom panel.
Figure 10B:
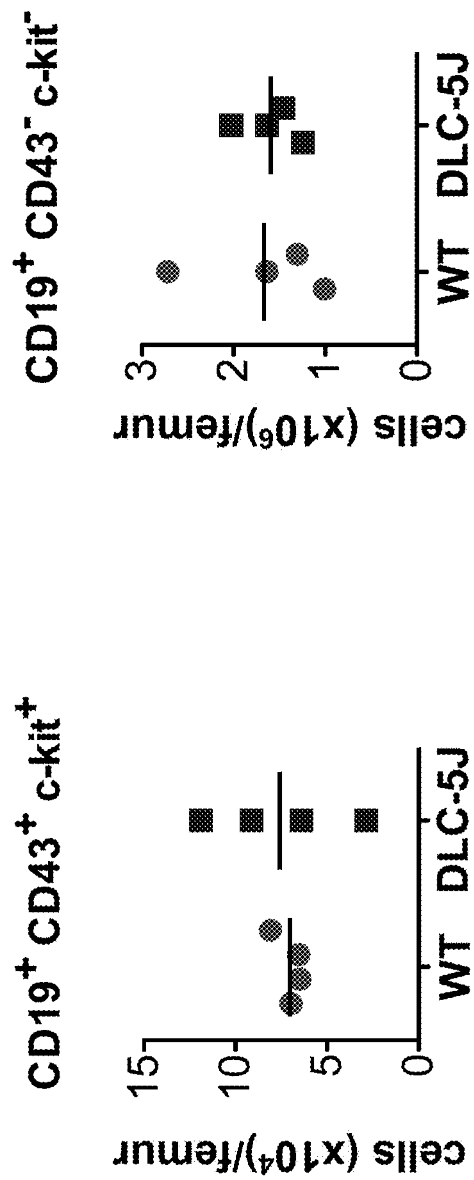
FIG. 10B shows the number of Pro (CD19$^+$CD43$^+$ckit$^+$) and Pre (CD19$^+$CD43$^-$ckir) B cells in bone marrow harvested from the femurs of wild type mice (WT) and mice homozygous for two human Vκ and five human Jκ gene segments (DLC-5J).
Figure 11A:
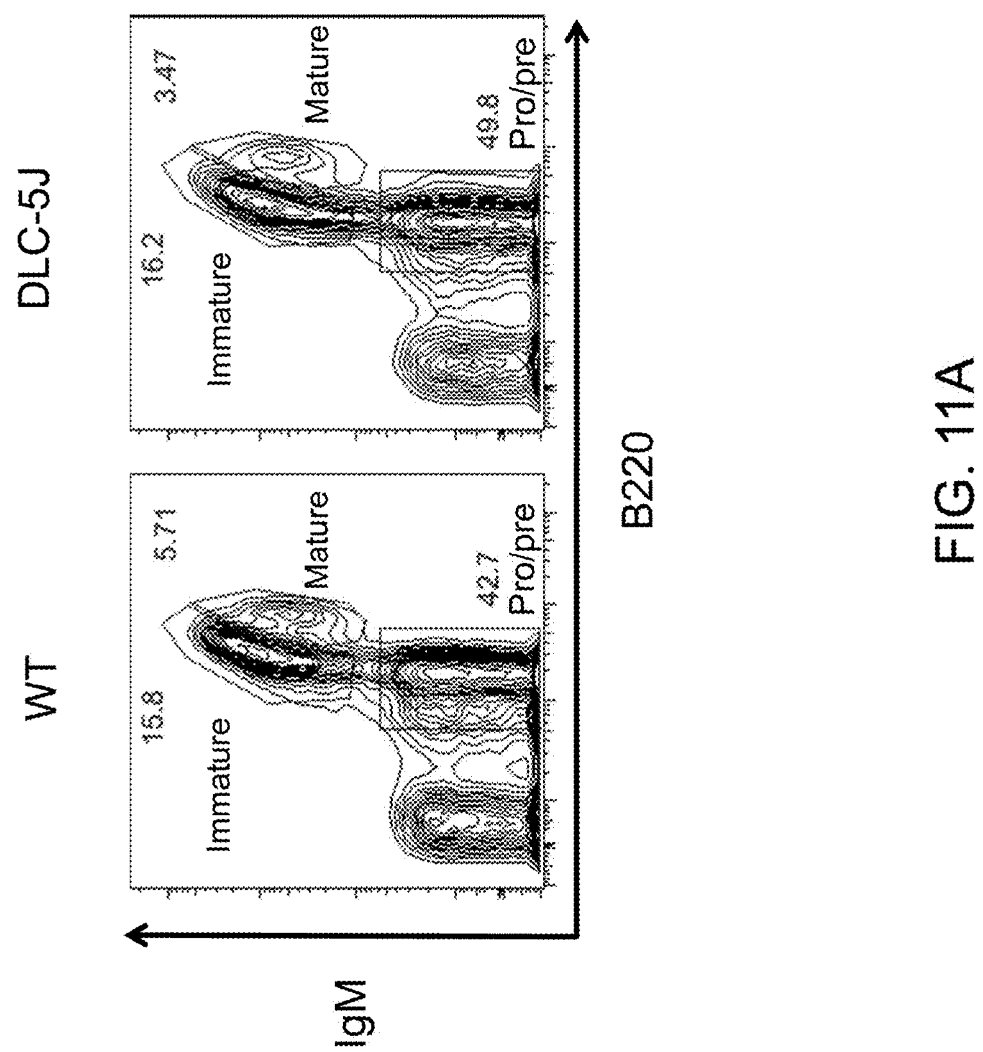
FIG. 11A shows representative contour plots of bone marrow gated on singlets stained for immunoglobulin M (IgM) and B220 from a wild type mouse (WT) and a mouse homozygous for two human Vκ and five human Jκ gene segments (DLC-5J). Immature, mature and pro/pre B cells are noted on each of the contour plots.
Figure 11B:
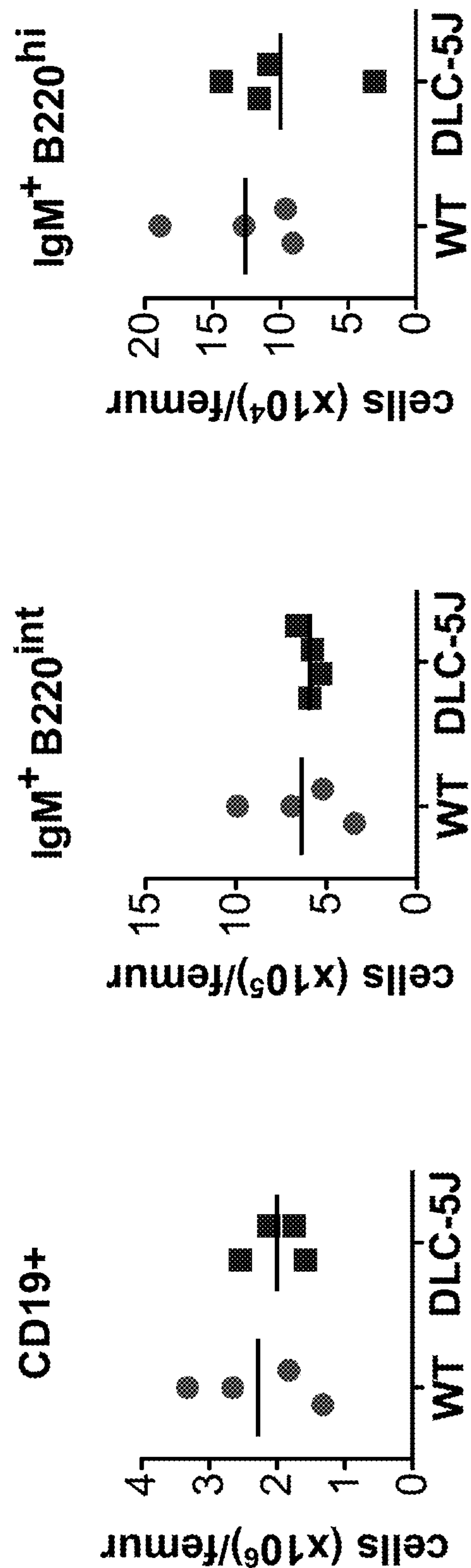
FIG. 11B shows the total number of B (CD19$^+$), immature B (B220$^{int}$IgM$^+$) and mature B (B220$^{hi}$IgM$^+$) cells in bone marrow isolated from the femurs of wild type mice (WT) and mice homozygous for two human Vκ and five human Jκ gene segments (DLC-5J).
Figure 12A:
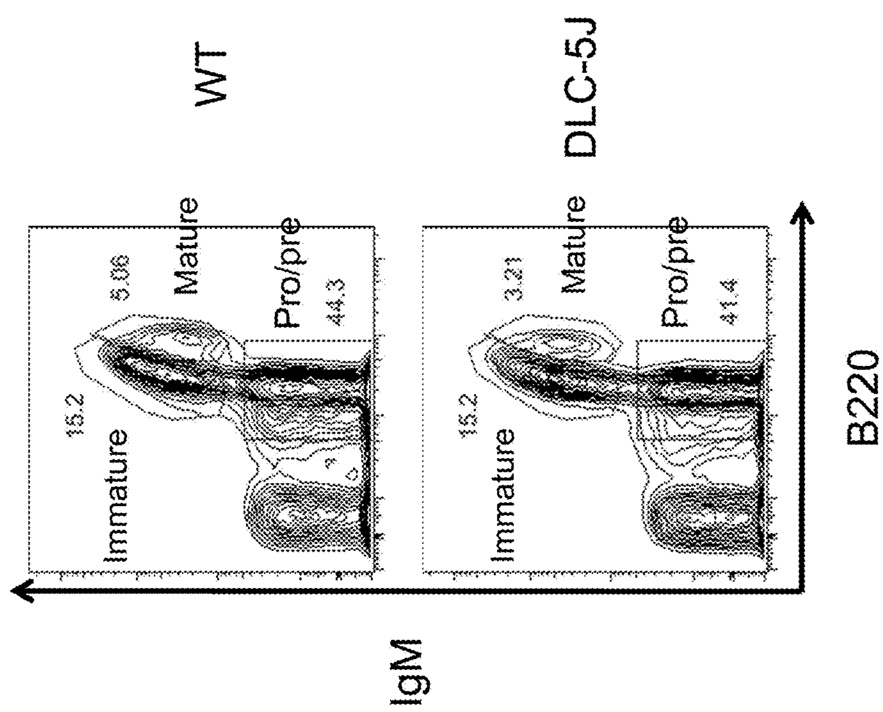
FIG. 12A shows representative contour plots of bone marrow gated on singlets stained for immunoglobulin M (IgM) and B220 from a wild type mouse (WT) and a mouse homozygous for two human Vκ and five human Jκ gene segments (DLC-5J). Immature, mature and pro/pre B cells are noted on each of the contour plots.
Figure 12B:
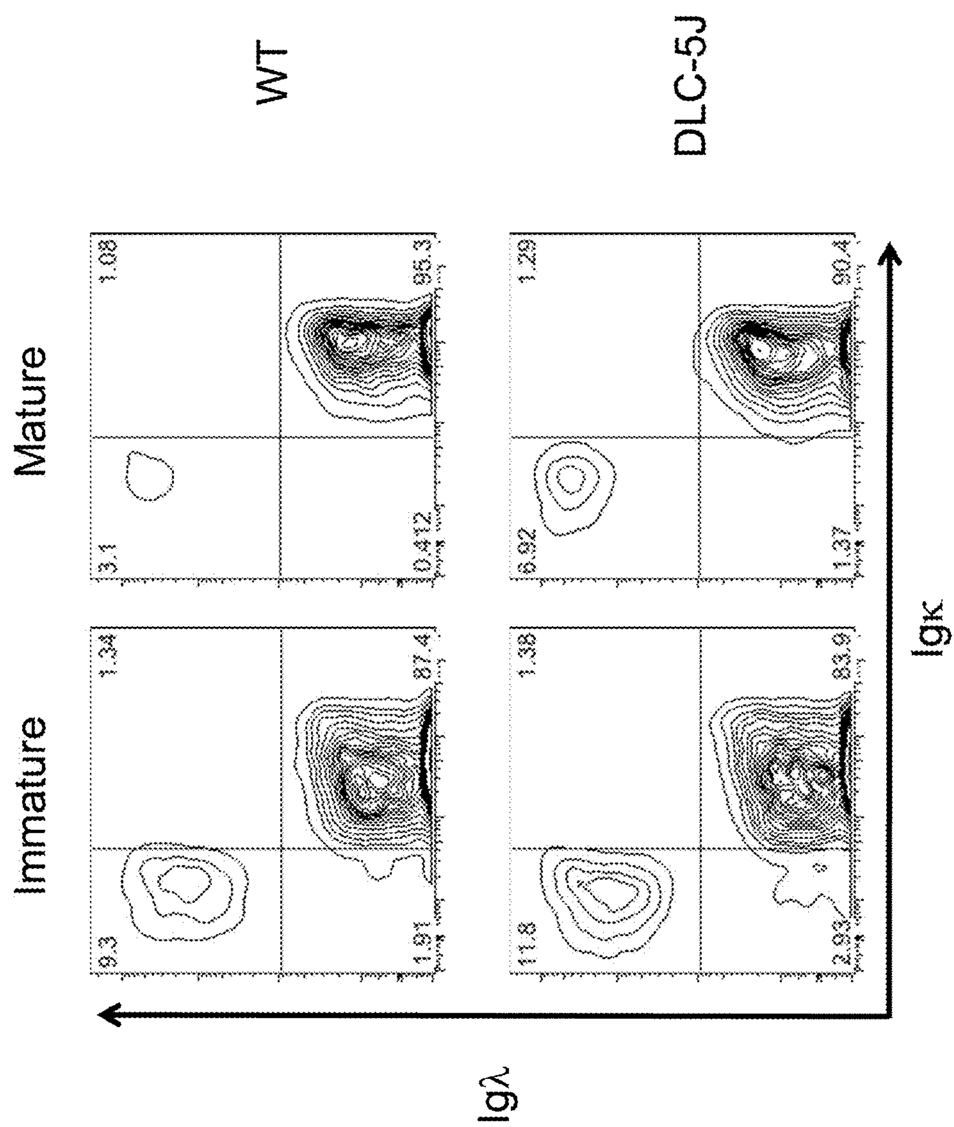
FIG. 12B shows representative contour plots of bone marrow gated on immature (B220$^{int}$IgM$^+$) and mature (B220$^{hi}$IgM$^+$) B cells stained for Igλ and Igκ expression isolated from the femurs of a wild type mouse (WT) and a mouse homozygous for two human Vκ and five human Jκ gene segments (DLC-5J).
Figure 13A:
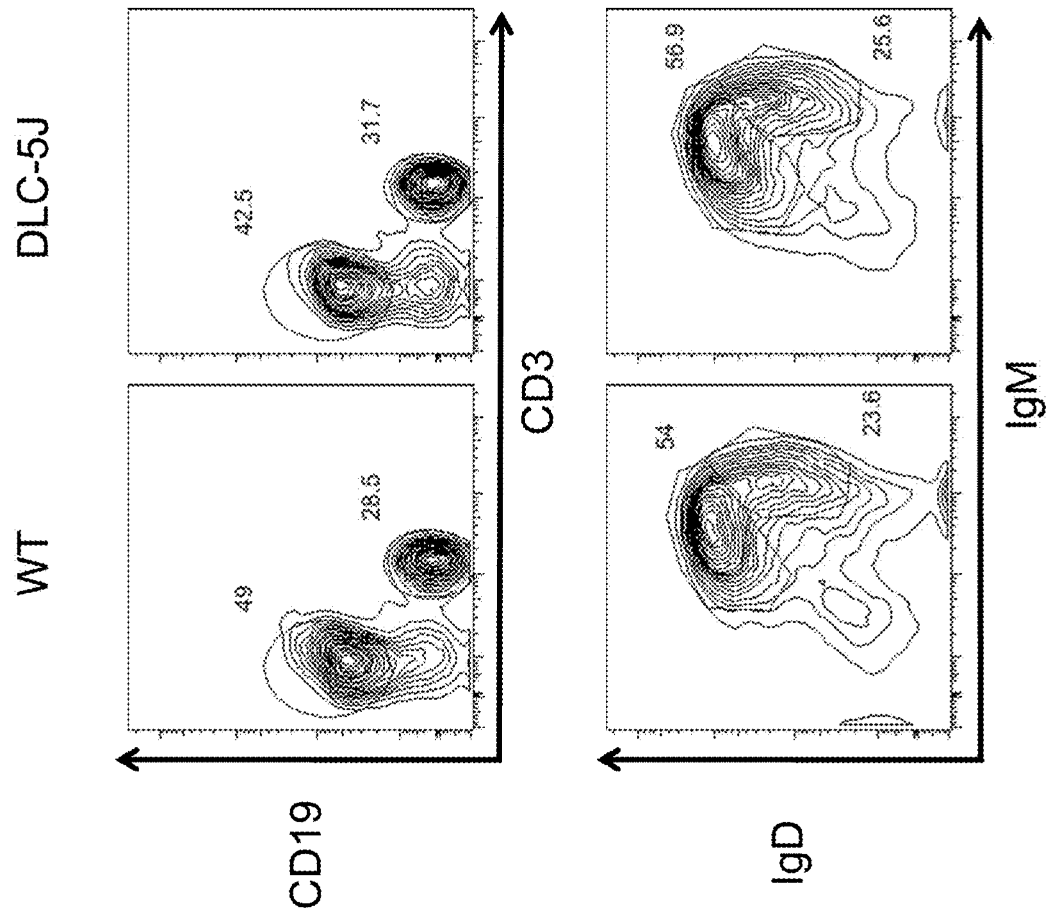
FIG. 13A, in the top panel, shows representative contour plots of splenocytes gated on singlets and stained for B and T cells (CD19$^+$ and CD3$^+$, respectively) from a wild type mouse (WT) and a mouse homozygous for two human Vκ and five human Jκ gene segments (DLC-5J). The bottom panel shows representative contour plots of splenocytes gated on CD19$^+$ and stained for immunoglobulin D (IgD) and immunoglobulin M (IgM) from a wild type mouse (WT) and a mouse homozygous for two human Vκ and five human Jκ gene segments (DLC-5J). Mature (54 for WT, 56.9 for DLC-5J) and transitional (23.6 for WT, 25.6 for DLC-5J) B cells are noted on each of the contour plots.
Figure 13B:
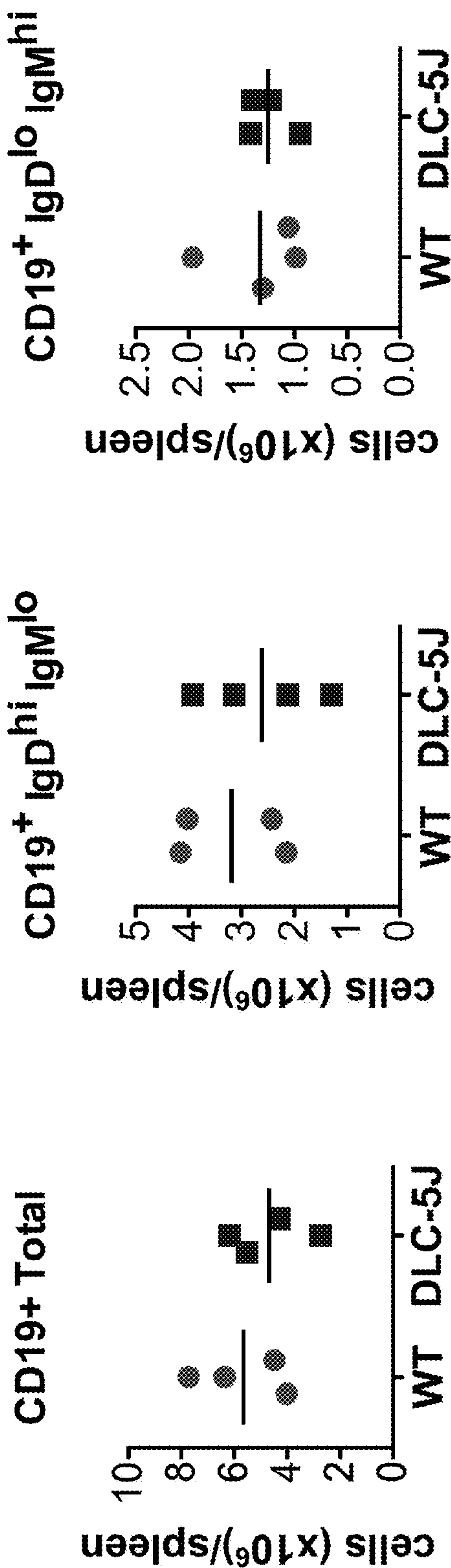
FIG. 13B shows the total number of CD19$^+$ B cells, transitional B cells (CD19$^+$IgM$^{hi}$IgD$^{lo}$) and mature B cells (CD19$^+$IgM$^{lo}$IgD$^{hi}$) in harvested spleens from wild type mice (WT) and mice homozygous for two human Vκ and five human Jκ gene segments (DLC-5J).
Figure 14A:
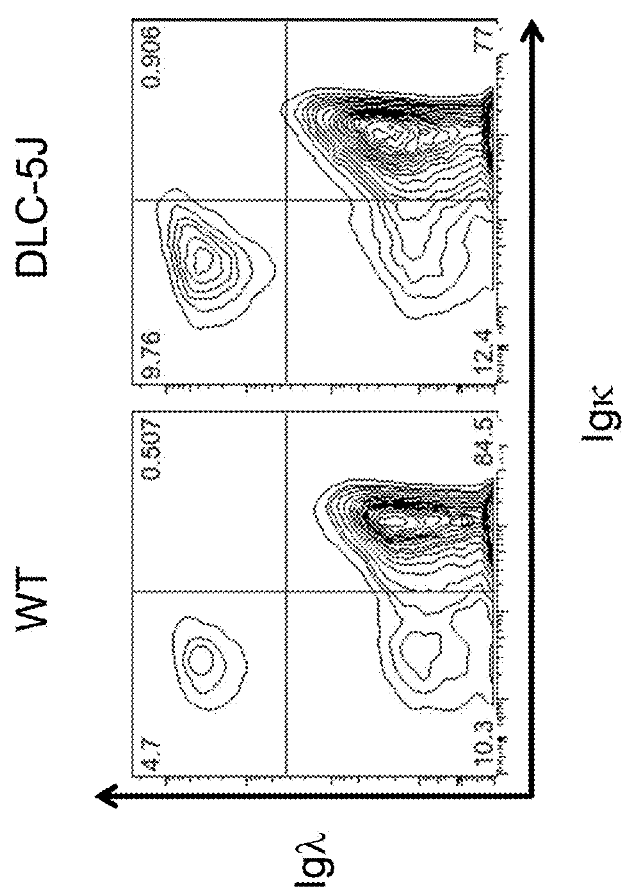
FIG. 14A shows representative contour plots of Igλ$^+$ and Igκ$^+$ splenocytes gated on CD19$^+$ from a wild type mouse (WT) and a mouse homozygous for two human Vκ and five human Jκ gene segments (DLC-5J).
Figure 14B:
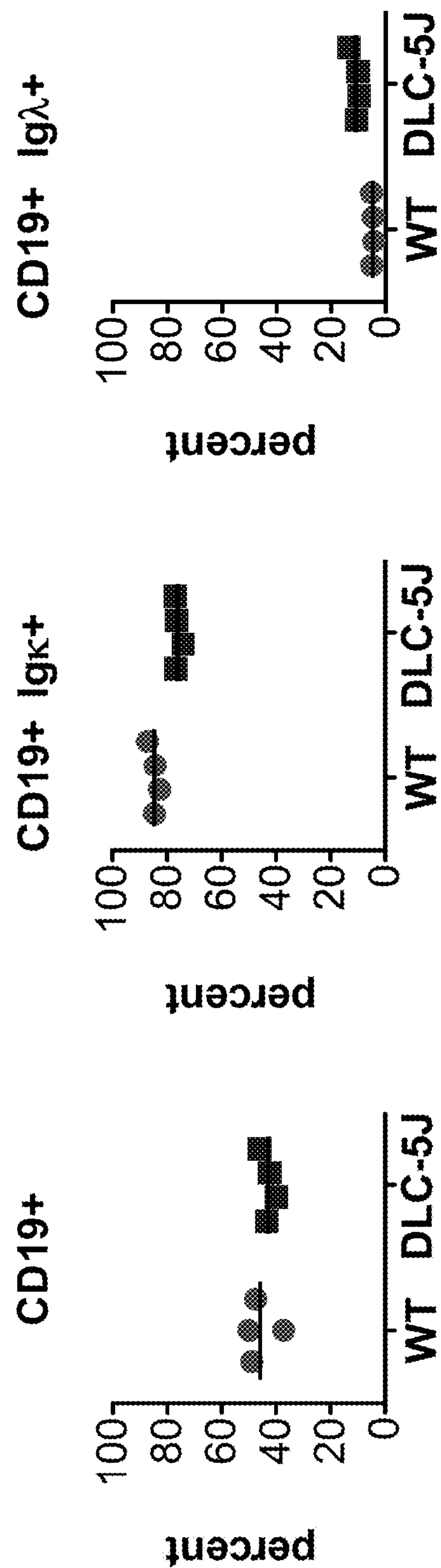
FIG. 14B shows the total number of B cells (CD19$^+$), Igκ$^+$ B cells (CD19$^+$Igκ$^+$) and Igλ$^+$ B cells (CD19$^+$Igλ$^+$) in harvested spleens from wild type (WT) and mice homozygous for two human Vκ and five human Jκ gene segments (DLC-5J).

Example 14. Generation and Analysis of Mice Expressing Two Human Light Chains Using the methods described above in Example 2, two additional engineered light chain loci containing two human Vκ gene segments (e.g., a human Vκ1-39 and human Vκ3-20 gene segment) were constructed (FIG. 9). One engineered light chain locus contained two human Vκgene segments and five human Jκ gene segments in unrearranged configuration (DLC-5J). The second engineered light chain locus contained two human Vκ gene segments and one human Jκ gene segment in unrearranged configuration (DLC-1J). For each of the two additional engineered light chain loci, the human gene segments were flanked 3' with recombination signal sequences to allow for in vivo rearrangement of the human gene segments in B cells.

Modified BAC DNA clones separately containing each of the the engineered light chain loci operably linked to mouse sequences (i.e., upstream and downstream sequences of the endogenous immunoglobulin κ light chain locus) were confirmed by PCR using primers located at sequences within each engineered light chain locus containing the two human Vκ gene segments followed by electroporation into ES cells to create mice that express either of the two human Vκgene segments (as described above). Positive ES cell clones that contain either of the engineered light chain loci described above were confirmed by TAQMAN™ screening and karyotyping using probes specific for the engineered light chain loci (as described above). Confirmed ES cell clones were then used to implant female mice to give rise to a litter of pups expressing a human light chain variable domain fused with a mouse Cκ domain, referred to herein as Dual Light Chain (DLC) mice.

Alternatively, ES cells bearing the engineered light chain locus may be transfected with a construct that expresses FLP in order to remove the FRTed neomycin cassette introduced by the targeting construct. Optionally, the neomycin cassette is removed by breeding to mice that express FLP recombinase (e.g., U.S. Pat. No. 6,774,279). Optionally, the neomycin cassette is retained in the mice.

Flow Cytometry. B cell populations and B cell development in DLC mice were validated by flow cytometry analysis of splenocyte and bone marrow preparations. Cell suspensions from mice homozygous for two human Vκ gene segments and five human Jκ gene segments (n=4), mice homozygous for two human Vκ gene segments and one human Jκ gene segment (n=4), and wild type mice (n=4) were made using standard methods (described above) and stained with fluorescently labeled antibodies (as described in Example 3).

Briefly, $1\times10^6$ cells were incubated with anti-mouse CD16/CD32 (clone 2.4G2, BD Pharmigen) on ice for 10 minutes, followed by labeling with the following antibody cocktail for 30 minutes on ice: APC-H7 conjugated anti-mouse CD19 (clone 1D3, BD Pharmigen), Pacific Blue conjugated anti-mouse CD3 (clone 17A2, BioLegend), FITC conjugated anti-mouse Igκ (clone 187.1, BD Pharmigen) or anti-mouse CD43 (clone 1B11, BioLegend), PE conjugated anti-mouse Igλ(clone RML-42, BioLegend) or anti-mouse c-kit (clone 2B8, BioLegend), PerCP-Cy5.5 conjugated anti-mouse IgD (BioLegend), PE-Cy7 conjugated anti-mouse IgM (clone 11/41, eBioscience), APC conjugated anti-mouse B220 (clone RA3-6B2, eBioscience). Following staining, cells were washed and fixed in 2% formaldehyde. Data acquisition was performed on an LSRII flow cytometer and analyzed with FlowJo (Tree Star, Inc.). Gating: total B cells ($CD19^+CD3^-$), $Ig\kappa^+$ B cells ($Ig\kappa Ig\lambda^-CD19^+CD3^-$), $Ig\lambda^+$ B cells ($Ig\kappa^-Ig\lambda^+CD19^+CD3^-$). Results for the bone marrow compartment are shown in FIG. 10A-FIG. 12B. Results for the splenic compartment are shown in FIG. 13A-FIG. 16.

Figure 15A:
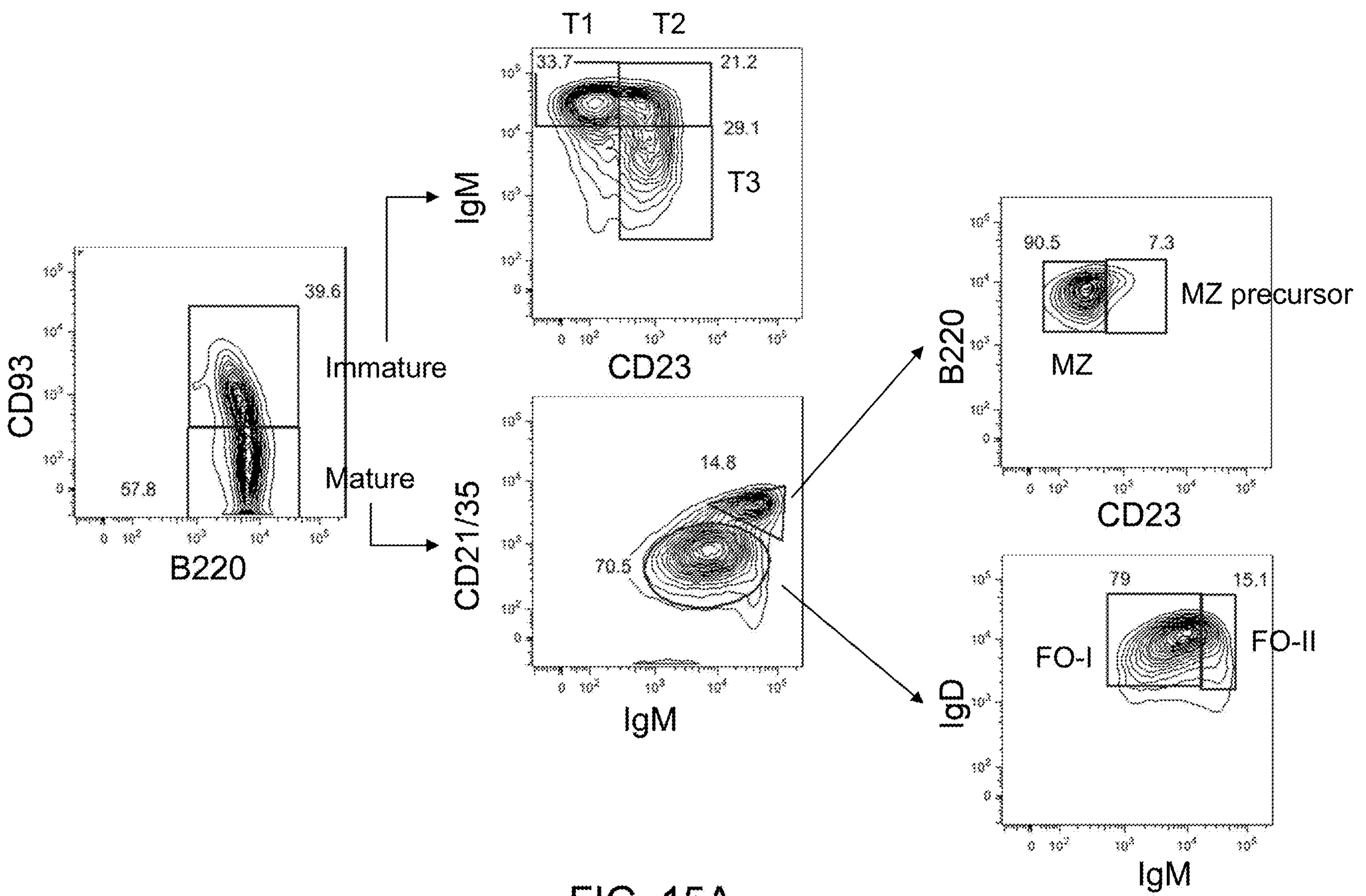
FIG. 15A shows the peripheral B cell development in mice homozygous for two human Vκ and five human Jκ gene segments. The first (far left) contour plot shows CD93$^+$ and B220$^+$ splenocytes gated on CD19$^+$ indicating immature (39.6) and mature (57.8) B cells. The second (top middle) contour plot shows IgM$^+$ and CD23$^+$ expression in immature B cells indicating T1 (33.7; IgD$^-$IgM$^+$CD21$^{lo}$CD23$^-$), T2 (21.2; IgD$^{hi}$IgM$^{hi}$CD21$^{mid}$CD23$^+$) and T3 (29.1) B cell populations. The third (bottom middle) contour plot shows CD21$^+$ (CD35$^+$) and IgM$^+$ expression of mature B cells indicating a small population (14.8) which give rise to marginal zone B cells and a second population (70.5) which gives rise to follicular (FO) B cells. The fourth (top right) contour plot shows B220$^+$ and CD23$^+$ expression in mature B cells indicating marginal zone (90.5; MZ) and marginal zone precursor (7.3; IgM$^{hi}$IgD$^{hi}$CD21$^{hi}$CD23$^+$) B cell populations. The fifth (bottom right) contour plot shows IgD$^+$ and IgM$^+$ expression in mature B cells indicating FO-I (79.0; IgD$^{hi}$IgM$^{lo}$CD21$^{mid}$CD23$^+$) and FO-II (15.1; IgD$^{hi}$IgM$^{hi}$CD21$^{mid}$CD23$^+$) B cell populations. Percentage of cells within each gated region is shown.
Figure 15B:
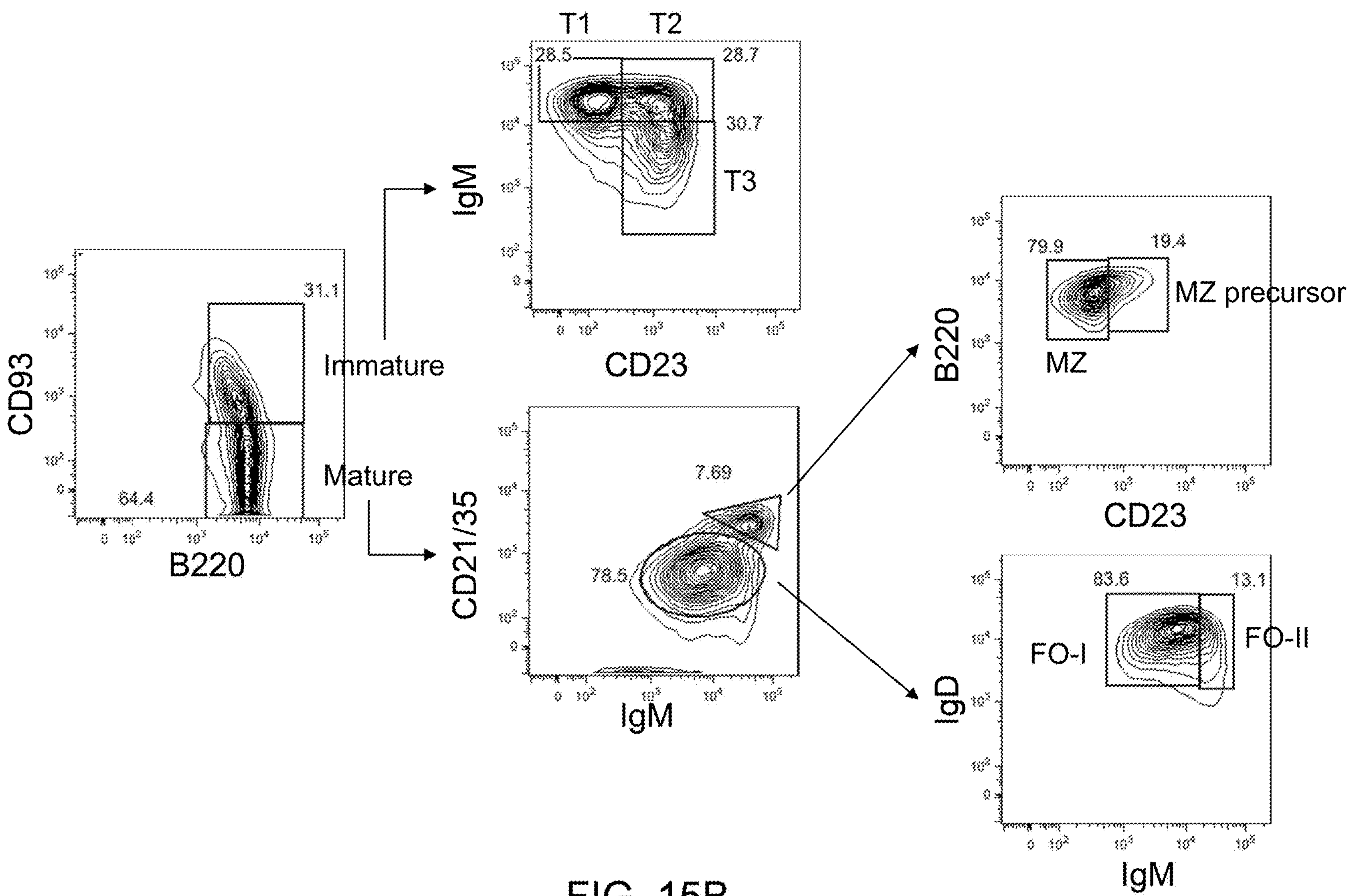
FIG. 15B shows the peripheral B cell development in wild type mice. The first (far left) contour plot shows CD93$^+$ and B220$^+$ splenocytes gated on CD19$^+$ indicating immature (31.1) and mature (64.4) B cells. The second (top middle) contour plot shows IgM$^+$ and CD23$^+$ expression in immature B cells indicating T1 (28.5; IgD$^-$IgM$^+$CD21$^{lo}$CD23$^-$), T2 (28.7; IgD$^{hi}$IgM$^{hi}$CD21$^{mid}$CD23$^+$) and T3 (30.7) B cell populations. The third (bottom middle) contour plot shows CD21$^+$ (CD35$^+$) and IgM$^+$ expression of mature B cells indicating a small population (7.69) which give rise to marginal zone B cells and a second population (78.5) which gives rise to follicular (FO) B cells. The fourth (top right) contour plot shows B220$^+$ and CD23$^+$ expression in mature B cells indicating marginal zone (79.9; MZ) and marginal zone precursor (19.4; IgM$^{hi}$IgD$^{hi}$CD21$^{hi}$CD23$^+$) B cell populations. The fifth (bottom right) contour plot shows IgD$^+$ and IgM$^+$ expression in mature B cells indicating FO-I (83.6; IgD$^{hi}$IgM$^{lo}$CD21$^{mid}$CD23$^+$) and FO-II (13.1; IgD$^{hi}$IgM$^{hi}$CD21$^{mid}$CD23$^+$) B cell populations. Percentage of cells within each gated region is shown.
Figure 16:
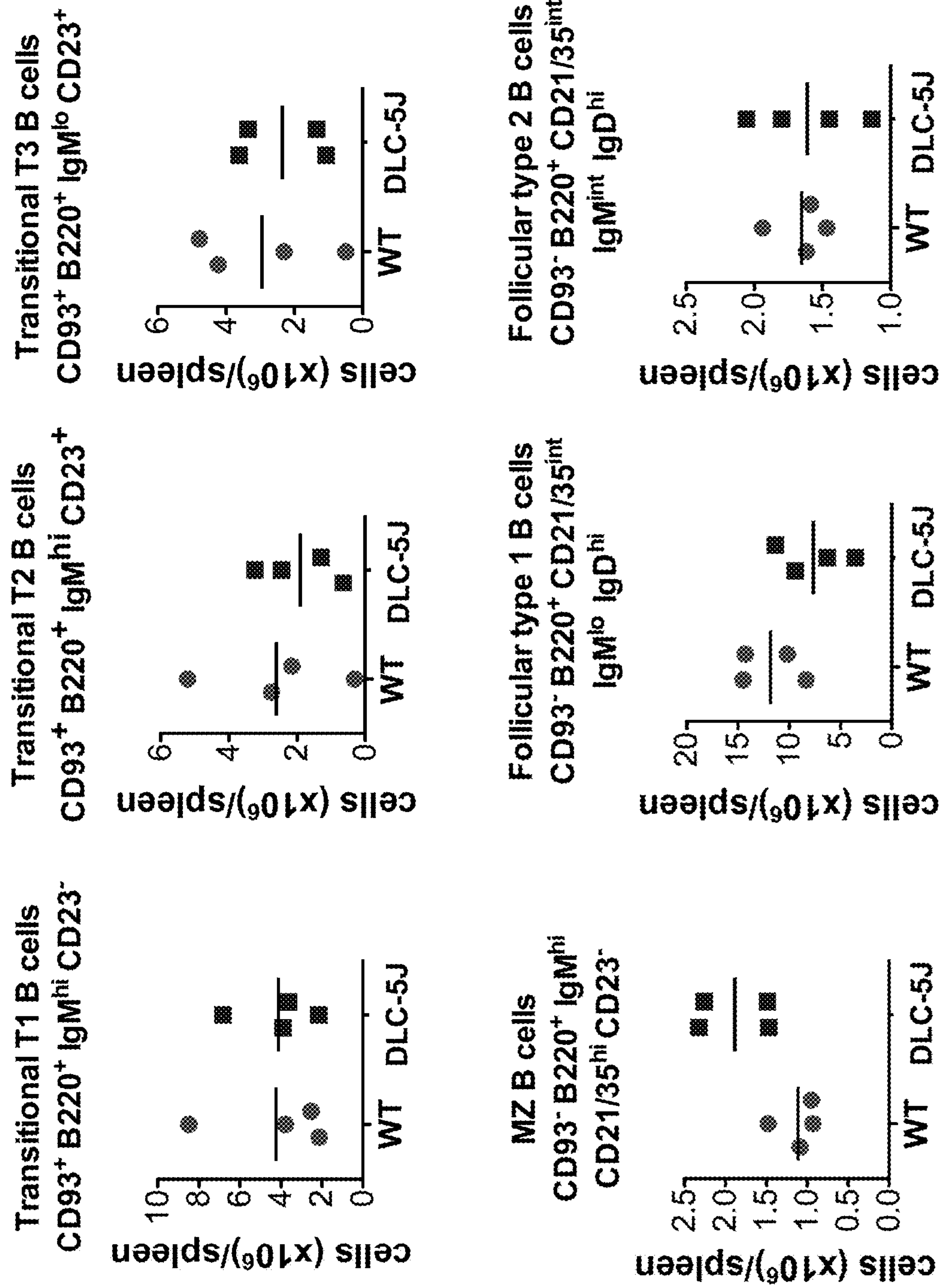
FIG. 16 shows the total number of transitional, marginal zone and follicular B cell populations in harvested spleens of wild-type (WT) and mice homozygous for two human Vκ and five human Jκ gene segments (DLC-5J).

As shown in this Example, DLC-5J mice demonstrate normal B cell populations within the splenic and bone marrow compartments (FIG. 10A-16). DLC-5J mice demonstrated immature, mature and pre/pro B cell populations within the bone marrow compartment that are substantially the same as observed in wild-type litter mates. In fact, the DLC-5J locus was capable of competing with the endogenous λ light chain locus to yield a κ:λ ratio that is substantially the same as that observed in wild-type mice (FIG. 14B). Also, DLC-5J mice demonstrate a normal peripheral B cell development as progression of B cells through various stages in the splenic compartment (e.g., immature, mature, T1, T2 T3, marginal zone precursor, marginal zone, follicular-I, follicular-II, etc.) occurs in a manner substantially the same as observed in wild type mice (FIG. 15A-16). In contrast, DLC-1J mice demonstrated a lower overall number of B cells and an increased λ light chain usage as compared to the engineered κ light chain (data not shown).

Dual Light Chain Expression. Expression of both human Vκ gene segments was analyzed in homozygous mice using a quantitative PCR assay in accordance with in Example 3. Briefly, $CD19^+$ B cells were purified from bone marrow and whole spleens of wild type mice, mice homozygous for a replacement of the mouse heavy chain and κ light chain variable loci with corresponding human heavy chain and κ light chain variable region loci (Hκ), as well as mice homozygous for an engineered κ light chain loci containing two human Vκ gene segments and either five human Jκ gene segments (DLC-5J) or one human Jκ gene segment (DLC-1J). Relative expression was normalized to expression of mouse Cκ region (n=3 to 5 mice per group). Results are shown in FIG. 17 and FIG. 18.

Figure 17:
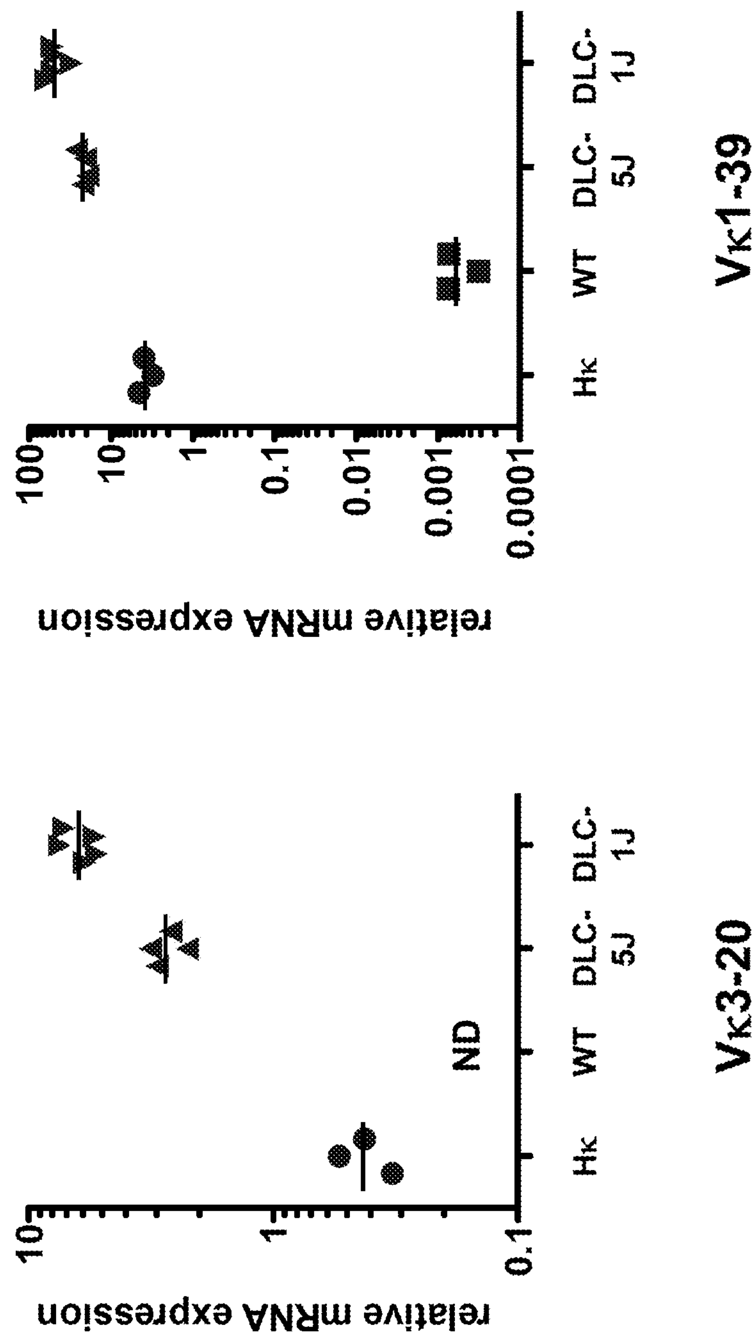
FIG. 17 shows the relative mRNA expression in bone marrow (y-axis) of Vκ3-20-derived and Vκ1-39-derived light chains in a quantitative PCR assay using probes specific for Vκ3-20 or Vκ1-39 gene segments in mice homozygous for a replacement of the endogenous Vκ and Jκ gene segments with human Vκ and Jκ gene segments (Hκ), wild type mice (WT), mice homozygous for two human Vκ gene segments and five human Jκ gene segments (DLC-5J) and mice homozygous for two human Vκ gene segments and one human Jκ gene segment (DLC-1J). Signals are normalized to expression of mouse Cκ. ND: not detected.
Figure 18:
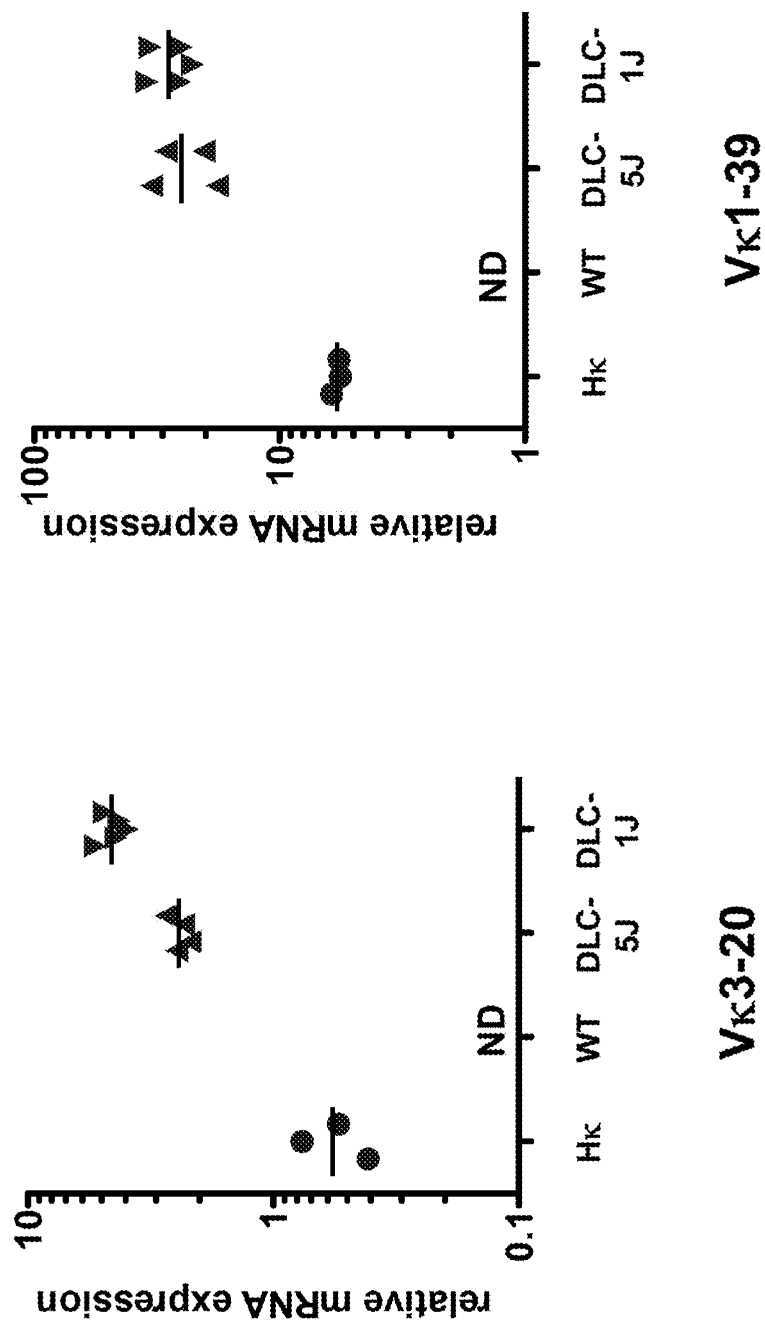
FIG. 18 shows the relative mRNA expression in whole spleens (y-axis) of Vκ3-20-derived and Vκ1-39-derived light chains in a quantitative PCR assay using probes specific for Vκ3-20 or Vκ1-39 gene segments in mice homozygous for a replacement of the endogenous Vκ and Jκ gene segments with human Vκ and Jκ gene segments (Hκ), wild type mice (WT), mice homozygous for two human Vκ gene segments and five human Jκ gene segments (DLC-5J) and mice homozygous for two human Vκ gene segments and one human Jκ gene segment (DLC-1J). Signals are normalized to expression of mouse Cκ. ND: not detected.
Figure 19:
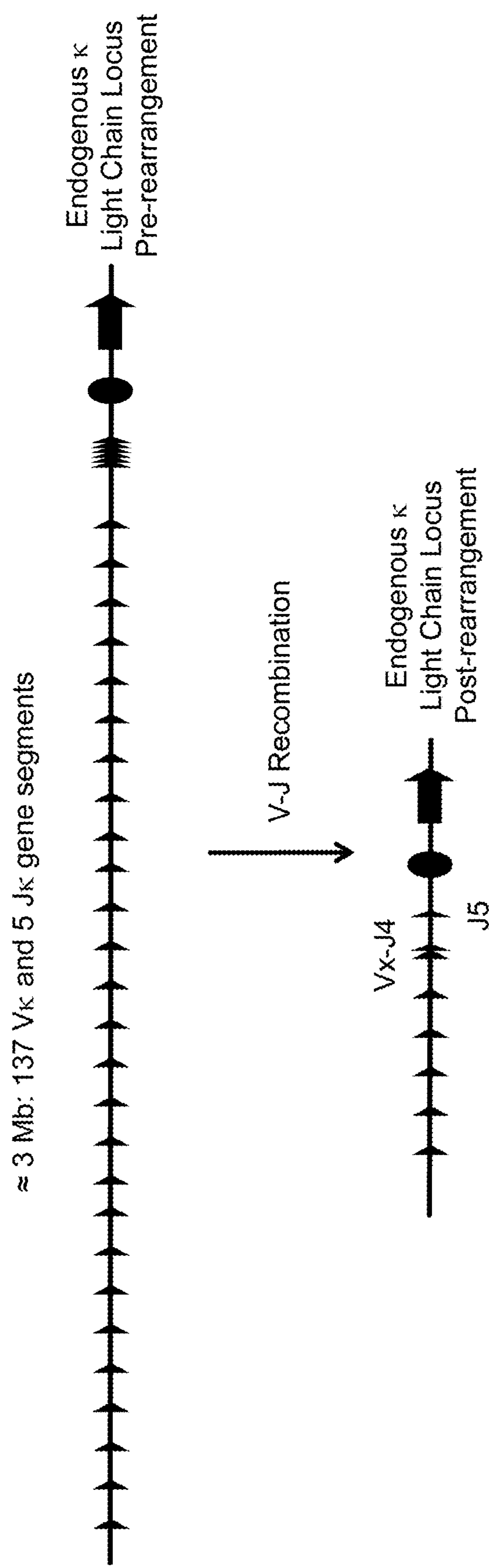
FIG. 19 shows a general illustration of recombination of a V and a J gene segment of an immunoglobulin κ light chain allele in a mouse and the structure of the light chain locus before rearrangement (top) and after rearrangement (bottom). Such a rearrangement as shown is only one of several possible rearrangement events.

Expression of light chains containing a rearranged human Vκ3-20 or human Vκ1-39 gene segment were detected in both the bone marrow and spleen of DLC-5J and DLC-1J mice (FIG. 17 and FIG. 18). In the bone marrow compartment, expression of both human Vκ3-20-derived and human Vκ1-39-derived light chains in both strains of DLC mice was significantly higher as compared to mice comprising a replacement of mouse Vκ and Jκ gene segment with corresponding human Vκ and Jκ gene segments (Hκ; FIG. 17). Human Vκ3-20-derived light chain expression was observed at about six-fold (DLC-5J) to fifteen-fold (DLC-1J) higher than in Hκ mice. DLC-1J mice demonstrated about two-fold higher expression of human Vκ3-20-derived light chains over DLC-5J mice in the bone marrow compartment. Human Vκ1-39-derived light chain expression was observed at about six-fold (DLC-5J) to thirteen-fold (DLC-1J) higher than in Hκ mice. DLC-1J mice demonstrated about two-fold higher expression of human Vκ1-39-derived light chains over DLC-5J mice in the bone marrow compartment.

In the splenic compartment, expression of both human Vκ3-20-derived and human Vκ1-39-derived light chains in both strains of DLC mice was significantly higher as compared to Hκ mice (FIG. 18). Human Vκ3-20-derived light chain expression was observed at about four-fold (DLC-5J) and eight-fold (DLC-1J) higher than in Hκ mice. DLC-1J mice demonstrated about two-fold higher expression of human Vκ3-20-derived light chains over DLC-5J mice in the splenic compartment. Human Vκ1-39-derived light chain expression was observed at about four-fold (DLC-5J) to five-fold (DLC-1J) higher than in Hκ mice. DLC-1J mice demonstrated similar expression of human Vκ1-39-derived light chains as compared to DLC-5J mice in the splenic compartment.

Human $V_L/J_L$ Usage in DLC-5J Mice. Mice homozygous for two unrearranged human Vκ gene segments and five unrearranged human Jκ gene segments (DLC-5J) were analyzed for human Vic/Jκ gene segment usage in splenic B cells by reverse-transcriptase polymerase chain reaction (RT-PCR).

Briefly, spleens from homozygous DLC-5J (n=3) and wild type (n=2) mice were harvested and meshed in 10 mL of RPMI 1640 (Sigma) containing 10% heat-inactivated fetal bovine serum using frosted glass slides to create single cell suspensions. Splenocytes were pelleted with a centrifuge (1200 rpm for five minutes) and red blood cells were lysed in 5 mL of ACK lysing buffer (GIBCO) for three minutes. Splenocytes were diluted with PBS (Irvine Scientific), filtered with a 0.7 μm cell strainer and centrifuged again to pellet cells, which was followed by resuspension in 1 mL of PBS.

RNA was isolated from pelleted splenocytes using AllPrep DNA/RNA mini kit (Qiagen) according to manufacturer's specifications. RT-PCR was performed on splenocyte RNA using 5' RACE (Rapid Amplification of cDNA ends) System with primers specific for the mouse Cκ gene according to manufacturer's specifications (Invitrogen). The primers specific for the mouse Cκ gene were 3' mIgκC RACE1 (AAGAAGCACA CGACTGAGGC AC; SEQ ID NO: 34) and mIgκC3'-1 (CTCACTGGAT GGTGGGAAGA TGGA; SEQ ID NO: 35). PCR products were gel-purified and cloned into pCR®2.1-TOPO® vector (TOPO® TA Cloning® Kit, Invitrogen) and sequenced with M13 Forward (GTAAAACGAC GGCCAG; SEQ ID NO: 36) and M13 Reverse (CAGGAAACAG CTATGAC; SEQ ID NO: 37) primers located within the vector at locations flanking the cloning site. Ten clones from each spleen sample were sequenced. Sequences were compared to the mouse and human immunoglobulin sets from the IMGT/V-QUEST reference directory sets to determine Vκ/Jκ usage. Table 25 sets forth the Vκ/Jκ combinations for selected clones observed in RT-PCR clones from each splenocyte sample. Table 26 sets forth the amino acid sequence of the human Vκ/human Jκ and human Jκ/mouse Cκ junctions of selected RT-PCR clones from DLC-5J homozygous mice. Lower case letters indicate mutations in the amino acid sequence of the variable region or non-template additions resulting from N and/or P additions during recombination.

As shown in this Example, mice homozygous for two unrearranged human Vκ gene segments and five unrearranged human Jκ gene segments (DLC-5J) operably linked to the mouse Cκ gene are able to productively recombine both human Vκ gene segments to multiple human Jκ gene segments to produce a limited immunoglobulin light chain repertoire. Among the rearrangements in DLC-5J homozygous mice shown in Table 25, unique human Vic/Jκ rearrangements were observed for Vκ1-39/Jκ2 (1), Vκ1-39/Jκ3 (1), Vκ3-20/Jκ1 (7), Vκ3-20/Jκ2 (4) and Vκ3-20/Jκ3 (1). Further, such unique rearrangements demonstrated junctional diversity through the presence of unique amino acids within the CDR3 region of the light chain (Table 26) resulting from either mutation and/or the recombination of the human Vκ and Jκ gene segments during development. All the rearrangements showed functional read through into mouse Cκ (Table 26).

Taken together, these data demonstrate that mice engineered to present a choice of no more than two human $V_L$ gene segments, both of which are capable of rearranging (e.g., with one or more and, in some embodiments, up to five human $J_L$ gene segments) and encoding a human $V_L$ domain of an immunoglobulin light chain have B cell numbers and development that is nearly wild-type in all aspects. Such mice produce a collection of antibodies having immunoglobulin light chains that have one of two possible human $V_L$ gene segments present in the collection. This collection of antibodies is produced by the mouse in response to antigen challenge and are associated with a diversity of reverse chimeric (human variable/mouse constant) heavy chains.

TABLE 25

| Mouse ID No. | Genotype | Clone | Vκ/Jκ Combination |
|---|---|---|---|
| 1089451 | DLC-5J | 1-2 | 1-39/3 |
| | | 1-4 | 3-20/2 |
| | | 1-7 | 3-20/1 |
| | | 1-8 | 3-20/2 |

TABLE 25-continued

| Mouse ID No. | Genotype | Clone | Vκ/Jκ Combination |
|---|---|---|---|
| 1089452 | DLC-5J | 2-2 | 3-20/1 |
| | | 2-3 | 3-20/1 |
| | | 2-6 | 3-20/2 |
| | | 2-8 | 3-20/2 |
| | | 2-9 | 3-20/1 |
| | | 2-10 | 1-39/2 |
| 1092594 | DLC-5J | 3-1 | 3-20/1 |
| | | 3-2 | 3-20/1 |
| | | 3-4 | 3-20/1 |
| | | 3-6 | 3-20/3 |
| | | 3-9 | 3-20/2 |
| 1092587 | WT | 1-1 | 19-93/1 |
| | | 1-2 | 6-25/1 |
| | | 1-3 | 4-91/5 |
| | | 1-5 | 3-10/4 |
| | | 1-6 | 4-86/4 |
| | | 1-8 | 19-93/1 |
| | | 1-10 | 19-93/2 |
| 1092591 | WT | 2-1 | 19-93/1 |
| | | 2-3 | 6-20/5 |
| | | 2-4 | 6-25/5 |
| | | 2-5 | 1-117/1 |
| | | 2-6 | 8-30/1 |
| | | 2-7 | 8-19/2 |
| | | 2-8 | 8-30/1 |
| | | 2-10 | 1-117/1 |

TABLE 26

| Clone | Vκ/Jκ | Sequence of hVκ/hJκ/mCκ Junction (CDR3 underlined, mIgκC italics) | SEQ ID NO: |
|---|---|---|---|
| 2-10 | 1-39/2 | QPEDFATYYCQQSYSTPYTFGQGTKLEIK*RADAAPTVSI* | 38 |
| 1-2 | 1-39/3 | QPEDFATYYCQQSYSTPFTFGPGTKVDIK*RADAAPTVSI* | 39 |
| 1-7 | 3-20/1 | EPEDFAVYYCQQYGSSPrTFGQGTKVEIK*RADAAPTVSI* | 40 |
| 2-2 | 3-20/1 | EPEDFAVYYCQQYGSSrTFGQGTKVEIK*RADAAPTVSI* | 41 |
| 2-3 | 3-20/1 | EPEDFAVYYCQQYGSSPWTFGQGTKVEIK*RADAAPTVSI* | 42 |
| 2-9 | 3-20/1 | dPEDFAVYYCQQYGSSPrTFGQGTKVEIK*RADAAPTVSI* | 44 |
| 3-1 | 3-20/1 | EPEDFAVYYCQQYGSSPrTFGQGTKVEIK*RADAAPTVSI* | 45 |
| 3-2 | 3-20/1 | EPEDFAVYYCQQYGSSPWTFGQGTKVEIK*RADAAPTVSI* | 46 |
| 3-4 | 3-20/1 | EPEDFAVYYCQQYGSSPPTFGQGTKVEIK*RADAAPTVSI* | 47 |
| 3-9 | 3-20/2 | EPEDFAVYYCQQYGSSPYTFGQGTKLEIK*RADAAPTVSI* | 48 |
| 3-6 | 3-20/3 | EPEDFAVYYCQQYGSSiFTFGPGTKVDIK*RADAAPTVSI* | 49 |

What is claimed is:

1. A method of making a mouse, comprising genetically modifying the germline genome of the mouse so that it includes:

a) exactly two unrearranged human immunoglobulin Vκ gene segments and five unrearranged human immunoglobulin Jκ gene segments operably linked to a mouse immunoglobulin light chain constant region sequence at the endogenous kappa light chain loci of the mouse, wherein the two unrearranged human immunoglobulin Vκ gene segments are a human Vκ1-39 gene segment and a human Vκ3-20 gene segment; and b) one or more unrearranged human immunoglobulin $V_H$ gene segments, one or more unrearranged human immunoglobulin $D_H$ gene segments, and one or more unrearranged human immunoglobulin $J_H$ gene segments operably linked to a mouse immunoglobulin heavy chain constant region sequence at the endogenous heavy chain loci of the mouse;

wherein the unrearranged human immunoglobulin heavy chain and kappa light chain gene segments are capable of rearranging and encoding human immunoglobulin variable domains of an antibody, and wherein the mouse does not comprise endogenous immunoglobulin Vκ or Jκ gene segments that are capable of rearranging to form an immunoglobulin light chain variable region sequence.

2. The method of claim 1, wherein the five unrearranged human immunoglobulin Jκ gene segments are a human Jκ1 gene segment, a human Jκ2 gene segment, a human Jκ3 gene segment, a human Jκ4 gene segment, and a human Jκ5 gene segment.

3. The method of claim 1, wherein the mouse light chain constant region is a mouse Cκ constant region.

4. The method of claim 1, wherein the human Vκ1-39 gene segment in the germline genome of the mouse is a human germline Vκ1-39 gene segment and the human Vκ3-20 gene segment in the germline genome of the mouse is a human germline Vκ3-20 gene segment.

5. The method of claim 2, wherein the germline genome of the mouse comprises in order: the human Vκ1-39 gene segment, the human Vκ3-20 gene segment, the human Jκ1 gene segment, the human Jκ2 gene segment, the human Jκ3 gene segment, the human Jκ4 gene segment, and the human Jκ5 gene segment.

6. The method of claim 1, wherein the mouse comprises a nonfunctional λ light chain locus.

7. A method for making an antibody that binds to an antigen of interest, wherein the method comprises:

(a) isolating one or more B lymphocytes from a mouse that has been exposed to an antigen of interest, wherein the one or more B lymphocytes express an antibody that binds the antigen of interest, and wherein the mouse comprises:

(i) exactly two unrearranged human immunoglobulin Vκ gene segments and five unrearranged human immunoglobulin Jκ gene segments operably linked to a mouse immunoglobulin light chain constant region sequence at the endogenous kappa light chain loci of the mouse, wherein the two unrearranged human immunoglobulin Vκ gene segments are a human Vκ1-39 gene segment and a human Vκ3-20 gene segment; and (ii) one or more unrearranged human immunoglobulin $V_H$ gene segments, one or more unrearranged human immunoglobulin $D_H$ gene segments, and one or more unrearranged human immunoglobulin $J_H$ gene segments operably linked to a mouse immunoglobulin heavy chain constant region sequence at the endogenous heavy chain loci of the mouse;

wherein the unrearranged human immunoglobulin heavy chain and kappa light chain gene segments are capable of rearranging and encoding human immunoglobulin variable domains of an antibody, and wherein the mouse does not comprise endogenous immunoglobulin Vκ or Jκ gene segments that are capable of rearranging to form an immunoglobulin light chain variable region sequence;

(b) identifying an amino acid sequence of human variable domain of the antibody that binds the antigen of interest or identifying a nucleotide sequence that encodes human variable domain of the antibody that binds that antigen of interest; and (c) employing the amino acid sequence or the nucleotide sequence of (b) to make an antibody that binds the antigen of interest.

8. The method of claim 7, wherein the five unrearranged human immunoglobulin Jκ gene segments are a human Jκ1 gene segment, a human Jκ2 gene segment, a human Jκ3 gene segment, a human Jκ4 gene segment, and a human Jκ5 gene segment.

9. The method of claim 7, wherein the mouse light chain constant region is a mouse Cκ constant region.

10. The method of claim 7, wherein the human Vκ1-39 gene segment in the germline genome of the mouse is a human germline Vκ1-39 gene segment and the human Vκ3-20 gene segment in the germline genome of the mouse is a human germline Vκ3-20 gene segment.

11. The method of claim 8, wherein the germline genome of the mouse comprises in order: the human Vκ1-39 gene segment, the human Vκ3-20 gene segment, the human Jκ1 gene segment, the human Jκ2 gene segment, the human Jκ3 gene segment, the human Jκ4 gene segment, and the human Jκ5 gene segment.

12. The method of claim 7, wherein the mouse comprises a nonfunctional 2 light chain locus.

* * * * *